United States Patent
South et al.

(10) Patent No.: US 11,041,162 B2
(45) Date of Patent: Jun. 22, 2021

(54) MICROORGANISMS ENGINEERED TO USE UNCONVENTIONAL SOURCES OF NITROGEN

(71) Applicant: Ginkgo Bioworks, Inc., Boston, MA (US)

(72) Inventors: Colin R. South, Lexington, MA (US); Arthur J. Shaw, IV, Belmont, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 16/392,322

(22) Filed: Apr. 23, 2019

(65) Prior Publication Data
US 2019/0316140 A1 Oct. 17, 2019

Related U.S. Application Data

(62) Division of application No. 15/679,312, filed on Aug. 17, 2017, now Pat. No. 10,316,323, which is a division of application No. 14/759,878, filed as application No. PCT/US2014/010332 on Jan. 6, 2014, now Pat. No. 9,765,348.

(60) Provisional application No. 61/782,351, filed on Mar. 14, 2013, provisional application No. 61/748,901, filed on Jan. 4, 2013.

(51) Int. Cl.
| | | |
|---|---|---|
| *C12N 15/81* | (2006.01) | |
| *C12P 3/00* | (2006.01) | |
| *C12N 1/20* | (2006.01) | |
| *C12N 9/14* | (2006.01) | |
| *C12N 9/88* | (2006.01) | |
| *C12N 15/70* | (2006.01) | |

(52) U.S. Cl.
CPC ............. *C12N 15/815* (2013.01); *C12N 1/20* (2013.01); *C12N 9/14* (2013.01); *C12N 9/88* (2013.01); *C12N 15/70* (2013.01); *C12N 15/81* (2013.01); *C12P 3/00* (2013.01); *C12Y 308/01* (2013.01); *C12Y 402/01069* (2013.01)

(58) Field of Classification Search
CPC .................................... C12N 9/88; C12N 1/20
USPC .................................................. 435/252.33
See application file for complete search history.

(56) References Cited

U.S. PATENT DOCUMENTS

| | | | | |
|---|---|---|---|---|
| 6,096,947 A | * | 8/2000 | Jayne ................. | C12N 15/8207 435/413 |
| 6,660,910 B1 | * | 12/2003 | Damm ............... | C12N 15/8274 800/300 |
| 10,316,323 B2 | | 6/2019 | South et al. | |
| 2011/0008809 A1 | | 1/2011 | Krebs | |
| 2011/0127108 A1 | | 6/2011 | Teichert | |
| 2011/0129566 A1 | | 6/2011 | Van Vuuren et al. | |

FOREIGN PATENT DOCUMENTS

WO WO 2003/040379 5/2003

OTHER PUBLICATIONS

Boundy-Mills et al., "The atzB Gene of *Pseudomonas* sp. Strain ADP Encodes the Second Enzyme of a Novel Atrazine Degradation Pathway," *Applied and Environmental Microbiology*, 1997, 63(3):916-923.
Cameron et al., "New Family of Biuret Hydrolases Involved in S-Triazine Ring Metabolism," *ACS Catal*, 2011, 1:1075-1082.
Cheng et al., "Allophanate Hydrolase, Not Urease, Function in Bacterial Cyanuric Acid Metabolism," *Appl. Environ. Microb.*, 2005, 71(8):4437-4445.
Copley, "Evolution of Efficient Pathways for Degradation of Anthropogenic Chemicals," *Nat. Chem. Biol.*, 2009, 5(8):559-566.
De Souza et al., "The atzABC Genes encoding Atrazine Catabolism Are Located on a Self-Transmissible Plasmid in *Pseudomonas* sp. Strain ADP," *Appl. Environ. Microb*, 1998, 64(6):2323-2326.
Dodge et al., "Plasmid Localization and Organization of Melamine Degradation Genes in *Rhodococcus* sp. Strain Mel." *Applied and Environmental Microbiology*, 78:1397-1403.
Eaton et al., "Cloning and analysis of s-Triazine catabolic genes from *Pseudomonas* sp. Strain NRRLB-12227," *Journal of Bacteriology*, 1991 173:1215-1222.
Eaton et al., "Cloning and comparison of the DNA encoding ammelide aminohydrolase and cyanuric acid amidohydrolase from three s-Triazine-degrading bacterial strains," *Journal of Bacteriology*, 1991, 173:1363-1366.
El-Sayed et al., "Biodegradation of melamine formaldehyde by *Micrococcus* sp. Strain MF-1 isolated from aminoplastic wastewater effluent," *International Biodeterioration & Biodegradation*, 2006, 57:75-81.
Fruchey et al., "On the Origins of Cyanuric Acid Hydrolase: Purification, Substrates, and Prevalence of AtzD from *Pseudomonas* sp. Strain ADP," *Appl. Environ. Microb.*, 2003, 69(6):3653-3657.
International Search Report and Written Opinion issued in International Patent Application No. PCT/US2014/10332, dated Jun. 24, 2014.

(Continued)

*Primary Examiner* — Tekchand Saidha
(74) *Attorney, Agent, or Firm* — Foley Hoag LLP

(57) ABSTRACT

Disclosed are genetically engineered organisms, such as yeast and bacteria, that have the ability to metabolize atypical nitrogen sources, such as melamine and cyanamide. Fermentation methods using the genetically engineered organisms are also described. The methods of the invention are robust processes for the industrial bioproduction of a variety of compounds, including commodities, fine chemicals, and pharmaceuticals.

9 Claims, 29 Drawing Sheets
Specification includes a Sequence Listing.

(56) References Cited

OTHER PUBLICATIONS

Kamo et al., "Limited distribution of natural cyanamide in higher plants: Occurrence in *Vicia villosa* subsp. *varia, V. cracca,* and *Robinia pseudo-acacia,*" *Phytochemistry*, 2008, 68:1166-1172.

Kamo et al., "Quantification of Cyanamide Contents in Herbaceous Plants," *Bioscience, Biotechnology, and Biochemistry*, 2006, 70:2310-2312.

Karns, "Gene Sequence and Properties of an s-Triazine Ring-Cleavage Enzyme from *Pseudomonas* sp. Strain NRRLB-12227," *Applied and Environmental Microbiology*, 1999, 65:3512-3517.

Leeson et al., "Biomineralization of atrazine ozonation products. Application to the Development of a Pesticide Waste Disposal System," *J. Agric. Food Chem.*, 1993, 41:983-987.

Maier-Greiner et al., "Isolation and properties of a nitrile hydratase from the soil fungus *Myrothecium verrucaria* that is highly specific for the fertilizer cyanamide and cloning of its gene," *Proceedings of the National Academy of Sciences*, 1991, 88:4260-4264.

Martinez et al., "Complete Nucleotide Sequence and Organization of the Atrazine Catabolic Plasmid pADP-1 from *Pseudomonas* sp. Strain ADP." *Journal of Bacteriology*, 2001, 183:5684-5697.

Mäser et al., "A Nucleoside Transporter from *Trypanosoma brucei* Involved in Drug Resistance," *Science*, 1999, 285:242-244.

Office action issued in corresponding Chinese Patent Application No. 201480012382.8, dated Mar. 12, 2018.

Schwarzer et al., "Physiological and electron microscopical investigations on syntrophic dicyandiamide degradation by soil bacteria," *Soil Biology and Biochemistry*, 1998, 30:385-391.

Seffernick et al., "Bacterial Ammeline Metabolism via Guanine Deaminase," *Journal of Bacteriology*, 2010, 192:1106-1112.

Seffernick et al., "Melamine Deaminse and Atrazine Chlorohydrolase: 98 Percent Identical but Functionally Different," *Journal of Bacteriology*, 2001, 183:2405-2410.

Shapir et al., "Evolution of Catabolic Pathways: Genomic Insights into Microbial s-Triazine Metabolism," *J. Bacteriol*, 2007, 189(3):674-682.

Shapir et al., "Purification and Characterization of Allophanate Hydrolase (AtzF) from *Pseudomonas* sp. Strain ADP," *J. Bacteriol*, 2005, 187(11):3731-3738.

Shapir et al., "Purification and Characterization of TrzF: Biuret Hydrolysis by Allophanate Hydrolase Supports Growth," *Applied and Environmental Microbiology*, 2006, 72:2491-2495.

Shapir et al., "Purification, Substrate Range, and Metal Center of AtzC: the N-Isopropylammelide Aminohydrolase Involved in Bacterial Atrazine Metabolism," *Journal of Bacteriology*, 184(19):5376-5384.

Shelton et al., "Metabolism and Melamine by *Klebsiella terragena.*" *Applied and Environmental Microbiology*, 1997, 63:2832-5.

Strong et al., "*Arthrobacter aurescens* TC1 Metabolizes Diverse s-Triazine Ring Compounds." *Applied and Environmental Microbiology*, 2002, 68:5973-5980.

Sýkora et al., "Biodegradability of ethylenediamine-based complexing agents." *Water Research*, 2001, 35:2010-2016.

Takagi et al., "Biodegradation of Melamine and its Hydroxy Derivatives by a Bacterial Consortium Containing a Novel *Nocardioides* Species," *Appl. Microbiol Biotechnol*, 2012, 94:1647-1656.

Ulanov et al., "Effect of the Expression of cyanamide hydratase on metabolites in cyanamide-treated soybean plants kept in the light or dark," *Journal of Experimental Botany*, 2007, 58:4319-4332.

Wackett et al., "Microbial Enzymes in Biodegradation," *Novel Approaches for Bioremediation of Organic Pollution*, Fass et al., 1999, p. 95-103.

Zeyer et al., "Microbial degradation of Ammeline." *Zbl. Bakt. Hyg., I. Abt. Orig. C.*, 1981, 2:289-298.

Shanks et al., "New yeast recombineering tools for bacteria," Plasmid, 62(2):88-97 (2009).

Shanks et al., "*Saccharomyces cerevisiae*-based molecular tool kit for manipulation of genes from gram-negative bacteria," Appl Environ Microbiol, 72(7): 5027-5036 (2006).

\* cited by examiner

Figure 2

| Compound | Formula | % N |
|---|---|---|
| Hydrazine | $N_2H_4$ | 88% |
| 5-Aminotetrazole | $CH_3N_5$ | 82% |
| Tetrazole | $CH_2N_4$ | 80% |
| Melamine | $C_3H_6N_6$ | 67% |
| Cyanamide | $CH_2N_2$ | 67% |
| 2-Cyanoguanidine | $C_2H_4N_4$ | 67% |
| Sodium azide | $NaN_3$ | 65% |
| Carbohydrazide | $CH_6N_4O$ | 62% |
| 1,2,3-Triazole | $C_2H_3N_3$ | 61% |
| 1,2,4-Triazole | $C_2H_3N_3$ | 61% |
| 1,3-Diaminoguanidine HCL | $CH_7N_5 \cdot HCl$ | 56% |
| Ammeline | $C_3H_5N_5O$ | 55% |
| 1,3,5-triazine | $C_3H_3N_3$ | 52% |
| Aminoacetonitrile | $C_2H_4N_2$ | 50% |
| Cyanoethylhydrazine | $C_3H_7N_3$ | 49% |
| Azodicarbonamide | $C_2H_4O_2N_4$ | 48% |
| Biurea | $C_2H_6N_4O_2$ | 47% |
| Formamidoxime | $CH_4N_2O$ | 47% |
| 1,2-Dimethylhydrazine | $C_2H_8N_2$ | 47% |
| 1,1-Dimethylhydrazine | $C_2H_8N_2$ | 47% |
| ethylhydrazine | $C_2H_8N_2$ | 47% |
| Ethylenediamine | $C_2H_8N_2$ | 47% |
| Sodium dicyanamide | $C_2N_3Na$ | 47% |
| Guanidine carbonate | $CH_5N_3 * \frac{1}{2} H_2CO_3$ | 47% |
| Methylamine | $CH_5N$ | 45% |
| Ammelide | $C_3H_4N_4O_2$ | 44% |
| Hydroxylamine | $NH_2OH$ | 42% |
| Malononitrile | $C_3H_2N_2$ | 42% |
| Biuret | $C_2H_5N_3O_2$ | 41% |
| Diethyltriamine | $C_4H_{13}N_3$ | 41% |

Figure 2 (continued)

| | | |
|---|---|---|
| Hexamethylenetetramine | $C_6H_{12}N_4$ | 40% |
| Triethylenetetramine | $C_6H_{18}N_4$ | 38% |
| 1,3-Diaminopropane | $C_3H_{10}N_2$ | 38% |
| Triethylenetetramine | $C_6H_{18}N_4$ | 38% |
| 1,3-Diaminopropane | $C_3H_{10}N_2$ | 38% |
| Hydroxyurea | $CH_4N_2O_2$ | 37% |
| Tetraethylenepentamine | $C_8H_{23}N_5$ | 37% |
| Thiourea | $CH_4N_2S$ | 37% |
| Succinonitrile | $C_4H_4N_2$ | 35% |
| Calcium cyanamide | $CaCN_2$ | 35% |
| Cyanuric acid | $C_3H_3N_3O_3$ | 33% |
| Aminoethylpiperazine | $C_6H_{15}N_3$ | 33% |
| Piperazine | $C_4H_{10}N_2$ | 33% |
| Dimethylamine | $C_2H_7N$ | 31% |
| Ethylamine | $C_2H_7N$ | 31% |
| dalfampridine | $C_5H_6N_2$ | 30% |
| Tetranitromethane | $CN_4O_8$ | 29% |
| Imidazolidinyl urea | $C_{11}H_{16}N_8O_8$ | 29% |
| Trinitromethane | $CHN_3O_6$ | 28% |
| malonamide | $C_3H_6N_2O_2$ | 27% |
| Chloramine | $NH_2Cl$ | 27% |
| Allophante | $C_2H_3N_2O_3$ | 27% |
| Trimethylamine | $C_3H_9N$ | 24% |
| Nitromethane | $CH_3NO_2$ | 23% |
| Acetaldoxime | $C_2H_5NO$ | 23% |
| Diazolidinyl urea | $C_8H_{14}N_4O_7$ | 20% |
| 1,2-Cyclohexanedione dioxime | $C_6H_{10}N_2O_2$ | 20% |
| Acetone oxime | $C_3H_7NO$ | 19% |
| Thioacetamide | $C_2H_5NS$ | 19% |
| Sodium thiocyanate | NaSCN | 17% |
| Isothiazole | $C_3H_3NS$ | 16% |
| Thiazole | $C_3H_3NS$ | 16% |

Figure 2 (continued)

| | | |
|---|---|---|
| Dimethylacetamide | $C_4H_9NO$ | 16% |
| Isothiazolinone | $C_3H_3NOS$ | 14% |
| Methylene blue | $C_{16}H_{18}N_3SCl$ | 13% |
| Diethanolamine | $C_4H_{11}NO_2$ | 13% |
| Aspartame | $C_{14}H_{18}N_2O_5$ | 10% |
| Benzisothiazolinone | $C_7H_5NOS$ | 7% |
| Acesulfame potassium | $C_4H_4KNO_4S$ | 7% |

Figure 3

| Enzyme | Gene | Source | EC | Genbank | Genbank Protein or Nucleotide Region |
|---|---|---|---|---|---|
| Melamine deaminase | trzA | Williamsia sp. NRRL B-15444R (formerly R. corallinus) | 3.5.4.- | JN241635 | |
| Melamine deaminase | triA | Pseudomonas sp. strain NRRL B-12227 (formerly Acidovorax citrulli) | 3.5.4.- | AF312304 | |
| Guanine (ammeline) deaminase | guaD | E. coli K12 strain MG1566 | 3.5.4.3 | NC_000913 | REGION: 3023788..3025107 |
| Guanine (ammeline) deaminase | blr3880 | Bradyrhizobium japonicum USDA 110 | 3.5.4.3 | NC_004463 | REGION: 4303362..4304759 |
| Guanine (ammeline) deaminase | GUD1/YDL238C | S. cerevisiae | 3.5.4.3 | Z74286 | |
| Guanine (ammeline) deaminase | YALI0E25740p | Y. lipolytica CLIB122 | 3.5.4.3 | NC_006071 | REGION: complement(3051691..3053046) |
| ammelide hydrolase | trzC | Pseudomonas sp. strain NRRL B-12227 (formerly Acidovorax citrulli) | 3.5.3.- | AAK00493 | |
| ammelide hydrolase | trzC | Rhodococcus sp. Mel | 3.5.3.- | AEX65049 | |
| N-isopropylammelide isopropylamino hydrolase | atzC | Pseudomonas sp. strain ADP | 3.5.99.4 | NC_004956 | REGION: complement(70219..71430) |
| Cyanuric acid amidohydrolase | trzD | Pseudomonas sp. strain NRRL B-12227 (formerly Acidovorax citrulli) | 3.5.2.15 | AF086815 | |
| Cyanuric acid amidohydrolase | atzD (trzD) | Rhodococcus sp. Mel | 3.5.2.15 | JN241637 | AEX65082 |
| Cyanuric acid amidohydrolase | atzD | Pseudomonas sp. strain ADP | 3.5.2.15 | NC_004956 | REGION: 101053..102144 |
| Biuret amidohydrolase | atzE | Pseudomonas sp. strain ADP | 3.5.1.84 | NC_004956 | REGION: 102427..103800 |
| Biuret amidohydrolase | trzE | Rhodococcus sp. Mel | 3.5.1.84 | AEX65081 | |
| Biuret amidohydrolase | trzE | Rhizobium leguminosarum bv. viciae 3841 | 3.5.1.84 | YP_770628 | |
| Allophanate hydrolase | atzF | Pseudomonas sp. strain ADP | 3.5.1.54 | NC_004956 | REGION: 104283..106100 |
| Allophanate hydrolase | DUR1,2 | S. cerevisiae | 6.3.4.6 / 3.5.1.54 | YSCUAMD | |
| Allophanate hydrolase | YALI0E07271g | Y. lipolytica CLIB122 | 6.3.4.6 / 3.5.1.54 | XM_503658 | |

Figure 11

| MOPS defined medium | mM |
|---|---|
| Glucose | 11.1 |
| $K_2HPO_4$ | 1.32 |
| $K_2SO_4$ | 0.28 |
| $FeSO_4$ | 0.01 |
| $CaCl_2$ | 5E-04 |
| $MgCl_2$ | 0.52 |
| NaCl | 50 |
| MOPS | 40 |
| Tricine | 4 |
| $(NH_4)_6Mo_7O_{24}$ | 3E-06 |
| $H_3BO_3$ | 4E-04 |
| $CoCl_2$ | 3E-05 |
| $CuSO_4$ | 1E-05 |
| $MnCl_2$ | 8E-05 |
| $ZnSO_4$ | 1E-05 |

|  | Optical Density 600 nm | | | |
| --- | --- | --- | --- | --- |
|  | NS100 | NS101 | NS111 | NS112 |
| no nitrogen | 0.18 | 0.19 | 1.31 | 0.99 |
| 10 mM urea | 3.12 | 3.60 | 3.68 | 3.05 |
| 10 mM cyanamide | 0.05 | 4.66 | 3.09 | 0.15 |

|  | Optical Density 600 nm | | |
|---|---|---|---|
|  | NS98 | NS99 | NS100 |
| no nitrogen | 1.43 | 1.37 | 1.09 |
| 10 mM urea | 5.09 | 5.26 | 5.22 |
| 10 mM biuret | 2.55 | 2.18 | 1.21 |

Figure 29

| Plasmid | Description | Genotype |
|---|---|---|
| pNC10 | *E. coli* and *S. cerevisiae* cloning/shuttle vector | Amp, ura3 |
| pNC53 | *E. coli* promoter (pTac)-terminator (trpT') cloning vector (AJS52) | Amp, ura3 |
| pNC67 | *E. coli*, *S. cerevisiae*, and *Y. lipolytica* shuttle vector | Amp, ura3, Hyg, Nat |
| pNC85 | *E. coli triA* expression vector (AJS69) | Amp, ura3 |
| pNC86 | *E. coli trzA, guaD, trzC* expression vector (AJS67) | Amp, ura3 |
| pNC87 | *E. coli trzD, trzE,* DUR1,2 expression vector (AJS68) | Amp, ura3 |
| pNC93 | *S. cerevisiae cah* expression vector (AJS76) | Amp, ura3, Hyg |
| pNC96 | *S. cerevisiae trzE MEL* expression vector (AJS79) | Amp, ura3, Hyg |
| pNC97 | *S. cerevisiae trzE Rl* expression vector (AJS80) | Amp, ura3, Hyg |
| pNC101 | E. coli *trzC_12227, guaD, triA* expression vector (AJS83) | Amp, ura3 |
| pNC120 | E. coli *trzD_12227, trzE,* DUR1,2 *trzC_12227, guaD, triA* expression vector (AJS88a) | Amp, ura3 |
| pNC121 | E. coli *atzD_ADP, trzE,* DUR1,2 *trzC_12227, guaD, triA* expression vector (AJS88b) | Amp, ura3 |

Figure 30

| Strain | Description | Culture Collection Designation |
|---|---|---|
| NS21 | Eschericha coli K12 | NRRL B-3707 |
| NS88 | Eschericha coli K12 with pNC85 | |
| NS89 | Eschericha coli K12 with pNC86 | |
| NS90 | Eschericha coli K12 with pNC87 | |
| NS91 | Eschericha coli K12 with pNC53 | |
| NS93 | Eschericha coli K12 with pNC85 selected for ammeline utilization | |
| NS103 | Eschericha coli K12 with pNC101 | |
| NS106 | Eschericha coli MG1655 | ATCC 47076 |
| NS107 | Eschericha coli B | ATCC 11303 |
| NS108 | Eschericha coli Crooks | ATCC 8739 |
| NS109 | Eschericha coli K12 with pNC120 | |
| NS110 | Eschericha coli K12 with pNC121 | |
| NS120 | Eschericha coli MG1655 with pNC53 | |
| NS121 | Eschericha coli MG1655 with pNC121 | |
| NS122 | Eschericha coli B with pNC121 | |
| NS123 | Eschericha coli Crooks with pNC53 | |
| NS124 | Eschericha coli Crooks with pNC121 | |
| NS8 | Saccharomyces cerevisiae | NRRL Y-2223 |
| NS22 | Saccharomyces cerevisiae industrial ethanol strain | |
| NS98 | Saccharomyces cerevisiae industrial ethanol strain with pNC96 | |
| NS99 | Saccharomyces cerevisiae industrial ethanol strain with pNC97 | |
| NS100 | Saccharomyces cerevisiae industrial ethanol strain with pNC67 | |
| NS101 | Saccharomyces cerevisiae industrial ethanol strain with pNC93 | |
| NS111 | Saccharomyces cerevisiae NRRL Y-2223 with pNC93 | |
| NS112 | Saccharomyces cerevisiae NRRL Y-2223 with pNC67 | |

Figure 31

*E. coli* Media

| MOPS defined medium | mM |
|---|---|
| Glucose | 11.1 |
| $K_2HPO_4$ | 1.32 |
| $K_2SO_4$ | 0.28 |
| $FeSO_4$ | 0.01 |
| $CaCl_2$ | 5E-04 |
| $MgCl_2$ | 0.52 |
| NaCl | 50 |
| MOPS | 40 |
| Tricine | 4 |
| $(NH_4)_6Mo_7O_{24}$ | 3E-06 |
| $H_3BO_3$ | 4E-04 |
| $CoCl_2$ | 3E-05 |
| $CuSO_4$ | 1E-05 |
| $MnCl_2$ | 8E-05 |
| $ZnSO_4$ | 1E-05 |
| Nitrogen source as indicated | 0.25-10 |

Additionally 100 ug/mL ampicillin is added for plasmid maintenance.

Figure 32

<u>S. cerevisiae Media</u>
YNB media (Per liter)
- Glucose          20 g
- Biotin 2 µg
- Calcium pantothenate 400 µg
- Folic acid 2 µg
- Inositol 2000 µg
- Niacin 400 µg
- p-Aminobenzoic acid 200 µg
- Pyridoxine hydrochloride 400 µg
- Riboflavin 200 µg
- Thiamine hydrochloride 400 µg
- Boric acid 500 µg
- Copper sulfate 40 µg
- Potassium iodide 100 µg
- Ferric chloride 200 µg
- Manganese sulfate 400 µg
- Sodium molybdate 200 µg
- Zinc sulfate 400 µg
- Potassium phosphate monobasic 1 g
- Magnesium sulfate 500 mg
- Sodium chloride 100 mg
- Calcium chloride 100 mg Additionally a nitrogen source at 10 mM concentration is added, as well as the antibiotics hygromycin (300 ug/mL) or nourseothricin (100 ug/mL) as appropriate for plasmid maintenance.

Figure 33

SC amino acid composition (total 2 g/L)

| SC amino acids | mg/L |
|---|---|
| Adenine | 21 |
| L-Alanine | 85.6 |
| L-Arginine | 85.6 |
| L-Asparagine | 85.6 |
| L-Aspartic Acid | 85.6 |
| L-Cysteine | 85.6 |
| Glutamine | 85.6 |
| L-Glutamic Acid | 85.6 |
| Glycine | 85.6 |
| L-Histidine | 85.6 |
| Myo-Inositol | 85.6 |
| L-Isoleucine | 85.6 |
| L-Leucine | 173.4 |
| L-Lysine | 85.6 |
| L-Methionine | 85.6 |
| Para-AminoBenzoic Acid (PABA) | 8.6 |
| L-Phenylalenine | 85.6 |
| L-Proline | 85.6 |
| L-Serine | 85.6 |
| L-Threonine | 85.6 |
| L-Tryptophan | 85.6 |
| L-Tyrosine | 85.6 |
| Uracil | 85.6 |
| L-Valine | 85.6 |

MICROORGANISMS ENGINEERED TO USE UNCONVENTIONAL SOURCES OF NITROGEN

RELATED APPLICATIONS

This application is a divisional application of U.S. patent application Ser. No. 15/679,312, filed Aug. 17, 2017, which is a divisional application of U.S. patent application Ser. No. 14/759,878, filed Jul. 8, 2015, which is a § 371 national stage application based on PCT/US2014/010332, filed Jan. 6, 2014, which claims the benefit of priority to U.S. Provisional Patent Application No. 61/782,351, filed Mar. 14, 2013, and U.S. Provisional Patent Application No. 61/748,901, filed Jan. 4, 2013, the contents of which are herein incorporated by reference in their entirety for all purposes.

SEQUENCE LISTING

The instant application contains a Sequence Listing which has been submitted electronically in .txt format and is hereby incorporated by reference in its entirety. Said .txt formatted copy was created on Apr. 18, 2019, is named NOVG-P0008US-D2_BI014-053-US-DIV2_sequence-listing-28803013_1 and is 279,000 bytes in size.

BACKGROUND

In the fermentation industry, cell culture media is typically formulated to provide all nutrients necessary for the growth of a host cell line, with particular emphasis on meeting the cell line's requirements for carbon, nitrogen, phosphorus, sulfur, and other major nutrients. Some cell lines require additional components, including amino acids, trace minerals and metals, and complex growth factors. The presence of these nutrients provides a suitable growth environment for the organism of choice and, unfortunately, for any potential contaminating organisms. In this environment the production organism is required to compete directly with any contaminant organism in the cell culture.

Even in robust hosts, the combination of opportunistic infections of the culture and the metabolic burden resulting from the demands of product manufacture is a major concern in monoculture operations. Industrial robustness is typically considered a multigenic trait specific to the host strain and thus difficult to engineer predictably into organisms late in the development process. Addition of selective growth inhibitors, such as bacterial antibiotics, is one method used to create a more robust fermentation environment for host organisms that are resistant to the growth inhibitor. However, antibiotic addition is often undesirable or unfeasible, and spontaneously resistant contaminations frequently result.

Accordingly, there exists a need for rationally engineered traits that, when engineered into a host organism, create a robust monoculture fermentation environment.

SUMMARY OF THE INVENTION

In certain embodiments, the invention relates to a genetically engineered organism, wherein the genetically engineered organism has been transformed by a nucleic acid molecule comprising any one or more of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of allophanate hydrolase, biuret amidohydrolase, cyanuric acid amidohydrolase, guanine deaminase, melamine deaminase, isopropylammelide isopropylaminohydrolase, cyanamide hydratase, urease, and urea carboxylase.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound of any one of Formulas I-III, or a salt thereof;

a native organism of the same species as the genetically engineered organism could not metabolize (i.e., use as a source of nitrogen) the nitrogen-containing compound;

the genetically engineered organism converts the substrate to a product; and the compound of formula I is

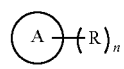

I wherein, independently for each occurrence,

is a five-, six, nine-, or ten-membered aryl or heteroaryl group;

R is —OH, —CO$_2$H, —NO$_2$, —CN, substituted or unsubstituted amino, or substituted or unsubstituted alkyl; and n is 0, 1, 2, 3, 4, or 5;

the compound of formula II is

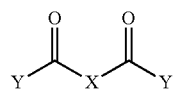

II wherein, independently for each occurrence,

X is —NH—, —N(alkyl)-, —O—, —C(R$^1$)$_2$—, —S—, or absent;

Y is —H, —NH$_2$, —N(H)(alkyl), —N(alkyl)$_2$, —CO$_2$H, —CN, or substituted or unsubstituted alkyl; and R$^1$ is —H, —OH, —CO$_2$H, —NO$_2$, —CN, substituted or unsubstituted amino, or substituted or unsubstituted alkyl; and the compound of formula III is

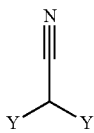

wherein, independently for each occurrence,
Y is —H, —NH$_2$, —N(H)(alkyl), —N(alkyl)$_2$, —CO$_2$H, —CN, or substituted or unsubstituted alkyl.

In certain embodiments, the invention relates to a method, comprising the step of
contacting any one of the aforementioned genetically engineered organisms with a substrate,
wherein
the substrate comprises a nitrogen-containing fraction and a non-nitrogen-containing fraction;
the nitrogen-containing fraction comprises, in an amount from about 10% by weight to about 100% by weight, a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
the genetically engineered organism converts the substrate to a product.

In certain embodiments, the invention relates to a method, comprising the step of
contacting any one of the aforementioned genetically engineered organisms with a substrate,
wherein
the substrate comprises a nitrogen-containing fraction and a non-nitrogen-containing fraction;
the nitrogen containing fraction consists essentially of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
the genetically engineered organism converts the substrate to a product.

In certain embodiments, the invention relates to a method comprising the step of
contacting any one of the aforementioned genetically engineered organisms with a substrate,
wherein
the substrate consists of a nitrogen-containing fraction and a non-nitrogen-containing fraction;
the nitrogen containing fraction consists of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
the genetically engineered organism converts the substrate to a product.

In certain embodiments, the invention relates to a product made by any one of the aforementioned methods.

In certain embodiments, the invention relates to a recombinant vector comprising a gene operably linked to a promoter, wherein the gene encodes an enzyme; and the enzyme is allophanate hydrolase, biuret amidohydrolase, cyanuric acid amidohydrolase, guanine deaminase, melamine deaminase, isopropylammelide isopropylaminohydrolase, cyanamide hydratase, urease, or urea carboxylase.

BRIEF DESCRIPTION OF THE FIGURES

FIG. 2 tabulates exemplary compounds capable of delivering nitrogen that could be accessed by an engineered organism.

FIG. 3 tabulates DNA and protein sequences encoding the melamine degradation pathway.

FIG. 11 tabulates the concentrations of the components in the MOPS medium used in Example 9.

FIG. 29 tabulates a summary of various plasmids of the invention.

FIG. 30 tabulates a summary of various organisms of the invention.

FIG. 31 tabulates the components and molar concentrations of each component in a MOPS defined medium, which is used, for example, with *E. coli*.

FIG. 32 tabulates the components and weight concentrations of each component in a YNB medium, which is used, for example, with *S. cerevisiae*.

FIG. 33 tabulates the components and weight concentrations of each component in a SC amino acid medium.

DETAILED DESCRIPTION OF THE INVENTION

Overview

Figure 1:
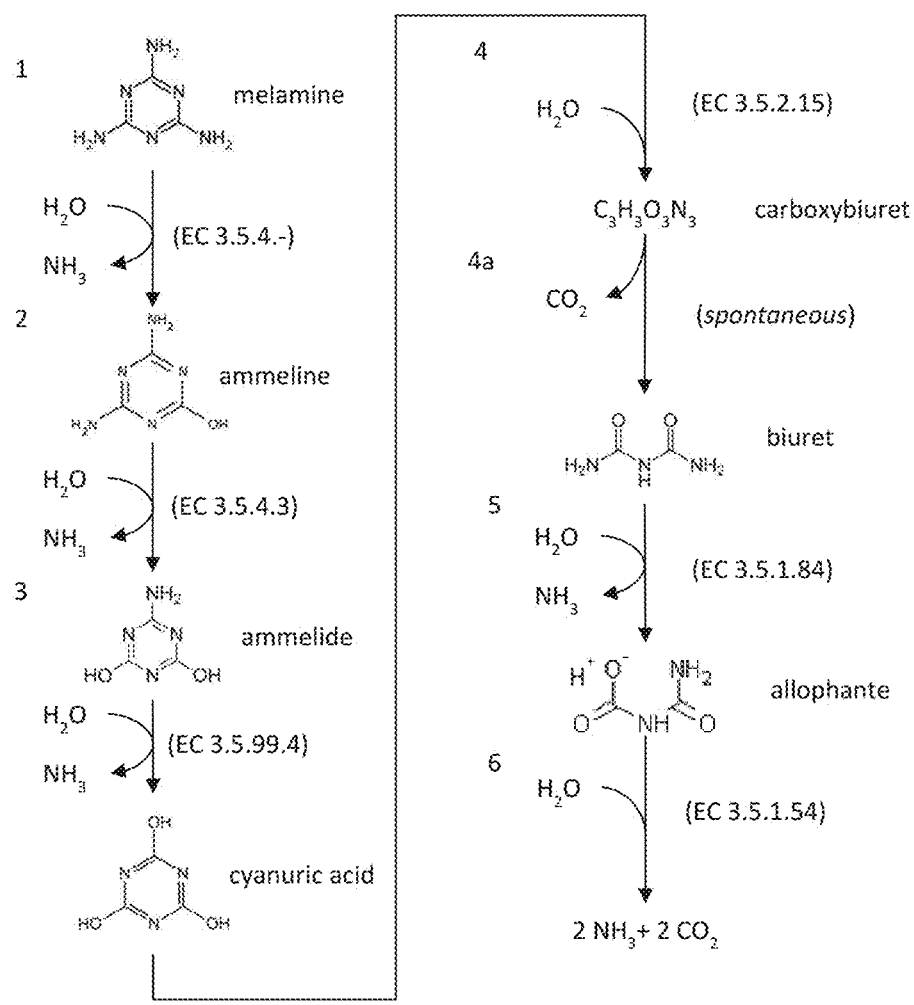
FIG. 1 depicts a schematic representation of the melamine degradation pathway. 1—Melamine deaminase (tzrA) (EC 3.5.4.-); 2—Ammeline deaminase (guanine deaminase) (EC 3.5.4.3); 3—N-isopropylammelide isopropylamino (Ammelide) hydrolyase (EC 3.5.99.4); 4—Cyanuric acid hydrolyase (EC 3.5.2.15); 4a—Carboxybiuret decarboxylase, spontaneous reaction; 5—Biuret amidohydrolase (EC 3.5.1.84); 6—Allophanate hydrolyase (EC 3.5.1.54). Nitrogen can be assimilated (as NH$_3$) by the action of the complete pathway acting on melamine, liberating 6 mol NH$_3$ per mol melamine, or via a subset of enzymes acting on pathway intermediates (e.g., steps 4, 4a, 5, and 6 acting on cyanuric acid releasing 3 mol NH$_3$ per mol cyanuric acid).
Figure 4:
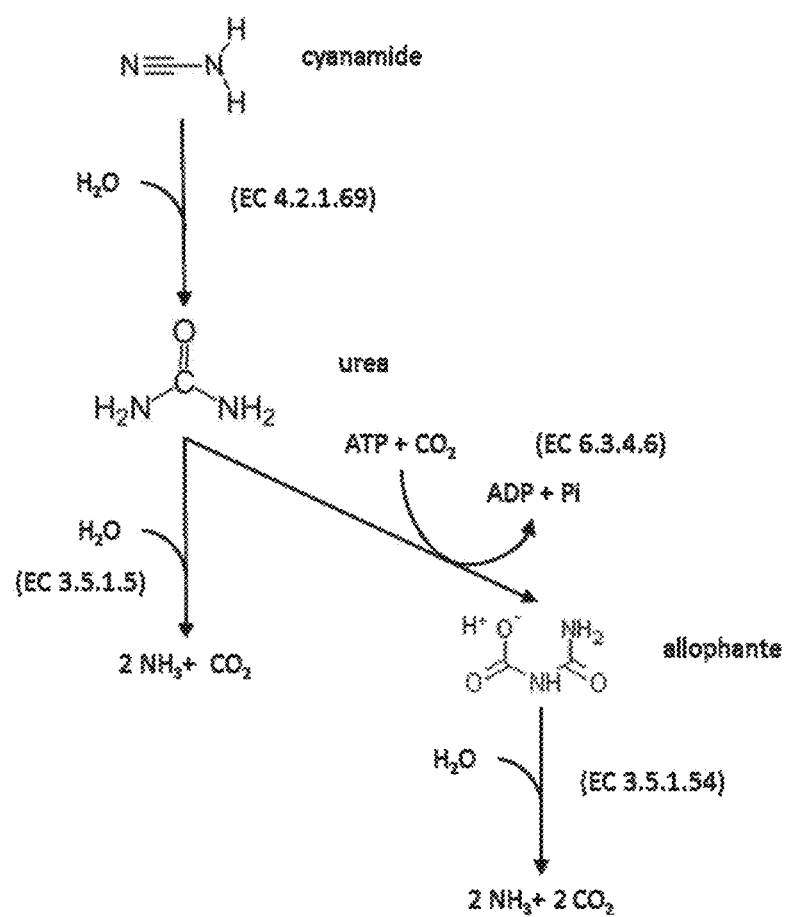
FIG. 4 depicts a schematic representation of the cyanamide assimilation pathway. After conversion of cyanamide to urea by cyanamide hydratase (EC 4.2.1.69), urea can be degraded either via urease (EC 3.5.1.5) or by urea carboxylase (EC 6.3.4.6) and allophanate hydrolyase (EC 3.5.1.54).

In certain embodiments, the invention relates to a genetically engineered host organism, wherein the genetically engineered host organism has a non-native ability to obtain a growth-limiting nutrient from a complex substrate; and the complex substrate could not have been metabolized or used as a nutrient by the native host organism. In certain embodiments, the non-native ability will provide the organism with a significant competitive advantage, and provide a major barrier to the success of contaminants in a fermentation. In certain embodiments, the genetically engineered host organism is a bacterium, a yeast, a fungus, a mammalian cell, or an insect cell. In certain embodiments, the genetically engineered host organism is a bacterium or a yeast.

In certain embodiments, the invention relates to a method of using the above-mentioned genetically engineered host organism, comprising contacting the genetically engineered host organism with a modified cell culture medium. In certain embodiments, the invention relates to a method of using the above-mentioned genetically engineered host organism, comprising contacting the genetically engineered host organism with a modified cell culture medium, wherein the genetically engineered host organism converts the cell culture medium to a product. In certain embodiments, using this approach provides a unique and targeted manner to promote the growth of the desired genetically engineered host organism. In certain embodiments, the above-mentioned methods minimize the growth of contaminant organisms, provide a valuable competitive advantage, and allow management of production of a range of valuable products.

In certain embodiments, the inventive methods decrease or eliminate the need for use of prophylactic antibiotics in large scale yeast cultures. Avoiding unnecessary antibiotics is an important benefit due to emerging environmental considerations and societal pressures. Additionally, in certain embodiments, the technique can be applied to bacterial systems in which antibiotics may not be added.

In certain embodiments, the genetically engineered host organism is a yeast; and the product is ethanol, isobutanol, lactic acid, an isoprenoid, a lipid, and enzyme product, or a high value specialty chemical.

In certain embodiments, the genetically engineered host organism is a bacterium; and the product is butanol, ethanol, isopropanol, 1,3-propanediol (PDO), 1,4-butanediol (BDO), succinic acid, itaconic acid, an enzyme product, a polyol, a protein product, or a high value specialty chemical.

In certain embodiments, the inventive technology is applicable in the production of one or more commodities, fine chemicals, and pharmaceuticals.

Definitions

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

"Exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Expression vector" or "expression construct" or "plasmid" or "recombinant DNA construct" is a vehicle for introducing a nucleic acid into a host cell. The nucleic acid can be one that has been generated via human intervention, including by recombinant means or direct chemical synthesis, with a series of specified nucleic acid elements that permit transcription and/or translation of a particular nucleic acid. The expression vector can be part of a plasmid, virus, or nucleic acid fragment, or other suitable vehicle. Typically, the expression vector includes a nucleic acid to be transcribed operably linked to a promoter.

"Inducible promoter" is a promoter that mediates transcription of an operably linked gene in response to a particular stimulus.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Osmotic shock" is the rupture of cells in a solution following a sudden reduction in osmotic pressure. Osmotic shock is sometimes induced to release cellular components of such cells into a solution.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements, in addition to the foreign gene, that facilitate transformation of a particular host cell. "Expression cassette" refers to a specific vector containing a foreign gene and having elements in addition to the foreign gene that allow for enhanced expression of that gene in a foreign host.

"Promoter" is a nucleic acid control sequence that directs transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

"Recombinant" is a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention.

Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Sonication" is a process of disrupting biological materials, such as a cell, by use of sound wave energy.

"Transformation" refers to the transfer of a nucleic acid fragment into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

Microbe Engineering

A. Overview

In certain embodiments of the invention, a microorganism is genetically modified to improve or provide de novo growth characteristics on a variety of feedstock materials.

Genes and gene products may be introduced into microbial host cells. Suitable host cells for expression of the genes and nucleic acid molecules are microbial hosts that can be found broadly within the fungal or bacterial families and which grow over a wide range of temperature, pH values, and solvent tolerances. Examples of suitable host strains include but are not limited to fungal or yeast species, such as *Aspergillus, Trichoderma, Saccharomyces, Pichia, Candida, Hansenula, Kluyveromyces*, or bacterial species, such as member of the proteobacteria and actinomycetes as well as the specific genera *Acinetobacter, Arthrobacter, Brevibacterium, Acidovorax, Bacillus, Clostridia, Streptomyces, Escherichia, Salmonella, Pseudomonas*, and Cornyebacterium.

*E. coli* is well suited to use as the host microorganism in the invention fermentative processes.

Microbial expression systems and expression vectors containing regulatory sequences that direct high level expression of foreign proteins are well known to those skilled in the art. Any of these could be used to construct chimeric genes to produce the any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and the aforementioned starting parent strain as a host can be transformed with the resulting plasmid. This approach can increase the copy number of each of the genes encoding the enzymes and, as a result, the activities of these enzymes can be increased. The plasmid is not particularly limited so long as it can autonomously replicate in the microorganism.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (see, for example, Molecular Cloning: A Laboratory Manual, Sambrook et al. (3d edition, 2001, Cold Spring Harbor Press; and U.S. Pat. No. 4,683,202 (incorporated by reference)). Alternatively, elements can be generated synthetically using known methods (see, for example, Gene. 1995 Oct. 16; 164(1):49-53).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the host genome resulting in gene targeting, gene conversion, gene deletion, gene duplication, gene inversion and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

This subsection is divided into subsections. Subsection 1 describes control sequences typically contained on vectors as well as novel control sequences provided by the present invention. Subsection 2 describes genes typically contained in vectors as well as novel codon optimization methods and genes prepared using them provided by the invention.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microbe contains a coding sequence for a desired gene product (for example, a selectable marker, or an enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration.

The promoter used to express an exogenous gene can be the promoter naturally linked to that gene or can be a heterologous promoter.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

2. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

D. Expression of Two or More Exogenous Genes

Further, a genetically engineered microorganism may comprise and express more than one exogenous gene. One or more genes can be expressed using an inducible promoter, which allows the relative timing of expression of these genes to be controlled. Expression of the two or more exogenous genes may be under control of the same inducible promoter or under control of different inducible promoters. In the latter situation, expression of a first exogenous gene can be induced for a first period of time (during which expression of a second exogenous gene may or may not be induced) and expression of a second or further exogenous gene can be induced for a second period of time (during which expression of a first exogenous gene may or may not be induced). Provided herein are vectors and methods for engineering microbes to grow on non-traditional growth media.

E. Transformation

Cells can be transformed by any suitable technique including, e.g., biolistics, electroporation, glass bead transformation and silicon carbide whisker transformation. Any convenient technique for introducing a transgene into a microorganism can be employed in the present invention. Transformation can be achieved by, for example, the method of D. M. Morrison (Methods in Enzymology 68, 326 (1979)), the method by increasing permeability of recipient cells for DNA with calcium chloride (Mandel, M. and Higa, A., J. Mol. Biol., 53, 159 (1970)), or the like.

Examples of expression of transgenes in oleaginous yeast (e.g., *Yarrowia lipolytica*) can be found in the literature (see, for example, Bordes et al., J Microbiol Methods, Jun. 27 (2007)). Examples of expression of exogenous genes in bacteria such as *E. coli* are well known; see, for example, Molecular Cloning: A Laboratory Manual, Sambrook et al. (3d edition, 2001, Cold Spring Harbor Press).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to an endogenous promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (see, for example, Protist 2004 December; 155(4):381-93). The transformed cells can be optionally selected based upon the ability to grow in the presence of the antibiotic or other selectable marker under conditions in which cells lacking the resistance cassette would not grow.

Nitrogen-Containing Compounds in Feedstocks

In certain embodiments, the invention relates to use of an atypical nitrogen-containing feedstock comprising, consisting essentially of, or consisting of a nitrogen-containing compound of any one of Formulas I-III. In certain embodiments, a non-genetically engineered organism, i.e., a native organism, could not metabolize (i.e., use as a source of nitrogen) the nitrogen-containing compounds in the feedstock.

In certain embodiments, the invention relates to any one of the aforementioned nitrogen-containing feedstocks, wherein the nitrogen-containing compound is a compound of formula I or a salt thereof:

I

wherein, independently for each occurrence,

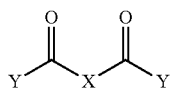

is a five-, six, nine-, or ten-membered aryl or heteroaryl group;

R is —OH, —CO₂H, —NO₂, —CN, substituted or unsubstituted amino, or substituted or unsubstituted alkyl; and n is 0, 1, 2, 3, 4, or 5.

In certain embodiments, the invention relates to any one of the aforementioned nitrogen-containing feedstocks, wherein the nitrogen-containing compound is a compound of formula II or a salt thereof:

$$\underset{Y}{\overset{O}{\parallel}}\overset{}{\underset{}{C}}-X-\overset{O}{\underset{}{\parallel}}\overset{}{C}-Y \qquad \text{II}$$

wherein, independently for each occurrence,
X is —NH—, —N(alkyl)-, —O—, —C(R¹)₂—, —S—, or absent;
Y is —H, —NH₂, —N(H)(alkyl), —N(alkyl)₂, —CO₂H, —CN, or substituted or unsubstituted alkyl; and
R¹ is —H, —OH, —CO₂H, —NO₂, —CN, substituted or unsubstituted amino, or substituted or unsubstituted alkyl.

In certain embodiments, the invention relates to any one of the aforementioned nitrogen-containing feedstocks, wherein the nitrogen-containing compound is a compound of formula III or a salt thereof:

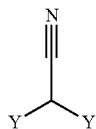

wherein, independently for each occurrence,
Y is —H, —NH₂, —N(H)(alkyl), —N(alkyl)₂, —CO₂H, —CN, or substituted or unsubstituted alkyl.

In certain embodiments, the invention relates to any one of the aforementioned nitrogen-containing feedstocks, wherein the nitrogen-containing compound is selected from the group consisting of:

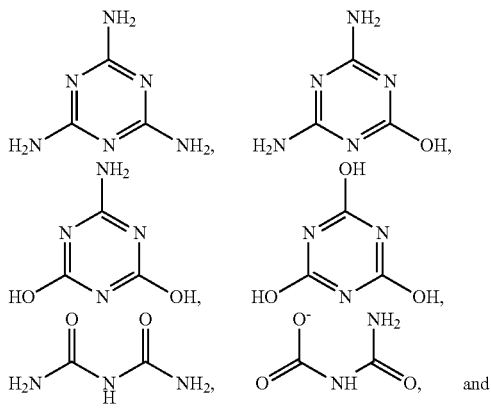

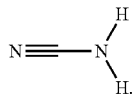

In certain embodiments, the invention relates to any one of the aforementioned nitrogen-containing feedstocks, wherein the nitrogen-containing compound is selected from the group consisting of Hydrazine, 5-Aminotetrazole, Tetrazole, Melamine, Cyanamide, 2-Cyanoguanidine, Sodium azide, Carbohydrazide, 1,2,3-Triazole, 1,2,4-Triazole, 1,3-Diaminoguanidine HCl, Ammeline, 1,3,5-triazine, Aminoacetonitrile, Cyanoethylhydrazine, Azodicarbonamide, Biurea, Formamidoxime, 1,2-Dimethylhydrazine, 1,1-Dimethylhydrazine, ethylhydrazine, Ethylenediamine, Sodium dicyanamide, Guanidine carbonate, Methylamine, Ammelide, Hydroxylamine, Malononitrile, Biuret, Diethyltriamine, Hexamethylenetetramine, Triethylenetetramine, 1,3-Diaminopropane, Triethylenetetramine, 1,3-Diaminopropane, Hydroxyurea, Tetraethylenepentamine, Thiourea, Succinonitrile, Calcium cyanamide, Cyanuric acid, Aminoethylpiperazine, Piperazine, Dimethylamine, Ethylamine, dalfampridine, Tetranitromethane, Imidazolidinyl urea, Trinitromethane, malonamide, Chloramine, Allophante, Trimethylamine, Nitromethane, Acetaldoxime, Diazolidinyl urea, 1,2-Cyclohexanedione dioxime, Acetone oxime, Thioacetamide, Sodium thiocyanate, Isothiazole, Thiazole, Dimethylacetamide, Isothiazolinone, Methylene blue, Diethanolamine, Aspartame, Benzisothiazolinone, and Acesulfame potassium.

Exemplary Isolated Nucleic Acid Molecules and Vectors

In certain embodiments, the invention relates to an isolated nucleic acid molecule, wherein the nucleic acid molecule encodes an enzyme that provides the organism with the ability to assimilate a nitrogen source that otherwise would not have been accessible to the native organism; and the enzyme is allophanate hydrolase, biuret amidohydrolase, cyanuric acid amidohydrolase, guanine deaminase, ammeline hydrolase, ammelide hydrolyase, melamine deaminase, isopropylammelide isopropylaminohydrolase, cyanamide hydratase, urease, or urea carboxylase.

In certain embodiments, the invention relates to an isolated nucleic acid molecule, wherein the nucleic acid molecule is selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CLIB122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from Bradyrhizobiumjaponicum USDA 110, GUD1/Y DL238C from *S. cerevisiae*, YAL10E2 5740p from *Y. lipolytica* CLIB122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to an isolated nucleic acid molecule comprising any one of the sequences disclosed herein. In certain embodiments, the invention relates to an isolated nucleic acid molecule having at least 85% sequence homology with any one of the sequences disclosed herein. In certain embodiments, the invention relates to an isolated nucleic acid molecule having at least 90% sequence homology with any one of the sequences disclosed herein. In certain embodiments, the invention relates to an isolated nucleic acid molecule having at least 95% sequence homology with any one of the sequences disclosed herein. In certain embodiments, the invention relates to an isolated nucleic acid molecule having at least 99% sequence homology with any one of the sequences disclosed herein. In certain embodiments, the invention relates to an isolated nucleic acid molecule having any one of the sequences disclosed herein.

A recombinant vector comprising any one of the aforementioned nucleic acid molecules operably linked to a promoter.

In certain embodiments, the invention relates to a recombinant vector comprising any one of the sequences disclosed herein. In certain embodiments, the invention relates to a recombinant vector having at least 85% sequence homology with any one of the sequences disclosed herein. In certain embodiments, the invention relates to a recombinant vector having at least 90% sequence homology with any one of the sequences disclosed herein. In certain embodiments, the invention relates to a recombinant vector having at least 95% sequence homology with any one of the sequences disclosed herein. In certain embodiments, the invention relates to a recombinant vector having at least 99% sequence homology with any one of the sequences disclosed herein.

Exemplary Genetically Engineered Organisms of the Invention

In certain embodiments, the invention relates to a genetically engineered organism, wherein the genetically engineered organism has been transformed by a nucleic acid molecule or a recombinant vector comprising any one of the sequences disclosed herein. In certain embodiments, the nucleic acid molecule or recombinant vector has at least 85% sequence homology with any one of the sequences disclosed herein. In certain embodiments, the nucleic acid molecule or recombinant vector has at least 90% sequence homology with any one of the sequences disclosed herein. In certain embodiments, the nucleic acid molecule or recombinant vector has at least 95% sequence homology with any one of the sequences disclosed herein. In certain embodiments, the nucleic acid molecule or recombinant vector has at least 99% sequence homology with any one of the sequences disclosed herein. In certain embodiments, the invention relates to a genetically engineered organism, wherein the genetically engineered organism has been transformed by a nucleic acid molecule or a recombinant vector having any one of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of allophanate hydrolase, biuret amidohydrolase, cyanuric acid amidohydrolase, guanine deaminase, ammeline hydrolase, ammelide hydrolyase, melamine deaminase, and isopropylammelide isopropylaminohydrolase, cyanamide hydratase, urease, or urea carboxylase.

In certain embodiments, the invention relates to any one of the aforementioned genetically engineered organisms, wherein the non-native gene is selected from the group consisting of atzF, DUR1,2 YALI0E 07271g, atzE, atzD, trzC, trzD, trzE, atzD, guaD, blr3880, GUD1/Y DL238C, YAL10E2 5740p, trzA, triA, atzC, and cah. In certain embodiments, the invention relates to any one of the aforementioned genetically engineered organisms, wherein the non-native gene is selected from the group consisting of atzF, DUR1,2 YALI0E 07271g, atzE, atzD, trzD, atzD, guaD, blr3880, GUD1/Y DL238C, YAL10E2 5740p, trzA, triA, atzC, and cah. Any organism may be used as a source of the non-native gene, as long as the organisms has the desired enzymatic activity. The non-native gene can each be obtained from chromosomal DNA of any one of the aforementioned microorganisms by isolating a DNA fragment complementing auxotrophy of a variant strain lacking the enzymatic activity. Alternatively, if the nucleotide sequence of these gene of the organism has already been elucidated (Biochemistry, Vol. 22, pp. 5243-5249, 1983; J. Biochem. Vol. 95, pp. 909-916, 1984; Gene, Vol. 27, pp. 193-199, 1984; Microbiology, Vol. 140, pp. 1817-1828, 1994; Mol. Gene Genet. Vol. 218, pp. 330-339, 1989; and Molecular Microbiology, Vol. 6, pp. 317-326, 1992), the genes can be obtained by PCR using primers synthesized based on each of the elucidated nucleotide sequences, and the chromosome DNA as a template.

In certain embodiments, the invention relates to any one of the aforementioned genetically engineered organisms, wherein the non-native gene is selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CLIB122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from *Bradyrhizobium japonicum* USDA 110, GUD1/Y DL238C from *S. cerevisiae*, YAL10E2 5740p from *Y. lipolytica* CLIB122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to any one of the aforementioned genetically engineered organisms, wherein the genetically engineered organism is a species of the genus *Yarrowia, Saccharomyces, Ogataea, Pichia*, or *Escherichia*.

In certain embodiments, the invention relates to any one of the aforementioned genetically engineered organisms, wherein the genetically engineered organism is selected from the group consisting of *Yarrowia lipolytica, Saccharomyces cerevisiae, Ogataea polymorpha*, Pichiapastoris, and *Escherichia coli*.

In certain embodiments, the genetically engineered organism is not *Rhodococcus* sp. Strain Mel.

Exemplary Methods of the Invention

In certain embodiments, the invention relates to a method, comprising the step of
  contacting any one of the aforementioned genetically
    engineered organisms with a substrate,
  wherein
    the substrate comprises a nitrogen-containing fraction and
      a non-nitrogen-containing fraction;

the nitrogen-containing fraction comprises, in an amount from about 10% by weight to about 100% by weight, a nitrogen-containing compound of any one of Formulas I-III;

a native organism of the same species as the genetically engineered organism could not metabolize (i.e., use as a source of nitrogen) the nitrogen-containing compound; and the genetically engineered organism converts the substrate to a product.

In certain embodiments, the invention relates to any one of the aforementioned methods, wherein the nitrogen-containing compounds have a low molecular weight. In certain embodiments, the invention relates to any one of the aforementioned methods, wherein the nitrogen-containing compounds have a molecular weight between about 30 Da and about 800 Da. In certain embodiments, the invention relates to any one of the aforementioned methods, wherein the nitrogen-containing compounds have a molecular weight between about 40 Da and about 600 Da. In certain embodiments, the invention relates to any one of the aforementioned methods, wherein the nitrogen-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, bout 560 Da, about 580 Da, or about 600 Da.

In certain embodiments, the invention relates to any one of the aforementioned methods, wherein the nitrogen-containing compounds have less than 12 carbon atoms. In certain embodiments, the invention relates to any one of the aforementioned methods, wherein the nitrogen-containing compounds have less than 8 carbon atoms. In certain embodiments, the invention relates to any one of the aforementioned methods, wherein the nitrogen-containing compounds have 1, 2, 3, 4, 5, 6, or 7 carbon atoms.

In certain embodiments, the invention relates to any one of the aforementioned methods, wherein the nitrogen-containing compounds have 1, 2, 3, 4, 5, 6, 7, 8, 9, or 10 nitrogen atoms.

In certain embodiments, the invention relates to any one of the aforementioned methods, wherein the nitrogen-containing compounds have 0, 1, 2, 3, 4, 5, 6, 7, or 8 oxygen atoms.

In certain embodiments, the invention relates to any one of the aforementioned methods, wherein the nitrogen-containing compounds have an octanol-water partition coefficient (log P) less than about 5. In certain embodiments, the invention relates to any one of the aforementioned methods, wherein the nitrogen-containing compounds have an octanol-water partition coefficient (log P) from about −0.5 to about 5. In certain embodiments, the invention relates to any one of the aforementioned methods, wherein the nitrogen-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the nitrogen-containing compounds are soluble in water at about 20° C. at a concentration of between about 0.01 g/L to about 1000 g/L. In certain embodiments, the invention relates to any one of the aforementioned methods, wherein the nitrogen-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the nitrogen-containing compounds move through the cell membrane by passive transport. Passive transport includes diffusion, facilitated diffusion, and filtration.

In certain embodiments, the invention relates to any one of the aforementioned methods, wherein the nitrogen-containing compounds move through the cell membrane by active transport, such as, for example, via an ATP-Binding Cassette (ABC) transporter or other known transmembrane transporter.

In certain embodiments, the invention relates to any one of the aforementioned methods, wherein the nitrogen-containing compounds are transported through the cell membrane.

In certain embodiments, the invention relates to any one of the aforementioned methods, wherein the nitrogen-containing compounds are substantially non-biocidal.

In certain embodiments, the invention relates to any one of the aforementioned methods, wherein the nitrogen-containing compounds are substantially biodegradable.

In certain embodiments, the invention relates to any one of the aforementioned methods, wherein the nitrogen-containing fraction comprises the nitrogen-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.'

In certain embodiments, the invention relates to any one of the aforementioned methods, wherein the nitrogen-containing fraction comprises the nitrogen-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate,
wherein
the substrate comprises a nitrogen-containing fraction and a non-nitrogen-containing fraction;
the nitrogen containing fraction consists essentially of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
the genetically engineered organism converts the substrate to a product.

In certain embodiments, the invention relates to a method, comprising the step of
contacting any one of the aforementioned genetically engineered organisms with a substrate,
wherein
the substrate consists of a nitrogen-containing fraction and a non-nitrogen-containing fraction;
the nitrogen containing fraction consists of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein the substrate does not comprise ammonium sulfate.

In certain embodiments, the invention relates to any one of the aforementioned methods, wherein the substrate does not comprise urea.

In certain embodiments, the invention relates to any one of the aforementioned methods, wherein a non-genetically engineered organism, i.e., a native organism, could not metabolize (i.e., use as a source of nitrogen) the nitrogen-containing compound. In certain embodiments, the genetically engineered organism is not *Rhodococcus* sp. Strain Mel.

In certain embodiments, the invention relates to any one of the aforementioned methods, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermentor.

In certain embodiments, the invention relates to any one of the aforementioned methods, wherein the genetically engineered organism is contacted with the substrate in an industrial-size fermentor.

In certain embodiments, the invention relates to any one of the aforementioned methods, wherein a plurality of genetically engineered organisms is contacted with a plurality of substrates in a plurality of fermentors, wherein the plurality of fermentors are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

Exemplary Products

In certain embodiments, the invention relates to a product made by any one of the aforementioned methods.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1

The oleaginous yeast *Yarrowia lipolytica* may be engineered to convert melamine into ammonia. Melamine ($C_3N_6H_6$) is a highly nitrogenous compound that can only be degraded by a very limited number of organisms including *Rhodococcus* sp. Strain Mel. Incorporating the pathway for melamine degradation into *Yarrowia*, accompanied with a modification in the media composition to use melamine as the predominant nitrogen source, will generate a more robust industrial production solution applicable to a number of applications. The advantage confirmed by this modification is significant enough to provide advantage in multiple applications including situations where the core technology may be significant genetic burden on the organism.

Example 2

Genes from FIG. 3, or suitable homologs, will be cloned into a host strain such as *Yarrowia lipolytica*, *Saccharomyces cerevisiae*, or *Escherichia coli*. Enzymes native to the host organism, such as allophante hydrolase or guanine deaminase may be overexpressed with a heterologous promoter. Functional expression will be assayed by enzymatic activity and the ability to confer nitrogen limited growth on the appropriate pathway intermediate. Ultimately, strains able to degrade melamine will be selected for improved utilization of the pathway via melamine limited continuous culturing or other selective methods. Similar strategies can be devised for nitrogen compounds listed in FIG. 2.

Example 3 Vector Construction Via Yeast Mediated Ligation

Base Vector

Vector pNC10 contains an *E. coli* pMB1 origin of replication and ampicillin resistance gene, a *S. cerevisiae* 2 μm origin of replication and URA3 gene, and a multiple cloning site containing the 8-bp recognition sequences for PacI, PmeI, and AscI. DNA of interest is inserted in the multiple cloning site via yeast mediated homologous recombination (YML) cloning. (Shanks et al. 2006; Shanks et al. 2009). Briefly, target DNA sequences are amplified by PCR using primers with 20-40 bp overhang homology to adjacent DNA segments in the final vector. pNC10 or another suitable base vector is then restriction digested, creating a linearized plasmid. PCR products and linear plasmid are transformed in *S. cerevisiae*, and the native *S. cerevisiae* gap repair mechanism assembles an intact plasmid based on homology overhangs.

Figure 5:
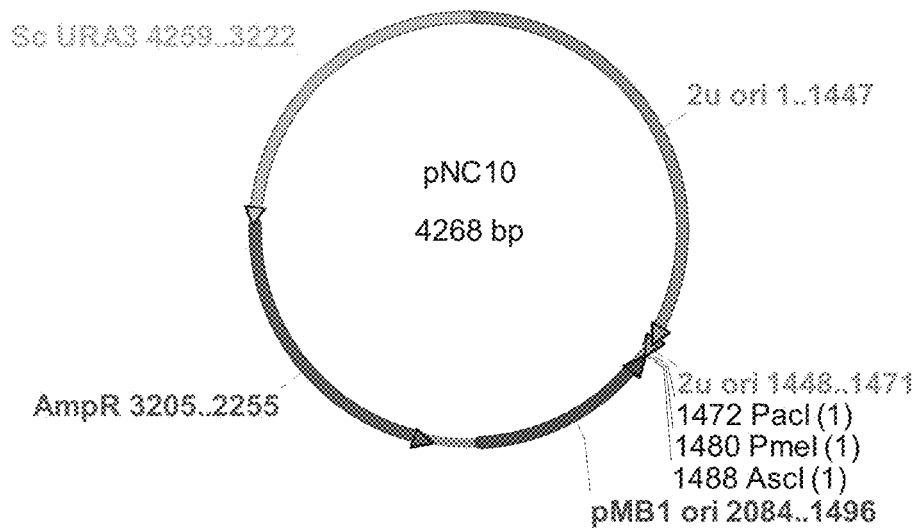
FIGS. 5-10 depict various plasmids of the invention.

The complete vector can then be isolated from *S. cerevisiae* via a DNA extraction protocol and used to transform *E. coli*. Concentrated vector can then be recovered from *E. coli* via DNA plasmid mini-prep or other suitable standard molecular biology protocols. See FIG. 5.

Example 4—*S. cerevisiae* Transformation

Grow overnight a 5 mL culture of a *S. cerevisiae* ura3 auxotroph strain in YPD at 30 C.

Transfer 1.5 mL of overnight culture to 50 mL fresh YPD (OD~0.3) and shake at 200 rpm, 30° C. in a flask. Allow to grow for approx. 4-5 hrs to an OD of 1.0.

Centrifuge cells at >5,000 rpm for 1 min, resuspend in 50 mL sterile water and repeat.

Add 1 mL of 100 mM Lithium acetate to cell pellet and transfer cells to a 1.5 mL tube.

Spin cells for 10 sec at >12,000 rpm, remove supernatant, and resuspend in 400-800 μL of 100 mM LiAc (each transformation uses 50 μL of this cell suspension).

Prepare a transformation master mix of the following, per sample

X number of transformations+1

| | |
|---|---|
| 50% PEG 3350 | 240 μL |
| 1M LiAc | 36 μL |
| Salmon sperm DNA* (2 mg/mL) | 50 μL |

*SS DNA should be first boiled for 10 min and rapidly cooled to 4° C.

Prepare one 1.5 mL tube for each transformation. Per tube, add: 5 μL of digested vector, 5 μL of each PCR insert (assuming a good PCR amplification, approx. 100-200 ng DNA), and water to bring the final volume to 34 μL. Add 326 μL master mix, and then 50 μL of cell suspension. Vortex tubes to completely mix contents.

Incubate for 30 min at 30° C., then mix by inverting and place in 42° C. water bath for 30 min. (Note optimal time at 42° C. varies strain to strain).

Spin down cells for 10 sec at >12,000 rpm, remove PEG mixture and resuspend in 1 mL sterile water. Spin down again, remove 800 μL, and use final 200 μL to resuspend and spread on SD-URA plates. Incubate at 30° C. for 2-4 days.

Example 5—Expression of Melamine Assimilation Enzymes in *S. cerevisiae*

Melamine assimilation genes, or a subset of them, can be expressed in *S. cerevisiae* by construction of a vector using the yeast mediated ligation described above. Expression vectors consist of an *S. cerevisiae* functional promoter, a gene encoding an enzyme of the melamine assimilation pathway, and an *S. cerevisiae* functional terminator. Assemblies of the promoter-gene-terminator motif can be incorporated into a single strain, either on a replicating plasmid or integrated into a chromosome. Possible promoters and terminators are listed below, see also Sun et al. 2012. A representative plasmid, expressing the trzA melamine hydratase under control of the *Y. lipolytica* TEF1 promoter and terminator is shown below.

Figure 6:
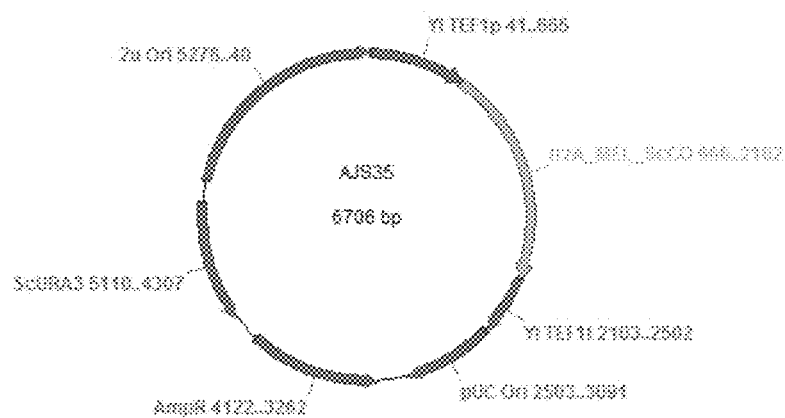

Plasmid AJS35 is an example of the melamine dehydratase trzA transcribed via the *Y. lipolytica* TEF1 promoter and terminator. See FIG. 6.

Strains NS98 and NS99 are industrial S. cereviaie strains carrying plasmids pNC96 (hyg$^R$, and a codon optimized trzE from *Rhodococcus* sp. MEL and pNC97 (hyg$^R$, and a codon optimized trzE from *Rhizobium leguminosarum*), respectively. Strain NS100 is the same industrial *S. cerevisiae* stain carrying plasmid pNC67 (hyg$^R$, nat$^R$) which serves as a control strain.

Figures 23, 24:
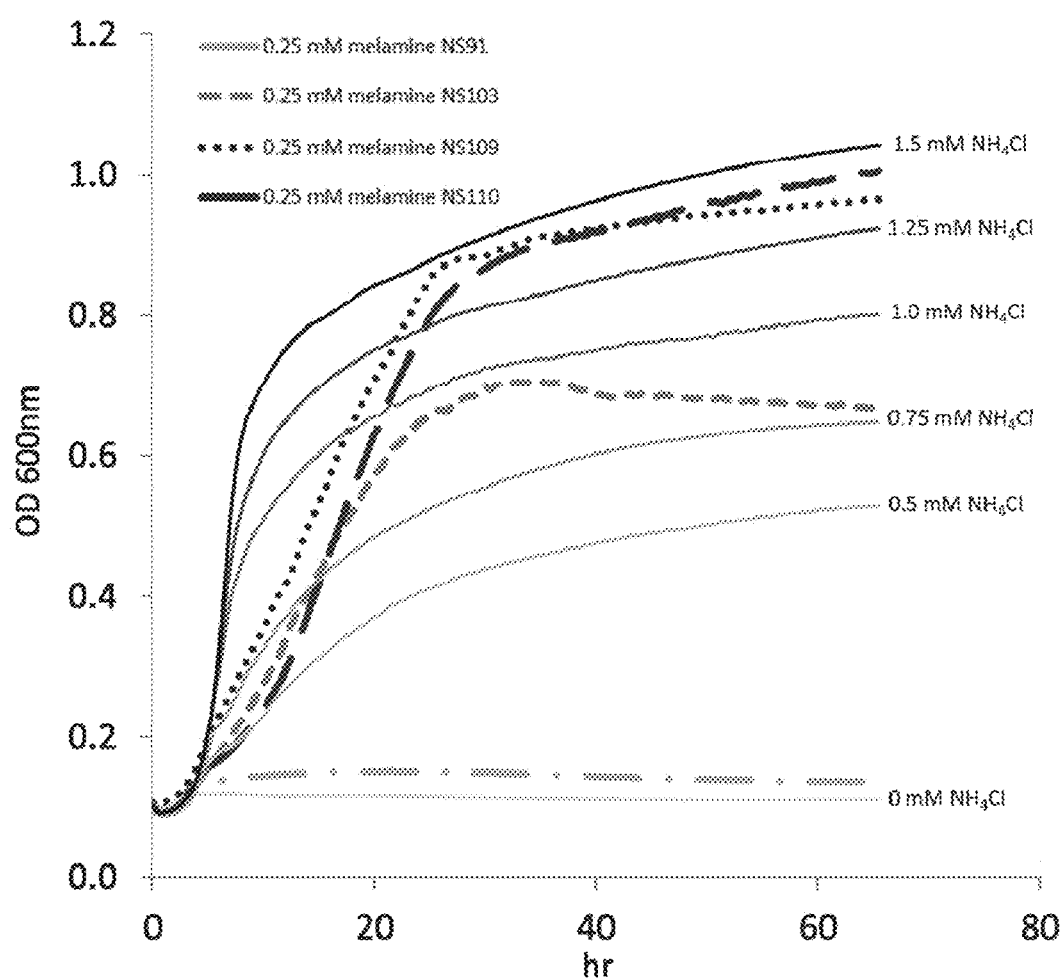
FIG. 23 tabulates the optical density at 600 nm after growth of three organisms of the invention on various media.
FIG. 24 depicts the growth of four organisms of the invention (NS91=control) on 0.25 mM melamine, as compared to the standard curves for a native organism on $NH_4Cl$. Because melamine has six nitrogen atoms, organisms having the ability to utilize melamine should be approximately six times more efficient (see, for example, NS110 on 0.25 mM melamine, as compared to a native organism on 1.5 mM $NH_4Cl$).

Strains NS98, NS99, and NS100 were grown in defined YNB medium with 10 mM urea and 100 μg/mL hygromycin to stationary phase aerobically at 30° C. 1/1000 v/v inoculations were then made into the same defined medium with either 10 mM urea, 10 mM biuret, or no additional nitrogen and grown under the same conditions. Optical density was measured after 72 hours, as shown in FIG. 23. Strains NS98 and NS99 were able to grow to an optical density approximately double that of NS100 in medium containing biuret, and also approximately double that with medium with no nitrogen supply. This shows that *S. cerevisiae* strains expressing trzE genes are advantaged in their utilization of biuret.

DNA that can be Used as Promoters for Gene Transcription in *S. cerevisiae*

S. cerevisiae TPI promoter (SEQ ID NO: 59)

aggaacccatcaggttggtggaaGATTACCCGTTCTAAGACTTTTCAG

CTTCCTCTATTGATGTTACACCTGGACACCCCTTTTCTGGCATCCAGT

TTTTAATCTTCAGTGGCATGTGAGATTCTCCGAAATTAATTAAAGCAA

TCACACAATTCTCTCGGATACCACCTCGGTTGAAACTGACAGGTGGTT

TGTTACGCATGCTAATGCAAAGGAGCCTATATACCTTTGGCTCGGCTG

CTGTAACAGGGAATATAAAGGGCAGCATAATTTAGGAGTTTAGTGAAC

TTGCAACATTTACTATTTTCCCTTCTTACGTAAATATTTTTCTTTTTA

ATTCTAAATCAATCTTTTTCAATTTTTTGTTTGTATTCTTTTCTTGCT

TAAAtctataactacaaaaaacacatacataaactaaaa

S. cerevisiae GPM1 promoter (SEQ ID NO: 60)

ttgctacgcaggctgcacaattacACGAGAATGCTCCCGCCTAGGATT

TAAGGCTAAGGGACGTGCAATGCAGACGACAGATCTAAATGACCGTGT

CGGTGAAGTGTTCGCCAAACTTTTCGGTTAACACATGCAGTGATGCAC

-continued

GCGCGATGGTGCTAAGTTACATATATATATATATATATATATATAT

ATATATAGCCATAGTGATGTCTAAGTAACCTTTATGGTATATTTCTTA

ATGTGGAAAGATACTAGCGCGCGCACCCACACACAAGCTTCGTCTTTT

CTTGAAGAAAAGAGGAAGCTCGCTAAATGGGATTCCACTTTCCGTTCC

CTGCCAGCTGATGGAAAAGGTTAGTGGAACGATGAAGAATAAAAGA

GAGATCCACTGAGGTGAAATTTCAGCTGACAGCGAGTTTCATGATCGT

GATGAACAATGGTAACGAGTTGTGGCTGTTGCCAGGGAGGGTGGTTCT

CAACTTTTAATGTATGGCCAAATCGCTACTTGGGTTTGTTATATAACA

AAGAAGAAATAATGAACTGATTCTCTTCCTCCTTCTTGTCCTTTCTTA

ATTCTGTTGTAATTACCTTCCTTTGTAATTTTTTTTGTAATTATTCTt ataataatccaaacaaacacacatattacaata S. cerevisiae TDH3 promoter
(SEQ ID NO: 61)
tgctgtaacccgtacatgcccaaaATAGGGGCGGGTTACACAGAATA

TATAACATCGTAGGTGTCTGGGTGAACAGTTTATTCCTGGCATCCACT

AAATATAATGGAGCCCGCTTTTTAAGCTGGCATCCAGAAAAAAAAGA

ATCCCAGCACCAAAATATTGTTTTCTTCACCAACCATCAGTTCATAGG

TCCATTCTCTTAGCGCAACTACAGAGAACAGGGGCACAAACAGGCAAA

AAACGGGCACAACCTCAATGGAGTGATGCAACCTGCCTGGAGTAAATG

ATGACACAAGGCAATTGACCCACGCATGTATCTATCTCATTTTCTTAC

ACCTTCTATTACCTTCTGCTCTCTCTGATTTGGAAAAAGCTGAAAAAA

AAGGTTGAAACCAGTTCCCTGAAATTATTCCCCTACTTGACTAATAAG

TATATAAAGACGGTAGGTATTGATTGTAATTCTGTAAATCTATTTCTT

AAACTTCTTAAATTCTACTTTTATAGTTAGTCTTTTTTTTAGTTTTAA

AACACCAAGAacttagtttcgaataaacacacataaacaaacaaa

S. cerevisiae FBA1 promoter
(SEQ ID NO: 62)
gcaccgctggcttgaacaacaataCCAGCCTTCCAACTTCTGTAAATA

ACGGCGGTACGCCAGTGCCACCAGTACCGTTACCTTTCGGTATACCTC

CTTTTCCCCATGTTTCCAATGCCCTTCATGCCTCCAACGGCTACTATCA

CAAATCCTCATCAAGCTGACGCAAGCCCTAAGAAATGAATAACAATAC

TGACAGTACTAAATAATTGCCTACTTGGCTTCACATACGTTGCATACG

TCGATATAGATAATAATGATAATGACAGCAGGATTATCGTAATACGTA

ATAGTTGAAAATCTCAAAAATGTGTGGGTCATTACGTAAATAATGATA

GGAATGGGATTCTTCTATTTTTCCTTTTTCCATTCTAGCAGCCGTCGG

GAAAACGTGGCATCCTCTCTTTCGGGCTCAATTGGAGTCACGCTGCCG

TGAGCATCCTCTCTTTCCATATCTAACAACTGAGCACGTAACCAATGG

AAAAGCATGAGCTTAGCGTTGCTCCAAAAAAGTATTGGATGGTTAATA

CCATTTGTCTGTTCTCTTCTGACTTTGACTCCTCAAAAAAAAAAATC

TACAATCAACAGATCGCTTCAATTACGCCCTCACAAAAACTTTTTTCC

TTCTTCTTCGCCCACGTTAAATTTTATCCCTCATGTTGTCTAACGGAT

TTCTGCACTTGATTTATTATAAAAAGACAAAGACATAATACTTCTCTA

TCAATTTCAGTTATTGTTCTTCCTTGCGTTATTCTTCTGTTCTTCTTT

-continued

TTCTTTTGTcatatataaccataaccaagtaatacatattcaaa

Y. lipolytica TEF1 promoter
(SEQ ID NO: 63)
tataaacggtattttcacaattgcACCCCAGCCAGACCGATAGCCGGT

CGCAATCCGCCACCCACAACCGTCTACCTCCCACAGAACCCCGTCACT

TCCACCCTTTTCCACCAGATCATATGTCCCAACTTGCCAAATTAAAAC

CGTGCGAATTTTCAAAATAAACTTTGGCAAAGAGGCTGCAAAGGAGGG

GCTGGTGAGGGCGTCTGGAAGTCGACCAGAGACCGGGTTGGCGGCGCA

TTTGTGTCCCAAAAAACAGCCCCAATTGCCCCAATTGACCCCAAATTG

ACCCAGTAGCGGGCCCAACCCCGGCGAGAGCCCCCTTCTCCCCACATA

TCAAACCTCCCCCGGTTCCCACACTTGCCGTTAAGGGCGTAGGGTACT

GCAGTCTGGAATCTACGCTTGTTCAGACTTTGTACTAGTTTCTTTGTC

TGGCCATCCGGGTAACCCATGCCGGACGCAAAATAGACTACTGAAAAT

TTTTTTGCTTTGTGGTTGGGACTTTAGCCAAGGGTATAAAAGACCACC

GTCCCCGAATTACCTTTCCTCTTCTTTTCTCTCTCTCCTTGTCAACTC

ACACCCGAAATCGTtaagcatttccttctgagtataagaatcattcaa a

S. cerevisiae PDC1 promoter
(SEQ ID NO: 64)
gcataatattgtccgctgcccgttTTTCTGTTAGACGGTGTCTTGATC

TACTTGCTATCGTTCAACACCACCTTATTTTCTAACTATTTTTTTTTT

AGCTCATTTGAATCAGCTTATGGTGATGGCACATTTTTGCATAAACCT

AGCTGTCCTCGTTGAACATAGGAAAAAAAAATATATAAACAAGGCTCT

TTCACTCTCCTTGGAATCAGATTTGGGTTTGTTCCCTTTATTTTCATA

TTTCTTGTCATATTCTTTTCTCAATTATTATCTTCTACTCATAacctc acgcaaaataacacagtcaaatcaatcaaa

S. cerevisiae TEF1 promoter
(SEQ ID NO: 65)
CATAGCTTCAAAATGTTTCTACTCCTTTTTTACTCTTCCAGATTTTCT

CGGACTCCGCGCATCGCCGTACCACTTCAAAACACCCAAGCACAGCAT

ACTAAATTTCCCCTCTTTCTTCCTCTAGGGTGTCGTTAATTACCCGTA

CTAAAGGTTTGGAAAAGAAAAAAGAGACCGCCTCGTTTCTTTTTCTTC

GTCGAAAAAGGCAATAAAAATTTTTATCACGTTTCTTTTTCTTGAAAA

TTTTTTTTTTGATTTTTTCTCTTTCGATGACCTCCCATTGATATTT

AAGTTAATAAACGGTCTTCAATTTCTCAAGTTTCAGTTTCATTTTTCT

TGTTCTATTACAACTTTTTTTACTTCTTGCTCATTAGAAAGAaagcat agcaatctaatctaagttttaattacaaa

DNA Sequences that can be Used as Terminators of Gene Transcription

S. cerevisiae TPI terminator
(SEQ ID NO: 66)
taagattaatataattatataaAAATATTATCTTCTTTTCTTTATATC

TAGTGTTATGTAAAATAAATTGATGACTACGGAAAGCTTTTTTATATT

GTTTCTTTTTCATTCTGAGCCACTTAAATTTCGTGAATGTTCTTGTAA

-continued
```
GGGACGGTAGATTTACAAGTGATACAACAAAAAGCAAGGCGCTTTTC

TAATAAAAGAAGAAAAGCATTTAACAATTGAACACCTCTATATCAAC

GAAGAATATTACTTTGTCTCTAAATCCTTGTAAAATGTGTACGATCTC

TATATGGGTTACTCATAAgtgtaccgaagactgcattgaaag
```

S. cerevisiae GPM1 terminator
(SEQ ID NO: 67)
```
gtctgaagaatgaatgatttgaTGATTTCTTTTTCCCTCCATTTTTCT

TACTGAATATATCAATGATATAGACTTGTATAGTTTATTATTTCAAAT

TAAGTAGCTATATATAGTCAAGATAACGTTTGTTTGACACGATTACAT

TATTCGTCGACATCTTTTTTCAGCCTGTCGTGGTAGCAATTTGAGGAG

TATTATTAATTGAATAGGTTCATTTTGCGCTCGCATAAACAGTTTTCG

TCAGGGACAGTATGTTGGAATGAGTGGTAATTAATGGTGACATGACAT

GTTATAGCAATAACCTTGATGTTTACATCGTAGTTTAATGTACACCCC

GCGAATTCGTTCAAGTAggagtgcaccaattgcaagggaa
```

S. cerevisiae TDH3 terminator
(SEQ ID NO: 68)
```
gtgaatttactttaaatcttgcATTTAAATAAATTTTCTTTTTATAGC

TTTATGACTTAGTTTCAATTTATATACTATTTTAATGACATTTTCGAT

TCATTGATTGAAAGCTTTGTGTTTTTCTTGATGCGCTATTGCATTGT

TCTTGTCTTTTTCGCCACATGTAATATCTGTAGTAGATACCTGATACA

TTGTGGATGCTGAGTGAAATTTTAGTTAATAATGGAGGCGCTCTTAAT

AATTTTGGGGATATTGGCTTTTTTTTTAAAGTTTACAAATGAATTTT

TTCCGCCAGGATAACGATTCTGAAGTTACTCTTAGCGTTCCTATCGGT

ACAGCCATCAAATCATGCCTATAAATCATGCCTATATTTGCGTGCAGT

CAGTATCATCTACATGAAAAAAACTCCCGCAATTTCTTATAGAATACG

TTGAAAATTAAATGTACGCGCCAAGATAAGATAACATATATCTAGATG

CAGTAATATACACAGATTCCCGCGGA
```

S. cerevisiae FBA1 terminator
(SEQ ID NO: 69)
```
gttaattcaaattaattgatatAGTTTTTTAATGAGTATTGAATCTGT

TTAGAAATAATGGAATATTATTTTTATTTATTTATATTATTGGT

CGGCTCTTTTCTTCTGAAGGTCAATGACAAAATGATATGAAGGAAATA

ATGATTTCTAAAATTTTACAACGTAAGATATTTTTACAaaagcctagc tcatctt
```

Y. lipolytica TEF1 terminator
(SEQ ID NO: 70)
```
gctgcttgtacctagtgcaaccccagtttgttaaaAATTAGTAGTCAA

AAACTTCTGAGTTAGAAATTTGTGAGTGTAGTGAGATTGTAGAGTATC

ATGTGTGTCCGTAAGTGAAGTGTTATTGACTCTTAGTTAGTTTATCTA

GTACTCGTTTAGTTGACACTGATCTAGTATTTTACGAGGCGTATGACT

TTAGCCAAGTGTTGTACTTAGTCTTCTCTCCAAACATGAGAGGGCTCT

GTCACTCAGTCGGCCTATGGGTGAGATGGCTTGGTGAGATCTTTCGAT

AGTCTCGTCAAGATGGTAGGATGATGGGGGAATACATTACTGCTCTCG

TCAAGGAAACCACAATCAGATCACACCATCCTCCATGGTAtccgatga ctctcttctccacagt
```

S. cerevisiae PDC1 terminator
(SEQ ID NO: 71)
```
acaagctaagttgactgctgctACCAACGCTAAGCAATAAGCGATTTA

ATCTCTAATTATTAGTTAAAGTTTTATAAGCATTTTTATGTAACGAAA

AATAAATTGGTTCATATTATTACTGCACTGTCACTTACCATGGAAAGA

CCAGACAAGAAGTTGCCGACACGACAGTCTGTTGAattggcttaagtc tgggtccgctt
```

S. cerevisiae CYC1 terminator
(SEQ ID NO: 72)
```
caggcccctttcctttgtcgaTATCATGTAATTAGTTATGTCACGCT

TACATTCACGCCCTCCTCCCACATCCGCTCTAACCGAAAAGGAAGGAG

TTAGACAACCTGAAGTCTAGGTCCCTATTTATTTTTTTAATAGTTAT

GTTAGTATTAAGAACGTTATTTATATTTCAAATTTTTCTTTTTTTCT

GTACAAACGCGTGTACGCATGTAACATTATACTGAAAACCTTGCTTGA

GAAGGTTTTGGGACGCTCGAAGGCTTTAATTTGC
```

Example 6—Expression of Melamine Assimilation Enzymes in E. coli

Melamine assimilation genes, or a subset of them, can be expressed in E. coli by construction of a vector using the yeast mediated ligation described above. Expression vectors consist of an E. coli functional promoter, a gene encoding an enzyme of the melamine assimilation pathway, and an E. coli functional terminator. Alternatively, several genes can be expressed from a single promoter as part of a gene operon; in this case inter-gene linker sequences are placed between genes. Sequences that can act as promoters, terminators, and linkers are listed below, as well as two representative E. coli expression plasmids, AJS67 (expressing genes for degradation of melamine to cyanuric acid with release of 3 $NH_3$ per melamine) and AJS68 (expressing genes for degradation of cyanuric acid to $NH_3$ and $CO_2$ with release of 3 $NH_3$ per cyanuric acid)

E. coli Ptach promoter
(SEQ ID NO: 73)
```
agctggtgacaattaatcatcggctcgtataatgtgtggaattgaatc
gatataaggaggttaatca
```

E. coli trpT' terminator
(SEQ ID NO: 74)
```
ctcaaaatatattttccctctatcttctcgttgcgcttaatttgacta
attctcattagcgaggcgcgccttccataggctccgcccc
``` inter-gene operon linkers
lacZ-lacY linker
(SEQ ID NO: 75)
```
ggaaatccatt
``` galT-galK linker
(SEQ ID NO: 76)
```
ggaacgacc
```

Figure 7:
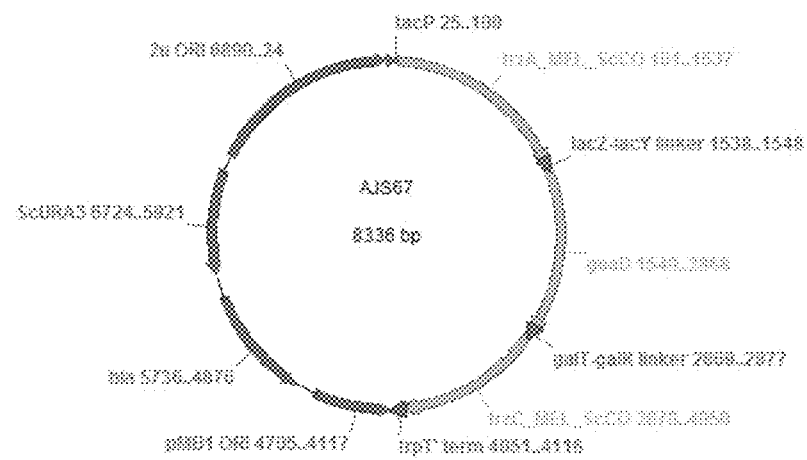
Figure 8:
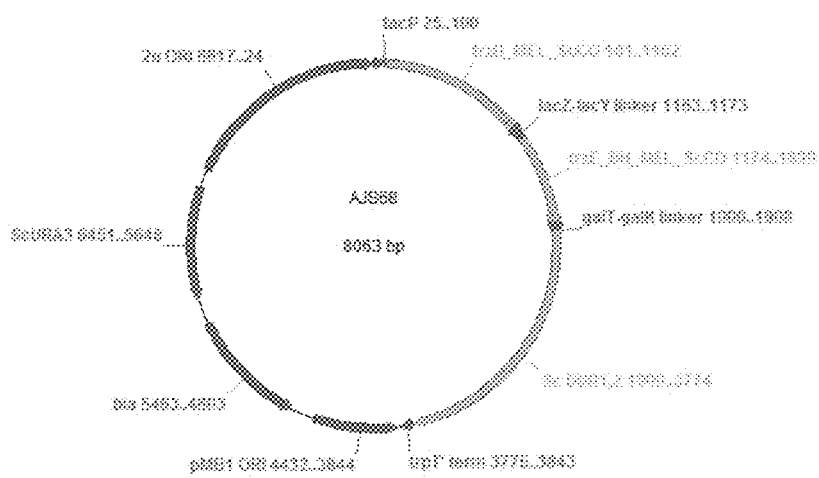

See FIG. 7 and FIG. 8.

Example 7—Expression of Cyanamide Assimilation Enzyme in S. cerevisiae

Figure 9:
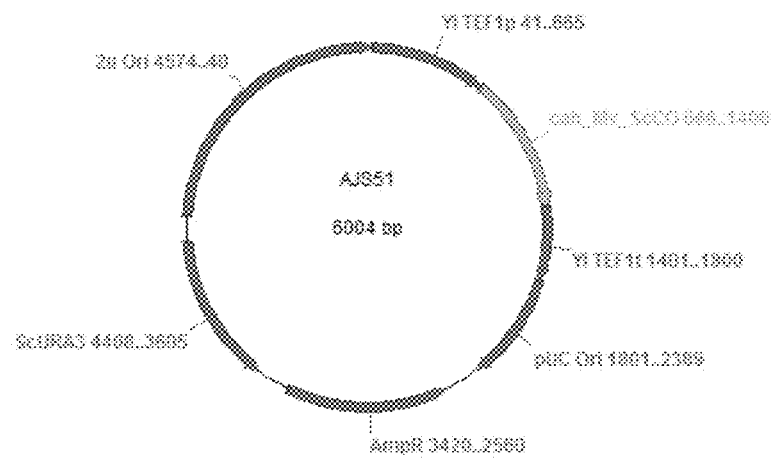

The gene expression methods described in example 5 can also be used in example 7. S. cerevisiae has the native ability to convert urea to NH$_3$ and CO$_2$ via the actions of urea carboxylase and allophante hydrolase, encoded in the fusion gene DUR1,2. Therefore, functional expression of cyanamide hydrolase is sufficient to convert cyanamide to NH$_3$. A representative cyanamide hydratase expression vector is shown below, with *Y. lipolytica* TEF1 promoter and terminator and a *S. cerevisiae* codon-optimized cyanamide hydratase (cah) from *Myrothecium verrucaria*. See FIG. 9.

Example 8—Expression of Cyanamide Assimilation Enzymes in *E. coli*

Figure 10:
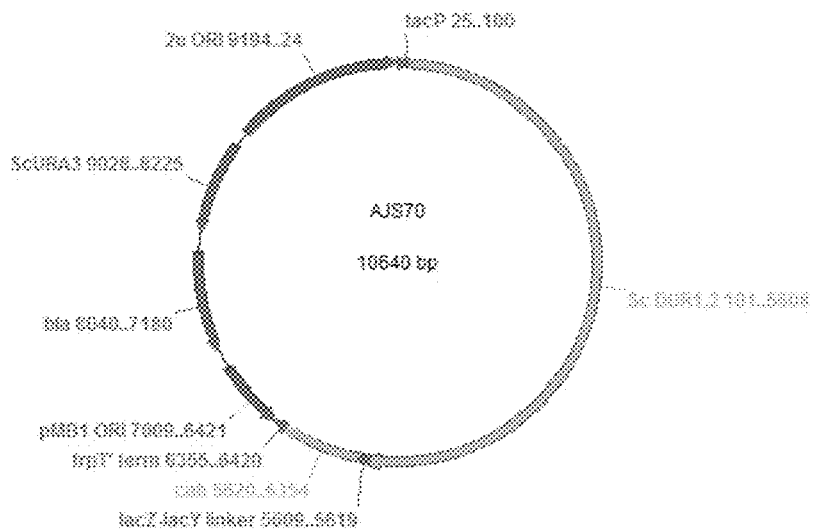

The gene expression methods described in Example 6 can also be used in example 8. Unlike *S. cerevisiae*, most *E. coli* strains are unable to utilize urea as a nitrogen source, so these additional conversion steps must also be engineered. Either a urea carboxylase/allophante hydrolase system or a urease enzyme with appropriate accessory enzymes must be expressed in addition to a cyanamide hydrolase. Urease can be found in some *E. coli* isolates (Collins and Falkow 1990) or heterologously expressed (Cussac et al. 1992). Alternatively, the DUR1,2 genes from *S. cerevisiae* could be expressed, as shown below in plasmid AJS70, along with a cyanamide hydratase. See FIG. 10.

Example 9—Expression of Melamine Assimilation Enzymes in *E. coli*

Several *E. coli* strains containing partial or complete melamine utilization pathways were constructed, as shown in FIGS. 29 and 30. Vector and strain construction was as described in example 6. All vectors contain the ampicillin resistance gene, and 100 ug/mL ampicillin was added to all culture medium. These strains were grown in MOPS defined medium with different nitrogen sources.

*E. coli* strains and melamine utilization genes
  NS88—triA (step 1)
  NS89—trzA, guaD, trzC (steps 1, 2, 3)
  NS90—trzD, trzE, DUR1,2 (steps 4, 5, 6)
  NS91—none (control strain)
  NS93—triA, native guaD selected for improved ammeline utilization (steps 1, 2)
  NS103—triA, guaD, trzC (steps 1, 2, 3)
  NS109—triA, guaD, trzC, trzD 12227, trzE, DUR1,2 (steps 1-6)
  NS110—triA, guaD, trzC, atzD ADP, trzE, DUR1,2 (steps 1-6)

Figure 12:
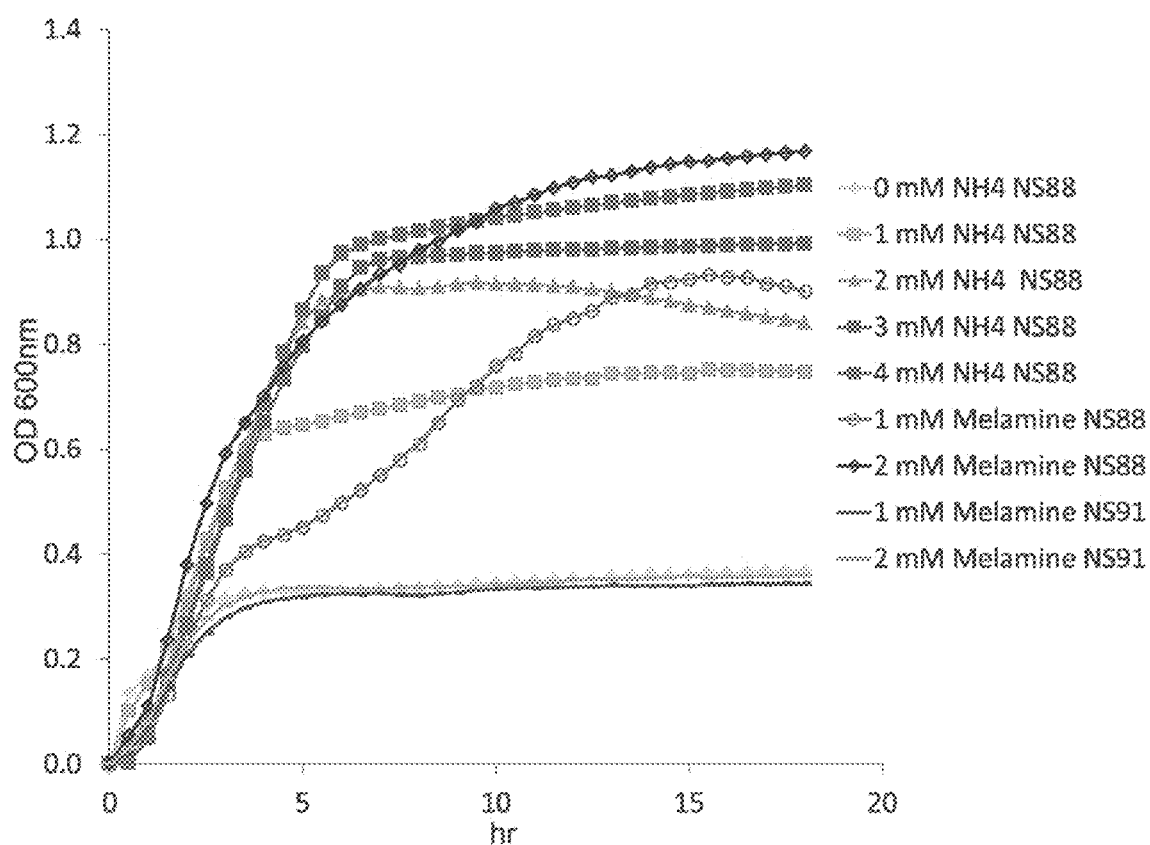
FIG. 12 depicts the growth progress of NS88 and NS91 (control) in media containing various concentrations of ammonium ion or melamine.

FIG. 12 shows the growth progress of NS88 and NS91 (control) in media containing various concentrations of ammonium chloride or melamine. NS88 grown on 1 mM melamine reaches an optical density comparable to that of the equivalent use of 2 mM ammonium chloride, suggesting that 2 mM ammonia are liberated from melamine by triA and the natively encoded guaD genes. The control strain NS91 does not grow with melamine as nitrogen source.

Figure 13:
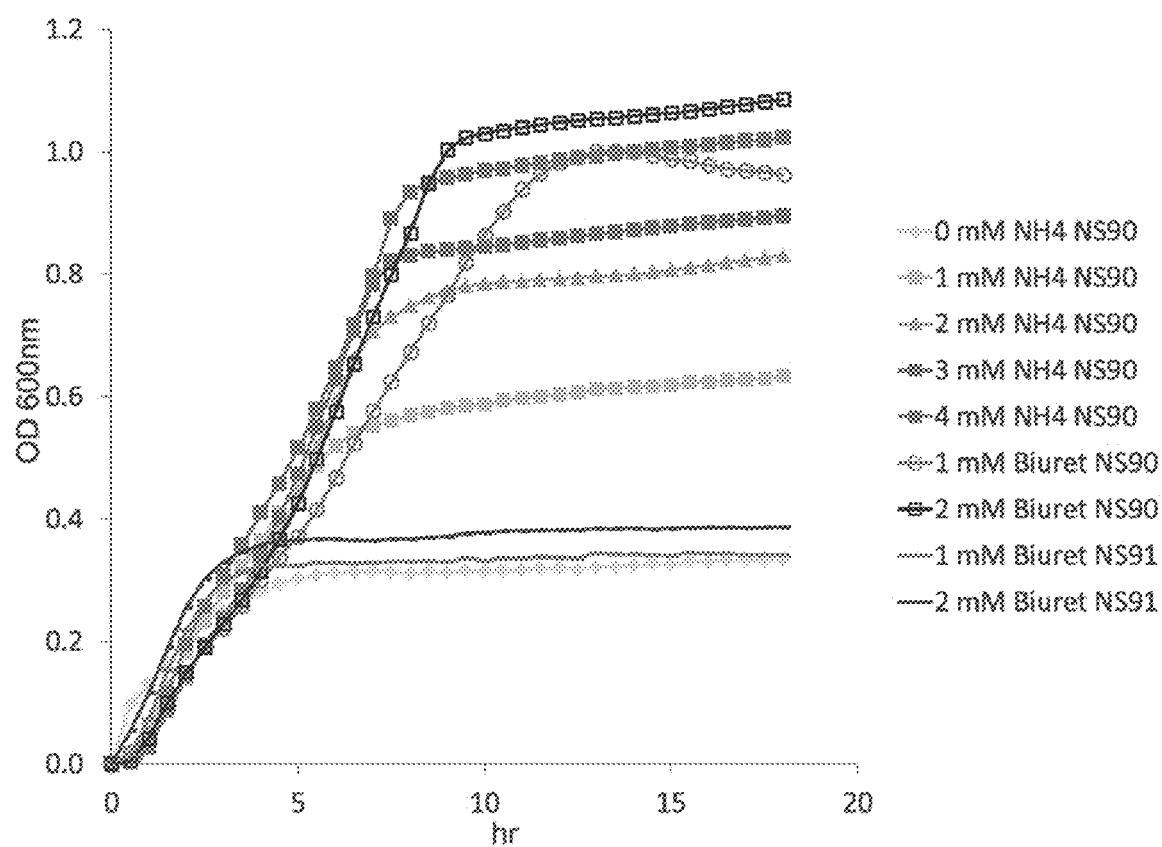
FIG. 13 depicts the growth progress of NS90 and NS91 (control) in media containing various concentrations of ammonium ion or biuret.

FIG. 13 shows the growth progress of NS90 and NS91 (control) in media containing various concentrations of ammonium chloride or biuret. NS90 grown on 1 mM biuret reaches an optical density comparable to that of the equivalent use of 3 mM ammonium chloride, suggesting that 3 mM ammonia are liberated from biuret by trzE and the DUR1,2. The control strain NS91 does not grow with biuret as nitrogen source.

FIG. 24 shows the growth progress of NS91, NS103, NS109, and NS110 in medium containing 0.25 mM melamine as sole nitrogen source. An average of all four strains grown on different ammonium chloride concentrations from 0 to 1.5 mM is also shown as a standard curve for growth with limiting nitrogen. NS91 grown on melamine is similar to the 0 mM ammonium chloride control. NS103 grown on 0.25 mM melamine is similar to 1-0.75 mM ammonium chloride, suggesting it is approximately utilizing the predicted 3 mM ammonia per 1 mM melamine. Strains NS109 and NS110 grown on 0.25 mM melamine are similar to 1.5-1.25 mM ammonium chloride, suggesting it is approximately utilizing the predicted 6 mM ammonia per 1 mM melamine.

Figure 25:
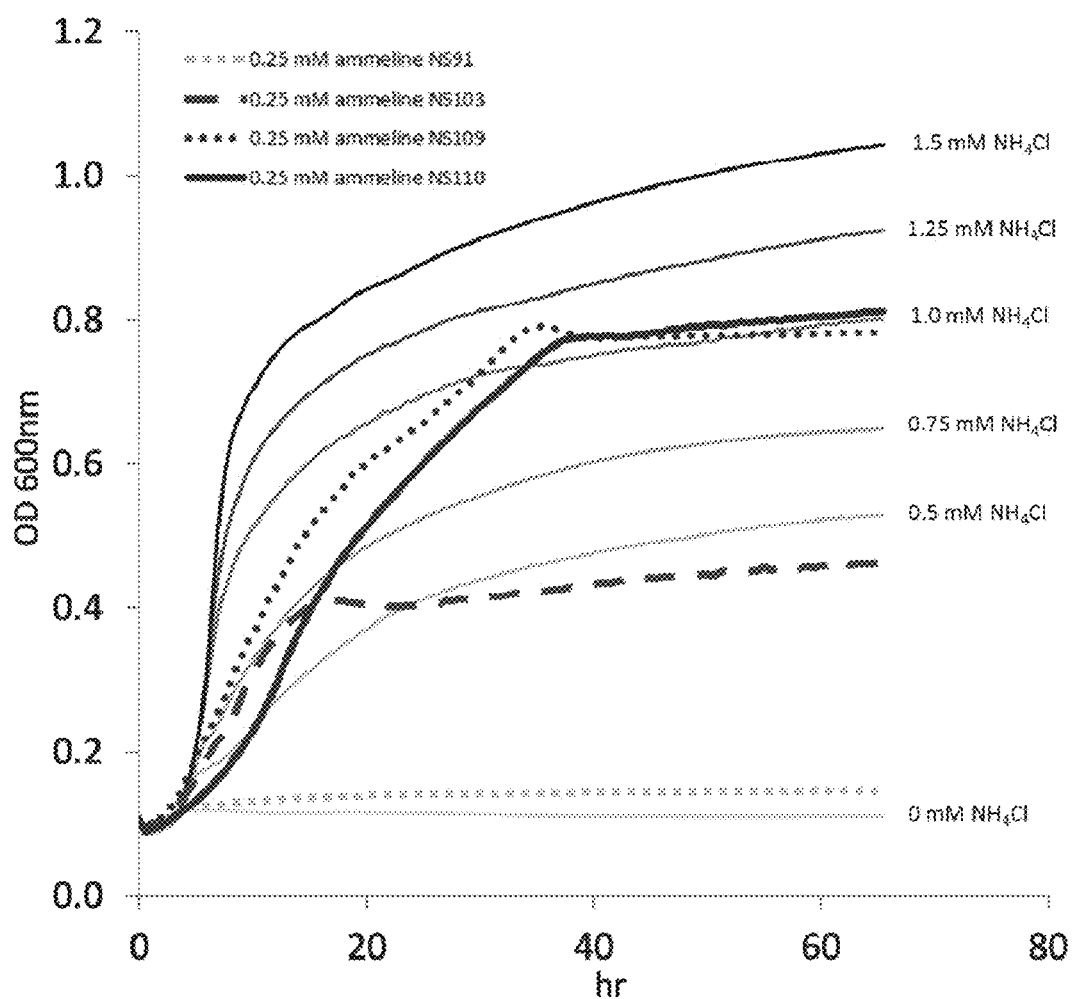
FIG. 25 depicts the growth of four organisms of the invention (NS91=control) on 0.25 mM ammeline, as compared to the standard curves for a native organism on $NH_4Cl$. Because ammeline has five nitrogen atoms, organisms having the ability to utilize melamine should be approximately five times more efficient (see, for example, NS110 on 0.25 mM ammeline, as compared to a native organism on 1.25 mM $NH_4Cl$).

FIG. 25 shows the growth progress of NS91, NS103, NS109, and NS110 in medium containing 0.25 mM ammeline as sole nitrogen source. An average of all four strains grown on different ammonium chloride concentrations from 0 to 1.5 mM is also shown as a standard curve for growth with limiting nitrogen. NS91 grown on ammeline is similar to the 0 mM ammonium chloride control. NS103 grown on 0.25 mM ammeline is similar to 0.5 mM ammonium chloride, suggesting it is approximately utilizating the predicted 2 mM ammonia per 1 mM ammeline. Strains NS109 and NS110 grown on 0.25 mM ammeline are similar to 1.25-1.0 mM ammonium chloride, suggesting it is approximately utilizating the predicted 5 mM ammonia per 1 mM ammeline.

Figure 26:
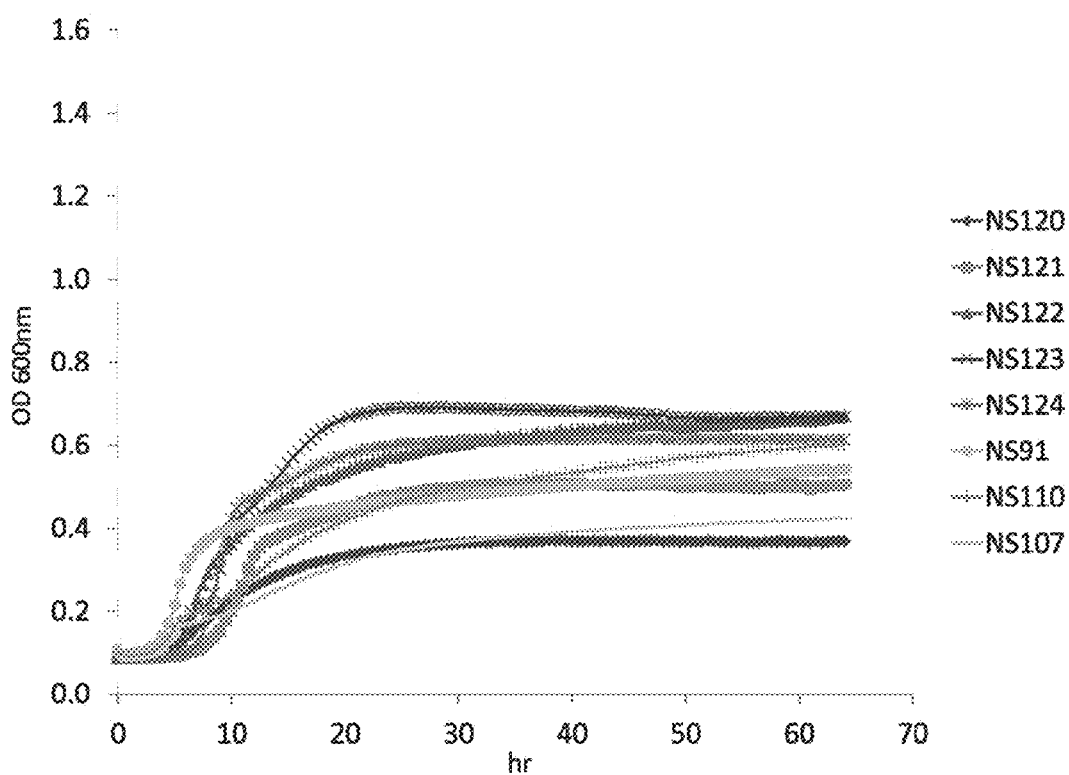
FIG. 26 depicts the growth of various organisms of the invention on 0.5 mM $NH_4Cl$. Importantly, the organisms described in FIGS. 26-28, for example NS120, NS91, NS107, and NS123, are *E. coli* strains derived from *E. coli* K12, *E. coli* B, *E. coli* Crooks, and *E. coli* MG1655 and are intended to show the breadth of the invention across various strains of *E. coli*.
Figure 27:
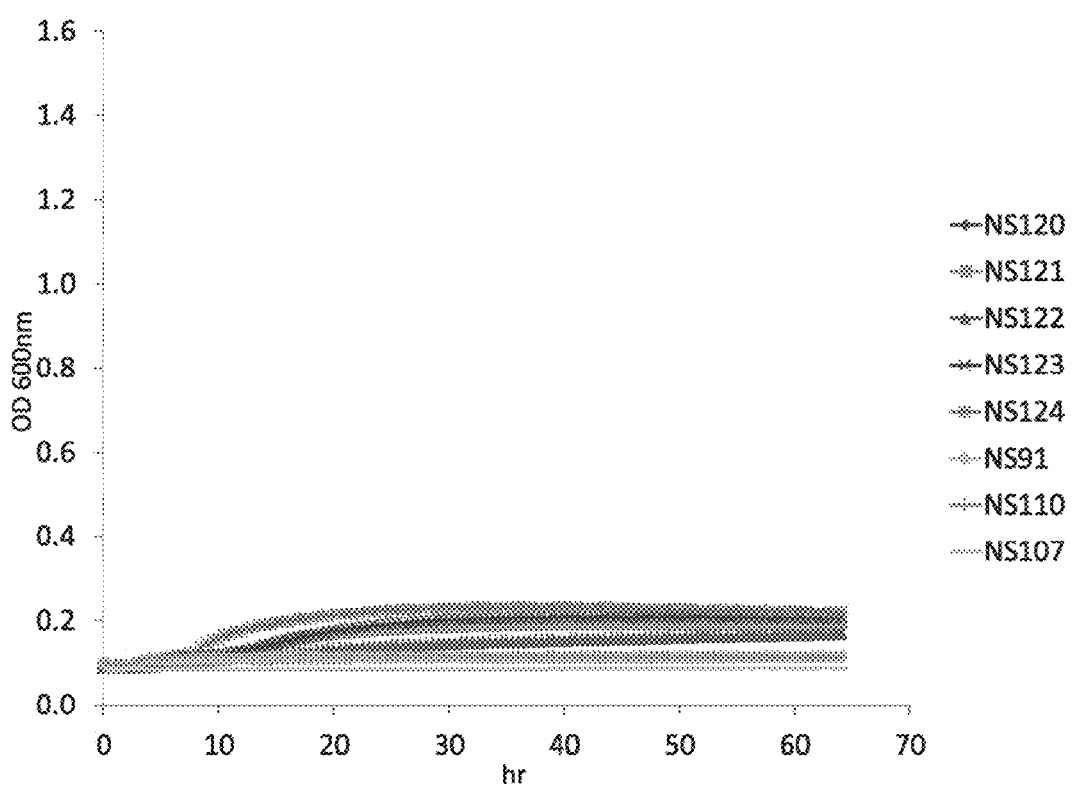
FIG. 27 depicts the growth of various organisms of the invention on a medium containing no nitrogen.
Figure 28:
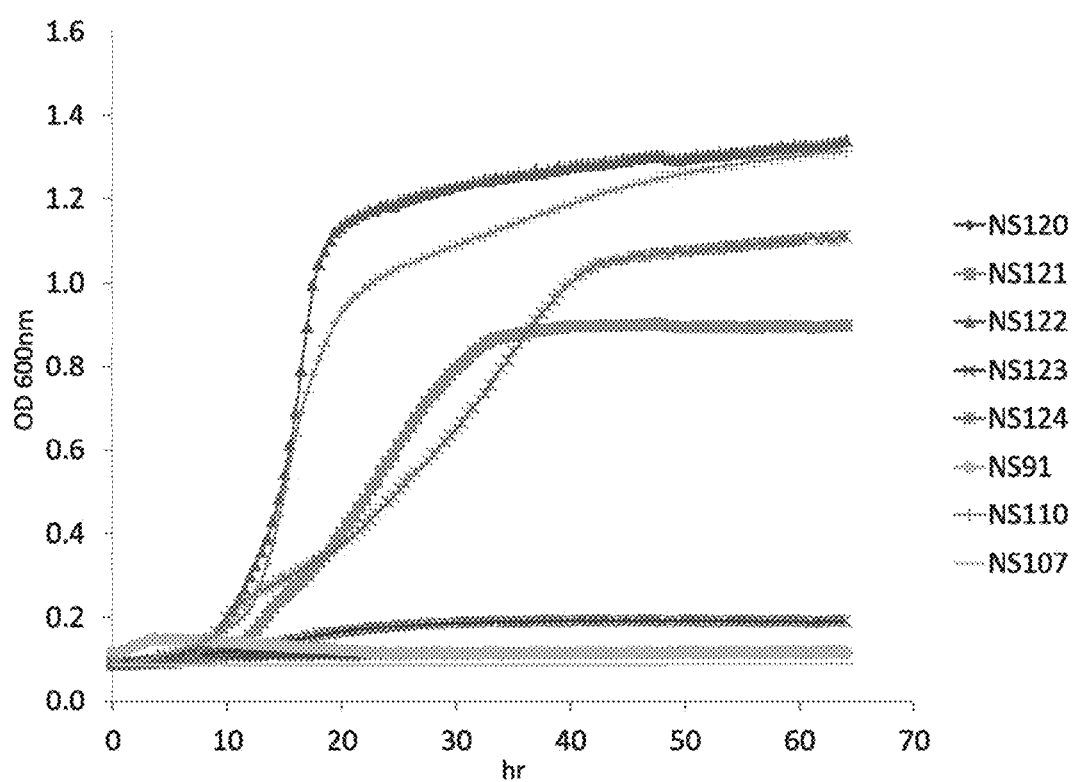
FIG. 28 depicts the growth of various organisms of the invention on a medium containing 0.5 mM melamine.

FIGS. 26, 27, and 28 show *E. coli* strains derived from *E. coli* K12, *E. coli* MG1655, *E. coli* B, and *E. coli* Crooks (C) containing either pNC121 with the complete melamine utilization pathway, or pNC53, a control vector. See FIGS. 29 and 30 for strain details. All the strains containing pNC121 are able to grow on 0.5 mM melamine as sole nitrogen source (FIG. 28). This indicates that the melamine utilization pathway is broadly applicable to *E. coli* strains that are commonly utilized for biotechnology applications.

Strains can also be selected for improved utilization of melamine derived nitrogen sources, in one example NS88 was passaged for 11 serial transfers in MOPS defined medium with 0.5 mM ammeline as sole nitrogen source. After the final passage, single colonies were isolated, and one was designated as NS93. NS93 and NS91 were grown overnight in medium with 0.5 mM ammonium chloride as sole nitrogen source, and then inoculated in medium with 0.5 mM ammeline as sole nitrogen source. NS91 exhibited a maximum growth rate of 0.024 hr$^{-1}$ on ammeline, while NS93 exhibited a maximum growth rate of 0.087 hr$^1$.

Media Utilization

Cultures grown aerobically at 37° C. with 100 mg/L ampicillin. Pre-cultures were grown in LB media with 100 mg/L ampicillin, washed once with an equal volume of MOPS media containing no nitrogen, and inoculated at 5% v/v of the final fermentation volume. The content of the MOPS medium is outlined in FIG. 11.

Imaging Cultures in Various Media

Figure 14:
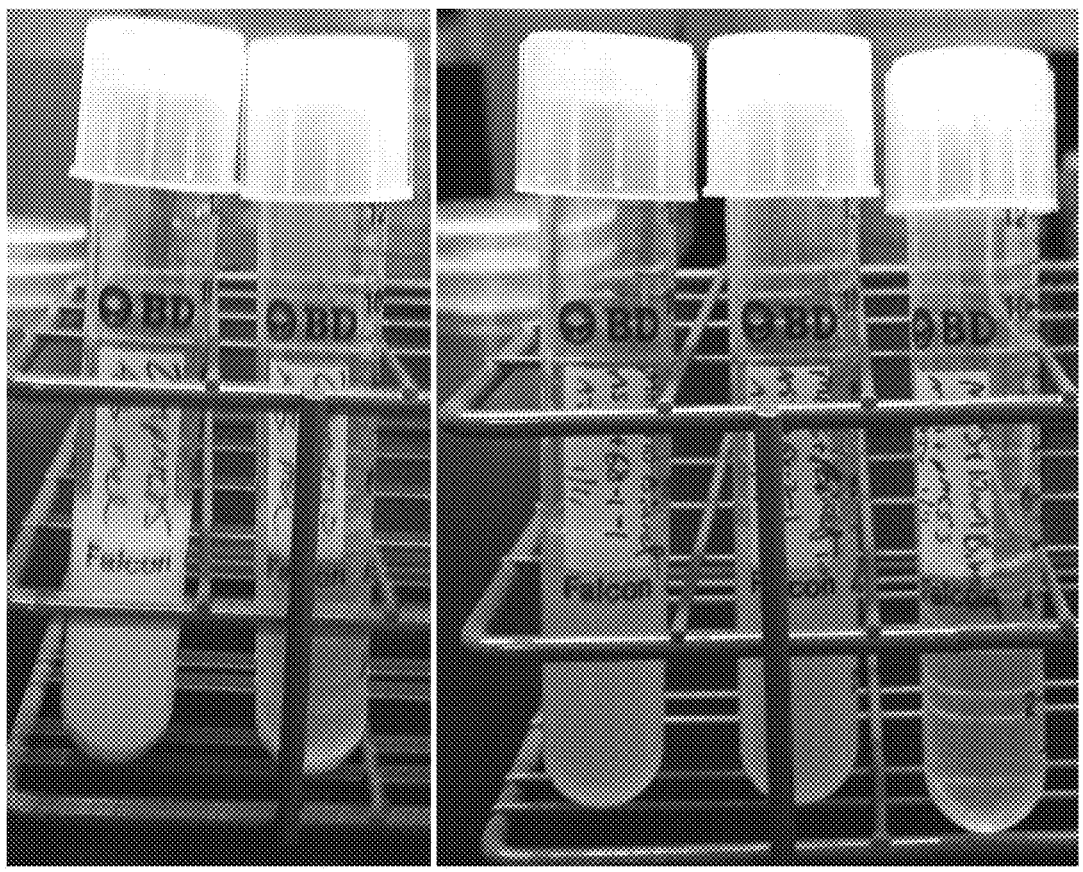
FIG. 14 depicts images, taken after 48 h, of cultures grown in MOPS media with different nitrogen sources. From left to right: NS88 with 10 mM melamine; NS91 with 10 mM melamine; NS90 with 10 mM biuret (replicate 1); NS90 with 10 mM biuret (replicate 2); and NS91 with 10 mM biuret.
Figure 15:
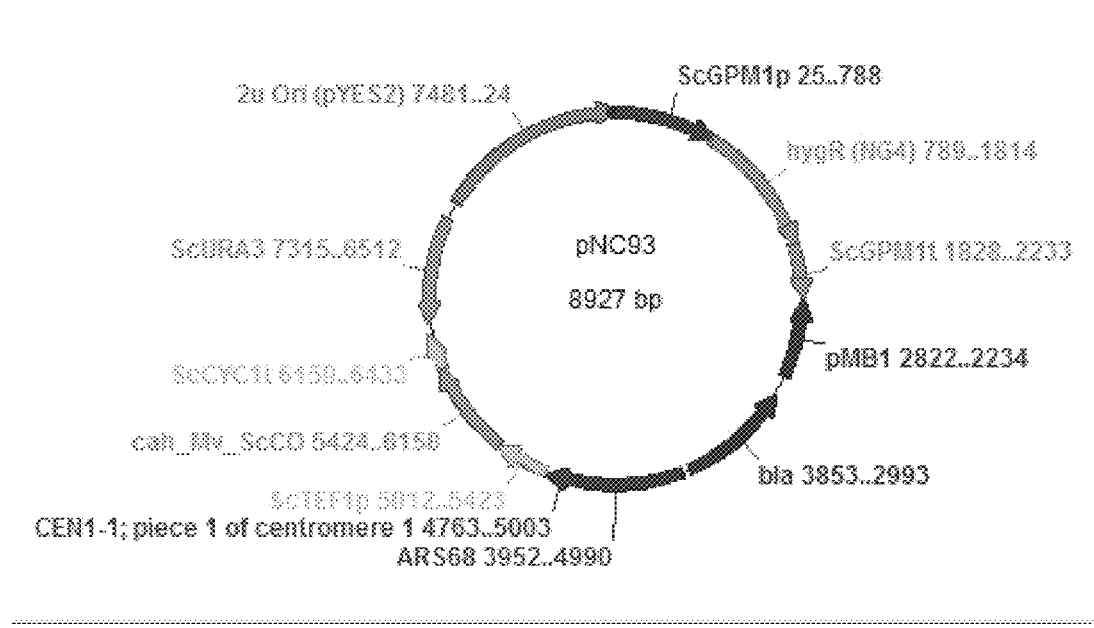
FIG. 15 depicts a plasmid of the invention.

Precultures were grown in LB media with 100 mg/L ampicillin, 0.1 mL were directly inoculated into 5 mL MOPS media with 100 mg/L ampicillin and the indicated nitrogen source. Grown at 37° C. in a drum roller at 30 rpm. See FIG. 14.

Example 10 Organisms Engineered to Utilize Cyanamide

Organisms
  NS100—industrial *S. cerevisiae* strain with pNC67 (hyg$^R$, nat$^R$)
  NS101—industrial *S. cerevisiae* strain with pNC93 (hyg$^R$, cah)

NS111—*S. cerevisiae* NRRL Y-2223 with pNC93 (hyg$^R$, cah)

NS112—*S. cerevisiae* NRRL Y-2223 with pNC67 (hyg$^R$, nat$^R$)

Figure 16:
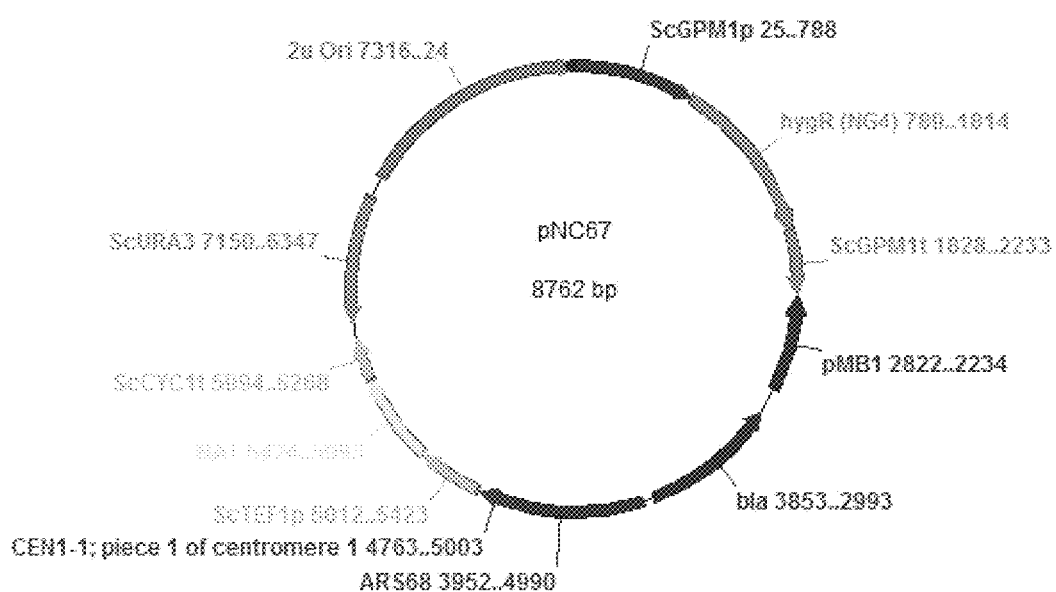
FIG. 16 depicts a plasmid of the invention.

See FIG. 16.

Utilization of Cyanamide in Defined Medium

Figure 17:
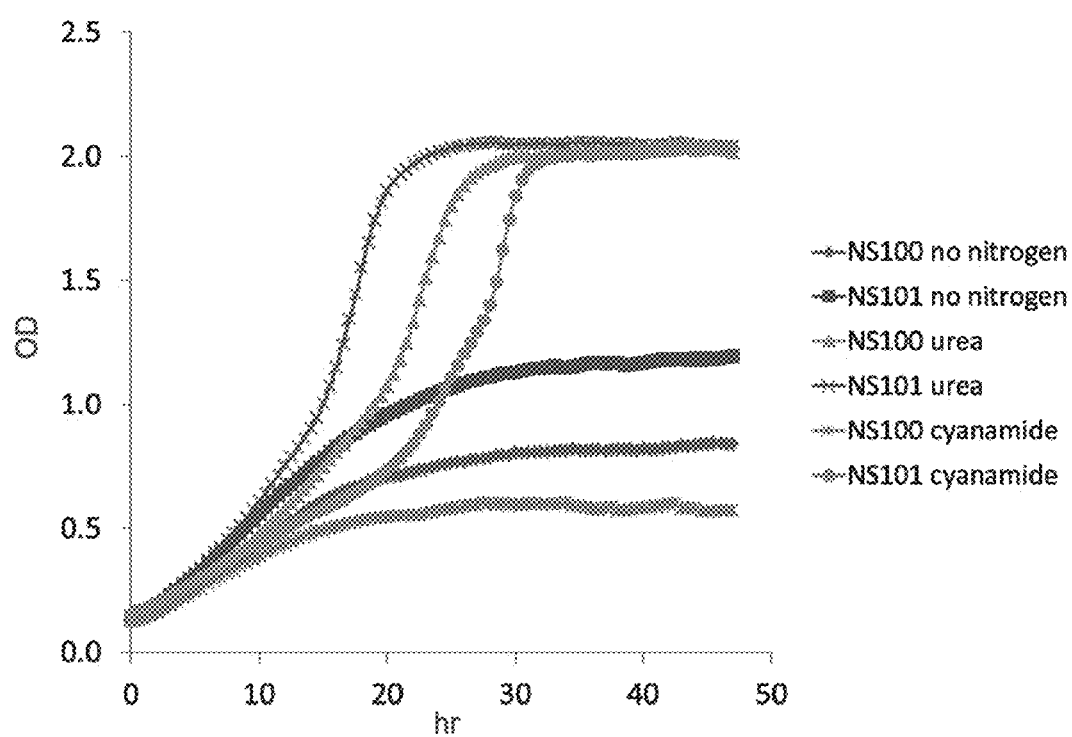
FIG. 17 depicts the growth progress of NS100 (control) and NS101 in media containing no nitrogen source, urea, or cyanamide.

Optical density of NS100 and NS101 grown in defined medium with different nitrogen sources. NS100 and NS101 were grown overnight in YPD medium, washed once in an equal volume of sterile water, and inoculated at 3.33% v/v. Strain NS101 is able to grow to an optical density with cyanamide comparable to that with urea, while NS100 grows to an optical density comparable to that with no nitrogen present in the medium. Data are averages of 3 replicate wells in a 96 well plate; 150 μL per well. 30° C., YNB medium contained 20 g/L glucose, 1.7 g/L YNB base medium without amino acids or ammonium sulfate, 5 g/L sodium sulfate, 100 μg/mL hygromycin, and either 10 mM urea, 10 mM cyanamide, or no nitrogen source. Inoculation was with 5 μL of culture pregrown for 24 hrs in the same medium with urea as nitrogen source. See FIG. 17.

Figures 21, 22:
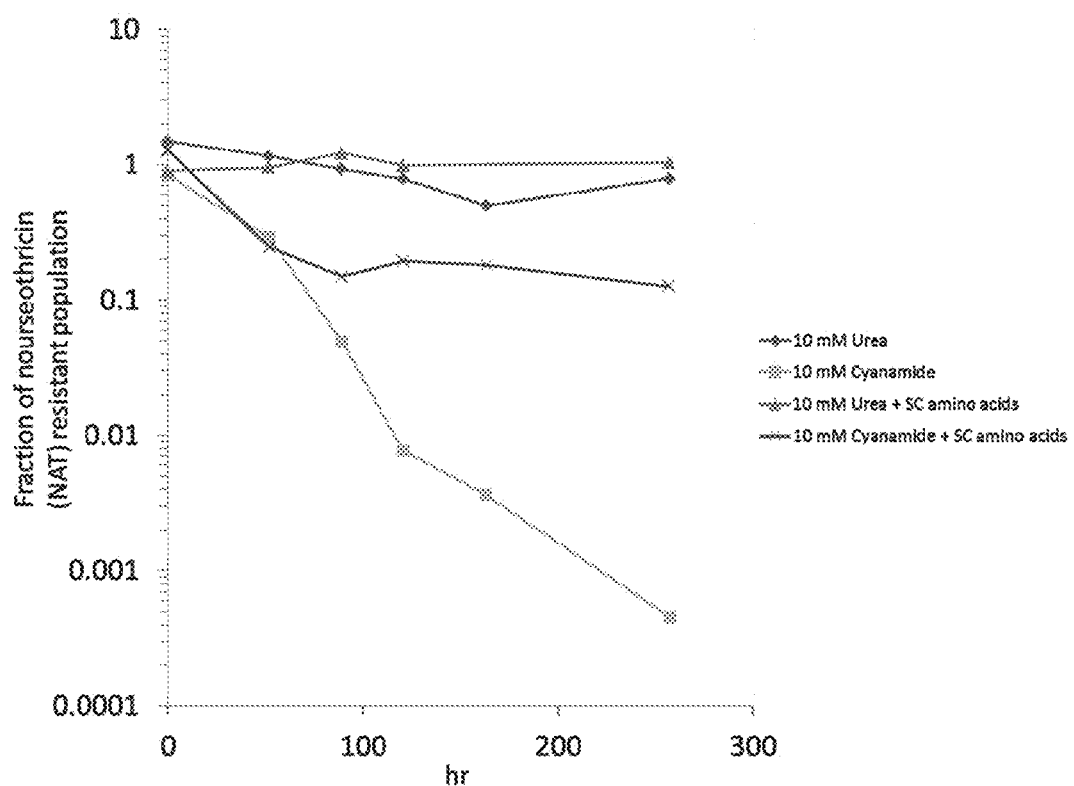
FIG. 21 depicts the growth of an organism of the invention in the presence of an antibiotic on various nitrogen-containing media (see FIG. 33 for composition of SC amino acid media).
FIG. 22 tabulates the optical density at 600 nm after growth of four organisms of the invention on various media.

Additionally, strains NS100, NS101, NS111, and NS112 were grown in defined YNB medium with 10 mM urea and 100 μg/mL hygromycin to stationary phase aerobically at 30° C. 1/1000 v/v inoculations were then made into the same defined medium with either 10 mM urea, 10 mM cyanamide, or no additional nitrogen and grown under the same conditions. Optical density was measured after 72 hours, as shown in FIG. 22. Strains NS101 and NS111, two different *S. cerevisiae* strains carrying the cah gene, were able to grow to an optical density comparable to that with urea; however, NS100 and NS112 only were able to grow to an optical density equal to or lower than in media with no nitrogen source. This shows that multiple *S. cerevisiae* strains are able to utilize cyanamide in the presence of the cah gene.

Competition in Defined Medium

Figure 18:
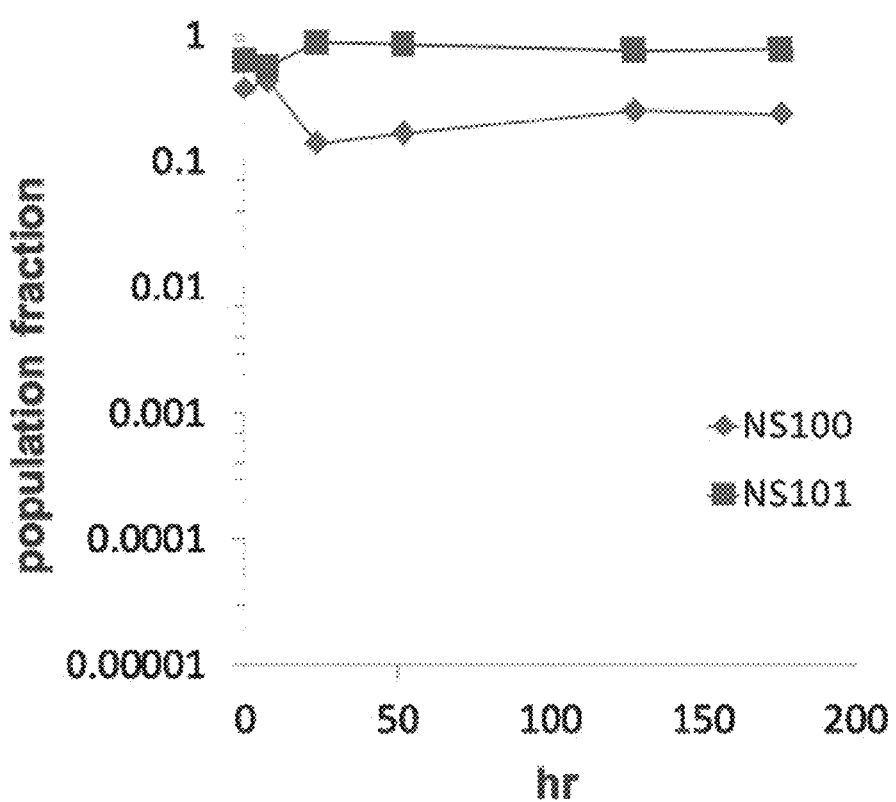
FIG. 18 depicts the population fraction of NS100 (control) and NS101 in a urea-containing medium.
Figure 19:
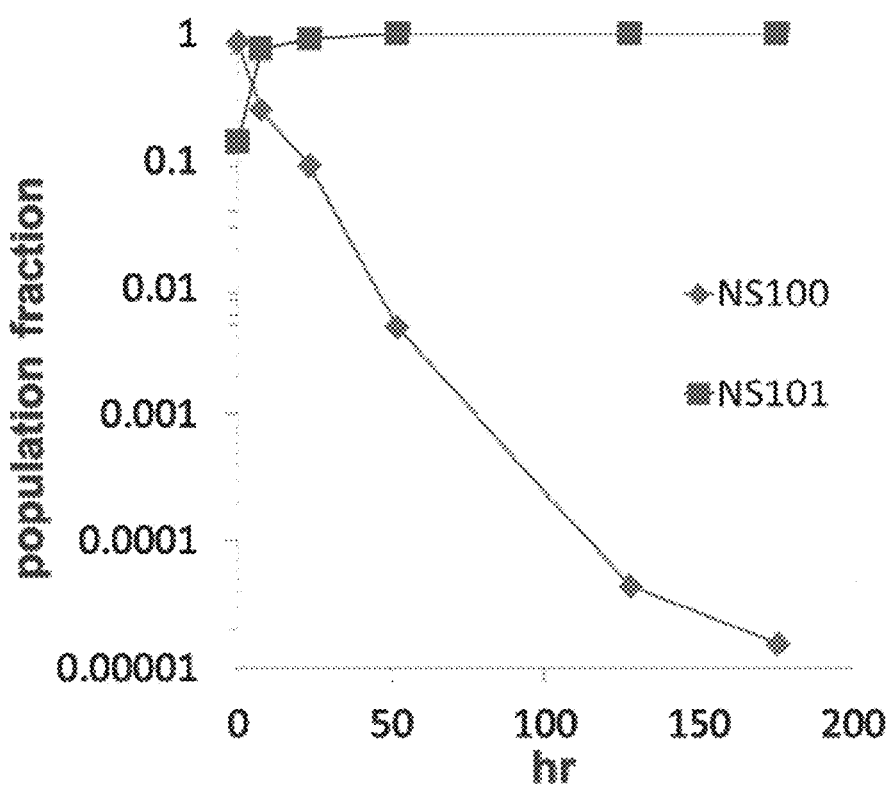
FIG. 19 depicts the population fraction of NS100 (control) and NS101 in a cyanamide-containing medium.

Strains NS100 (hyg$^R$, nat$^R$) and NS101 (hyg$^R$, cah) were grown in defined medium with 100 μg/mL hygromycin with urea as nitrogen source, and then both inoculated into defined medium containing either 10 mM urea or 10 mM cyanamide as nitrogen source. Upon growth to stationary phase, 1/100 v/v serial transfers were made to fresh medium with the same composition. The culture population was monitored via counting the number of hyg$^R$, nat$^R$ colony forming units and subtracting from the number of hyg$^R$ colony forming units. See FIG. 18 and FIG. 19 for one experiment in defined minimal medium. A second experiment is shown in FIG. 21. The second experiment included both defined minimal (YNB) and defined complex (YNB+SC amino acids) medium compositions. The defined YNB medium contained 20 g/L glucose, 1.7 g/L YNB base medium without amino acids or ammonium sulfate, 5 g/L sodium sulfate, and either 10 mM urea, 10 mM cyanamide, or no nitrogen source. Medium compositions are additionally given in FIGS. 32 and 33. Growth occurred aerobically at 30° C. Colony forming units were counted by serial dilutions in YPD media with either 300 μg/mL hygromycin or 100 μg/mL nourseothricin, and are the average of 3 dilution counts. See FIG. 18 and FIG. 19.

Utilization of Cyanamide in Rich Medium

Optical density of NS100 and NS101 grown in rich YPD medium with 100 μg/mL hygromycin and with and without 10 mM cyanamide. NS100 and NS101 were grown overnight in YPD medium, and inoculated at 3.33% v/v. NS101 experiences a shorter lag phase than NS100 in the presence of 10 mM cyanamide. Thus, cyanamide, in addition to functioning as a sole source of nitrogen, can also act as a deterrent for microbial growth. Data are averages of 3 replicate wells in a 96 well plate; 150 μL per well. 30° C., YPD medium or YPD medium with 10 mM cyanamide. Inoculation was with 5 μL of culture pregrown for 24 hrs in the YNB medium with urea as nitrogen source.

Figure 20:
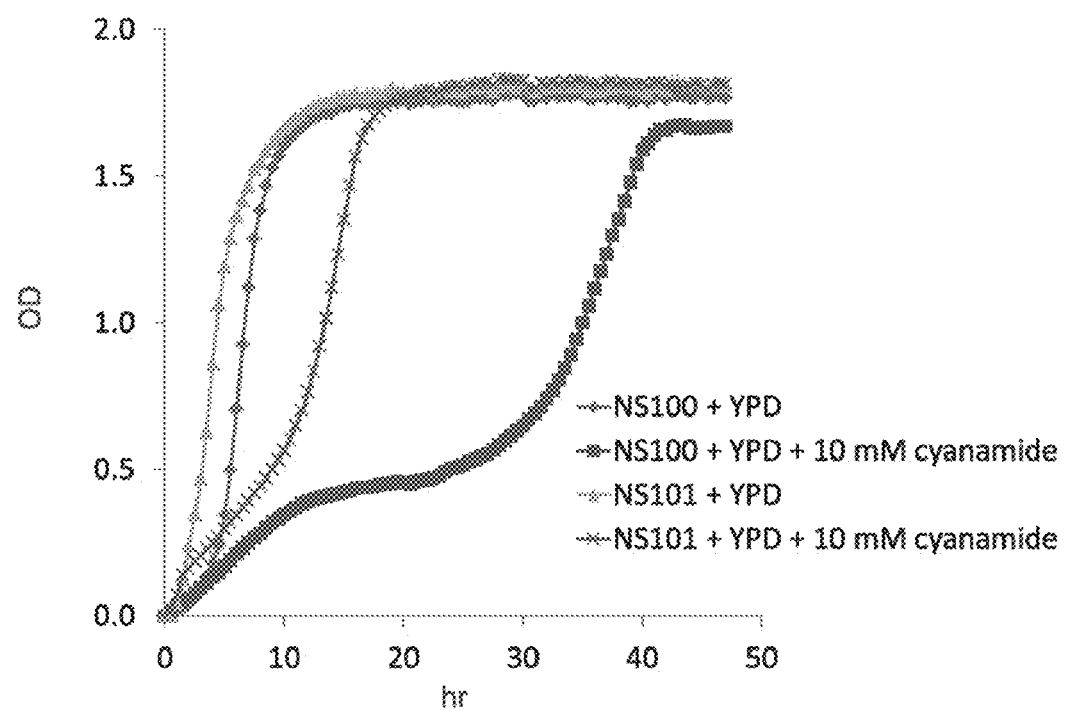
FIG. 20 depicts the growth progress of NS100 (control) and NS101 in media containing no nitrogen source, or media containing cyanamide.

See FIG. 20.

Example 11—Cyanamide Hydratase Activity Assay

This assay measured the conversion rate of cyanamide to urea. In the first step, cyanamide was hydrated to urea by cyanamide hydratase, which was detected in cell free extract of a *S. cerevisiae* strain expressing the cah gene and a control strain without cah. In the second step of the assay, a commercial kit (Megazyme, Ireland) was used to detect urea via enzymatic conversion of urea to ammonia followed by NADPH linked conversion of ammonia and 2-oxoglutarate to NADP+, $H_2O$, and glutamic acid.

Cell free extracts were prepared by growing *S. cerevisiae* strains in 50 mL yeast extract, peptone, dextrose (YPD) medium with 300 μg/mL hygromycin to an optical density between 1-2. Cells were harvested by centrifugation, washed once in an equal volume of water, and re-suspended in Y-PER lysis buffer (Thermo Scientific, USA) following the manufacturer's instructions. After incubation at room temperature for 20 minutes, the lysate was centrifuged at 14,000×g for 10 min and the supernatant was recovered as the cell free extract. Total protein was measured by a Nanodrop spectrophotometer (Thermo Scientific, USA).

Protocol

Add together in a 100 μL volume:
  10 μL of 50 mM NaPO4, pH 7.7;
  10 μL of 200 mM cyanamide made fresh
  5-20 μL cell free extract
  balance water (60 μL for 20 μL CFE)
add 100 uL of above sample to 2.9 mL Megazyme urea/ammonia assay reagents and monitor at 340 nm.

| Strain | Genotype | Cyanamide hydratase activity | | |
|---|---|---|---|---|
| | | μmol mg$^{-1}$ | min$^{-1}$ | Standard Deviation |
| NS100 | hyg$^R$ nat$^R$ | 0.019 | | 0.001 |
| NS101 | hyg$^R$ cah | 0.073 | | 0.002 |

Example 12—Exemplary Sequences of the Invention

Sequence 1 is the DNA sequence of the allophanate hydrolase atzF gene in *Pseudomonas* sp. strain ADP.

Sequence 2 is the DNA sequence of allophanate hydrolase DUR1,2 gene in *S. cerevisiae*.

Sequence 3 is the DNA sequence of allophanate hydrolase YALI0E07271g gene in *Y. lipolytica* CLIB122.

Sequence 4 is the DNA sequence of the biuret amidohydrolase atzE gene in *Pseudomonas* sp. strain ADP.

Sequence 5 is the DNA sequence of the cyanuric acid amidohydrolase atzD gene in *Pseudomonas* sp. strain ADP.

Sequence 6 is the DNA sequence of the cyanuric acid amidohydrolase trzD gene in *Pseudomonas* sp. strain NRRLB-12227 (formerly *Acidovorax citrulli*).

Sequence 7 is the DNA sequence of the cyanuric acid amidohydrolase atzD trzD gene in *Rhodococcus* sp. Mel.

Sequence 8 is the DNA sequence of the guanine deaminase guaD gene in *E. coli* K12 strain MG1566.

Sequence 9 is the DNA sequence of the guanine deaminase blr3880 gene in *Bradyrhizobium japonicum* USDA 110.

Sequence 10 is the DNA sequence of the guanine deaminase GUD1/YDL238C gene in *S. cerevisiae*.

Sequence 11 is the DNA sequence of the guanine deaminase YALI0E25740p gene in *Y. lipolytica* CLIB122.

Sequence 12 is the DNA sequence of the melamine deaminase trzA gene in *Williamsia* sp. NRRL B-15444R (formerly *R. corallinus*).

Sequence 13 is the DNA sequence of the melamine deaminase triA gene in *Pseudomonas* sp. strain NRRL B-12227 (formerly *Acidovorax citrulli*).

Sequence 14 is the DNA sequence of the isopropylammelide isopropylamino-hydrolase atzC gene in *Pseudomonas* sp. strain ADP.

Sequence 15 is the cDNA sequence of the *Myrothecium verrucaria* cyanamide hydratase (cah) gene.

Sequences 16-21 are DNA sequences of the invention.

Sequences 22-37 are the sequences of various cyanamide hydratase (cah) genes for use in the invention.

Sequences 38 and 39 are the sequences of various trzC genes for use in the invention.

Sequences 40 and 41 are the sequences of various trzE genes for use in the invention.

Sequence 42 is the sequence of plasmid pNC10.
Sequence 43 is the sequence of plasmid pNC53.
Sequence 44 is the sequence of plasmid pNC67.
Sequence 45 is the sequence of plasmid pNC85.
Sequence 46 is the sequence of plasmid pNC86.
Sequence 47 is the sequence of plasmid pNC87.
Sequence 48 is the sequence of plasmid pNC93.
Sequence 49 is the sequence of plasmid pNC96.
Sequence 50 is the sequence of plasmid pNC97.
Sequence 51 is the sequence of plasmid pNC101.
Sequence 52 is the sequence of plasmid pNC120.
Sequence 53 is the sequence of plasmid pNC121.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A genetically engineered organism, wherein the genetically engineered organism has been transformed by a nucleic acid molecule; the nucleic acid molecule comprises the non-native gene cah and the non-native gene DUR1,2.

2. The genetically engineered organism of claim 1, wherein the non-native gene cah is cah from *Fusarium oxysporum* Fo5176, cah from *F. pseudograminaearum* CS3096, cah from *Gibberella zeae* PH-I, cah from *Aspergillus kawachii* IFO 4308, cah from *A. niger* CBS 513.88, cah from *A. niger* ATCC 1015, cah from *A. oryzae* 3.042, or cah from *S. cerevisiae* FostersB; or the non-native gene DUR1,2 is DUR1,2 from *S. cerevisiae*.

3. The genetically engineered organism of claim 1, wherein the genetically engineered organism is a species of the genus *Yarrowia, Saccharomyces, Ogataea, Pichia*, or *Escherichia*.

4. The genetically engineered organism claim 1, wherein the genetically engineered organism is selected from the group consisting of *Yarrowia lipolytica, Saccharomyces cerevisiae, Ogataea polymorpha, Pichiapastoris*, and *Escherichia coli*.

5. A recombinant vector comprising a gene operably linked to a promoter, wherein the gene encodes cyanamide hydratase, and the vector further comprises a DUR1,2 gene.

6. The recombinant vector of claim 5, wherein the DUR1,2 gene is DUR1,2 from *S. cerevisiae*, or the gene encoding cyanamide hydratase is cah from *Myrothecium verrucaria*.

7. The genetically engineered organism of claim 1, wherein the nucleic acid molecule comprises the sequence of SEQ ID NO: 15.

8. The genetically engineered organism of claim 1, wherein the non-native gene cah and the non-native gene DUR1,2 are expressed from a single promoter as part of a gene operon.

9. The recombinant vector of claim 5, wherein the gene encoding cyanamide hydratase and the DUR1,2 gene are operably linked to the same promoter as part of a gene operon.

\* \* \* \* \*

SEQUENCE LISTING

```
<160> NUMBER OF SEQ ID NOS: 76

<210> SEQ ID NO 1
<211> LENGTH: 1818
<212> TYPE: DNA
<213> ORGANISM: Pseudomonas sp.

<400> SEQUENCE: 1
atgaatgacc gcgcgcccca ccctgaaaga tctggtcgag tcacgccgga tcacctgacc      60
gatctggctt cctatcaggc tgcctatgcc gccggtacag acgccgccga cgtcatttcg     120
gacctgtatg cccgtatcaa agaagacggc gaaaatccga tctggattag cctgttgccc     180
ttggaaagcg cattggcgat gctggccgac gcgcagcaac gcaaggacaa gggagaagcg     240
ttgccgctct ttggcatccc cttcggcgtc aaggacaaca tcgacgtcgc aggccttccg     300
acgactgccg ggtgtacggg gttcgcgcgt acgccccgac agcacgcctt cgtcgtacag     360
cgcctggtgg acgctggcgc gatcccgatc ggaaaaacga acctcgatca attcgcgacc     420
gggttgaacg gcactcgcac gccgtttggc attccgcgct gcgtgttcaa cgagaactac     480
gtatccggcg gctccagcag tggctccgca gtggccgtcg ccaacggcac ggtaccgttc     540
tcgctcggga cggacactgc cggttccggc cgcattcctg ctgcgttcaa caatctggtg     600
ggcttgaaac cgaccaaagg cctgttctcg ggcagtggac tggttcccgc ggcgcgaagc     660
cttgactgca tcagcgtcct cgcccatacc gtagatgacg cccttgcggt cgcacgcgtc     720
gccgccggct acgatgctga tgacgctttt tcgcgcaagg cgggcgccgc cgcactgaca     780
gaaaagagtt ggcctcgtcg cttcaatttc ggggtcccag cggcggaaca tcgccagttt     840
ttcggtgacg cggaagccga ggcgcttttc aataaagcgg ttcgcaagct tgaagagatg     900
ggtggcacct gcatctcgtt tgactatacc cccttcaggc aggctgctga actgctctac     960 gccggcccctt gggttgcgga gcgcctggcg gccatcgaga gccttgcgga cgagcatccc    1020
gaggtgctcc acccggtcgt tcgtgacatc atcttgtccg cgaagcgaat gagcgcagtc    1080
gacacgttca acggtatcta tcgcctggcc gaccttgtca gggctgcaga gagcacttgg    1140
```

-continued

```
gaaaagatcg atgtgatgct gctgccgacg gcgccgacca tctacactgt agaagacatg    1200
ctcgccgatc cggtacgcct caacagcaat ctgggcttct acacgaactt cgtgaacttg    1260
atggatttgt ccgcgattgc tgttcccgca ggcttccgaa ccaatggcct gccatttggc    1320
gtcactttca tcggtcgggc gttcgaagat ggggcgatcg caagcttggg aaaagctttc    1380
gtggagcacg acctcgccaa gggcaacgcg ccacggcgg cgccacccaa ggataccgtc     1440
gcaatcgccg tggtaggtgc acatctctcc gaccagccct tgaatcatca gctcacggag    1500
agcggcggaa agctacgggc aacaacgcgt actgcgccgg atatgccttt gtacgcactc    1560
cgtgatgcga cgccggctaa gcctggaatg ttgcgcgacc agaatgcggt cgggagcatc    1620
gaagtggaaa tctgggatct gccggtcgcc gggttcggtg cgtttgtaag tgaaattccg    1680
gcgccgttgg gtatcgggac aataacactc gaagacggca gccatgtgaa aggctttctg    1740
tgcgagccac atgccatcga cggcgctc gacatcactc actacggcgg ctggcgagca     1800
tacctcgcgg ctcaatag                                                 1818
```

<210> SEQ ID NO 2
<211> LENGTH: 5508
<212> TYPE: DNA
<213> ORGANISM: Saccharomyces cerevisiae

<400> SEQUENCE: 2

```
atgacagtta gttccgatac aactgctgaa atatcgttag gttggtcaat ccaagactgg     60
attgatttcc acaagtcatc aagctcccag gcttcactaa ggcttcttga atcactacta    120
gactctcaaa atgttgcgcc agtcgataat gcgtggatat cgctaatttc aaaggaaaat    180
ttactgcacc aattccaaat tttaaagagc agagaaaata agaaactct acctctctac     240 ggtgtcccta ttgctgttaa ggacaacatc gacgttagag gtctacgcac caccgctgca    300
tgtccatcct ttgcatatga gccttccaaa gactctaaag tagtagaact actaagaaat    360
gcaggtgcaa taatcgtggg taagacaaac ttggaccaat ttgccacagg attagtcggc    420
acacggtctc catatgggaa acaccttgc gcttttagca aagagcatgt atctggtggt     480
tcctccgctg ggtcagcatc ggtggtcgcc agaggtatcg taccaattgc attgggtact    540
gatacagcag gttctggtag agtcccagcc gccttgaaca acctgattgg cctaaagcca    600
acaaagggcg tcttttcctg tcaaggtgta gttcccgctt gtaaatcttt agactgcgtc    660
tccatctttg cattaaacct aagtgatgct gaacgctgct ccgcatcat gtgccagcca    720 gatcctgata tgatgaata ttctagaccc tatgttcca acccaaagaa aaattttca      780 agcaatgtaa cgattgctat tcctaaaaat atcccatggt atggtgaaac caagaatcct    840
gtactgtttt ccaatgctgt cgaaaatcta tcaagaacgg cgctaacgt catagaaatt     900 gattttgagc ctcttttaga gttagctcgc tgtttatacg aaggtacttg ggtggccgag    960
cgttatcaag ctattcaatc gttttttggac agtaaaccac caaggaatc tttgaccct   1020 actgttattt caattataga aggggccaag aaatacagtg cagtagactg cttcagtttt   1080
gaatacaaaa gacaaggcat cttgcaaaaa gtgagacgac ttctcgaatc agtcgatgtc   1140
ttgtgtgtgc ccacatgtcc cttaaatcct actatgcaac aagttgcgga tgaaccagtc   1200
ctagtcaatt caagacaagg cacatggact aattttgtca acttggcaga tttggcagcc   1260
cttgctgttc ccgcagggtt ccgagacgat ggtttgccaa atggtattac tttaatcggt   1320
aaaaaattca cagattacgc actattagag ttggctaacc gctatttcca aaatatgttc   1380
```

```
cccaacggtt ccagaacata cggtactttt acctcttctt cagtaaagcc agcaaacgat   1440
caattagtgg gaccagacta tgacccatct acgtccataa aattggctgt tgtcggtgca   1500
catcttaagg gtctgcctct acattggcaa ttggaaaagg tcaatgcaac atatttatgt   1560
acaacaaaaa catcaaaagc ttaccagctt tttgctttgc ccaaaaatgg accagtttta   1620
aaacctggtt tgagaagagt tcaagatagc aatggctctc aaatcgaatt agaagtgtac   1680
agtgttccaa aagaactgtt cggtgctttt atttccatgg ttcctgaacc attgggaata   1740
ggttcagtgg agttagaatc tggtgaatgg atcaaatcct ttatttgtga agaatctggt   1800
tacaaagcca aaggtacagt tgatatcaca aagtatggtg gatttagagc atattttgaa   1860
atgttgaaga aaaagagtc ccaaaagaag aagttatttg ataccgtgtt aattgccaat   1920
agaggtgaaa ttgccgttcg tattatcaag acattaaaaa aattgggtat tagatcagtt   1980
gcagtttatt ccgaccctga taaatattct caacacgtta ctgatgcaga tgtttctgta   2040 cccttcatg gcacaaccgc agcccaaact tatttagaca tgaataagat catagatgcc   2100
gctaagcaaa ctaatgcaca ggccattatt cctggttatg gtttcttgtc ggaaaatgcg   2160 gattttctg atgcgtgcac cagtgctggc attacctttg ttggtccttc gggagatatt   2220
atcagaggtt tagggttaaa acattctgct agacagattc acagaaggc tggcgttcct   2280 ctagtgccag gctctttgct tatcacatca gttgaagagg ctaagaaagt cgcagcggaa   2340
ttggaatacc cagttatggt gaagtcaact gctggtggcg tggtattgg tttgcagaaa   2400 gtcgattctg aagaggacat cgagcatatt tttgagactg tgaaacatca aggtgaaaca   2460
tttttcggtg acgctggtgt atttctgaaa cggtttatcg aaaatgccag gcatgttgaa   2520
gtccaactta tgggagatgg ttttggtaag gccattgctt gggcgaacg tgattgttct   2580 ttacagcgtc gtaaccaaaa agttatcgaa gaaactcctg caccaaattt gccagaaaag   2640
acgaggttgg cgttaagaaa ggcagctgaa agtttgggat ctttattgaa ttacaagtgt   2700
gctggtacgt tgaatttat ttacgatgag aaaaaggacg agttttactt tttagaagtt   2760
aatacaagat tacaagttga acatccaata acagaaatgg ttacagggtt agacttggtc   2820
gagtggatga tcaggattgc cgctaatgat gcacctgatt ttgattctac aaaggtagaa   2880
gtcaatgggg tttcaatgga ggcacgttta tatgctgaaa atccattgaa aaatttcaga   2940
ccttctccag gttacttgt cgatgtgaaa tttcctgatt gggcaagagt ggatacttgg   3000
gttaagaaag gtactaatat ttctcccgaa tatgatccaa cattggccaa aattatcgtt   3060
catgggaaag accgtgatga tgcaatttcc aagttaaatc aagcgttaga agaaacaaaa   3120
gtttacggat gtattactaa cattgactac ctgaagtcta tcattaccag tgatttcttt   3180
gctaaagcaa aagtttctac aaacattttg aactcttatc aatatgagcc taccgccatc   3240
gaaattactt tgcccggtgc acacactagt attcaggatt accccggtag agttgggtac   3300
tggagaattg gtgttccgcc ctctggtcca atggacgcat attcgtttag attggcgaac   3360
agaattgttg gtaatgacta caggactcct gccattgaag taacgttgac tggtccatcc   3420
atcgttttcc attgtgaaac tgtcattgcc attactggtg gtaccgctct atgtacatta   3480
gacggccaag aaattcccca acacaaaccg gtcgaagtta agaggggatc tactttatcc   3540
attggcaagt tgacaagcgg ctgtagagca tacttaggta tcagggtgg cattgatgtg   3600 cctaaatact tgggctctta ttctactttc actctaggaa atgtcggtgg atacaatgga   3660
agggtgctaa aacttgggaga cgtactattc ttaccaagca atgaagaaaa taatcagtt   3720 gagtgccttc cacagaatat tcctcaatca ttaattcctc aaatttccga aactaaggaa   3780
```

```
tggagaattg gtgtaacatg tggtccccat gggtctccag attttttaa acctgagtcc      3840 atcgaagaat ttttcagtga gaagtggaag gttcattaca actccaatag atttggtgtc      3900
cgtttgattg gacctaaacc taagtgggca agaagtaatg gtggtgaagg tggtatgcat      3960
ccttcaaaca ctcacgatta cgtttattct ctgggtgcaa ttaatttcac gggtgatgag      4020
ccagttatta ttacttgcga tggtccttcc ttaggtggtt ttgtgtgtca agctgttgtc      4080
ccagaagcag aactgtggaa ggttggacag gttaaacccg tgattccat tcagtttgtg       4140 ccactttctt acgaaagctc gagatcctta aggaatctc aggaagttgc aattaaatca       4200
ttggatggta ctaagttaag gcgcttagac tctgtttcaa ttttaccatc attcgaaacg      4260
cctattcttg cacaaatgga aaagtgaat gagctttcac caaggttgt atacagacaa        4320 gcaggtgatc gttatgtttt ggtggaatac ggtgataatg aaatgaattt taatatttcc      4380
tatagaattg aatgcctgat ctcccttgtg aaaagaata agactattgg tattgttgaa      4440
atgtcccaag gtgttagatc tgtgttgata gaatttgatg gttacaaagt cactcaaaaa      4500
gaattgctta agtattggt ggcatatgaa acagaaatcc agtttgatga aaattggaag       4560
ataacttcta atataataag attaccgatg gctttcgaag actcgaagac tttggcatgt     4620
gttcaaaggt atcaagaaac aattcgttcg tctgctccat ggttgccaaa taacgttgat      4680
ttcattgcca atgtaaatgg aatttcaagg aatgaagttt atgatatgtt gtattctgcc      4740
agatttatgg ttttaggttt aggtgatgtc ttcctagggt cgccttgtgc tgttccatta      4800
gatcctcgtc acagattttt gggaagcaag tacaacccaa gtagaacata tacagaaaga     4860
ggtgcagtcg gtattggcgg tatgtatatg tgcatatatg ctgctaacag tcctggtggg     4920
taccaattag tgggtagaac aataccaatt tgggacaaac tatgtctggc cgcatcttct     4980
gaggttccgt ggttgatgaa cccatttgac caagtcgaat tttacccagt ttctgaagaa     5040
gatttggata aaatgactga agattgtgat aatggtgttt ataaagtcaa tatcgaaaag     5100 agtgttttg atcatcaaga atacttgaga tggatcaacg caaacaaaga ttccatcaca       5160
gcattccagg agggccagct tggtgaaaga gcagaggaat tgccaaaatt gattcaaaat     5220
gcaaactctg aactaaaaga aagtgtcaca gtcaaacctg acgaggaaga agacttccca      5280
gaaggtgcag aaattgtata ttctgagtat tctgggcgtt tttggaaatc catagcatct      5340
gttgagatgt ttattgaagc aggtcaaggg ctactaatta ttgaagccat gaaagcggaa     5400
atgattatat ccgctcctaa atcgggtaag attatcaaga tttgccatgg caatggtgat     5460
atggttgatt ctggtgacat agtggccgtc atagagacat tggcatga                  5508
```

<210> SEQ ID NO 3
<211> LENGTH: 5463
<212> TYPE: DNA
<213> ORGANISM: Yarrowia lipolytica

<400> SEQUENCE: 3

```
atgtgcaaat caatcggctg gactattgcc gaatggaagg aggcacagac caactcgtct       60
tacgaggagg cccgacatcg actgttggac ctcgtggcca ccttcaagga ctacaagcat      120
ggtgatccgc cttggatcac tgtcgcctca acagagcata tcaacaagca atggaaggag     180
cttcagttga tgaagaagaa cccagagtcc cttcccttt acggagttcc tttcgctgta      240
aaggacaaca ttgatgtcat cgactttccc acaaccgctg catgccccgc ctatctctac     300
atccccaagg aagacgccac catggtccgt ctgatcaaag aggctggagg tatcgttgtc     360
```

-continued

| | |
|---|---|
| ggcaaaacca acctcgatca gttcgctact ggtctggtcg gaacccgatc tccttacgga | 420 |
| aagactccca acaccttctc cgacaagcac gtatctggag gttcgtctgc tggctctgct | 480 |
| tccgtagtcg cccgaggcct ggttcccttt tctcttggaa cagatactgc aggctcaggt | 540 |
| cgggttcccg cctctctcaa caacctggta ggcctaaagc caaccgttgg cgcattttca | 600 |
| gccaagggtg tggtacccgc ctgcaagtcg cttgattgcg tctccatttt ctcgctggtc | 660 |
| ctgtctgacg ctcagctggt gttcaacatt gccgcccact ttgacaagga cgattgctac | 720 |
| tcgcgacgtt tcccccagcg acctctcaag tcgtttggcc ccactccagt atttgccgtc | 780 |
| cccgaaaccc ctctgtggtt tggagatgag ctcaaccctg ctctcttcga cgacgccgtt | 840 |
| gagcgtttgc gacaacaggg cgtaaaggtc gtcaagattg acttcactcc tctgttcgac | 900 |
| ctcgccaagt gcctctacga aggtccctgg gtggctgagc gatacgctgc catcaaggac | 960 |
| tttgtgcaga accgaaagga agacatggac gaaactgtgt atggcattgt caagcaggct | 1020 |
| gagaacttca ctgctgcaga cgcctttgcc tacgagtaca acgacgagc cattgtgcga | 1080 |
| aagattgagg agatcttctc ttccattgac ggtctgatcg tgcccacatg tcctctattc | 1140 |
| cccaccatgg agtctgtggc taaggagcct gtcactgtca atgcccacca gggtacctac | 1200 |
| accaactttg tcaacctcgc tgatctctct gctctagcta tccctgtcgg attccgaaag | 1260 |
| gacggtttcc cctttggaat cactctcatc tctcaaaagt tcaacgacta cgctctgctg | 1320 |
| gacatggctc agaagttcct gcctgcttct cgacctctgg gtgctctgcc aaaggacaag | 1380 |
| ttcaccgcca agaagggaga tcttcttgcc tcttctatcg tcgacaacat gcctcgaacc | 1440 |
| atccctctgg ctgttgtagg agcccatctc accggcatgc ctctcaactg gcagcttcaa | 1500 |
| aaggtcgagg ctactcttgc ccgacgaacc aaaactgccg actactaccg actctacgct | 1560 |
| ctggcgaaca ccgtgcctac aaagcctggt ctccgacggg ttcttccctc tgacactact | 1620 |
| ctccgaggcg aggctattga ggttgaaatc tgggacgtgc cttacagaaa ctttggagag | 1680 |
| ttcgtatcaa tggtccctca tcctcttggt atcggaacca ttgagcttgc cgacggaaaa | 1740 |
| tgggtcaagg gtttcatttg cgagcagctg ggatacgacg acgctgagga catcaccaag | 1800 |
| tttggcggct ggagagcgta caaggctgag actacccaga acctggagtc caagcctttc | 1860 |
| gagactgttc tggtcgccaa ccgaggtgag attgccgttc gactcatcaa aactcttcga | 1920 |
| aagatggata ttcgagctgt ggctgtcttc tccgagcctg atcggttcgc tcaacatgtt | 1980 |
| cttgatgctg atgactctgt gtctctggaa ggtaccactg ccgccgagac ttacttgtcc | 2040 |
| atccccaaga ttatcgctgc ttgcaagaag actggagccc aagccattct tcctggctac | 2100 |
| ggtttcctgt ctgagaatgc tgacttctcc gacgcctgtg ccgaggctgg tatcgtattc | 2160 |
| attggcccca ctggtgactc cattcgaaag ctcggtctca gcactctgc acgagagatt | 2220 |
| gctcttgctt ctgacgtgcc tcttgtgccc ggtacaggcc tgatcgagac tgtttccgag | 2280 |
| gcctccgagg ctgccgagaa gctcgagtac cccctgatga tcaagagtac cgctggtgga | 2340 |
| ggtggtattg gtcttcagaa ggtcgacaaa cccgaggatc tcaagcgggc ttttgagacc | 2400 |
| gtcaagcacc aaggtaagtc tttctttgga gacgatggtg tcttcatgga gcgatttgtc | 2460 |
| gagaatgctc gacacgtgga ggttcagatt cttggtgacg gcaagggcaa cgctctcgct | 2520 |
| attggcgagc gagactgttc tcttcagcga cgaaaccaga aggtcgtcga agagactcct | 2580 |
| gcccccaact tccctgctga gactcgaact cgaatgatga aggcgtccga aatgctggca | 2640 |
| aagaacctca actatcgagg tgccggcact gtggagttca ttttcgatga gaagcgaaac | 2700 |
| gagttctact tccttgaggt taacgctcgt ctgcaggtcg agcatcccat cactgagtcc | 2760 |

```
gtcactggac tggatcttgt cgagtggatg attctcattg gagctggcaa ggccccagac   2820
ttcgaggccc agcgtgccaa gaccccccag ggtgcttcta tcgaggcccg tctgtacgcc   2880
gagaaccccg tcaaggactt tgtgccttct cccggtcagc tcaccgacgt gcagttccct   2940
agtgatgctc gagtcgacac ctgggtcagc cgtggaacca agatctcagc agagtacgat   3000
cccactcttg ccaagattat tgttcacggc tctgaccgag ctgacgccct gcgaaagctc   3060
cagagagctc tggacgagac agtggttgcc ggcgtgacca ccaacctgga ctaccttaag   3120
tccattgtcg gatctcagat gtttgccgag gccaaggtgt ccacccgagt actggactct   3180
tacaactaca ctcccaatgc cattgagatc acttcccccg ctcctacac cactattcag   3240 gattaccccg gtcgaaccaa gctgtggcat attggtgttc ctccttctgg acccatggat   3300
gcctacgcct tccgggtggc caaccagatt gtgggcaacc accccaaggc tcctgctatc   3360
gaagctacac ttgtgggccc ctcaattatg ttccacagcg acactgtgat tgccatcacc   3420
ggtggatctg ctgaggccac tcttaatggt gagcccatcg agttctggaa gcctgtgact   3480
gtcaaggctg ccagactctc cgcaactggc cgtctcactt ctggctgcag attgtacatt   3540
gcgattcgaa acgtctgtc tattccagag taccttggtt ctcgatccac cttcgctctc   3600
ggtaaccttg gaggcttcaa cggtcgaact ctcaagtttg gcgatgtcat tttcatgggc   3660
gagcccgagc ttccctcctg ctccattcct gctcccatct ccgagcatgc tcctgcctct   3720
gatgacatga tccccaagta tggcaacgcc tggactgttg gagtcacttg cggccctcac   3780
ggctcgccag acttttttgc tcacggctgg atggatacct tcttcgatgc caagtggaag   3840
atccattaca actccaaccg atttggtgtt cgtctgattg gccccaagcc cgagtgggct   3900
cgaaaggatg gaggagaggc tggtctgcat ccttccaacc agcacgacta tgtctactct   3960
ctgggtgcca tcaatttcac cggtgatgag cctgtcattc tgacctgcga tggtccttct   4020
ctcggtggct ttgtctgtgc tgctgttgtt gtagaggccg agctgtggaa gattggccag   4080
gtcaagcccg agacactgt gcagtttgtg cccatgacta ttgactctgc tcgacagctc   4140
aagaaggccc aggacagaac cattaccaac ctgtgcggtt ccccgtacga gtctgttgat   4200
gctcttctcg ctctggagga ttacgagaac cccatcatct acaccgtccc tgcctctacc   4260
tccactcctc gagtcgtcta ccgacaggct ggagaccgat acattctggt cgagtacggt   4320
gacaacaaca tggacattaa cctgtcctat cgaatccatc ggctcattga ggaagctcag   4380
cagtctatca agggcattgt cgaaatgtct cgaggtgttc gttctgtgct gatcgagttc   4440
catccttctg cctctcgatc cactctcatg caggctttgg tcgactttga gaagcgactt   4500
cagtttgtcg agacctggca ggttccctct cgaattattc gactgccgat gtgctttgag   4560
gactccaaga ccctggacgc tgtcaaacgg taccaggaga ccattcggtc aaaggctccc   4620
tggcttccca caacgtcga cttcattcga gacgtcaaca gttctccga ccgatctcag   4680 gtccgagaca ttgtctacac tgcccgattc ctggttctgg gtcttggaga cgtgttcctt   4740
ggtgctcctt gcgcggtacc tcttgatccc cgacacagac tgcttggaac aaagtacaat   4800
ccctctcgaa cctacactcc caacggcact gtcggaattg gaggaatgta catgtgtatc   4860
tacaccatgg aatctcctgg aggctaccag ttggttggtc gaactatccc catctgggac   4920
aagctgtctc tcggccagga ccgaccttgg ctgctgtcac ccttcgacca gattgagtac   4980
taccccgtcg acgaggagga gctcaaccac attaccaccg aggtgagaa cggtcgatat   5040 gctgtgggaga tggagcagtc cgtctttgat tatggcaagt attctgcctg gctcaaggac   5100
```

```
aactctaagt ccattgaggc tcacattgct tctcaggcag agggtctgga cgacttcgcc    5160
aacctgatca aggtcgccaa cgaggatctg gcctctggaa agactggagc caccaaggag    5220
gagactcctc tgtcggcctc tgccgtccag gtcttctccg aggtcactgg ccgtttctgg    5280
aagggcctgg ttgccgtcgg agatactgtt gacaagggcc agggtatcgt tgtggtggag    5340
gccatgaaga ccgagatggt cgtcaacgcc cctgttgctg aaaggttgt caagttgtac     5400 aacaccaatg agatatggt ggatactgga gattgtgtgg ctgtcatcga gcccattgtt     5460
taa                                                                  5463
```

<210> SEQ ID NO 4
<211> LENGTH: 1374
<212> TYPE: DNA
<213> ORGANISM: Pseudomonas sp.

<400> SEQUENCE: 4

```
atgaagacag tagaaattat tgaaggtatc gcctctggca gaaccagtgc gcgcgacgtg     60
tgcgaagagg cgctcgcaac catcggcgcg accgatggac tcatcaatgc ctttacatgc    120
cgtacggttg aacgagcccg cgcagaggcg gatgccatcg atgttcgacg ggcgcgcggc    180
gaggtacttc cgcctcttgc cggcctcccc tacgcggtaa agaatctgtt cgacatcgaa    240
ggcgtgacga cgcttgccgg ctcgaagatc aaccgtactc tcccgcctgc gcgcgcagac    300
gccgtgctgg tgcaacggct gaaagctgcc ggcgccgtgc tcctgggcgg cctcaatatg    360
gacgagtttg cctatggatt tacgaccgaa aatacgcact atgggccgac ccggaacccg    420
catgacaccg ggcgtatcgc tggtggttcg tcagggggt ctggagcggc aatcgctgcg     480
gggcaggtac cactatcgct cggatcggac accaacggtt ccatacgcgt gccagcatca    540
ttgtgtggcg tgtgggggct gaagcctacc ttcggccgcc tgtcccggcg agggacatac    600
ccgtttgttc acagcattga tcacctcggg ccattggccg atagcgtgga aggcttggcg    660
ttggcctacg atgcaatgca gggcccggat ccgctcgacc ccggatgcag cgcatcgcgc    720 atccaacccct cggtaccggt cctcagtcag ggtatcgctg gctccggat cggcgtgctg    780 ggtggctggt tcgggacaa tgccggcccg ccgcgcgag ccgcggtcga tgttgccgcg      840
cttacgctcg cgccagcga agtcgtcatg tggcccgacg cggagatcgg gcgcgcagcc    900
gccttcgtta tcactgccag cgagggaggc tgtctgcatc tcgatgatct tcgcatccgt    960
ccgcaagact tcgagcctct gtccgtagat cgctttatct cgggggtttt acaaccggtc   1020
gcgtggtact gcgtgcaca gcggtttcga cgtgtctatc gagataaggt gaatgctctt   1080
ttccgtgact gggacatat aatcgctccc gcaacgccaa tagtgctcc cgcaatcggc    1140 accgaatgga tcgaggtaaa cggtacacgc catccgtgcc gccggtcat gggacttctc   1200 actcagccgg tctccttcgc aggctgtccg gtggtcgccg ctccaacgtg gcctggagaa   1260
aacgatggca tgccgatcgg ggtacagctc atcgcggcgc cctggaacga atctctatgc    1320
ctgcgcgcag gcaaggtatt acaagacacc ggtatcgccc gactgaaatg ttaa          1374
```

<210> SEQ ID NO 5
<211> LENGTH: 1092
<212> TYPE: DNA
<213> ORGANISM: Pseudomonas sp.

<400> SEQUENCE: 5

```
atgtatcaca tcgacgtttt ccgaatccct tgccacagcc tggtgatac atcgggtctc     60 gaggatttga ttgaaacagg ccgcgttgcc cccgccgaca tcgtcgcggt aatgggcaag    120
```

```
accgagggca atggctgcgt caacgattac acgcgtgaat acgccaccgc catgcttgct      180
gcgtgccttg ggcgtcattt gcaactccca ccccatgagg tggaaaagcg ggtcgcgttt      240
gtgatgtcag gtgggacgga aggcgtgctg tccccccacc acacggtatt cgcaagacgt      300
ccggcaatcg acgcgcatcg tcccgctggc aaacgtctca cgcttggaat cgccttcacg      360
cgtgattttc tgccggagga aattggccgc cacgctcaga taacggagac agccggcgcc      420
gtcaaacgcg caatgcgaga tgccgggatc gcttcgattg acgatctgca ttttgtgcag      480
gtgaagtgtc cgctgctgac accagcaaag atcgcctcgg cgcgatcacg cggatgcgct      540
ccagtcacga cggatacgta tgaatcgatg ggctattcgc gcggcgcttc ggccctgggc      600
atcgctctcg ctacagaaga ggtgccctcc tcgatgctcg tagacgaatc agtgctgaat      660
gactggagtc tctcatcgtc actggcgtcg gcgtctgcag gcatcgaact ggagcacaac      720
gtggtgatcg ctattggcat gagcgagcag gccaccagtg aactggtcat tgcccacggc      780
gtgatgagcg acgcgatcga gcggcctcg gtgcggcgaa cgattgaatc gctgggcata      840
cgtagcgatg acgagatgga tcgcatcgtc aacgtattcg ccaaagcgga ggcgagcccg      900
gacggggttg tacgaggtat gcggcacacg atgctaagtg actccgacat taattcgacc      960
cgccatgcgc gggcggtcac cggcgcggcc attgcctcgg tagttgggca tggcatggtg     1020
tatgtgtccg gtggcgccga gcatcaggga cctgccggcg gcggcccttt tgcagtcatt     1080
gcccgcgctt aa                                                         1092

<210> SEQ ID NO 6
<211> LENGTH: 1113
<212> TYPE: DNA
<213> ORGANISM: Pseudomonas sp.

<400> SEQUENCE: 6
atgcaagcgc aagttttcg agttccaatg agtaatccag ccgatgttag tggcgtagcc       60
aagctcatcg atgagggagt gatccgtgcc gaagaggtcg tctgcgttct cggcaagacc      120
gaaggcaacg gctgtgtcaa tgacttcacg cgtggctaca ccaccctcgc gttcaaggtc      180
tacttctccg agaaactggg cgtgtcccgg caagaggtcg gcgagcgcat cgctttcatc      240
atgtccggcg gtaccgaagg cgtcatggcg cctcactgca ccatcttcac cgtgcagaag      300
acggacaaca agcagaagac cgccgctgaa ggcaagcgac ttgccgttca gcagatcttt      360
acccgcgagt tcctgccgga ggagatcggc cgcatgccgc aggtcacgga aacagccgac      420
gctgttcgcc gcgccatgcg cgaagccggc atcgcggatg catccgatgt ccacttcgtt      480
caggtcaagt gcccactgct cactgccggc cgcatgcatg acgctgtcga gcgcgggcat      540
acggttgcca ccgaagatac ctatgagtcc atgggctact cccgcggcgc atccgcgctt      600
ggtatcgccc tggccctcgg ggaagtcgag aaggccaacc tcagtgatga agttattacc      660
gcagactaca gtctctactc ctcggttgcc tcaacttcgg cgggtatcga gttgatgaac      720
aacgagatca tcgtcatggg caacagccgc gcatggggtg gtgacctcgt catcggccac      780
gccgagatga aggacgccat cgacggtgca gcggtccggc aggccctgcg cgacgtcggg      840
tgctgcgaga acgacctgcc gaccgtcgac gagctcggcc gcgtggtcaa tgtatttgcc      900
aaggctgaag cctccccgga cggtgaggtt cgtaaccgcc gccacacgat gctggacgat      960
tcggacatta acagcacgcg ccatgcgcga cggtcgtca atgcagttat cgcttcgatc     1020
gtgggagatc ccatggttta tgtctccggc ggctccgagc atcagggccc cgccggtggc     1080
```

```
ggtcccgttg cagttatcgc gcgcacagct taa                     1113
```

<210> SEQ ID NO 7
<211> LENGTH: 1113
<212> TYPE: DNA
<213> ORGANISM: Rhodococcus sp.

<400> SEQUENCE: 7

```
atgcaagcgc aagttttttcg agttccaatg agtaatccag ccgatgttag tggcgtagcc    60
aagctcatcg atgagggagt gatccgtgcc gaagaggtcg tctgcgttct cggcaagacc   120
gaaggcaacg gctgtgtcaa tgacttcacg cgtggctaca ccaccctcgc gttcaaggtc   180
tacttctccg agaaactggg cgtgtcccgg caagaggtcg gcgagcgcat cgctttcatc   240
atgtccggcg gtaccgaagg cgtcatggcg cctcactgca ccatcttcac cgtgcagaag   300
acggacaaca agcagaagac cgccgctgaa ggcaagcgac ttgccgttca gcagatcttt   360
acccgcgagt tcctgccgga ggagatcggc cgcatgccgc aggtcacgga aacagccgac   420
gctgttcgcc gcgccatgcg cgaagccggc atcgcggatg catccgatgt ccacttcgtt   480
caggtcaagt gcccactgct cactgccggc cgcatgcatg acgctgtcga gcgcgggcat   540
acggttgcca ccgaagatac ctatgagtcc atgggctact cccgcggcgc atccgcgctt   600
ggtatcgccc tggccctcgg ggaagtcgag aaggccaacc tcagtgatga agttattacc   660
gcagactaca gtctctactc ctcggttgcc tcaacttcgg cgggtatcga gttgatgaac   720
aacgagatca tcgtcatggg caacagccgc gcatggggtg gtgacctcgt catcggccac   780
gccgagatga aggacgccat cgacggtgca gcggtccggc aggccctgcg cgacgtcggg   840
tgctgcgaga cgacctgcc gaccgtcgac gagctcggcc gcgtggtcaa tgtatttgcc   900
aaggctgaag cctccccgga cggtgaggtt cgtaaccgcc gccacacgat gctggacgat   960
tcggacatta acagcacgcg ccatgcgcga gcggtcgtca atgcagttat cgcttcgatc  1020
gtgggagatc ccatggttta tgtctccggc ggctccgagc atcagggccc cgccggtggc  1080
ggtcccgttg cagttatcgc gcgcacagct taa                                1113
```

<210> SEQ ID NO 8
<211> LENGTH: 1320
<212> TYPE: DNA
<213> ORGANISM: Escherichia coli

<400> SEQUENCE: 8

```
atgatgtcag agaacacac gttaaaagcg gtacgaggca gttttattga tgtcacccgt    60
acgatcgata acccggaaga gattgcctct gcgctgcggt ttattgagga tggtttatta   120
ctcattaaac agggaaaagt ggaatggttt ggcgaatggg aaaacggaaa gcatcaaatt   180
cctgacacca ttcgcgtgcg cgactatcgc ggcaaactga tagtaccggg ctttgtcgat   240
acacatatcc attatccgca agtgaaaatg tgggggcct atggtgagca attgctggag   300
tggttgaata aacacacctt ccctactgaa cgtcgttatg aggatttaga gtacgcccgc   360
gaaatgtcgg cgttcttcat caagcagctt ttacgtaacg gaaccaccac ggcgctggtg   420
tttggcactg ttcatccgca atctgttgat gcgctgtttg aagccgccag tcatatcaat   480
atgcgtatga ttgccggtaa ggtgatgatg accgcaacg caccggatta tctgctcgac   540
actgccgaaa gcagctatca ccaaagcaaa gaactgatcg aacgctggca caaaaatggt   600
cgtctgctat atgcgattac gccacgcttc gccccgacct catctcctga acagatggcg   660
atggcgcaac gcctgaaaga agaatatccg gatacgtggg tacataccca tctctgtgaa   720
```

```
aacaaagatg aaattgcctg ggtgaaatcg ctttatcctg accatgatgg ttatctggat        780
gtttaccatc agtacggcct gaccggtaaa aactgtgtct ttgctcactg cgtccatctc        840
gaagaaaaag agtgggatcg tctcagcgaa accaaatcca gcattgcttt ctgtccgacc        900
tccaaccttt acctcggcag cggcttattc aacttgaaaa agcatggca gaagaaagtt        960 aaagtgggca tgggaacgga tatcggtgcc ggaaccactt caacatgct gcaaacgctg       1020 aacgaagcct acaaagtatt gcaattacaa ggctatcgcc tctcggcata tgaagcgttt       1080
tacctggcca cgctcggcgg agcgaaatct ctgggccttg acgatttgat tggcaacttt       1140
ttacctggca aagaggctga tttcgtggtg atggaaccca ccgccactcc gctacagcag       1200
ctgcgctatg acaactctgt ttctttagtc gacaaattgt tcgtgatgat gacgttgggc       1260
gatgaccgtt cgatctaccg cacctacgtt gatggtcgtc tggtgtacga acgcaactaa       1320
```

<210> SEQ ID NO 9
<211> LENGTH: 1398
<212> TYPE: DNA
<213> ORGANISM: Bradyrhizobium japonicum

<400> SEQUENCE: 9

```
atgaccaccg tcggtattcg cggcacgttc ttcgatttcg tcgacgatcc ctggaagcac         60
atcggcaacg agcaggcggc tgcgcgcttt catcaggacg gcctcatggt cgtcaccgac        120
ggcgtcatca aggcgttcgg tccgtacgag aagatcgccg ccgcgcatcc gggcgttgag        180
atcacccata tcaaggaccg catcatcgtc ccgggcttca tcgacggcca catccatctg        240
cctcagaccc gcgtgctcgg tgcctatggc gagcagctct gccgtggct gcagaagtcg        300 atctatcccg aggagatcaa gtacaaggat cgcaactacg cgcgcgaagg cgtgaagcgt        360
tttctcgatg cactgctcgc cgccggcacc accacctgcc aggccttcac cagctcctca        420
ccggtcgcga ccgaagagct gttcgaggag caagcaggc gcaacatgcg cgtgatcgcg        480
ggtctcaccg ggatcgaccg caacgcgccg gccgaattca tcgatacgcc cgagaatttc        540
tatcgcgaca gcaagcggct gatcgcgcag tatcacgaca agggccgtaa cctctacgct        600
atcacgccgc gcttcgcctt cggcgcctcg cccgagctgc tgaaggcgtg tcagcgcctc        660
aagcacgagc atccggactg ctgggtcaat acccacatct ccgagaaccc ggccgaatgc        720
agcggcgtgc tggtcgagca cccggactgc caggattatc tcggcgtcta cgagaagttc        780
gacctggtcg gcccaaagtt ctccggcggc cacggcgtct atctctcgaa caacgaattc        840
cgccgcatgt ccaagaaagg cgcggcggta gtgttctgcc cgtgctcgaa cctgttcctc        900
ggcagcggcc tgttccgtct cggccgcgcc accgatccgg agcatcgcgt gaagatgtcg        960
ttcggcaccg atgtcggcgg cggcaaccgc ttctcgatga tctccgtgct cgacgacgct       1020
tacaaggtcg gcatgtgcaa caacacgctg ctcgacggca gcatcgatcc gtcgcgcaag       1080
gacctcgcga agccgagcg caacaagctc tcgccctatc gtggcttctg gtcggtcacg       1140
ctcggcggcg ccgaaggcct ctacatcgac gacaagctcg gcaatttcga gcccggcaag       1200
gaggccgatt tcgtcgcgct cgatccgaac ggcggacaac tggcgcaacc ctggcaccag       1260
tcgctgattg ccgacggtgc aggtccgcgc acgttgatg aggccgcgag catgctgttc       1320
gccgtcatga tggtcggcga cgatcgctgc gtcgacgaga cctgggtgat gggcaagcgc       1380
ctctacaaga agagctga                                                    1398
```

<210> SEQ ID NO 10

```
<211> LENGTH: 1470
<212> TYPE: DNA
<213> ORGANISM: Saccharomyces cerevisiae

<400> SEQUENCE: 10
atgacaaaaa gtgatttatt atttgataaa ttcaacgaca acatggaaa gtttctagtt       60 ttttttggta cctttgtaga taccccctaaa ttaggagagc tgagaatcag agagaaaaca    120
tctgttggag ttctcaacgg aatcatcagg tttgtgaaca gaaattcact cgatcctgtc    180
aaagattgtt tagatcacga tagtagctta tcaccagagg atgtcacggt ggttgacata    240
attggaaaag acaagactcg aaataacagc ttttattttc caggttttgt tgacacgcat    300
aaccatgtct cgcaatatcc aaatgtcggc gtatttggga attctaccct gctggattgg    360
ctagagaagt ataccttccc catagaagcc gcactagcaa acgaaaatat tgcgagagaa    420
gtttacaata aggtaataag taagacgctt tctcacggta caacgactgt ggcttactat    480
aataccattg atctcaagtc cactaagctc ttggctcaac taagctcctt attggggcag    540
cgtgttcttg ttggaaaagt gtgcatggat accaatggtc ccgagtatta tattgaagat    600
actaaaactt cctttgaaag cactgtgaaa gttgttaagt acatacggga accatttgt    660 gatcccctcg taaatcctat agtgacacca aggttcgcgc cctcttgttc tagagaacta    720
atgcaacagt tgtccaagct agtcaaggat gaaaacatac acgttcaaac ccacttgtcg    780
gaaaataagg aggagataca gtgggttcaa gatttatttc ccgaatgtga gagctatact    840
gatgtatacg acaaatatgg gctgctcaca gaaaaaacag tattggcaca ttgtattcat    900
ctaacagatg ccgaagcgcg tgtgattaaa cagcgtcgct gtggtatatc tcattgtccc    960
atttccaact cctctctgac ttctggagag tgtagggttc gatggttgct ggaccagggc   1020
ataaaggttg gtctaggcac cgacgtttca gccggtcatt cttgtagcat actcaccacc   1080
ggaaggcagg cctttgcagt ttcaaggcat ttggcaatga gagaaactga tcatgcaaaa   1140
ctttcagtct ccgagtgcct atttcttgct acaatgggcg gagcacaagt cttgcgtatg   1200
gatgagacct tggggacttt tgacgtcggt aagcagtttg acgctcaaat gatcgatacc   1260
aatgctcccg gctcaaacgt ggatatgttt cattggcagc taaaggagaa ggatcaaatg   1320
caagagcaag agcaagagca agggcaagac ccttataaga cccaccgct gcttactaat   1380 gaagacataa tcgcaaaatg gttctttaac ggtgatgatc gcaacaccac taaagtttgg   1440
gtagccggcc agcaagtcta ccagatttag                                     1470

<210> SEQ ID NO 11
<211> LENGTH: 1356
<212> TYPE: DNA
<213> ORGANISM: Yarrowia lipolytica

<400> SEQUENCE: 11
atgactgctt caaacaccac agttttttc ggagccatcg tcaatcccgc cagaagagca       60
cttgaatacc tgccccaagc tgctatcggt gtcagggaag gggaaatcgt cttttttcgac    120 agacatgctg aatcggcttc ggcgtctgct gccaccccaca acattaagaa cttcgacacg    180
gtggacttgt cgaaaaccac ctcgttcctt ttccccggtt tcatcgacac tcacattcat    240
gcgccccagt accccaacag cggtattttc ggcaagacca cactgctaga ctggctgact    300
acctacacct tcccccctgga gtcgtctctc aaggacccca aaatcgccca ggacgtgtac    360
tccagggtag tcaagaagac tctcgccaac ggaactacaa cggctgctta ctacgccact    420
gtccacgtgg agtccacaaa gaaactggct gacatttgtc tgtctcaagg tcagagagca    480
```

-continued

```
cttgtgggaa gagtgtgcat ggaccaaaac actcctgatt actacagaga tgcaagcgtg      540
gaggaggcca agaagagcga ccgggaagtt gttgagtata ttcagtctct taacaaaccc      600
gatcgcatcc tccccatcat cacaccccgt tttgcgccct cttgcactgg tgaaatcatg      660
tcctggcagg gagactatgc ccagaagaac aacctgcaca tccagactca catttctgaa      720
aacaagggcg agattgcctg ggtcaaggag ctgtaccctg cttgcaaatc gtatgcagac      780
acataccacc agcatggact gctgacagaa aagacgcttc tggcccatgc catctatctg      840
accgacgaag aactcaacct ggtggagcag caaaagtgtg actttcccca ttgccccatt      900
tccaactcgt cgctgacatc aggcgagttc atgctcgaa aaattctcga caggaacatt       960 cccttttggtc tgggaaccga tgtttctgga ggttacgctc cttccattct cagcacagcc   1020
agacacggtc ttctggtgtc tcgtcacgtg gccatgaagt ccgaaaacga cgccgacaag    1080
ctgtctgtgg atgaggtact gtacttggcc actctgggtg gcgccgaggc tctcaaactg    1140
gactcaaaga ttggttcttt cgaggtgggc aagaagttcg acgccagca gattgatctc     1200 gagactaacg gttctcctgt tgacattttt gactgggaat tgcctatttc cgagggaaac    1260
aagctcgaga acctggtgca caagtggttg tttaatggag acgaccgaaa cacttctact    1320
gtctgggtca acggagacaa ggtggtgacc aagtag                               1356
```

<210> SEQ ID NO 12
<211> LENGTH: 1437
<212> TYPE: DNA
<213> ORGANISM: Williamsia sp.

<400> SEQUENCE: 12

```
atgaccagaa tcgcaatcac cggcggacga gtcctgacca tggacccga gcgccgcgtg       60 ctcgaaccag gaacggttgt ggtcgaggac cagttcatcg cacaagtggg atccccggac     120
gacgtcgaca tccgcggcgc cgaaatcatc gacgccaccg ggatggcagt gctccccggc     180
ttcgtcaaca cccacaccca cgtcccacaa atcctcctca ggggtggtgc atcccatgac    240
cgcaacctcc tcgaatggct gcacaacgtg ctctatcccg gcctcgctgc ctacacagac    300
gacgacatcc gagtcggaac actgctgtac tgcgccgaag cccttcgttc tggcatcacc    360
actgtcgtcg acaacgagga cgtccgaccc aacgacttcg cccgcgccgg ggccgccggg    420
atcggcgcct tcaccgacgc aggaatccga gccatttacg cgcgcatgta cttcgacgcg    480
ccacgcgccg aactcgaaga actcgtcgcc accatccacg ccaaggcccc cggcgccgtg    540
cgcatggacg aatcagccag caccgaccac gtactggcag acctagacca actcatcacc    600
cgccacgacc gcacagcaga tggccgcatc agggtgtggc ccgcacccgc catcccccttc   660 atggtcagtg aaaaaggaat gaaggcagcg caagagatcg cagcgagccg caccgacggc    720
tggaccatgc acgtcagcga ggatcccatc gaggcccgag tgcactccat gaacgcccg     780 gaatatttac accacctcgg ctgcctcgac accgactcc ttgccgcgca ctgcgtgcat     840
atcgacagcc gagacatccg cctgttccgc cagcacgacg taaaaatttc tacccaacca    900
gtatcgaaca gctacctggc ggccggaatt gcaccggtcc ccgaaatgct cgcccacggc    960
gtgaccgtgg gcatcggtac cgacgacgcc aactgcaacg cagcgtgaa cctcatctcg    1020 gacatgaaag tgctagcgct cattcaccga gctgcacatc gagatgcctc aatcatcaca    1080
cctgaaaaaa tcatcgaaat ggccaccatc gacggagccc gctgcatcgg tatggccgat    1140
cagattggtt ccctcgaggc gggtaaacgc gccgacatca tcaccctcga ccttcgtcac    1200
```

```
gcccaaacaa ccccagcgca cgacttggcg gccaccatcg tctttcaggc ctacggcaac    1260
gaggtcaacg acgtcctcgt caatggctcg gtagtgatgc gcgatcgagt actttctttt    1320
ctgccgactc cccaagaaga aaaagcgctc tacgacgatg cgtcggagcg atcggctgca    1380
atgctcgcac gggccggcct caccggcaca cgcacatggc aaacactggg atcgtag       1437

<210> SEQ ID NO 13
<211> LENGTH: 1425
<212> TYPE: DNA
<213> ORGANISM: Pseudomonas sp.

<400> SEQUENCE: 13
atgcaaacgc tcagcatcca gcacggtacc ctcgtcacga tggatcagta ccgcagagtc      60
cttggggata gctgggttca cgtgcaggat ggacggatcg tcgcgctcgg agtgcacgcc     120
gagtcggtgc ctccgccagc ggatcgggtg atcgatgcac gcgcaaggt cgtgttaccc      180 ggtttcatca tgcccacac ccatgtgaac cagatcctcc tgcgcggagg gccctcgcac      240
gggcgtcaac tctatgactg ctgttcaac gttttgtatc cggacaaaa ggcgatgaga       300 ccggaggacg tagcggtggc ggtgaggttg tattgtgcgg aagctgtgcg cagcgggatt     360
acgacgatca acgacaacgc cgattcggcc atctacccag caacatcga ggccgcgatg      420 gcggtctatg gtgaggtggg tgtgagggtc gtctacgccc gcatgttctt tgatcggatg     480
gacgggcgca ttcaagggta tgtggacgcc ttgaaggctc gctctcccca gtcgaactg      540 tgctcgatca tggaggaaac ggctgtggcc aaagatcgga tcacagccct gtcagatcag     600
tatcatggca cggcaggagg tcgtatatca gtttggcccg ctcctgccat taccccggcg    660
gtgacagttg aaggaatgcg atgggcacaa gccttcgccc gtgatcgggc ggtaatgtgg     720
acgcttcaca tggcggagag cgatcatgat gagcggcttc attggatgag tcccgccgag    780
tacatggagt gttacggact cttggatgag cgtctgcagg tcgcgcattg cgtgtacttt    840
gaccggaagt atgttcggct gctgcaccgc acaatgtga aggtcgcgtc gcaggttgtg      900
agcaatgcct acctcggctc aggggtggcc ccgtgccag agatggtgga gcgcggcatg     960
gccgtgggca ttgaacaga tgacgggaat tgtaatgact ccgtaaacat gatcggagac      1020
atgaagttta tggcccatat tcaccgcgcg gtgcatcggg atgcggacgt gctgacccca    1080
gagaagattc ttgaaatggc gacgatcgat ggggcgcgtt cgttgggaat ggaccacgag    1140
attggttcca tcgaaaccgg caagcgcgcg gaccttatcc tgcttgacct gcgtcaccct    1200
cagacgactc ctcaccatca tttgcggcc acgatcgtgt tcaggctta cggcaatgag     1260 gtggacactg tcctgattga cggaaacgtt gtgatggaga accgccgctt gagctttctt    1320 cccctgaac gtgagttggc gttccttgag gaagcgcaga gccgcgccac agctattttg    1380
cagcgggcga acatggtggc taacccagct tggcgcagcc tctag                     1425

<210> SEQ ID NO 14
<211> LENGTH: 1212
<212> TYPE: DNA
<213> ORGANISM: Pseudomonas sp.

<400> SEQUENCE: 14
atgagtaaag attttgattt aatcattaga aacgcctatc taagtgaaaa agacagtgta     60
tatgatattg ggattgttgg tgacagaata atcaaaatag aagctaaaat tgaaggaacc    120
gtaaaagacg aaattgatgc aaagggtaac cttgtgtctc ccggatttgt cgatgcacat    180
acccatatgg ataagtcatt tacgagcaca ggtgaaagat taccgaagtt ttggagcaga    240
```

```
ccttatacaa gggatgctgc catcgaggat ggcttgaaat attataaaaa tgctacccac      300
gaagaaataa aaagacatgt gatagaacat gctcacatgc aggtactcca tgggacttta      360
tacacccgga cccatgtaga tgtagattca gttgctaaaa caaaagcagt ggaagcagtt      420
ttagaagcca aggaagagtt aaaggatctt atcgatatac aagtcgtagc ctttgcacag      480
agtggatttt tcgttgattt ggaatctgaa tcattgatta gaaaatcctt ggatatgggc      540
tgtgatttag ttgggggagt tgatcctgct acgcgggaaa ataatgttga gggttcttta      600
gacctatgct ttaaattagc aaaggaatac gatgttgata tcgactatca catacatgat      660
attggaactg ttggagtata ttcgataaat cgtcttgccc aaaagacaat tgaaaatggg      720
tataagggta gagtaactac gagtcatgcc tggtgttttg cagatgctcc gtccgaatgg      780
ctcgatgagg caatcccatt gtacaaggat tcgggtatga aatttgttac ctgttttagt      840
agtacaccgc tactatgcc ggtgataaag ctgcttgaag ctggcatcaa tcttggctgt      900
gcttcggaca atatcagaga ttttttgggtt ccctttggca acggtgatat ggtacaaggg      960
gctctgatcg aaactcagag attagagtta aagacaaaca gagatttggg actaatttgg      1020
aaaatgataa cgtcagaggg tgctagagtt ttaggaattg aaaagaacta tgggatagaa      1080
gttggtaaaa aggccgatct tgttgtatta aattcgttgt caccacaatg gcaataatc      1140 gaccaagcaa aaagactatg cgtaattaaa aatggacgta tcattgtgaa ggatgaggtt      1200
atagttgcct aa                                                         1212

<210> SEQ ID NO 15
<211> LENGTH: 735
<212> TYPE: DNA
<213> ORGANISM: Myrothecium verrucaria

<400> SEQUENCE: 15
atgtcttctt cagaagtcaa agccaacgga tggactgccg ttccagtcag cgcaaaggcc       60
attgttgact ccctgggaaa gcttggtgat gtctcctcat attctgtgga agatatcgcg      120
ttccctgcgg cagacaaact tgttgccgag gcacaggcct tgtgaaggc ccgattgagt      180 cccgaaacct acaatcactc catgcgcgtt ttctactggg gaaccgtcat cgcgagacgt      240
ttacttcccg agcaagctaa agacttgtct ccaagtacat gggcactgac atgtcttctg      300
catgacgttg gtactgcgga ggcatacttt acatctacac gaatgtcctt cgatatttac      360
ggtggcatta aggctatgga ggtgctcaag gtccttggga gtagcaccga ccaggctgag      420
gctgttgccg aggccatcat tcgtcatgag gatgtggggg tagatggcaa catcacattc      480
ctcggtcagt tgatccagct ggctacgctt tatgacaatg tcggggccta cgatgggatt      540
gatgattttg gtagctgggt tgatgacacc acacgcaaca gtatcaacac ggcattccca      600
cgacatggtt ggtgttcttg gtttgcctgc acggttcgta aggaagaaag taacaagcct      660
tggtgccaca caacgcatat ccctcagttc gataaacaga tggaagcgaa cacttttgatg      720 aagccttggg agtaa                                                       735

<210> SEQ ID NO 16
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
```

```
ttatcgatga taagctgtca aagatgagaa ttaattccac ggactataga ctatactaga    60
tactccgtct actgtacgat acacttccgc tcaggtcctt gtcctttaac gaggccttac   120
cactcttttg ttactctatt gatccagctc agcaaaggca gtgtgatcta agattctatc   180
ttcgcgatgt agtaaaacta gctagaccga gaaagagact agaaatgcaa aaggcacttc   240
tacaatggct gccatcatta ttatccgatg tgacgctgca gcttctcaat gatattcgaa   300
tacgctttga ggagatacag cctaatatcc gacaaactgt tttacagatt tacgatcgta   360
cttgttaccc atcattgaat tttgaacatc cgaacctggg agttttccct gaaacagata   420
gtatatttga acctgtataa taatatatag tctagcgctt tacggaagac aatgtatgta   480
tttcggttcc tggagaaact attgcatcta ttgcataggt aatcttgcac gtcgcatccc   540
cggttcattt tctgcgtttc catcttgcac ttcaatagca tatctttgtt aacgaagcat   600
ctgtgcttca ttttgtagaa caaaaatgca acgcgagagc gctaattttt caaacaaaga   660
atctgagctg catttttaca gaacagaaat gcaacgcgaa agcgctattt taccaacgaa   720
gaatctgtgc ttcatttttg taaaacaaaa atgcaacgcg acgagagcgc taattttttca   780
aacaaagaat ctgagctgca tttttacaga acagaaatgc aacgcgagag cgctatttta   840
ccaacaaaga atctatactt cttttttgtt ctacaaaaat gcatcccgag agcgctattt   900
ttctaacaaa gcatcttaga ttactttttt tctcctttgt gcgctctata atgcagtctc   960
ttgataactt tttgcactgt aggtccgtta aggttagaag aaggctactt ggtgtctat   1020
tttctcttcc ataaaaaaag cctgactcca cttcccgcgt ttactgatta ctagcgaagc  1080
tgcgggtgca tttttttcaag ataaaggcat ccccgattat attctatacc gatgtggatt  1140
gcgcatactt tgtgaacaga aagtgatagc gttgatgatt cttcattggt cagaaaatta  1200
tgaacggttt cttctatttt gtctctatat actacgtata ggaaatgttt acattttcgt  1260
attgttttcg attcactcta tgaatagttc ttactacaat ttttttgtct aaagagtaat  1320
actagagata aacataaaaa atgtagaggt cgagtttaga tgcaagttca aggagcgaaa  1380
ggtggatggg taggttatat agggatatag cacagagata tatagcaaag agatactttt  1440
gagcaatgtt tgtggaagcg gtattcgcaa tttaattaag tttaaacggc gcgcctttcc  1500
ataggctccg ccccctgac gagcatcaca aaaatcgacg ctcaagtcag aggtggcgaa  1560
acccgacagg actataaaga taccaggcgt ttccccctgg aagctccctc gtgcgctctc  1620
ctgttccgac cctgccgctt accggatacc tgtccgcctt ctcccttcg ggaagcgtgg   1680
cgctttctca tagctcacgc tgtaggtatc tcagttcggt gtaggtcgtt cgctccaagc  1740
tgggctgtgt gcacgaaccc cccgttcagc ccgaccgctg cgccttatcc ggtaactatc  1800
gtcttgagtc caacccggta agacacgact tatcgccact ggcagcagcc actggtaaca  1860
ggattagcag agcgaggtat gtaggcggtg ctacagagtt cttgaagtgg tggcctaact  1920
acggctacac tagaagaaca gtatttggta tctgcgctct gctgaagcca gttaccttcg  1980
gaaaaagagt tggtagctct tgatccggca acaaaccac cgctggtagc ggtggttttt   2040
ttgtttgcaa gcagcagatt acgcgcagaa aaaaaggatc tcaagaagat cctttgatct  2100
tttctacggg gtctgacgct cagtggaacg aaaactcacg ttaagggatt ttggtcatga  2160
gattatcaaa aaggatcttc acctagatcc ttttaaatta aaaatgaagt tttaaatcaa  2220
tctaaagtat atatgagtaa acttggtctg acagttacca atgcttaatc agtgaggcac  2280
ctatctcagc gatctgtcta tttcgttcat ccatagttgc ctgactcccc gtcgtgtaga  2340
```

```
taactacgat acgggagggc ttaccatctg gccccagtgc tgcaatgata ccgcgagacc    2400
cacgctcacc ggctccagat ttatcagcaa taaaccagcc agccggaagg gccgagcgca    2460
gaagtggtcc tgcaacttta tccgcctcca tccagtctat taattgttgc cgggaagcta    2520
gagtaagtag ttcgccagtt aatagtttgc gcaacgttgt tgccattgct acaggcatcg    2580
tggtgtcacg ctcgtcgttt ggtatggctt cattcagctc cggttcccaa cgatcaaggc    2640
gagttacatg atcccccatg ttgtgcaaaa aagcggttag ctccttcggt cctccgatcg    2700
ttgtcagaag taagttggcc gcagtgttat cactcatggt tatggcagca ctgcataatt    2760
ctcttactgt catgccatcc gtaagatgct tttctgtgac tggtgagtac tcaaccaagt    2820
cattctgaga atagtgtatg cggcgaccga gttgctcttg cccggcgtca atacgggata    2880
ataccgcgcc acatagcaga actttaaaag tgctcatcat tggaaaacgt tcttcggggc    2940
gaaaactctc aaggatctta ccgctgttga tccagttcga tgtaaccc actcgtgcac    3000 ccaactgatc ttcagcatct tttactttca ccagcgtttc tgggtgagca aaaacaggaa    3060
ggcaaaatgc cgcaaaaaag gaataagggc gacacggaa atgttgaata ctcatactct    3120
tcctttttca atattattga agcatttatc agggttattg tctcatgagc ggatacatat    3180
ttgaatgtat ttagaaaaat aaacagcgat cgcgcggccg cgggtaataa ctgatataat    3240
taaattgaag ctctaatttg tgagtttagt atacatgcat ttacttataa tacagttttt    3300
tagttttgct ggccgcatct tctcaaatat gcttcccagc ctgcttttct gtaacgttca    3360
ccctctacct tagcatccct tccctttgca aatagtcctc ttccaacaat aataatgtca    3420
gatcctgtag agaccacatc atccacggtt ctatactgtt gacccaatgc gtctcccttg    3480
tcatctaaac ccacaccggg tgtcataatc aaccaatcgt aaccttcatc tcttccaccc    3540
atgtctcttt gagcaataaa gccgataaca aaatctttgt cgctcttcgc aatgtcaaca    3600
gtacccttag tatattctcc agtagctagg gagcccttgc atgacaattc tgctaacatc    3660
aaaaggcctc taggttcctt tgttacttct tccgccgcct gcttcaaacc gctaacaata    3720
cctgggccca ccacaccgtg tgcattcgta atgtctgccc attctgctat tctgtataca    3780
cccgcagagt actgcaattt gactgtatta ccaatgtcag caattttct gtcttcgaag    3840 agtaaaaaat tgtacttggc ggataatgcc tttagcggct taactgtgcc ctccatggaa    3900
aaatcagtca agatatccac atgtgttttt agtaaacaaa ttttgggacc taatgcttca    3960
actaactcca gtaattcctt ggtggtacga acatccaatg aagcacacaa gtttgtttgc    4020
ttttcgtgca tgatattaaa tagcttggca gcaacaggac taggatgagt agcagcacgt    4080
tccttatatg tagctttcga catgatttat cttcgtttcc tgcaggtttt tgttctgtgc    4140
agttgggtta agaatactgg gcaatttcat gtttcttcaa caccacatat gcgtatatat    4200
accaatctaa gtctgtgctc cttccttcgt tcttccttct gctcggagat taccgaatca    4260
aagctagc                                                            4268
```

<210> SEQ ID NO 17
<211> LENGTH: 6706
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gatactttg agcaatgttt gtggaagcgg tattcgcaat tataaacggt attttcacaa      60
```

```
ttgcaccoca gccagaccga tagccggtcg caatccgcca cccacaaccg tctacctccc      120
acagaacccc gtcacttcca cccttttcca ccagatcata tgtcccaact tgccaaatta      180
aaaccgtgcg aattttcaaa ataaactttg gcaaagaggc tgcaaaggag gggctggtga      240
gggcgtctgg aagtcgacca gagaccgggt tggcggcgca tttgtgtccc aaaaaacagc      300
cccaattgcc ccaattgacc ccaaattgac ccagtagcgg gcccaacccc ggcgagagcc      360
cccttctccc cacatatcaa acctccccg gttcccacac ttgccgttaa gggcgtaggg       420
tactgcagtc tggaatctac gcttgttcag actttgtact agtttctttg tctggccatc      480
cgggtaaccc atgccggacg caaaatagac tactgaaaat ttttttgctt tgtggttggg      540
actttagcca agggtataaa agaccaccgt ccccgaatta cctttcctct tcttttctct      600
ctctccttgt caactcacac ccgaaatcgt taagcatttc cttctgagta taagaatcat      660
tcaaaatgac tagaatcgct atcacaggtg gtagagtttt gactatggac ccagaaagaa      720
gagtattaga accaggtaca gttgttgttg aagatcaatt cattgcacaa gtcggttcac      780
cagatgacgt agacatcaga ggtgctgaaa ttatagatgc cactggtatg gctgtattac      840
caggtttcgt taatacacat acccacgttc ctcaaatttt gttaagaggt ggtgcttcac      900
atgatagaaa tttgttggaa tggttgcaca acgtcttata tccaggtttg gctgcataca      960
ctgatgacga tatcagagtt ggtacattgt tatattgtgc tgaagcattg agatccggta     1020
ttactacagt tgtcgacaat gaagatgtta gacctaacga ttttgccaga gctggtgccg     1080
ctggtattgg tgcattcact gatgccggta tcagagcaat ctatgccaga atgtactttg     1140
atgctccaag agcagaattg gaagaattag tcgcaacaat acatgcaaaa gccccctggtg    1200 ccgtaagaat ggacgaatct gcttcaaccg atcatgtttt ggcagactta gatcaattga     1260
ttaccagaca tgcagaact gctgatggta gaattagagt atggccagct cctgcaatac      1320
cattcatggt ttctgaaaag ggtatgaagg cagcccaaga aatagctgca tccagaactg     1380
acggttggac aatgcatgtt agtgaagatc caatcgaagc cagagtccac tctatgaatg     1440
ctcctgaata tttgcatcac ttgggttgtt tagacgatag attgttagcc gctcattgcg     1500
ttcacataga ctcaagagat atcagattgt ttagacaaca tgatgttaag atatccacac     1560
aacctgtctc caatagttac ttagcagccg gtatagcacc agttcctgaa atgttggctc     1620
atggtgtcac agtaggtatt ggtaccgacg atgctaattg taacgactcc gtaaacttaa     1680
tcagtgatat gaaggttttg gcattgatac atagagctgc acacagagat gctagtatca     1740
ttaccccaga aaagataatc gaaatggcca ctattgacgg tgctagatgc attggtatgg     1800
ctgatcaaat cggttctttg gaagctggta aaagagcaga cataatcact ttggatttga     1860
gacatgcaca aaccactcct gcccacgatt tggccgctac aattgtctttt caagcttatg     1920 gtaatgaagt aaacgatgtt ttggtcaacg gttctgtagt tatgagagat agagtttgt      1980 cattcttacc aacccctcaa gaagaaaagg ctttatacga cgatgcatct gaaagatcag     2040
cagccatgtt agccagagct ggtttgactg gtacaagaac ctggcaaact ttgggttctt     2100
aagctgcttg tacctagtgc aaccccagtt tgttaaaaat tagtagtcaa aaacttctga    2160
gttagaaatt tgtgagtgta gtgagattgt agagtatcat gtgtgtccgt aagtgaagtg    2220
ttattgactc ttagttagtt tatctagtac tcgtttagtt gacactgatc tagtatttta    2280
cgaggcgtat gacttagcc aagtgttgta cttagtcttc tctccaaaca tgagagggct     2340
ctgtcactca gtcggcctat gggtgagatg gcttggtgag atctttcgat agtctcgtca    2400
agatggtagg atgatggggg aatacattac tgctctcgtc aaggaaacca caatcagatc    2460
```

```
acaccatcct ccatggtatc cgatgactct cttctccaca gttttccata ggctccgccc    2520
ccctgacgag catcacaaaa atcgacgctc aagtcagagg tggcgaaacc cgacaggact    2580
ataaagatac caggcgtttc ccctggaag ctccctcgtg cgctctcctg ttccgaccct     2640
gccgcttacc ggatacctgt ccgcctttct cccttcggga agcgtggcgc tttctcatag    2700
ctcacgctgt aggtatctca gttcggtgta ggtcgttcgc tccaagctgg gctgtgtgca    2760 cgaaccccc gttcagcccg accgctgcgc cttatccggt aactatcgtc ttgagtccaa     2820
cccggtaaga cacgacttat cgccactggc agcagccact ggtaacagga ttagcagagc    2880
gaggtatgta ggcggtgcta cagagttctt gaagtggtgg cctaactacg gctacactag    2940
aagaacagta tttggtatct gcgctctgct gaagccagtt accttcggaa aaagagttgg    3000
tagctcttga tccggcaaac aaaccaccgc tggtagcggt ggttttttg tttgcaagca     3060 gcagattacg cgcagaaaaa aaggatctca agaagatcct ttgatctttt ctacggggtc    3120
tgacgctcag tggaacgaaa actcacgtta agggattttg gtcatgagat tatcaaaaag    3180
gatcttcacc tagatccttt taaattaaaa atgaagtttt aaatcaatct aaagtatata    3240
tgagtaaact tggtctgaca gttaccaatg cttaatcagt gaggcaccta tctcagcgat    3300
ctgtctattt cgttcatcca tagttgcctg actccccgtc gtgtagataa ctacgatacg    3360
ggagggctta ccatctggcc ccagtgctgc aatgataccg cgagacccac gctcaccggc    3420
tccagattta tcagcaataa accagccagc cggaagggcc gagcgcagaa gtggtcctgc    3480
aactttatcc gcctccatcc agtctattaa ttgttgccgg gaagctagag taagtagttc    3540
gccagttaat agtttgcgca acgttgttgc cattgctaca ggcatcgtgg tgtcacgctc    3600
gtcgtttggt atggcttcat tcagctccgg ttcccaacga tcaaggcgag ttacatgatc    3660
ccccatgttg tgcaaaaaag cggttagctc cttcggtcct ccgatcgttg tcagaagtaa    3720
gttggccgca gtgttatcac tcatggttat ggcagcactg cataattctc ttactgtcat    3780
gccatccgta agatgctttt ctgtgactgg tgagtactca accaagtcat tctgagaata    3840
gtgtatgcgg cgaccgagtt gctcttgccc ggcgtcaata cgggataata ccgcgccaca    3900
tagcagaact ttaaaagtgc tcatcattgg aaaacgttct cggggcgaaa actctcaag    3960 gatcttaccg ctgttgagat ccagttcgat gtaacccact cgtgcaccca actgatcttc    4020
agcatctttt actttcacca gcgtttctgg gtgagcaaaa acaggaaggc aaaatgccgc    4080
aaaaaaggga ataagggcga cacggaaatg ttgaatactc atactcttcc ttttcaata    4140 ttattgaagc atttatcagg gttattgtct catgagcgga tacatatttg aatgtatta    4200 gaaaaataaa cagcgatcgc gcggccgcgg gtaataactg atataattaa attgaagctc    4260
taatttgtga gtttagtata catgcattta cttataatac agttttttag ttttgctggc    4320
cgcatcttct caaatatgct tcccagcctg cttttctgta acgttcaccc tctaccttag    4380
catcccttcc ctttgcaaat agtcctcttc aacaataat aatgtcagat cctgtagaga    4440
ccacatcatc cacggttcta tactgttgac ccaatgcgtc tcccttgtca tctaaaccca    4500
caccgggtgt cataatcaac caatcgtaac cttcatctct tccacccatg tctctttgag    4560
caataaagcc gataacaaaa tctttgtcgc tcttcgcaat gtcaacagta cccttagtat    4620
attctccagt agctagggag cccttgcatg acaattctgc taacatcaaa aggcctctag    4680 gttccttgt tacttcttcc gccgcctgct tcaaaccgct aacaataacct gggcccacca    4740 caccgtgtgc attcgtaatg tctgcccatt ctgctattct gtatacacccc gcagagtact    4800
```

```
gcaatttgac tgtattacca atgtcagcaa atttctgtc ttcgaagagt aaaaaattgt    4860
acttggcgga taatgccttt agcggcttaa ctgtgccctc catggaaaaa tcagtcaaga    4920
tatccacatg tgtttttagt aaacaaattt tgggacctaa tgcttcaact aactccagta    4980
attccttggt ggtacgaaca tccaatgaag cacacaagtt tgtttgcttt tcgtgcatga    5040
tattaaatag cttggcagca acaggactag gatgagtagc agcacgttcc ttatatgtag    5100
ctttcgacat gatttatctt cgtttcctgc aggttttgt tctgtgcagt tgggttaaga    5160
atactgggca atttcatgtt tcttcaacac cacatatgcg tatatatacc aatctaagtc    5220
tgtgctcctt ccttcgttct tccttctgct cggagattac cgaatcaaag ctagcttatc    5280
gatgataagc tgtcaaagat gagaattaat tccacggact atagactata ctagatactc    5340
cgtctactgt acgatacact tccgctcagg tccttgtcct ttaacgaggc cttaccactc    5400
ttttgttact ctattgatcc agctcagcaa aggcagtgtg atctaagatt ctatcttcgc    5460
gatgtagtaa aactagctag accgagaaag agactagaaa tgcaaaaggc acttctacaa    5520
tggctgccat cattattatc cgatgtgacg ctgcagcttc tcaatgatat tcgaatacgc    5580
tttgaggaga tacagcctaa tatccgacaa actgttttac agatttacga tcgtacttgt    5640
tacccatcat tgaattttga acatccgaac ctgggagttt tccctgaaac agatagtata    5700
tttgaacctg tataataata tatagtctag cgctttacgg aagacaatgt atgtatttcg    5760
gttcctggag aaactattgc atctattgca taggtaatct tgcacgtcgc atccccggtt    5820
cattttctgc gtttccatct tgcacttcaa tagcatatct ttgttaacga agcatctgtg    5880 cttcatttg tagaacaaaa atgcaacgcg agagcgctaa tttttcaaac aaagaatctg    5940
agctgcattt ttacagaaca gaaatgcaac gcgaaagcgc tattttacca acgaagaatc    6000
tgtgcttcat ttttgtaaaa caaaaatgca acgcgacgag agcgctaatt tttcaaacaa    6060
agaatctgag ctgcattttt acagaacaga aatgcaacgc gagagcgcta ttttaccaac    6120
aaagaatcta tacttctttt tgttctaca aaaatgcatc ccgagagcgc tatttttcta    6180
acaaagcatc ttagattact tttttctcc tttgtgcgct ctataatgca gtctcttgat    6240 aacttttgc actgtaggtc cgttaaggtt agaagaaggc tactttggtg tctatttct    6300 cttccataaa aaagcctga ctccacttcc cgcgtttact gattactagc gaagctgcgg    6360
gtgcattttt tcaagataaa ggcatccccg attatattct ataccgatgt ggattgcgca    6420
tactttgtga acagaaagtg atagcgttga tgattcttca ttggtcagaa aattatgaac    6480
ggtttcttct attttgtctc tatatactac gtataggaaa tgtttacatt ttcgtattgt    6540
tttcgattca ctctatgaat agttcttact acaattttt tgtctaaaga gtaatactag    6600
agataaacat aaaaaatgta gaggtcgagt ttagatgcaa gttcaaggag cgaaaggtgg    6660
atgggtaggt tatataggga tatagcacag agatatatag caaaga                   6706
```

<210> SEQ ID NO 18
<211> LENGTH: 8336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gtttgtggaa gcggtattcg caatttaatt aaagctggtg acaattaatc atcggctcgt      60
ataatgtgtg gaattgaatc gatataagga ggttaatcat atgactagaa tcgctatcac     120
```

```
aggtggtaga gttttgacta tggacccaga aagaagagta ttagaaccag gtacagttgt      180
tgttgaagat caattcattg cacaagtcgg ttcaccagat gacgtagaca tcagaggtgc      240
tgaaattata gatgccactg gtatggctgt attaccaggt ttcgttaata cacataccca      300
cgttcctcaa attttgttaa gaggtggtgc ttcacatgat agaaatttgt tggaatggtt      360
gcacaacgtc ttatatccag gtttggctgc atacactgat gacgatatca gagttggtac      420
attgttatat tgtgctgaag cattgagatc cggtattact acagttgtcg acaatgaaga      480
tgttagacct aacgattttg ccagagctgg tgccgctggt attggtgcat tcactgatgc      540
cggtatcaga gcaatctatg ccagaatgta ctttgatgct ccaagagcag aattggaaga      600
attagtcgca acaatacatg caaaagcccc tggtgccgta agaatggacg aatctgcttc      660
aaccgatcat gttttggcag acttagatca attgattacc agacatgaca gaactgctga      720
tggtagaatt agagtatggc cagctcctgc aataccattc atggtttctg aaaagggtat      780
gaaggcagcc caagaaatag ctgcatccag aactgacggt tggacaatgc atgttagtga      840
agatccaatc gaagccagag tccactctat gaatgctcct gaatatttgc atcacttggg      900
ttgtttagac gatagattgt tagccgctca ttgcgttcac atagactcaa gagatatcag      960
attgtttaga caacatgatg ttaagatatc cacacaacct gtctccaata gttacttagc     1020
agccggtata gcaccagttc ctgaaatgtt ggctcatggt gtcacagtag gtattggtac     1080
cgacgatgct aattgtaacg actccgtaaa cttaatcagt gatatgaagg ttttggcatt     1140
gatacataga gctgcacaca gagatgctag tatcattacc ccagaaaaga taatcgaaat     1200
ggccactatt gacggtgcta gatgcattgg tatggctgat caaatcggtt ctttggaagc     1260
tggtaaaaga gcagacataa tcactttgga tttgagacat gcacaaacca ctcctgccca     1320
cgatttggcc gctacaattg tctttcaagc ttatggtaat gaagtaaacg atgttttggt     1380
caacggttct gtagttatga gagatagagt tttgtcattc ttaccaaccc ctcaagaaga     1440
aaaggcttta tacgacgatg catctgaaag atcagcagcc atgttagcca gagctggttt     1500
gactggtaca agaacctggc aaactttggg ttcttaagga aatccattat gatgtcagga     1560
gaacacacgt taaaagcggt acgaggcagt tttattgatg tcacccgtac gatcgataac     1620
ccggaagaga ttgcctctgc gctgcggttt attgaggatg gtttattact cattaaacag     1680
ggaaaagtgg aatggtttgg cgaatgggaa acggaaagc atcaaattcc tgacaccatt      1740
cgcgtgcgcg actatcgcgg caaactgata gtaccgggct ttgtcgatac acatatccat     1800
tatccgcaaa gtgaaatggt gggggcctat ggtgagcaat tgctggagtg gttgaataaa     1860
cacaccttcc ctactgaacg tcgttatgag gatttagagt acgcccgcga aatgtcggcg     1920
ttcttcatca gcagcttttt acgtaacgga accaccacgg cgctggtgtt tggcactgtt     1980
catccgcaat ctgttgatgc gctgtttgaa gccgccagtc atatcaatat gcgtatgatt     2040
gccggtaagg tgatgatgga ccgcaacgca ccggattatc tgctcgacac tgccgaaagc     2100
agctatcacc aaagcaaaga actgatcgaa cgctggcaca aaaatggtcg tctgctatat     2160
gcgattacgc cacgcttcgc cccgacctca tctcctgaac agatggcgat ggcgcaacgc     2220
ctgaaagaag aatatccgga tacgtgggta catacccatc tctgtgaaaa caaagatgaa     2280
attgcctggg tgaaatcgct ttatcctgac catgatggtt atctggatgt ttaccatcag     2340
tacggcctga ccgtaaaaa ctgtgtcttt gctcactgcg tccatctcga agaaaaagag      2400
tgggatcgtc tcagcgaaac caaatccagc attgctttct gtccgacctc caacctttac     2460
ctcggcagcg gcttattcaa cttgaaaaaa gcatggcaga agaaagttaa agtgggcatg     2520
```

```
ggaacggata tcggtgccgg aaccactttc aacatgctgc aaacgctgaa cgaagcctac    2580
aaagtattgc aattacaagg ctatcgcctc tcggcatatg aagcgtttta cctggccacg    2640
ctcggcggag cgaaatctct gggccttgac gatttgattg caactttttt acctggcaaa    2700
gaggctgatt tcgtggtgat ggaacccacc gccactccgc tacagcagct gcgctatgac    2760
aactctgttt ctttagtcga caaattgttc gtgatgatga cgttgggcga tgaccgttcg    2820
atctaccgca cctacgttga tggtcgtctg gtgtacgaac gcaactaagg aacgaccatg    2880
agagaagtcc aattgttaga tggtagaaga gttgatgtcg cctgtgctgg tcctttgatt    2940
agtgaaatag gtgcccactt agatttgact gctccagttg aaattgattg tggtggtggt    3000
ttagcaacta gaccttttac tgaacctcat ttgcacttag acaaagcagg tactgccgat    3060
agattgcctg ccggtgcttc cacaatcggt gacgctattg ctgcaatgca aagtgtcaag    3120
gtaaccgaaa gagataatgt cgccgctgta gcagccagaa tgcatagagt tttaaacaga    3180
atcgtcgatg acggttccca cgctattaga gcattggttg atgtcgacga gtttggggt    3240 ttaacagctt ttcatgctgc acaacaagtc caagccgctt tggccccaag agctgttgtc    3300
caaattgtcg ctttcccaca acacggttta accccctcaag tattggcaat gttagaacaa    3360
gcagccgctg aaggtgcagg tgccttgggt gctcatactg atgttgaccc agatcctgca    3420
gcccacgttg gtgccgtcgc tgcaatagcc gctggtgctt ccttgccatt agaagttcat    3480
actgacgaag gtgctagtcc agataaattt tatttgcctg cagtattgga agttttagat    3540
agattcccag gtttgtctac tacattagct cattgtttgt cattaggtac aattgcacct    3600
aagcaacaac aacattggat cgaagaatta gctcacagag atatcaaagt atgcgttgca    3660
ccatctattt tgggtttcgg tttgccatta gcacctgtta gagccttaat agaagctggt    3720
gtcggtatct tagtaggttc agacaatttg caagatgttt tctttccttt gggtacaggt    3780
agagcaattg aaaacgttag attgttagcc accgcagccc aattaactgc accagaattg    3840
gccggtcctt taattgctgg tgtaaccgac atagcttacg caaccgttac tggtgctgca    3900
gatgccttgg ctgttgaatc tccagctaca ttagtagttc atgatgctac ctcacctgca    3960
gaattgttaa gaggtataga cggtacaaga attaccgtta tagatggttt gttgacatct    4020
ccattgcaat tggataaagg tatcaagtaa gtttaaacta atcccacagc cgccagttcc    4080 gctgcggca ttttaacttt ctttaatggg cgcgcctttc cataggctcc gccccctga    4140 cgagcatcac aaaaatcgac gctcaagtca gaggtggcga aacccgacag gactataaag    4200
ataccaggcg tttcccctg gaagctccct cgtgcgctct cctgttccga ccctgccgct    4260
taccggatac ctgtccgcct ttctcccttc gggaagcgtg gcgctttctc atagctcacg    4320
ctgtaggtat ctcagttcgg tgtaggtcgt tcgctccaag ctgggctgtg tgcacgaacc    4380
ccccgttcag cccgaccgct gcgccttatc cggtaactat cgtcttgagt ccaacccggt    4440
aagacacgac ttatcgccac tggcagcagc cactggtaac aggattagca gagcgaggta    4500
tgtaggcggt gctacagagt tcttgaagtg gtggcctaac tacggctaca ctagaagaac    4560
agtatttggt atctgcgctc tgctgaagcc agttaccttc ggaaaaagag ttggtagctc    4620
ttgatccggc aaacaaacca ccgctggtag cggtggtttt tttgtttgca agcagcagat    4680
tacgcgcaga aaaaaaggat ctcaagaaga tcctttgatc ttttctacgg ggtctgacgc    4740
tcagtggaac gaaaactcac gttaagggat tttggtcatg agattatcaa aaaggatctt    4800
cacctagatc cttttaaatt aaaaatgaag ttttaaatca atctaaagta tatatgagta    4860
```

```
aacttggtct gacagttacc aatgcttaat cagtgaggca cctatctcag cgatctgtct   4920
atttcgttca tccatagttg cctgactccc cgtcgtgtag ataactacga tacgggaggg   4980
cttaccatct ggccccagtg ctgcaatgat accgcgagac ccacgctcac cggctccaga   5040
tttatcagca ataaaccagc cagccggaag ggccgagcgc agaagtggtc ctgcaacttt   5100
atccgcctcc atccagtcta ttaattgttg ccgggaagct agagtaagta gttcgccagt   5160
taatagtttg cgcaacgttg ttgccattgc tacaggcatc gtggtgtcac gctcgtcgtt   5220
tggtatggct tcattcagct ccggttccca acgatcaagg cgagttacat gatcccccat   5280
gttgtgcaaa aaagcggtta gctccttcgg tcctccgatc gttgtcagaa gtaagttggc   5340
cgcagtgtta tcactcatgg ttatggcagc actgcataat tctcttactg tcatgccatc   5400
cgtaagatgc ttttctgtga ctggtgagta ctcaaccaag tcattctgag aatagtgtat   5460
gcggcgaccg agttgctctt gcccggcgtc aatacgggat aataccgcgc cacatagcag   5520
aactttaaaa gtgctcatca ttggaaaacg ttcttcgggg cgaaaactct caaggatctt   5580
accgctgttg agatccagtt cgatgtaacc cactcgtgca cccaactgat cttcagcatc   5640
ttttactttc accagcgttt ctgggtgagc aaaaacagga aggcaaaatg ccgcaaaaaa   5700
gggaataagg gcgacacgga aatgttgaat actcatactc ttccttttt aatattattg   5760
aagcatttat cagggttatt gtctcatgag cggatacata tttgaatgta tttagaaaaa   5820
taaacagcga tcgcgcggcc gcgggtaata actgatataa ttaaattgaa gctctaattt   5880
gtgagtttag tatacatgca tttacttata atacagtttt ttagttttgc tggccgcatc   5940
ttctcaaata tgcttcccag cctgcttttc tgtaacgttc accctctacc ttagcatccc   6000
ttcccttgc aaatagtcct cttccaacaa taataatgtc agatcctgta gagaccacat   6060
catccacggt tctatactgt tgacccaatg cgtctccctt gtcatctaaa cccacaccgg   6120
gtgtcataat caaccaatcg taaccttcat ctcttccacc catgtctctt tgagcaataa   6180
agccgataac aaaatctttg tcgctcttcg caatgtcaac agtaccctta gtatattctc   6240
cagtagctag ggagcccttg catgacaatt ctgctaacat caaaaggcct ctaggttcct   6300
ttgttacttc ttccgccgcc tgcttcaaac cgctaacaat acctgggccc accacaccgt   6360
gtgcattcgt aatgtctgcc cattctgcta ttctgtatac acccgcagag tactgcaatt   6420
tgactgtatt accaatgtca gcaaattttc tgtcttcgaa gagtaaaaaa ttgtacttgg   6480
cggataatgc ctttagcggc ttaactgtgc cctccatgga aaaatcagtc aagatatcca   6540
catgtgtttt tagtaaacaa attttgggac ctaatgcttc aactaactcc agtaattcct   6600
tggtggtacg aacatccaat gaagcacaca agtttgtttg cttttcgtgc atgatattaa   6660
atagcttggc agcaacagga ctaggatgag tagcagcacg ttccttatat gtagctttcg   6720
acatgattta tcttcgtttc ctgcaggttt ttgttctgtg cagttgggtt aagaatactg   6780
ggcaatttca tgtttcttca acaccacata tgcgtatata taccaatcta agtctgtgct   6840
ccttccttcg ttcttccttc tgctcggaga ttaccgaatc aaagctagct tatcgatgat   6900
aagctgtcaa agatgagaat taattccacg gactatagac tatactagat actccgtcta   6960
ctgtacgata cacttccgct caggtccttg tcctttaacg aggccttacc actcttttgt   7020
tactctattg atccagctca gcaaaggcag tgtgatctaa gattctatct tcgcgatgta   7080
gtaaaactag ctagaccgag aaagagacta gaaatgcaaa aggcacttct acaatggctg   7140
ccatcattat tatccgatgt gacgctgcag cttctcaatg atattcgaat acgctttgag   7200
gagatacagc ctaatatccg acaaactgtt ttacagattt acgatcgtac ttgttaccca   7260
```

```
tcattgaatt ttgaacatcc gaacctggga gttttccctg aaacagatag tatatttgaa    7320
cctgtataat aatatatagt ctagcgcttt acgaagacaa atgtatgtat ttcggttcct    7380
ggagaaacta ttgcatctat tgcataggta atcttgcacg tcgcatcccc ggttcatttt    7440
ctgcgtttcc atcttgcact tcaatagcat atctttgtta acgaagcatc tgtgcttcat    7500
tttgtagaac aaaaatgcaa cgcgagagcg ctaattttc aaacaaagaa tctgagctgc     7560
atttttacag aacagaaatg caacgcgaaa gcgctatttt accaacgaag aatctgtgct    7620 tcattttgt aaaacaaaaa tgcaacgcga cgagagcgct aatttttcaa acaaagaatc     7680
tgagctgcat ttttacagaa cagaaatgca acgcgagagc gctattttac caacaaagaa    7740
tctatacttc ttttttgttc tacaaaatg catcccgaga gcgctatttt ctaacaaag     7800 catcttagat tactttttttt ctcctttgtg cgctctataa tgcagtctct tgataacttt    7860
ttgcactgta ggtccgttaa ggttagaaga aggctacttt ggtgtctatt ttctcttcca    7920
taaaaaaagc ctgactccac ttcccgcgtt tactgattac tagcgaagct gcgggtgcat    7980
tttttcaaga taaaggcatc cccgattata ttctataccg atgtggattg cgcatacttt    8040
gtgaacagaa agtgatagcg ttgatgattc ttcattggtc agaaaattat gaacggtttc    8100
ttctattttg tctctatata ctacgtatag gaaatgttta cattttcgta ttgttttcga    8160
ttcactctat gaatagttct tactacaatt ttttgtcta aagagtaata ctagagataa     8220
acataaaaaa tgtagaggtc gagtttagat gcaagttcaa ggagcgaaag gtggatgggt    8280
aggttatata gggatatagc acagagatat atagcaaaga gatacttttg agcaat        8336
```

<210> SEQ ID NO 19
<211> LENGTH: 8063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gtttgtggaa gcggtattcg caatttaatt aaagctggtg acaattaatc atcggctcgt      60
ataatgtgtg gaattgaatc gatataagga ggttaatcat atgtcctcca cagcattata     120
caccgttcct accgcaggtc cagacgatgt tgccgccttg aaagcattag atggtcattc     180
cgcctccgat attttggctg taataggtaa acagagggt aatggttgtg ttaacgactt      240
tagtagaacc ttatctgctg cagttttggca tccattgtta aagattcag ccattacagt     300 cttttccggt ggtgcagaag gtgtaataag tccacatgta aacatcttcg ttagagatga     360
aagacaatat tctggtcacc ctagaggttt ggtaactgct gttggtagaa caagagttat     420
cggtccagaa gaaattggta gacctgctca agtcgatgca gtacatgaaa ccgttgtcgc     480
attgttaact gaattgggtg ttggtccaga tgacgttcac ttggtcttga ttaaatgccc     540
tttgttatct tcagacgcta tagcaggtgt tcatagaaga ggtttaagac ctgtcactac     600
agatacttac gaatctatgt caagatccag agccgcttct gctttgggta tagccatggc     660
tttaaaggaa tgtgatagag acagagcatt gttagccttg gaaggtagag atgacgtttg     720
gtcagcaaga gcctccgctt ccagtggtgc tgaattggat gactgccaca ttttagtagt     780
tgcagaatca gatgcagccg ctaatccatt aagagcagcc catactgcca tgagagatgc     840
tttggacatc caagctttaa cagaagttttt tgacagaatt gctgcagaag gtaccgt       900 cagacaaata ttcgcaaagg ccgaagctga tccttcaggt gctatcagag gttatagaca     960
```

```
taccatgtta actgattccg acgtcaatgc aacaagacac gccagagccg ctgtaggtgg      1020
tttgattgca gccttacatg gtaacggtgc tgtctatgta tcaggtggtg cagaacacca      1080
aggtccaagt ggtggtggtt ctgttactgt tatatatgat gttcctgcaa cagccaacgc      1140
taccggtgaa gcttctagat aaggaaatcc attatgatat actcaacagt caacgctaat      1200
ccttacgctt ggccttacga tggttcaata gaccctgctc acaccgcttt aatcttaatc      1260
gattggcaaa tagacttttg tggtccaggt ggttatgtcg attccatggg ttacgactta      1320
tccttgacta gaagtggttt agaacctaca gcaagagtat tggctgcagc cagagatact      1380
ggtatgacag ttatccatac tagagaaggt cacagaccag atttggctga cttgccacct      1440
aataagagat ggagatctgc atcagccggt gctgaaatcg gttcagttgg tccatgtggt      1500
agaattttag tcagaggtga acctggttgg gaaatagtac cagaagttgc acctagagaa      1560
ggtgaaccaa ttatagataa acctggtaaa ggtgctttct acgcaacaga tttggacttg      1620
ttgttgagaa caagaggtat cacccatttg attttgaccg gtataactac agatgtttgc      1680
gtccacacca ctatgagaga agccaacgat agaggttacg aatgtttaat tttgtctgat      1740
tgcaccggtg ctactgacag aaagcatcac gaagctgcat tatctatggt caccatgcaa      1800
ggtggtgtat tcggtgcaac tgcccattca gatgactat tggccgcttt gggtacaacc      1860
gttccagcag ccgctggtcc tagagctaga acagaataag gaacgaccat gacagttagt      1920
tccgatacaa ctgctgaaat atcgttaggt tggtcaatcc aagactggat tgatttccac      1980
aagtcatcaa gctcccaggc ttcactaagg cttcttgaat cactactaga ctctcaaaat      2040
gttgcgccag tcgataatgc gtggatatcg ctaatttcaa aggaaaattt actgcaccaa      2100
ttccaaattt taaagagcag agaaaataaa gaaactctac ctctctacgg tgtccctatt      2160
gctgttaagg acaacatcga cgttagaggt ctacccacca ccgctgcatg tccatccttt      2220
gcatatgagc cttccaaaga ctctaaagta gtagaactac taagaaatgc aggtgcgata      2280
atcgtgggta agacaaactt ggaccaattt gccacaggat tagtcggcac acggtctcca      2340
tatgggaaaa caccttgcgc ttttagcaaa gagcatgtat ctggtggttc ctccgctggg      2400
tcagcatcgg tggtcgccag aggtatcgta ccaattgcat gggtactga tacagcaggt      2460 tctggtagag tcccagccgc cttgaacaac ctgattggcc taaagccaac aaagggcgtc      2520
ttttcctgtc aaggtgtagt tcccgcttgt aaatctttag actgcgtctc catctttgca      2580
ttaaacctaa gtgatgctga acgctgcttc cgcatcatgt gccagccaga tcctgataat      2640
gatgaatatt ctagacccta tgtttccaac cctttgaaaa aatttcaag caatgtaacg      2700 attgctattc ctaaaaatat cccatggtat ggtgaaacca agaatcctgt actgttttcc      2760
aatgctgtcg aaaatctatc aagaacgggc gctaacgtca tagaaattga ttttgagcct      2820
cttttagagt tagctcgctg tttatacgaa ggtacttggg tggccgagcg ttatcaagct      2880
attcaatcgt ttttggacag taaaccacca aaggaatctt tggaccctac tgttatttca      2940
attatagaag gggccaagaa atacagtgca gtagactgct tcagttttga atacaaaaga      3000
caaggcatct tgcaaaaagt gagacgactt ctcgaatcag tcgatgtatt gtgtgtgccc      3060
acatgtcctt taaatcctac tatgcaacaa gttgcggatg aaccagtcct agtcaattca      3120
agacaaggca catggactaa ttttgtcaac ttggcagatt tggcagccct tgctgttccc      3180
gcagggttcc gagacgatgg tttgccaaat ggtattactt taatcggtaa aaaattcaca      3240
gattacgcac tattagagtt ggctaaccgc tatttccaaa atatattccc caacggttcc      3300
```

```
agaacatacg gtacttttac ctcttcttca gtaaagccag caaacgatca attagtggga    3360
ccagactatg acccatctac gtccataaaa ttggctgttg tcggtgcaca tcttaagggt    3420
ctgcctctac attggcaatt ggaaaaggtc aatgcaacat atttatgtac aacaaaaaca    3480
tcaaaagctt accagctttt tgctttgccc aaaaatggac cagttttaaa acctggtttg    3540
agaagagttc aagatagcaa tggctctcaa atcgaattag aagtgtacag tgttccaaaa    3600
gaactgttcg gtgcttttat ttccatggtt cctgaaccat taggaatagg ttcagtggag    3660
ttagaatctg gtgaatggat caaatccttt atttgtgaag aatctggtta caaagccaaa    3720
ggtacagttg atatcacaaa gtatggtgga tttagagcat attttgaaat gttgtaagtt    3780
taaactaatc ccacagccgc cagttccgct ggcggcattt taactttctt taatgggcgc    3840
gcctttccat aggctccgcc ccctgacga gcatcacaaa aatcgacgct caagtcagag    3900
gtggcgaaac ccgacaggac tataaagata ccaggcgttt ccccctggaa gctccctcgt    3960
gcgctctcct gttccgaccc tgccgcttac cggatacctg tccgcctttc tcccttcggg    4020
aagcgtggcg ctttctcata gctcacgctg taggtatctc agttcggtgt aggtcgttcg    4080
ctccaagctg ggctgtgtgc acgaaccccc cgttcagccc gaccgctgcg ccttatccgg    4140
taactatcgt cttgagtcca acccggtaag acacgactta tcgccactgg cagcagccac    4200
tggtaacagg attagcagag cgaggtatgt aggcggtgct acagagttct gaagtggtg    4260
gcctaactac ggctacacta agaacagt atttggtatc tgcgctctgc tgaagccagt    4320
taccttcgga aaaagagttg gtagctcttg atccggcaaa caaaccaccg ctggtagcgg    4380
tggttttttt gtttgcaagc agcagattac gcgcagaaaa aaaggatctc aagaagatcc    4440
tttgatcttt tctacggggt ctgacgctca gtggaacgaa aactcacgtt aagggatttt    4500
ggtcatgaga ttatcaaaaa ggatcttcac ctagatcctt ttaaattaaa aatgaagttt    4560
taaatcaatc taaagtatat atgagtaaac ttggtctgac agttaccaat gcttaatcag    4620
tgaggcacct atctcagcga tctgtctatt tcgttcatcc atagttgcct gactccccgt    4680
cgtgtagata actacgatac gggagggctt accatctggc cccagtgctg caatgatacc    4740
gcgagaccca cgctcaccgg ctccagattt atcagcaata aaccagccag ccggaagggc    4800
cgagcgcaga agtggtcctg caactttatc cgcctccatc cagtctatta attgttgccg    4860
ggaagctaga gtaagtagtt cgccagttaa tagtttgcgc aacgttgttg ccattgctac    4920
aggcatcgtg gtgtcacgct cgtcgtttgg tatggcttca ttcagctccg gttcccaacg    4980
atcaaggcga gttacatgat cccccatgtt gtgcaaaaaa gcggttagct ccttcggtcc    5040
tccgatcgtt gtcagaagta agttggccgc agtgttatca ctcatggtta tggcagcact    5100
gcataattct cttactgtca tgccatccgt aagatgcttt tctgtgactg gtgagtactc    5160
aaccaagtca ttctgagaat agtgtatgcg gcgaccgagt tgctcttgcc cggcgtcaat    5220
acgggataat accgcgccac atagcagaac tttaaaagtg ctcatcattg gaaaacgttc    5280
ttcggggcga aaactctcaa ggatcttacc gctgttgaga tccagttcga tgtaacccac    5340
tcgtgcaccc aactgatctt cagcatcttt tactttcacc agcgtttctg ggtgagcaaa    5400
aacaggaagg caaaatgccg caaaaaaggg aataagggcg acacggaaat gttgaatact    5460
catactcttc ctttttcaat attattgaag catttatcag ggttattgtc tcatgagcgg    5520
atacatattt gaatgtattt agaaaaataa acagcgatcg cgcggccgcg gtaataact    5580
gatataatta aattgaagct ctaatttgtg agtttagtat acatgcattt acttataata    5640
cagttttttta gttttgctgg ccgcatcttc tcaaatatgc ttcccagcct gcttttctgt    5700
```

```
aacgttcacc ctctacctta gcatcccttc cctttgcaaa tagtcctctt ccaacaataa    5760
taatgtcaga tcctgtagag accacatcat ccacggttct atactgttga cccaatgcgt    5820
ctcccttgtc atctaaaccc acaccggtg tcataatcaa ccaatcgtaa ccttcatctc     5880
ttccacccat gtctctttga gcaataaagc cgataacaaa atctttgtcg ctcttcgcaa    5940
tgtcaacagt acccttagta tattctccag tagctaggga gcccttgcat gacaattctg    6000
ctaacatcaa aaggcctcta ggttcctttg ttacttcttc cgccgcctgc ttcaaaccgc    6060
taacaatacc tgggcccacc acaccgtgtg cattcgtaat gtctgcccat tctgctattc    6120
tgtatacacc cgcagagtac tgcaatttga ctgtattacc aatgtcagca aattttctgt    6180
cttcgaagag taaaaaattg tacttggcgg ataatgcctt tagcggctta actgtgccct    6240
ccatggaaaa atcagtcaag atatccacat gtgtttttag taaacaaatt ttgggaccta    6300
atgcttcaac taactccagt aattccttgg tggtacgaac atccaatgaa gcacacaagt    6360
ttgtttgctt ttcgtgcatg atattaaata gcttggcagc aacaggacta ggatgagtag    6420
cagcacgttc cttatatgta gctttcgaca tgatttatct tcgtttcctg caggtttttg    6480
ttctgtgcag ttgggttaag aatactgggc aatttcatgt ttcttcaaca ccacatatgc    6540
gtatatatac caatctaagt ctgtgctcct tccttcgttc ttccttctgc tcggagatta    6600
ccgaatcaaa gctagcttat cgatgataag ctgtcaaaga tgagaattaa ttccacggac    6660
tatagactat actagatact ccgtctactg tacgatacac ttccgctcag gtccttgtcc    6720
tttaacgagg ccttaccact cttttgttac tctattgatc cagctcagca aaggcagtgt    6780
gatctaagat tctatcttcg cgatgtagta aaactagcta gaccgagaaa gagactagaa    6840
atgcaaaagg cacttctaca atggctgcca tcattattat ccgatgtgac gctgcagctt    6900
ctcaatgata ttcgaatacg ctttgaggag atacagccta atatccgaca aactgtttta    6960
cagatttacg atcgtacttg ttacccatca ttgaattttg aacatccgaa cctgggagtt    7020
ttccctgaaa cagatagtat atttgaacct gtataataat atatagtcta gcgctttacg    7080
gaagacaatg tatgtatttc ggttcctgga gaaactattg catctattgc ataggtaatc    7140
ttgcacgtcg catccccggt tcatttctg cgtttccatc ttgcacttca atagcatatc     7200
tttgttaacg aagcatctgt gcttcatttt gtagaacaaa aatgcaacgc gagagcgcta    7260 attttttcaaa caaagaatct gagctgcatt tttacagaac agaaatgcaa cgcgaaagcg    7320 ctatttttacc aacgaagaat ctgtgcttca tttttgtaaa acaaaaatgc aacgcgacga    7380
gagcgctaat ttttcaaaca aagaatctga gctgcatttt tacagaacag aaatgcaacg    7440
cgagagcgct attttaccaa caaagaatct atacttcttt tttgttctac aaaaatgcat    7500
cccgagagcg ctatttttct aacaaagcat cttagattac ttttttttctc ctttgtgcgc    7560 tctataatgc agtctcttga aactttttg cactgtaggt ccgttaaggt tagaagaagg     7620
ctactttggt gtctattttc tcttccataa aaaaagcctg actccacttc ccgcgtttac    7680
tgattactag cgaagctgcg ggtgcatttt ttcaagataa aggcatcccc gattatattc    7740
tataccgatg tggattgcgc atactttgtg aacagaaagt gatagcgttg atgattcttc    7800
attggtcaga aaattatgaa cggtttcttc tattttgtct ctatatacta cgtataggaa    7860
atgtttacat tttcgtattg ttttcgattc actctatgaa tagttcttac tacaattttt    7920
ttgtctaaag agtaatacta gagataaaca taaaaaatgt agaggtcgag tttagatgca    7980
agttcaagga gcgaaaggtg gatgggtagg ttatataggg atatagcaca gagatatata    8040
```
gcaaagagat acttttgagc aat                                              8063

<210> SEQ ID NO 20
<211> LENGTH: 6004
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

| | | | | | |
|---|---|---|---|---|---|
| gatactttg | agcaatgttt | gtggaagcgg | tattcgcaat | tataaacggt | attttcacaa | 60 |
| ttgcacccca | gccagaccga | tagccggtcg | caatccgcca | cccacaaccg | tctacctccc | 120 |
| acagaacccc | gtcacttcca | cccttttcca | ccagatcata | tgtcccaact | tgccaaatta | 180 |
| aaaccgtgcg | aattttcaaa | ataaactttg | gcaaagaggc | tgcaaaggag | gggctggtga | 240 |
| gggcgtctgg | aagtcgacca | gagaccgggt | tggcggcgca | tttgtgtccc | aaaaaacagc | 300 |
| cccaattgcc | ccaattgacc | ccaaattgac | ccagtagcgg | gcccaacccc | ggcgagagcc | 360 |
| cccttctccc | cacatatcaa | acctcccccg | gttcccacac | ttgccgttaa | gggcgtaggg | 420 |
| tactgcagtc | tggaatctac | gcttgttcag | actttgtact | agtttctttg | tctggccatc | 480 |
| cgggtaaccc | atgccggacg | caaaatagac | tactgaaaat | ttttttgctt | tgtggttggg | 540 |
| acttagccca | agggtataaa | agaccaccgt | ccccgaatta | cctttcctct | tcttttctct | 600 |
| ctctccttgt | caactcacac | ccgaaatcgt | taagcatttc | cttctgagta | taagaatcat | 660 |
| tcaaaatgtc | atcctcagaa | gtaaaagcaa | atggttggac | cgcagttcct | gtttccgcaa | 720 |
| aagcaatagt | agactccttg | ggtaaattag | gagatgtctc | ttcatattcc | gtagaagata | 780 |
| ttgccttttcc | agctgcagac | aaattggtag | ccgaagctca | agcattcgtt | aaggctagat | 840 |
| tatctcctga | aacctacaac | cattcaatga | gagttttcta | ttggggtact | gtcattgcca | 900 |
| gaagattgtt | accagaacaa | gctaaagatt | tgtctccttc | aacatgggca | ttaacctgtt | 960 |
| tgttacacga | cgttggtact | gccgaagctt | atttttacctc | cactagaatg | agtttcgata | 1020 |
| tctacggtgg | tattaaagct | atggaagtat | tgaaggtttt | aggttccagt | acagatcaag | 1080 |
| cagaagccgt | tgctgaagca | attataagac | atgaagatgt | tggtgtcgac | ggtaacatca | 1140 |
| cattttggg | tcaattgatc | caattggcaa | cattgtacga | taacgtcggt | gcctacgacg | 1200 |
| gtattgatga | cttcggttcc | tgggttgatg | acactacaag | aaacagtata | aacactgctt | 1260 |
| tcccaagaca | tggttggtgt | tcttggttcg | catgcacagt | tagaaaagaa | gaatcaaaca | 1320 |
| agccttggtg | ccacaccaca | cacataccac | aattcgacaa | acaaatggaa | gcaaacacct | 1380 |
| tgatgaaacc | ttgggaataa | gctgcttgta | cctagtgcaa | ccccagtttg | ttaaaaatta | 1440 |
| gtagtcaaaa | acttctgagt | tagaaatttg | tgagtgtagt | gagattgtag | agtatcatgt | 1500 |
| gtgtccgtaa | gtgaagtgtt | attgactctt | agttagttta | tctagtactc | gtttagttga | 1560 |
| cactgatcta | gtattttacg | aggcgtatga | ctttagccaa | gtgttgtact | tagtcttctc | 1620 |
| tccaaacatg | agagggctct | gtcactcagt | cggcctatgg | gtgagatggc | ttggtgagat | 1680 |
| cttttcgatag | tctcgtcaag | atggtaggat | gatgggggaa | tacattactg | ctctcgtcaa | 1740 |
| ggaaaccaca | atcagatcac | accatcctcc | atggtatccg | atgactctct | tctccacagt | 1800 |
| tttccatagg | ctccgccccc | ctgacgagca | tcacaaaaat | cgacgctcaa | gtcagaggtg | 1860 |
| gcgaaacccg | acaggactat | aaagatacca | ggcgtttccc | cctggaagct | ccctcgtgcg | 1920 |
| ctctcctgtt | ccgaccctgc | cgcttaccgg | atacctgtcc | gcctttctcc | cttcgggaag | 1980 |

```
cgtggcgctt tctcatagct cacgctgtag gtatctcagt tcggtgtagg tcgttcgctc    2040
caagctgggc tgtgtgcacg aacccccgt  tcagcccgac cgctgcgcct tatccggtaa    2100
ctatcgtctt gagtccaacc cggtaagaca cgacttatcg ccactggcag cagccactgg    2160
taacaggatt agcagagcga ggtatgtagg cggtgctaca gagttcttga agtggtggcc    2220
taactacggc tacactagaa gaacagtatt tggtatctgc gctctgctga agccagttac    2280
cttcggaaaa agagttggta gctcttgatc cggcaaacaa accaccgctg gtagcggtgg    2340 ttttttttgtt tgcaagcagc agattacgcg cagaaaaaaa ggatctcaag aagatccttt    2400
gatcttttct acggggtctg acgctcagtg gaacgaaaac tcacgttaag ggattttggt    2460
catgagatta tcaaaaagga tcttcaccta gatccttttta aattaaaaat gaagttttaa    2520
atcaatctaa agtatatatg agtaaacttg gtctgacagt taccaatgct taatcagtga    2580
ggcacctatc tcagcgatct gtctatttcg ttcatccata gttgcctgac tccccgtcgt    2640
gtagataact acgatacggg agggcttacc atctggcccc agtgctgcaa tgataccgcg    2700
agacccacgc tcaccggctc cagatttatc agcaataaac cagccagccg aagggccga    2760 gcgcagaagt ggtcctgcaa ctttatccgc ctccatccag tctattaatt gttgccggga    2820
agctagagta agtagttcgc cagttaatag tttgcgcaac gttgttgcca ttgctacagg    2880
catcgtggtg tcacgctcgt cgtttggtat ggcttcattc agctccggtt cccaacgatc    2940
aaggcgagtt acatgatccc ccatgttgtg caaaaaagcg gttagctcct tcggtcctcc    3000
gatcgttgtc agaagtaagt tggccgcagt gttatcactc atggttatgg cagcactgca    3060
taattctctt actgtcatgc catccgtaag atgcttttct gtgactggtg agtactcaac    3120
caagtcattc tgagaatagt gtatgcggcg accgagttgc tcttgcccgg cgtcaatacg    3180
ggataatacc gcgccacata gcagaacttt aaaagtgctc atcattggaa aacgttcttc    3240
ggggcgaaaa ctctcaagga tcttaccgct gttgagatcc agttcgatgt aacccactcg    3300
tgcacccaac tgatcttcag catctttac tttcaccagc gtttctgggt gagcaaaaac    3360
aggaaggcaa aatgccgcaa aaaagggaat aagggcgaca cggaaatgtt gaatactcat    3420
actcttcctt tttcaatatt attgaagcat ttatcagggt tattgtctca tgagcggata    3480
catatttgaa tgtatttaga aaaataaaca gcgatcgcgc ggccgcgggt aataactgat    3540
ataattaaat tgaagctcta atttgtgagt ttagtataca tgcatttact tataatacag    3600 tttttttagtt ttgctggccg catcttctca aatatgcttc ccagcctgct tttctgtaac    3660
gttcaccctc tacctttagca tcccttccct ttgcaaatag tcctcttcca acaataataa    3720
tgtcagatcc tgtagagacc acatcatcca cggttctata ctgttgaccc aatgcgtctc    3780
ccttgtcatc taaacccaca ccgggtgtca taatcaacca atcgtaacct tcatctcttc    3840
cacccatgtc tctttgagca ataaagccga taacaaaatc tttgtcgctc ttcgcaatgt    3900
caacagtacc cttagtatat tctccagtag ctagggagcc cttgcatgac aattctgcta    3960
acatcaaaag gcctctaggt tcctttgtta cttcttccgc cgcctgcttc aaaccgctaa    4020
caatacctgg gccccaccaca ccgtgtgcat tcgtaatgtc tgcccattct gctattctgt    4080
atacacccgc agagtactgc aatttgactg tattaccaat gtcagcaaat tttctgtctt    4140
cgaagagtaa aaaattgtac ttggcggata atgcctttag cggcttaact gtgccctcca    4200
tggaaaaatc agtcaagata tccacatgtg tttttagtaa acaaattttg ggacctaatg    4260
cttcaactaa ctccagtaat tccttggtgg tacgaacatc caatgaagca cacaagtttg    4320
tttgcttttc gtgcatgata ttaaatagct tggcagcaac aggactagga tgagtagcag    4380
```

| | |
|---|---|
| cacgttcctt atatgtagct ttcgacatga tttatcttcg tttcctgcag gttttttgttc | 4440 |
| tgtgcagttg ggttaagaat actgggcaat ttcatgtttc ttcaacacca catatgcgta | 4500 |
| tatataccaa tctaagtctg tgctccttcc ttcgttcttc cttctgctcg gagattaccg | 4560 |
| aatcaaagct agcttatcga tgataagctg tcaaagatga gaattaattc cacggactat | 4620 |
| agactatact agatactccg tctactgtac gatacacttc cgctcaggtc cttgtccttt | 4680 |
| aacgaggcct taccactctt tgttactct attgatccag ctcagcaaag gcagtgtgat | 4740 |
| ctaagattct atcttcgcga tgtagtaaaa ctagctagac cgagaaagag actagaaatg | 4800 |
| caaaaggcac ttctacaatg gctgccatca ttattatccg atgtgacgct gcagcttctc | 4860 |
| aatgatattc gaatacgctt tgaggagata cagcctaata tccgacaaac tgttttacag | 4920 |
| atttacgatc gtacttgtta cccatcattg aattttgaac atccgaacct gggagttttc | 4980 |
| cctgaaacag atagtatatt tgaacctgta taataatata tagtctagcg ctttacggaa | 5040 |
| gacaatgtat gtatttcggt tcctggagaa actattgcat ctattgcata ggtaatcttg | 5100 |
| cacgtcgcat ccccggttca ttttctgcgt ttccatcttg cacttcaata gcatatcttt | 5160 |
| gttaacgaag catctgtgct tcattttgta gaacaaaaat gcaacgcgag agcgctaatt | 5220 |
| tttcaaacaa agaatctgag ctgcattttt acagaacaga aatgcaacgc gaaagcgcta | 5280 |
| ttttaccaac gaagaatctg tgcttcattt ttgtaaaaca aaaatgcaac gcgacgagag | 5340 |
| cgctaatttt tcaaacaaag aatctgagct gcattttac agaacagaaa tgcaacgcga | 5400 |
| gagcgctatt ttaccaacaa agaatctata cttcttttt gttctacaaa atgcatccc | 5460 |
| gagagcgcta tttttctaac aaagcatctt agattacttt ttttctcctt tgtgcgctct | 5520 |
| ataatgcagt ctcttgataa cttttttgcac tgtaggtccg ttaaggttag aagaaggcta | 5580 |
| ctttggtgtc tatttttctct tccataaaaa aagcctgact ccacttcccg cgtttactga | 5640 |
| ttactagcga agctgcgggt gcattttttc aagataaagg catccccgat tatattctat | 5700 |
| accgatgtgg attgcgcata ctttgtgaac agaaagtgat agcgttgatg attcttcatt | 5760 |
| ggtcagaaaa ttatgaacgg tttcttctat tttgtctcta tatactacgt ataggaaatg | 5820 |
| tttacatttt cgtattgttt tcgattcact ctatgaatag ttcttactac aattttttg | 5880 |
| tctaaagagt aatactagag ataaacataa aaaatgtaga ggtcgagttt agatgcaagt | 5940 |
| tcaaggagcg aaaggtggat gggtaggtta tagggata tagcacagag atatatagca | 6000 |
| aaga | 6004 |

<210> SEQ ID NO 21
<211> LENGTH: 10640
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

| | |
|---|---|
| gtttgtggaa gcggtattcg caatttaatt aaagctggtg acaattaatc atcggctcgt | 60 |
| ataatgtgtg gaattgaatc gatataagga ggttaatcat atgacagtta gttccgatac | 120 |
| aactgctgaa atatcgttag gttggtcaat ccaagactgg attgatttcc acaagtcatc | 180 |
| aagctcccag gcttcactaa ggcttcttga atcactacta gactctcaaa atgttgcgcc | 240 |
| agtcgataat gcgtggatat cgctaatttc aaaggaaaat ttactgcacc aattccaaat | 300 |
| tttaaagagc agagaaaata aagaaactct acctctctac ggtgtcccta ttgctgttaa | 360 |

-continued

| | |
|---|---|
| ggacaacatc gacgttagag gtctacccac caccgctgca tgtccatcct ttgcatatga | 420 |
| gccttccaaa gactctaaag tagtagaact actaagaaat gcaggtgcga taatcgtggg | 480 |
| taagacaaac ttggaccaat ttgccacagg attagtcggc acacggtctc catatgggaa | 540 |
| aacaccttgc gcttttagca aagagcatgt atctggtggt cctccgctg gtcagcatc | 600 |
| ggtggtcgcc agaggtatcg taccaattgc attgggtact gatacagcag gttctggtag | 660 |
| agtcccagcc gccttgaaca acctgattgg cctaaagcca acaaagggcg tcttttcctg | 720 |
| tcaaggtgta gttcccgctt gtaaatcttt agactgcgtc tccatctttg cattaaacct | 780 |
| aagtgatgct gaacgctgct ccgcatcat gtgccagcca gatcctgata atgatgaata | 840 |
| ttctagaccc tatgtttcca acccttgaa aaaattttca agcaatgtaa cgattgctat | 900 |
| tcctaaaaat atcccatggt atggtgaaac caagaatcct gtactgtttt ccaatgctgt | 960 |
| cgaaaatcta tcaagaacgg gcgctaacgt catagaaatt gattttgagc ctcttttaga | 1020 |
| gttagctcgc tgtttatacg aaggtacttg ggtggccgag cgttatcaag ctattcaatc | 1080 |
| gttttttggac agtaaaccac caaaggaatc tttggaccct actgttattt caattataga | 1140 |
| aggggccaag aaatacagtg cagtagactg cttcagtttt gaatacaaaa gacaaggcat | 1200 |
| cttgcaaaaa gtgagacgac ttctcgaatc agtcgatgta ttgtgtgtgc ccacatgtcc | 1260 |
| tttaaatcct actatgcaac aagttgcgga tgaaccagtc ctagtcaatt caagacaagg | 1320 |
| cacatggact aattttgtca acttggcaga tttggcagcc cttgctgttc ccgcagggtt | 1380 |
| ccgagacgat ggtttgccaa atggtattac tttaatcggt aaaaaattca cagattacgc | 1440 |
| actattagag ttggctaacc gctatttcca aaatatattc cccaacggtt ccagaacata | 1500 |
| cggtactttt acctcttctt cagtaaagcc agcaaacgat caattagtgg gaccagacta | 1560 |
| tgacccatct acgtccataa aattggctgt tgtcggtgca catcttaagg gtctgcctct | 1620 |
| acattggcaa ttgaaaaagg tcaatgcaac atatttatgt acaacaaaaa catcaaaagc | 1680 |
| ttaccagctt tttgctttgc ccaaaaatgg accagtttta aaacctggtt tgagaagagt | 1740 |
| tcaagatagc aatggctctc aaatcgaatt agaagtgtac agtgttccaa agaactgtt | 1800 |
| cggtgctttt atttccatgg ttcctgaacc attaggaata ggttcagtgg agttagaatc | 1860 |
| tggtgaatgg atcaaatcct ttatttgtga agaatctggt tacaaagcca aaggtacagt | 1920 |
| tgatatcaca aagtatggtg gatttagagc atattttgaa atgttgaaga aaaaagagtc | 1980 |
| ccaaaagaag aagttatttg ataccgtgtt aattgccaat agaggtgaaa ttgccgttcg | 2040 |
| tattatcaag acattaaaaa aattgggtat tagatcagtt gcagtttatt ccgaccctga | 2100 |
| taaatattct caacacgtta ctgatgcaga tgtttctgta ccccttcatg cacaaccgc | 2160 |
| agcccaaact tatttagaca tgaataagat catgatgcc gctaagcaaa ctaatgcaca | 2220 |
| ggccattatt cctggttatg gtttcttgtc ggaaaatgcg gatttttctg atgcgtgcac | 2280 |
| cagtgctggc attaccttg ttggtccttc gggagatatt atcagaggtt tagggttaaa | 2340 |
| acattctgct agacagattg cacagaaggc tggcgttcct ctagtgccag gctctttgct | 2400 |
| tatcacatca gttgaagagg ctaagaaagt cgcagcggaa ttggaatacc cagttatggt | 2460 |
| gaagtcaact gctggtggcg gtggtattgg tttcagaaaa gtcgattctg aagaggacat | 2520 |
| cgagcatatt tttgagactg tgaaacatca aggtgaaaca ttttttcggtg acgctggtgt | 2580 |
| atttctggaa cggtttatcg aaaatgccag gcatgttgaa gtccaactta gggagatgg | 2640 |
| ttttggtaag gccattgctt gggcgaacg tgattgttct ttacagcgtc gtaaccaaaa | 2700 |

```
agttatcgaa gaaactcctg caccaaattt gccagaaaag acgaggttgg cgttaagaaa    2760
ggcagctgaa agtttgggat ctttattgaa ttacaagtgt gctggtacgg ttgaatttat    2820
ttacgatgag aaaaaggacg agttttactt tttagaagtt aatacaagat tacaagttga    2880
acatccaata acagaaatgg ttacagggtt agacttggtc gagtggatga tcaggattgc    2940
cgctaatgat gcacctgatt ttgattctac aaaggtagaa gtcaatgggg tttcaatgga    3000
ggcacgttta tatgctgaaa atccattgaa aaatttcaga ccttctccag gtttacttgt    3060
cgatgtgaaa tttcctgatt gggcaagagt ggatacttgg gttaagaaag gtactaatat    3120
ttctcccgaa tatgatccaa cattggccaa aattatcgtt catgggaaag accgtgatga    3180
tgcaatttcc aagttaaatc aagcgttaga agaaacaaaa gtttacggat gtattactaa    3240
cattgactac ctgaagtcta tcattaccag tgatttcttt gctaaagcaa aagtttctac    3300
aaacattttg aactcttatc aatatgagcc taccgccatc gaaattactt tgcccggtgc    3360
acacactagt attcaggatt accccggtag agttgggtac tggagaattg gtgttccgcc    3420
ctctggtcca atggacgcat attcgtttag attggcgaac agaattgttg gtaatgacta    3480
caggactcct gccattgaag taacgttgac tggtccatcc atcgttttcc attgtgaaac    3540
tgtcattgcc attactggtg gtaccgctct atgtacatta gacggccaag aaattcccca    3600
acacaaaccg gtcgaagtta agaggggatc tactttatcc attggcaagt tgacaagcgg    3660
ctgtagagca tacttaggta tcaggggtgg cattgatgtg cctaaatact ggggctctta    3720
ttctactttc actctaggaa atgtcggtgg atacaatgga agggtgctaa acttggaga    3780 cgtactattc ttaccaagca atgaagaaaa taaatcagtt gagtgccttc cacagaatat    3840
tcctcaatca ttaattcctc aaatttccga aactaaggaa tggagaattg gtgtaacatg    3900
tggtccccat gggtctccag atttttttaa acctgagtcc atcgaagaat ttttcagtga    3960
gaagtggaag gttcattaca actccaatag atttggtgtc cgtttgattg gacctaaacc    4020
taagtgggca agaagtaatg gtggtgaagg tggtatgcat ccttcaaaca ctcacgatta    4080
cgtttattct ctgggtgcaa ttaatttcac gggtgatgag ccagttatta ttacttgcga    4140 tggtcctttcc ttaggtggtt ttgtgtgtca agctgttgtc ccagaagcag aactgtggaa    4200
ggttggacag gttaaacccg gtgattccat tcagtttgtg ccactttctt acgaaagctc    4260
gagatcctta aggaatctc aggatgttgc aattaaatca ttggatggta ctaagttaag    4320
gcgcttagac tctgtttcaa ttttaccatc attcgaaacg cctattcttg cacaaatgga    4380
aaaagtgaat gagctttcac caaaggttgt atacagacaa gcaggtgatc gttatgtttt    4440
ggtggaatac ggtgataatg aaatgaattt taatatttcc tatagaattg aatgcctgat    4500
ctcccttgtg aaaagaata agactattgg tattgttgaa atgtcccaag gtgttagatc    4560
tgtattgata gaatttgatg gttacaaagt cactcaaaaa gaattgctta agtattggt    4620 ggcatatgaa acagaaatcc agtttgatga aaattggaag ataacttcta atataataag    4680
attaccgatg gctttcgaag actcgaagac tttggcatgt gttcaaaggt atcaagaaac    4740
aattcgttcg tctgctccat ggttgccaaa taacgttgat ttcattgcca atgtaaatgg    4800
aatttcaagg aatgaagttt atgatatgtt gtattctgcc agatttatgg ttttaggttt    4860
aggtgatgtc ttcctagggt cgccttgtgc tgttccatta gatcctcgtc acagattttt    4920
gggaagcaag tacaacccaa gtagaacata tacagaaaga ggtgcagtcg gtattggcgg    4980
tatgtatatg tgcatatatg ctgctaacag tcctggtggg taccaattag tgggtagaac    5040
aataccaatt tgggacaaac tatgtctggc cgcatcttct gaggttccgt ggttgatgaa    5100
```

```
cccatttgac caagtcgaat tttacccagt ttctgaagaa gatttggata aaatgactga    5160
agattgtgat aatggtgttt ataaagtcaa tatcgaaaag agtgttttg atcatcaaga     5220 atacttgaga tggatcaacg caaacaaaga ttccatcaca gcattccagg agggccagct    5280
tggtgaaaga gcagaggaat tgccaaatt gattcaaaat gcaaactctg aactaaaaga    5340
aagtgtcaca gtcaaacctg acgaggaaga agactttccca gaaggtgcag aaattgtata  5400
ttctgagtat tctgggcgtt tttgaaatc catagcatct gttggagatg ttattgaagc    5460
aggtcaaggg ctactaatta ttgaagccat gaaagcggaa atgattatat ccgctcctaa   5520
atcgggtaag attatcaaga tttgccatgg caatggtgat atggttgatt ctggtgacat   5580
agtggccgtc atagagacat tggcatgagg aaatccatta tgtcatcctc agaagtaaaa   5640
gcaaatggtt ggaccgcagt tcctgtttcc gcaaaagcaa tagtagactc cttgggtaaa   5700
ttaggagatg tctcttcata ttccgtagaa gatattgcct ttccagctgc agacaaattg   5760
gtagccgaag ctcaagcatt cgttaaggct agattatctc ctgaaaccta caaccattca   5820
atgagagttt tctattgggg tactgtcatt gccagaagat tgttaccaga acaagctaaa   5880
gatttgtctc cttcaacatg ggcattaacc tgtttgttac acgacgttgg tactgccgaa   5940
gcttatttta cctccactag aatgagtttc gatatctacg gtggtattaa agctatggaa   6000
gtattgaagg ttttaggttc cagtacagat caagcagaag ccgttgctga agcaattata   6060
agacatgaag atgttggtgt cgacggtaac atcacatttt tgggtcaatt gatccaattg   6120
gcaacattgt acgataacgt cggtgcctac gacggtattg atgacttcgg ttcctgggtt   6180
gatgacacta caagaaacag tataaacact gctttcccaa gacatggttg gtgttcttgg   6240
ttcgcatgca cagttagaaa agaagaatca aacaagcctt ggtgccacac cacacacata   6300
ccacaattcg acaaacaaat ggaagcaaac accttgatga aaccttggga ataagtttaa   6360
actaatccca cagccgccag ttccgctggc ggcattttaa ctttcttaa tgggcgcgcc    6420 tttccatagg ctccgccccc ctgacgagca tcacaaaaat cgacgctcaa gtcagaggtg   6480
gcgaaacccg acaggactat aaagatacca ggcgtttccc cctggaagct ccctcgtgcg   6540
ctctcctgtt ccgaccctgc cgcttaccgg atacctgtcc gcctttctcc cttcgggaag   6600
cgtggcgctt tctcatagct cacgctgtag gtatctcagt tcggtgtagg tcgttcgctc   6660
caagctgggc tgtgtgcacg aaccccccgt tcagcccgac cgctgcgcct tatccggtaa   6720
ctatcgtctt gagtccaacc cggtaagaca cgacttatcg ccactggcag cagccactgg   6780
taacaggatt agcagagcga ggtatgtagg cggtgctaca gagttcttga agtggtggcc   6840
taactacggc tacactagaa gaacagtatt tggtatctgc gctctgctga agccagttac   6900
cttcggaaaa agagttggta gctcttgatc cggcaaacaa accaccgctg gtagcggtgg   6960 ttttttttgtt tgcaagcagc agattacgcg cagaaaaaaa ggatctcaag aagatccttt   7020
gatcttttct acggggtctg acgctcagtg gaacgaaaac tcacgttaag ggattttggt   7080
catgagatta tcaaaaagga tcttcaccta gatccttta aattaaaaat gaagttttaa    7140
atcaatctaa agtatatatg agtaaacttg gtctgacagt taccaatgct taatcagtga   7200
ggcacctatc tcagcgatct gtctatttcg ttcatccata gttgcctgac tccccgtcgt   7260
gtagataact acgatacggg agggcttacc atctggcccc agtgctgcaa tgataccgcg   7320
agacccacgc tcaccggctc cagatttatc agcaataaac cagccagccg gaagggccga   7380
gcgcagaagt ggtcctgcaa ctttatccgc ctccatccag tctattaatt gttgccggga   7440
```

```
agctagagta agtagttcgc cagttaatag tttgcgcaac gttgttgcca ttgctacagg   7500
catcgtggtg tcacgctcgt cgtttggtat ggcttcattc agctccggtt cccaacgatc   7560
aaggcgagtt acatgatccc ccatgttgtg caaaaaagcg gttagctcct tcggtcctcc   7620
gatcgttgtc agaagtaagt tggccgcagt gttatcactc atggttatgg cagcactgca   7680
taattctctt actgtcatgc catccgtaag atgcttttct gtgactggtg agtactcaac   7740
caagtcattc tgagaatagt gtatgcggcg accgagttgc tcttgcccgg cgtcaatacg   7800
ggataatacc gcgccacata gcagaacttt aaaagtgctc atcattggaa aacgttcttc   7860
ggggcgaaaa ctctcaagga tcttaccgct gttgagatcc agttcgatgt aacccactcg   7920
tgcacccaac tgatcttcag catctttac tttcaccagc gtttctgggt gagcaaaaac    7980
aggaaggcaa aatgccgcaa aaaagggaat aagggcgaca cggaaatgtt gaatactcat   8040
actcttcctt tttcaatatt attgaagcat ttatcagggt tattgtctca tgagcggata   8100
catatttgaa tgtatttaga aaaataaaca gcgatcgcgc ggccgcgggt aataactgat   8160
ataattaaat tgaagctcta atttgtgagt ttagtataca tgcatttact tataatacag   8220
ttttttagtt ttgctggccg catcttctca aatatgcttc ccagcctgct tttctgtaac   8280
gttcaccctc taccttagca tcccttccct ttgcaaatag tcctcttcca acaataataa   8340
tgtcagatcc tgtagagacc acatcatcca cggttctata ctgttgaccc aatgcgtctc   8400
ccttgtcatc taaacccaca ccgggtgtca taatcaacca atcgtaacct tcatctcttc   8460
cacccatgtc tctttgagca ataaagccga taacaaaatc tttgtcgctc ttcgcaatgt   8520
caacagtacc cttagtatat tctccagtag ctagggagcc cttgcatgac aattctgcta   8580
acatcaaaag gcctctaggt tcctttgtta cttcttccgc cgcctgcttc aaaccgctaa   8640
caatacctgg gccaccaca ccgtgtgcat tcgtaatgtc tgcccattct gctattctgt    8700
atacacccgc agagtactgc aatttgactg tattaccaat gtcagcaaat tttctgtctt   8760
cgaagagtaa aaaattgtac ttggcggata atgcctttag cggcttaact gtgccctcca   8820
tggaaaaatc agtcaagata tccacatgtg tttttagtaa acaaattttg ggacctaatg   8880
cttcaactaa ctccagtaat tccttggtgg tacgaacatc caatgaagca cacaagtttg   8940
tttgcttttc gtgcatgata ttaaatagct tggcagcaac aggactagga tgagtagcag   9000
cacgttcctt atatgtagct ttcgacatga tttatcttcg tttcctgcag gttttttgttc  9060
tgtgcagttg ggttaagaat actgggcaat ttcatgtttc ttcaacacca catatgcgta   9120
tatataccaa tctaagtctg tgctccttcc ttcgttcttc cttctgctcg gagattaccg   9180
aatcaaagct agcttatcga tgataagctg tcaaagatga gaattaattc cacggactat   9240
agactatact agatactccg tctactgtac gatacacttc cgctcaggtc cttgtccttt   9300
aacgaggcct taccactctt tgttactct attgatccag ctcagcaaag gcagtgtgat    9360
ctaagattct atcttcgcga tgtagtaaaa ctagctagac cgagaaagag actagaaatg   9420
caaaaggcac ttctacaatg gctgccatca ttattatccg atgtgacgct gcagcttctc   9480
aatgatattc gaatacgctt tgaggagata cagcctaata tccgacaaac tgttttacag   9540
atttacgatc gtacttgtta cccatcattg aattttgaac atccgaacct gggagttttc   9600
cctgaaacag atagtatatt tgaacctgta taataatata tagtctagcg ctttacggaa   9660
gacaatgtat gtatttcggt tcctggagaa actattgcat ctattgcata ggtaatcttg   9720
cacgtcgcat ccccggttca ttttctgcgt ttccatcttg cacttcaata gcatatcttt   9780
gttaacgaag catctgtgct tcatttgta gaacaaaaat gcaacgcgag agcgctaatt    9840
```

```
tttcaaacaa agaatctgag ctgcattttt acagaacaga aatgcaacgc gaaagcgcta   9900
ttttaccaac gaagaatctg tgcttcattt ttgtaaaaca aaaatgcaac gcgacgagag   9960
cgctaatttt tcaaacaaag aatctgagct gcatttttac agaacagaaa tgcaacgcga  10020
gagcgctatt ttaccaacaa agaatctata cttctttttt gttctacaaa aatgcatccc  10080
gagagcgcta tttttctaac aaagcatctt agattacttt ttttctcctt tgtgcgctct  10140
ataatgcagt ctcttgataa ctttttgcac tgtaggtccg ttaaggttag aagaaggcta  10200
ctttggtgtc tattttctct tccataaaaa aagcctgact ccacttcccg cgtttactga  10260
ttactagcga agctgcgggt gcattttttc aagataaagg catccccgat tatattctat  10320
accgatgtgg attgcgcata ctttgtgaac agaaagtgat agcgttgatg attcttcatt  10380
ggtcagaaaa ttatgaacgg tttcttctat tttgtctcta tatactacgt ataggaaatg  10440
tttacatttt cgtattgttt tcgattcact ctatgaatag ttcttactac aatttttttg  10500
tctaaagagt aatactagag ataaacataa aaaatgtaga ggtcgagttt agatgcaagt  10560
tcaaggagcg aaaggtggat gggtaggtta tatagggata tagcacagag atatatagca  10620
aagagatact tttgagcaat                                              10640
```

<210> SEQ ID NO 22
<211> LENGTH: 244
<212> TYPE: PRT
<213> ORGANISM: Fusarium oxysporum

<400> SEQUENCE: 22

```
Met Leu Pro Thr Glu Val Glu Ala Asn Gly Trp Thr Ala Val Pro Val
1               5                   10                  15

Ser Ala Lys Ala Ile Lys Asp Ser Val Gly Gln Leu Val Pro Thr Gln
            20                  25                  30

Thr Tyr Thr Leu Gln Asp Ile Val Phe Pro Ser Glu Asp Lys Leu Val
        35                  40                  45

Ser Glu Ala Gln Ala Phe Val Lys Ala Arg Leu Ser Gln Glu Ala Tyr
    50                  55                  60

Asn His Ser Met Arg Val Phe Tyr Trp Gly Ser Ile Ile Ala Lys Arg
65                  70                  75                  80

Leu Leu Pro Lys His Ala Glu Ala Leu Ser Pro Ser Thr Trp Ala Leu
                85                  90                  95

Thr Cys Leu Leu His Asp Ile Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125

Leu Lys Val Leu Gly Ser Ser Asp Asp Gln Ala Glu Ala Val Ala Glu
    130                 135                 140

Ala Ile Ile Arg His Glu Asp Met Gly Val Asp Gly Ser Ile Thr Phe
145                 150                 155                 160

Leu Gly Gln Leu Ile Gln Leu Ala Thr Leu Tyr Asp Asn Val Gly Thr
                165                 170                 175

Tyr Glu Gly Ile Asp Asp Phe Gly Gly Trp Ile Asp Glu Ala Thr Arg
            180                 185                 190

Asp Asn Val Asn Lys Ala Ile Pro Arg His Gly Trp Cys Ser Trp Phe
        195                 200                 205

Ala Cys Thr Val Arg Lys Glu Glu Ser Asn Lys Pro Trp Cys His Thr
    210                 215                 220
```

Thr His Ile Pro Gln Phe Asp Lys Gln Met Glu Ala Asn Thr Leu Met
225                 230                 235                 240

Lys Gln Trp Glu

<210> SEQ ID NO 23
<211> LENGTH: 735
<212> TYPE: DNA
<213> ORGANISM: Fusarium oxysporum

<400> SEQUENCE: 23

```
atgttgccca ccgaagtcga ggccaacggc tggactgccg tgcctgtcag cgccaaggca    60
atcaaggact cggtcggaca gcttgtaccc acgcaaacct acactctcca agacatcgtt   120
ttcccctctg aggacaaact tgtgtctgaa gctcaagcct tgtcaaggc acggctaagt    180
caagaagctt ataaccactc tatgcgagtt ttctactggg gatccattat tgccaagcgt   240
ttgctaccca agcacgcaga ggccctgtcc ccgtccacct gggcgctgac atgtcttttg   300
catgatatcg gtactgctga gcttacttc acttcaactc gcatgtcttt tgatatctat   360
ggtggaatca aggcaatgga ggtgctcaaa gtcctcggta gcagcgacga tcaggccgag   420
gcagtcgcag aggctatcat ccgtcatgaa gacatgggcg tggacggttc gattactttc   480
ctaggccagt taattcagct tgctacgctg tatgacaacg ttgggacgta cgagggcatt   540
gacgattttg gcggctggat tgacgaagct actcgggata tgtcaacaa agctattcct   600
cgtcacggtt ggtgctcctg gtttgcctgt actgtccgca aggaggaatc caacaagcct   660
tggtgccata ctacccatat tcctcaattt gataagcaga tggaggcaaa cactttgatg   720
aaacagtggg agtag                                                   735
```

<210> SEQ ID NO 24
<211> LENGTH: 245
<212> TYPE: PRT
<213> ORGANISM: Fusarium pseudograminearum

<400> SEQUENCE: 24

Met Ser Ser Pro Glu Val Lys Ile Asn Gly Trp Thr Ala Val Pro Leu
1               5                   10                  15

Asn Ala Lys Asn Ile Leu Asp Ser Val Gly Lys Leu Ala Glu Val Pro
                20                  25                  30

Thr Tyr Lys Ala Glu Asp Ile Lys Phe Pro Ser Asn Asp Lys Leu Val
            35                  40                  45

Ala Glu Ala Gln Ala Phe Val Lys Ala Arg Leu Ser Pro Glu Ala Tyr
        50                  55                  60

Asn His Ser Met Arg Val Phe Tyr Trp Gly Asn Ile Leu Ala Lys Arg
65                  70                  75                  80

Leu Leu Pro Glu His Phe Glu Ala Leu Ser Thr Ser Thr Trp Ala Leu
                85                  90                  95

Thr Cys Leu Leu His Asp Ile Gly Thr Ala Asp Ala Phe Phe Thr Ser
            100                 105                 110

Thr His Met Ser Phe Asp Leu Tyr Gly Gly Ile Lys Ala Met Glu Val
        115                 120                 125

Leu Lys Val Leu Gly Gly Thr Thr Asp Gln Ala Glu Ala Val Ala Glu
    130                 135                 140

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
                165                 170                 175

Tyr Glu Gly Ile Glu Asp Tyr Gly Ser Trp Val Asp Glu Val Thr Arg
            180                 185                 190

Asp Asn Ile Asn Arg Glu Phe Pro Arg His Lys Trp Ala Ser Cys Phe
        195                 200                 205

Ala Ser Val Ile Arg Gln Glu Glu Ser Asn Lys Pro Trp Cys His Ser
    210                 215                 220

Thr His Ile Val Gly Phe Pro Glu Lys Leu Glu Ala Asn Thr Leu Met
225                 230                 235                 240

Lys Pro Trp Glu Glu
                245

<210> SEQ ID NO 25
<211> LENGTH: 738
<212> TYPE: DNA
<213> ORGANISM: Fusarium pseudograminearum

<400> SEQUENCE: 25
atgtcttcac ctgaagtcaa gattaacggt tggactgctg tccccctcaa cgccaagaac      60
attctcgatt ctgtaggaaa actcgcagaa gttcccacct acaaggcaga ggatattaaa     120
ttcccatcaa atgacaagct cgtcgccgaa gcccaggcct ttgtcaaggc gcgactgagc     180
ccagaagcgt ataatcactc catgagagta ttttactggg gaaacattct gcaaagcgt     240 ttgctgcccg agcattttga agctttgtcc acgtctacct gggcactcac ctgtctctta     300
cacgacatag gaacggccga tgccttcttc acctccacgc acatgtcgtt cgatctctat     360
ggcggcataa aggctatgga agtgctcaag gtgctcggcg gtactaccga ccaagctgaa     420
gctgtcgccg aggccatcat acgtcatcag gatgtgggcg tggacggcac catcactttt     480
cttgggcagc tgattcaact tgccacactt tacgacaacg tcggcgttta tgagggcatt     540
gaggactatg gcagttgggt tgatgaggtc actcgcgata atatcaatag gaatttcct     600 cggcacaagt gggcatcttg ctttgcttct gtcattcgtc aggaggagtc caacaaaccc     660
tggtgccatt ctacacatat tgtaggcttt cctgaaaagc ttgaggccaa cactcttatg     720
aagccttggg aggagtag                                                    738

<210> SEQ ID NO 26
<211> LENGTH: 245
<212> TYPE: PRT
<213> ORGANISM: Fusarium graminearum

<400> SEQUENCE: 26

Met Ser Ser Pro Glu Ala Lys Thr Asn Gly Trp Thr Ala Val Pro Leu
1               5                   10                  15

Asn Ala Lys Asn Ile Leu Asp Thr Val Gly Lys Leu Ala Glu Val Pro
20 25 30

Thr Tyr Lys Ala Glu Asp Ile Gln Phe Pro Ser Asp Asp Lys Leu Val
35 40 45

Ala Glu Ala Gln Ala Phe Ala Lys Ala Arg Leu Ser Pro Glu Ala Tyr
50 55 60

Asn His Ser Met Arg Val Phe Tyr Trp Gly Asn Ile Leu Ala Lys Arg
65 70 75 80

Leu Leu Pro Glu His Phe Gly Ala Leu Ser Thr Ser Thr Trp Ala Leu
85 90 95

Thr Cys Leu Leu His Asp Ile Gly Thr Ala Asp Val Phe Phe Thr Ser
100 105 110

Thr His Met Ser Phe Asp Leu Tyr Gly Gly Ile Lys Ala Met Glu Val
         115                 120                 125

Leu Lys Val Leu Gly Gly Thr Thr Asp Gln Ala Glu Ala Val Ala Glu
     130                 135                 140

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
                 165                 170                 175

Tyr Glu Gly Ile Gln Asp Tyr Gly Ser Trp Val Asp Glu Ala Thr Arg
             180                 185                 190

Asp Asn Ile Asn Arg Ala Phe Pro Arg His Lys Trp Thr Ser Cys Phe
         195                 200                 205

Ala Ser Val Ile Arg Gln Glu Glu Ser Asn Lys Pro Trp Cys His Ser
     210                 215                 220

Thr His Ile Val Asp Phe Pro Glu Lys Leu Glu Ala Asn Thr Leu Met
225                 230                 235                 240

Lys Pro Trp Glu Glu
             245

<210> SEQ ID NO 27
<211> LENGTH: 738
<212> TYPE: DNA
<213> ORGANISM: Fusarium graminearum

<400> SEQUENCE: 27
atgtcttcac ctgaagccaa aactaacggt tggactgctg tccccctcaa cgctaagaat      60
attctcgaca ctgtaggaaa gctcgcagaa gttcccacct acaaggcaga ggatattcaa     120
tttccatcag acgacaagct agtcgccgaa gcccaagccc ttgccaaggc acgactaagc     180
cctgaagcct ataatcactc catgcgagta ttttactggg aaacattctc tgcaaagcgt     240
ttgctgccag agcattttgg agctttgtcc acgtctacct gggcactcac ctgtctctta     300
cacgacatag gaacggccga tgtcttcttc acatccacac acatgtcgtt cgatctctat     360
ggcggcataa aggctatgga agtgctcaag gtgctcggtg gtaccaccga ccaagctgaa     420
gctgtcgccg aggccatcat acgtcatcag gatgtgggcg tggacggcac catcactttt     480
cttgggcagc tgattcaact tgccacactt tatgataacg tcggcgttta tgagggcatt     540
caagactatg gcagttgggt tgatgaggcc actcgcgata tatcaatag ggcatttcct     600 cgacacaagt ggacgtcttg ctttgcttcc gtcattcgtc aggaggagtc aacaaaccc      660 tggtgccatt ctacacatat tgtggacttt cctgaaaagc ttgaggccaa cactcttatg     720
aagccttggg aggagtag                                                   738

<210> SEQ ID NO 28
<211> LENGTH: 244
<212> TYPE: PRT
<213> ORGANISM: Aspergillus kawachii

<400> SEQUENCE: 28

Met Cys Asn Asp Glu Ile Lys Ala Asn Gly Trp Ser Ser Met Pro Ala
1               5                   10                  15

Asn Ala Gly Ala Ile Phe Thr Asp Gln Ser Phe Ile Glu Arg Ala Glu
             20                  25                  30

Ala Met Gln Leu Asp Thr Ile Ile Phe Pro Phe Asp Asp Pro Val Val
         35                  40                  45

Ser Lys Thr Trp Glu Tyr Ala Arg Ala Val Leu His Pro Gln Thr Leu

```
                50                  55                  60
Asn His Ser Met Arg Val Tyr Phe Tyr Gly Met Val Ile Thr Thr Gln
 65                  70                  75                  80

Gln Phe Pro Glu Ile Ala Ala Ser Leu Asn Pro Val Thr Trp Ala Leu
                 85                  90                  95

Thr Cys Leu Leu His Asp Ile Gly Thr Ala Glu Glu Asn Leu Thr Ala
            100                 105                 110

Thr Arg Met Ser Phe Asp Ile Tyr Gly Gly Ile Lys Ala Leu His Val
             115                 120                 125

Leu Lys Glu Phe Gly Ala Thr Ala Asp Gln Ala Glu Ala Val Ala Glu
130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Val
                165                 170                 175

His Pro His Val Lys Ser Phe Glu Gly Leu Val His Gln Thr Thr Arg
            180                 185                 190

Lys Gln Ile Asn Glu Ala Tyr Pro Arg Leu Lys Trp Cys Glu Phe Phe
            195                 200                 205

Ser Gly Met Ile Arg Lys Glu Thr Ile Lys Pro Trp Cys His Ser
210                 215                 220

Thr His Leu Val Asp Phe Asp Arg Glu Ile Glu Asn Thr Leu Met
225                 230                 235                 240

Arg Glu Trp Glu

<210> SEQ ID NO 29
<211> LENGTH: 735
<212> TYPE: DNA
<213> ORGANISM: Aspergillus kawachii

<400> SEQUENCE: 29
atgtgcaacg acgaaataaa agccaacggc tggtccagca tgcccgccaa tgccggtgcc      60
atatttacgg accaatcctt catcgaaagg gcagaagcca tgcagctcga tacaatcata     120
ttccccttcg acgatcctgt cgtttcaaag acctgggaat acgccagggc tgttcttcac     180
ccccagacat tgaaccattc catgagggtc tacttctacg gaatggtaat caccacccag     240
caattccctg aaatagcagc atccctcaac ccagtcacct gggctctgac ctgcctcctc     300
cacgacatcg gtactgcgga ggagaaccta actgcaacgc gcatgtcatt cgatatctat     360
ggcggtatca aggccctcca tgtgctgaag gagtttggtg ccactgcgga ccaggccgag     420
gccgttgctg aggcgatcat tcgacatgag gatatgggcg tcgatggaac tattacatat     480
ttcggtcagc ttattcagtt ggctactaca tatgataata ccggagttca tccgcatgtg     540
aagagttttg agggcttggt gcatcagaca actcgcaaac agatcaatga ggcgtatccg     600
cggttgaagt ggtgtgaatt tttctcgggg atgattagga aggaagagac gatcaagcct     660
tggtgtcatt cgacccattt ggtggacttt gacagggaga tagaagagaa tacgcttatg     720
agggagtggg agtaa                                                     735

<210> SEQ ID NO 30
<211> LENGTH: 244
<212> TYPE: PRT
<213> ORGANISM: Aspergillus niger

<400> SEQUENCE: 30
```

| Met | Cys | His | Asp | Glu | Ile | Lys | Ala | Asn | Gly | Trp | Ser | Ser | Thr | Pro | Ala |
|---|---|---|---|---|---|---|---|---|---|---|---|---|---|---|---|
| 1 | | | | 5 | | | | | 10 | | | | | 15 | |

Asn Ala Gly Ala Ile Phe Thr Asp Gln Ser Phe Ile Glu Arg Ala Glu
              20                  25                  30

Ala Val Glu Leu Asp Thr Ile Gln Phe Pro Phe Asp Asp Pro Val Val
          35                  40                  45

Ser Lys Thr Leu Glu Tyr Val Lys Ala Val Leu His Pro Glu Thr Leu
    50                  55                  60

Asn His Ser Met Arg Val Tyr Tyr Gly Met Val Ile Thr Thr Gln
65                  70                  75                  80

Gln Phe Pro Glu Gln Ala Ala Ser Ile Asn Pro Val Thr Trp Ala Leu
                    85                  90                  95

Thr Cys Leu Leu His Asp Leu Gly Thr Ala Glu Glu Asn Leu Thr Ala
                100                 105                 110

Thr Arg Met Ser Phe Asp Ile Tyr Gly Gly Ile Lys Ala Leu His Val
            115                 120                 125

Leu Lys Glu Phe Gly Ala Thr Ala Asp Gln Ala Glu Ala Ala Ala Glu
    130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Ile
                165                 170                 175

His Pro His Val Lys Gly Phe Glu Gly Leu Val His Arg Thr Thr Arg
                180                 185                 190

Lys Gln Ile Asn Glu Ala Tyr Pro Arg Leu Lys Trp Cys Ala Phe Phe
            195                 200                 205

Ser Gly Leu Ile Arg Lys Glu Glu Thr Ile Lys Pro Trp Cys His Ser
    210                 215                 220

Thr His Leu Val Asp Phe Asp Lys Glu Ile Glu Glu Asn Thr Leu Met
225                 230                 235                 240

Arg Glu Trp Glu

<210> SEQ ID NO 31
<211> LENGTH: 735
<212> TYPE: DNA
<213> ORGANISM: Aspergillus niger

<400> SEQUENCE: 31

```
atgtgccacg acgaaatcaa agccaacggc tggtccagca ctcccgccaa tgccggtgcc      60
atatttacgg accaatcctt cattgaaagg gcagaagccg tggagctcga tacgatccag     120
ttccccttg acgaccctgt agtctcgaag acattggaat atgtcaaggc tgttcttcac     180
cccgagactt tgaatcattc catgagggtt tactattacg gaatggtaat caccacccaa     240
caattccccg aacaagcagc atccataaac ccagtgacct gggctctgac ttgtctcctc     300
cacgacctcg gaaccgcgga ggagaacctc accgcaacgc gcatgtcatt cgatatctac     360
ggcggcatca aagccctcca tgtgctgaag gagtttggtg ccactgcgga ccaggccgaa     420
gcagcagctg aggcaatcat tcgacatgaa gatatgggag tcgatggaac gattacctac     480
ttcggtcagc ttattcagct ggctacgacg tatgataata ccggattca tccgcatgtg     540
aagggctttg aggggttggt ccatcgcacg actcgcaagc agattaatga ggcgtatccg     600
cggttgaagt ggtgtgcgtt tttctccggg ttgattagaa aggaggagac gattaagcct     660
tggtgtcatt cgactcattt ggtggatttt gataaggaga tcgaggagaa tacgcttatg     720
```

```
agggagtggg agtaa                                                      735
```

<210> SEQ ID NO 32
<211> LENGTH: 241
<212> TYPE: PRT
<213> ORGANISM: Aspergillus niger

<400> SEQUENCE: 32

| Met | Cys | His | Asp | Lys | Ile | Pro | Leu | Asn | Gly | Trp | Thr | Ser | Thr | Pro | Ala |
|---|---|---|---|---|---|---|---|---|---|---|---|---|---|---|---|
| 1 | | | | 5 | | | | | 10 | | | | | 15 | |

| Asn | Ala | Gly | Ala | Ile | Phe | Pro | Asp | Lys | Pro | Phe | Ile | His | Pro | Pro | Thr |
|---|---|---|---|---|---|---|---|---|---|---|---|---|---|---|---|
| | | | 20 | | | | | 25 | | | | | 30 | | |

| Pro | Ile | Ser | Ile | Thr | Asp | Ile | Pro | Phe | Pro | Ser | Thr | Asp | Pro | Leu | Val |
|---|---|---|---|---|---|---|---|---|---|---|---|---|---|---|---|
| | | | 35 | | | | | 40 | | | | 45 | | | |

| Ala | Lys | Thr | Leu | Glu | Tyr | Val | Gln | Ser | Leu | Leu | Pro | Arg | Glu | Thr | Val |
|---|---|---|---|---|---|---|---|---|---|---|---|---|---|---|---|
| | 50 | | | | | 55 | | | | | 60 | | | | |

| Asn | His | Ser | Met | Arg | Val | Tyr | Ser | Tyr | Gly | Met | Ile | Leu | Leu | Thr | Gln |
|---|---|---|---|---|---|---|---|---|---|---|---|---|---|---|---|
| 65 | | | | | 70 | | | | | 75 | | | | | 80 |

| Gln | Phe | Pro | Ser | His | His | Leu | Ser | Pro | Thr | Thr | Trp | Ala | Leu | Thr | Cys |
|---|---|---|---|---|---|---|---|---|---|---|---|---|---|---|---|
| | | | | 85 | | | | | 90 | | | | | 95 | |

| Leu | Leu | His | Asp | Ile | Gly | Thr | Ala | Pro | Ser | Leu | Leu | Thr | Ser | Thr | Asn |
|---|---|---|---|---|---|---|---|---|---|---|---|---|---|---|---|
| | | | 100 | | | | | 105 | | | | | 110 | | |

| Met | Ser | Phe | Asp | Leu | Tyr | Gly | Gly | Ile | Lys | Ala | His | Ser | Val | Leu | Thr |
|---|---|---|---|---|---|---|---|---|---|---|---|---|---|---|---|
| | | 115 | | | | | 120 | | | | | 125 | | | |

| Ser | Phe | Asp | Cys | Pro | Ala | Asp | Val | Ala | Asp | Ala | Val | Ala | Glu | Ala | Ile |
|---|---|---|---|---|---|---|---|---|---|---|---|---|---|---|---|
| 130 | | | | | 135 | | | | | 140 | | | | | |

| Ile | Arg | His | Gln | Asp | Leu | Gly | Val | Asp | Gly | Asn | Ile | Thr | Phe | Leu | Gly |
|---|---|---|---|---|---|---|---|---|---|---|---|---|---|---|---|
| 145 | | | | | 150 | | | | | 155 | | | | | 160 |

| Gln | Leu | Ile | Gln | Leu | Ala | Thr | Ile | Tyr | Asp | Asn | Val | Gly | Glu | His | Pro |
|---|---|---|---|---|---|---|---|---|---|---|---|---|---|---|---|
| | | | | 165 | | | | | 170 | | | | | 175 | |

| His | Val | Lys | Asp | Phe | Gly | Gly | Leu | Ile | His | Glu | Asp | Ala | Arg | Arg | Glu |
|---|---|---|---|---|---|---|---|---|---|---|---|---|---|---|---|
| | | | 180 | | | | | 185 | | | | | 190 | | |

| Val | Asn | Glu | Arg | Trp | Arg | Arg | Glu | Gly | Trp | Cys | Gly | Val | Phe | Ala | Asp |
|---|---|---|---|---|---|---|---|---|---|---|---|---|---|---|---|
| | | 195 | | | | | 200 | | | | | 205 | | | |

| Val | Val | Lys | Leu | Glu | Val | Gly | Arg | Lys | Pro | Trp | Cys | His | Ser | Thr | His |
|---|---|---|---|---|---|---|---|---|---|---|---|---|---|---|---|
| | 210 | | | | | 215 | | | | | 220 | | | | |

| Ile | Val | Gly | Phe | Glu | Gly | Lys | Val | Arg | Gly | Asn | Ala | Leu | Phe | Gly | Glu |
|---|---|---|---|---|---|---|---|---|---|---|---|---|---|---|---|
| 225 | | | | | 230 | | | | | 235 | | | | | 240 |

Lys

<210> SEQ ID NO 33
<211> LENGTH: 726
<212> TYPE: DNA
<213> ORGANISM: Aspergillus niger

<400> SEQUENCE: 33

```
atgtgccacg acaagatccc cctcaacggc tggaccagca cccccgccaa cgctggtgcc     60
atcttccccg acaagccctt catccaccca cccacgccca tctccatcac cgacatcccc    120
ttcccctcca ccgatcccct cgtcgccaag accctcgaat acgtccaatc cctcctcccc    180
cgcgagaccg tcaaccactc catgcgcgta tactcctacg gaatgatcct cctcacccag    240
caattccctt cccaccatct atctccaaca acctgggccc taacctgcct tctgcatgac    300
atcggcaccg cccctccct cctcacctca acaaacatgt cctttgacct ctacggcggc    360
atcaaagccc actccgtact tacttccttc gactgtcccg ctgatgttgc tgacgccgta    420
```

```
gcggaagcta ttatccggca tcaggatcta ggcgtggatg ggaatatcac gttcctggga      480
cagttgatcc agctggctac catttatgat aatgtggggg aacatccgca cgtcaaggac      540
tttggagggt tgattcatga ggatgcgagg agggaggtta atgagcgctg agaagggag       600 ggatggtgtg gggtgtttgc tgatgtggtg aagttggagg tggggaggaa gccgtggtgt      660
cattcgacgc atattgtggg gtttgagggg aaggttaggg ggaatgcgct ttttggggag      720
aaatag                                                                 726
```

<210> SEQ ID NO 34
<211> LENGTH: 242
<212> TYPE: PRT
<213> ORGANISM: Aspergillus oryzae

<400> SEQUENCE: 34

```
Met Ser Pro Thr Arg Ala Ala Gln Val Glu Glu Tyr Gly Trp Thr Ala
1               5                   10                  15

Val Ser Cys Asp Pro Gln Gln Arg Ala Ala Thr Asn Pro Pro Thr Lys
            20                  25                  30

Pro Ser Val Pro Gln Leu Val Lys Asp Thr Thr Leu Pro Asp Thr Pro
        35                  40                  45

Leu Val Lys Asp Ala Met Glu Tyr Val Lys Ala Glu Leu Pro Ala His
    50                  55                  60

Thr Phe Asn His Ser Met Arg Val Tyr Tyr Gly Leu Ala Ile Ala
65                  70                  75                  80

Arg Gln His Phe Pro Glu Trp Lys Phe Ser Asp Glu Thr Trp Leu Leu
                85                  90                  95

Thr Cys Leu Phe His Asp Ile Gly Thr Ile Asp Lys Tyr Thr Gln Asp
            100                 105                 110

Val Phe Met Ser Phe Asp Ile Tyr Gly Gly Ile Val Ala Leu Asn Val
        115                 120                 125

Leu Thr Glu Lys Gly Ala Pro Ala Pro Gln Ala Glu Ser Val Ala Glu
    130                 135                 140

Ala Ile Ile Arg His Gln Asp Pro Val Lys Val Gly Thr Ile His Ser
145                 150                 155                 160

Val Gly Leu Leu Ile Gln Leu Ala Thr Gln Phe Asp Asn Leu Gly Ala
                165                 170                 175

His Lys Glu Tyr Val His Pro Asp Thr Val Glu Asp Val Asn Gln His
            180                 185                 190

Tyr Pro Arg Arg Gln Trp Ser Lys Cys Phe Ser Ser Lys Leu Arg Glu
        195                 200                 205

Glu Ile Gly Leu Lys Pro Trp Cys His Thr Thr Ala Glu Gly Glu Gly
    210                 215                 220

Phe Pro Val Gly Ile Glu Asn Asn Thr Leu Met Glu Pro Tyr Asp Gly
225                 230                 235                 240

Arg Phe
```

<210> SEQ ID NO 35
<211> LENGTH: 729
<212> TYPE: DNA
<213> ORGANISM: Aspergillus oryzae

<400> SEQUENCE: 35

```
atgtcaccca ccagagcagc tcaagtcgaa gaatacggtt ggacagcggt gtcctgcgat      60
cctcagcagc gagctgctac aaacccacct accaagcctt ctgttcccca gttggtcaaa     120
```

```
gatacaactc ttcccgatac tcctctagtc aaagatgcca tggaatatgt taaggcagag    180
ctacccgctc acactttaa ccacagcatg cgtgtctact attatggcct tgcaatcgcc    240
agacaacact tcccagaatg gaagttcagc gatgaaacct ggcttctcac ctgcctcttc    300
cacgacatcg gcactatcga caagtacacc caagacgtct ttatgtcctt cgatatctac    360
ggtggaattg tcgctctgaa cgtcctcacg gagaaaggtg cgccagcacc ccaggctgaa    420
agtgtcgcag aagccatcat ccgtcatcag gatccggtga agttgggac tattcattct     480 gtcggtttac ttattcagct tgctacgcag tttgacaacc ttggtgccca aaggagtat    540 gtccaccctg atactgtgga agatgtgaac cagcattatc cgcgtcgtca gtggtcgaag    600
tgcttctcga gtaagctgag ggaggaaatt gggctcaagc cttggtgcca tactactgcg    660
gagggcgagg ggttccctgt tgggatcgag aacaacactt tgatggagcc ttatgatgga    720
cgcttctag                                                           729
```

<210> SEQ ID NO 36
<211> LENGTH: 243
<212> TYPE: PRT
<213> ORGANISM: Saccharomyces cerevisiae

<400> SEQUENCE: 36

Met Lys Leu Leu Arg Thr Val Phe Leu Pro Cys Ser Ser Lys Glu
1               5                   10                  15

Ser Ile Met Ser Gln Tyr Gly Phe Val Arg Val Pro Arg Glu Val Glu
            20                  25                  30

Lys Ala Ile Pro Val Val Asn Ala Ser Arg Pro Arg Ala Val Val Pro
        35                  40                  45

Pro Pro Asn Ser Glu Thr Ala Arg Leu Val Arg Glu Tyr Ala Ala Lys
    50                  55                  60

Glu Leu Thr Ala Pro Val Leu Asn His Ser Leu Arg Val Phe Gln Tyr
65                  70                  75                  80

Ser Leu Ala Ile Ile Arg Asp Gln Phe Pro Ala Trp Asp Leu Asp Gln
                85                  90                  95

Glu Val Leu Tyr Val Thr Cys Leu Leu His Asp Ile Ala Thr Thr Asp
            100                 105                 110

Lys Asn Met Arg Ala Thr Lys Met Ser Phe Glu Tyr Tyr Gly Gly Ile
        115                 120                 125

Leu Ser Arg Glu Leu Val Phe Asn Ala Thr Gly Gly Asn Gln Asp Tyr
    130                 135                 140

Ala Asp Ala Val Thr Glu Ala Ile Ile Arg His Gln Asp Leu Thr Gly
145                 150                 155                 160

Thr Gly Tyr Ile Thr Thr Leu Gly Leu Ile Leu Gln Ile Ala Thr Thr
                165                 170                 175

Leu Asp Asn Val Gly Ser Asn Thr Asp Leu Ile His Ile Asp Thr Val
            180                 185                 190

Arg Ala Ile Asn Glu Gln Phe Pro Arg Leu His Trp Leu Ser Cys Phe
        195                 200                 205

Ala Thr Val Val Asn Thr Glu Asn Ser Arg Lys Pro Trp Gly His Thr
    210                 215                 220

Ser Ser Leu Gly Asp Asp Phe Ser Lys Lys Val Ile Cys Asn Thr Phe
225                 230                 235                 240

Gly Tyr Asn

<210> SEQ ID NO 37

<211> LENGTH: 732
<212> TYPE: DNA
<213> ORGANISM: Saccharomyces cerevisiae

<400> SEQUENCE: 37

```
ttagttatac ccaaatgtat tgcatatgac tttctttgaa aaatcatcac ccaaagaact    60
ggtgtggccc cacggttttc tcgagttttc agtgttcacc accgtagcaa acatgataa   120
ccagtgcagt cttggaaatt gctcattaat ggctctaact gtatcgatat gaatcagatc   180
ggtattggat ccgacattgt caagcgtagt agcaatctgc agaatgagcc ccaaggtggt   240
aatgtagcca gtcccagtca atcctggtg acgaatgatg gcctcagtta ctgcatctgc   300
atagtcctga tttccacctg tcgcattaaa tacaagctcc cttgaaagta tgccaccata   360
atactcaaat gacatcttcg tggctctcat attcttatct gttgttgcaa tatcatgaag   420
taagcaggtg acgtacaaaa cttcctgatc caagtcccat gctggaaatt ggtctcttat   480
gatagctaaa ctatattgaa aaacacgcaa agagtggttt agaacggggg cagtcaattc   540
tttagcggca tattcccgaa caagcctagc agtttcactg tttggaggcg aacaacggc   600
ccgtggtcta gatgcattca ccactggaat ggccttttct acctctctag gaactcttac   660
aaatccgtac tgtgacatga ttgattcttt tgaagaggag caaggcaaaa aacagtacg   720
aagcaacttc at                                                      732
```

<210> SEQ ID NO 38
<211> LENGTH: 390
<212> TYPE: PRT
<213> ORGANISM: Rhodococcus sp.

<400> SEQUENCE: 38

```
Met Arg Glu Val Gln Leu Leu Asp Gly Arg Arg Val Asp Val Ala Cys
  1               5                  10                  15

Ala Gly Pro Leu Ile Ser Glu Ile Gly Ala His Leu Asp Leu Thr Ala
             20                  25                  30

Pro Val Glu Ile Asp Cys Gly Gly Gly Leu Ala Thr Arg Pro Phe Thr
         35                  40                  45

Glu Pro His Leu His Leu Asp Lys Ala Gly Thr Ala Asp Arg Leu Pro
     50                  55                  60

Ala Gly Ala Ser Thr Ile Gly Asp Ala Ile Ala Ala Met Gln Ser Val
 65                  70                  75                  80

Lys Val Thr Glu Arg Asp Asn Val Ala Ala Val Ala Ala Arg Met His
                 85                  90                  95

Arg Val Leu Asn Arg Ile Val Asp Asp Gly Ser His Ala Ile Arg Ala
            100                 105                 110

Leu Val Asp Val Asp Glu Val Trp Gly Leu Thr Ala Phe His Ala Ala
        115                 120                 125

Gln Gln Val Gln Ala Ala Leu Ala Pro Arg Ala Val Val Gln Ile Val
    130                 135                 140

Ala Phe Pro Gln His Gly Leu Thr Pro Gln Val Leu Ala Met Leu Glu
145                 150                 155                 160

Gln Ala Ala Ala Glu Gly Ala Gly Ala Leu Gly Ala His Thr Asp Val
                165                 170                 175

Asp Pro Asp Pro Ala Ala His Val Gly Ala Val Ala Ala Ile Ala Ala
            180                 185                 190

Gly Ala Ser Leu Pro Leu Glu Val His Thr Asp Glu Gly Ala Ser Pro
        195                 200                 205
```

```
Asp Lys Phe Tyr Leu Pro Ala Val Leu Glu Val Leu Asp Arg Phe Pro
    210                 215                 220

Gly Leu Ser Thr Thr Leu Ala His Cys Leu Ser Leu Gly Thr Ile Ala
225                 230                 235                 240

Pro Lys Gln Gln Gln His Trp Ile Glu Glu Leu Ala His Arg Asp Ile
                245                 250                 255

Lys Val Cys Val Ala Pro Ser Ile Leu Gly Phe Gly Leu Pro Leu Ala
            260                 265                 270

Pro Val Arg Ala Leu Ile Glu Ala Gly Val Gly Ile Leu Val Gly Ser
        275                 280                 285

Asp Asn Leu Gln Asp Val Phe Phe Pro Leu Gly Thr Gly Arg Ala Ile
290                 295                 300

Glu Asn Val Arg Leu Leu Ala Thr Ala Ala Gln Leu Thr Ala Pro Glu
305                 310                 315                 320

Leu Ala Gly Pro Leu Ile Ala Gly Val Thr Asp Ile Ala Tyr Ala Thr
                325                 330                 335

Val Thr Gly Ala Ala Asp Ala Leu Ala Val Glu Ser Pro Ala Thr Leu
            340                 345                 350

Val Val His Asp Ala Thr Ser Pro Ala Glu Leu Leu Arg Gly Ile Asp
        355                 360                 365

Gly Thr Arg Ile Thr Val Ile Asp Gly Leu Leu Thr Ser Pro Leu Gln
370                 375                 380

Leu Asp Lys Gly Ile Lys
385                 390

<210> SEQ ID NO 39
<211> LENGTH: 412
<212> TYPE: PRT
<213> ORGANISM: Pseudomonas sp.

<400> SEQUENCE: 39

Met Ser Met Glu Thr His Ser Tyr Val Asp Val Ala Ile Arg Asn Ala
1               5                   10                  15

Arg Leu Ala Asp Thr Glu Gly Ile Val Asp Ile Leu Ile His Asp Gly
            20                  25                  30

Arg Ile Ala Ser Ile Val Lys Ser Thr Lys Thr Lys Gly Ser Val Glu
        35                  40                  45

Ile Asp Ala His Glu Gly Leu Val Thr Ser Gly Leu Val Glu Pro His
    50                  55                  60

Ile His Leu Asp Lys Ala Leu Thr Ala Asp Arg Val Pro Ala Gly Ser
65                  70                  75                  80

Ile Gly Asp Leu Arg Thr Arg Gly Leu Glu Met Ala Ile Arg Ala
                85                  90                  95

Thr Arg Asp Ile Lys Arg Thr Phe Thr Val Glu Asp Val Arg Glu Arg
                100                 105                 110

Ala Ile Arg Ala Ala Leu Met Ala Ser Arg Ala Gly Thr Thr Ala Leu
            115                 120                 125

Arg Thr His Val Asp Val Asp Pro Ile Val Gly Leu Ala Gly Ile Arg
        130                 135                 140

Gly Val Leu Glu Ala Arg Glu Val Cys Ala Gly Leu Ile Asp Ile Gln
145                 150                 155                 160

Ile Val Ala Phe Pro Gln Glu Gly Leu Phe Cys Ser Ala Gly Ala Val
                165                 170                 175

Asp Leu Met Arg Glu Ala Ile Lys Leu Gly Ala Asp Ala Val Gly Gly
            180                 185                 190
```

```
Ala Pro Ala Leu Asp Asp Arg Pro Gln Asp His Val Arg Ala Val Phe
        195                 200                 205

Asp Leu Ala Ala Glu Phe Gly Leu Pro Val Asp Met His Val Asp Glu
    210                 215                 220

Ser Asp Arg Arg Glu Asp Phe Thr Leu Pro Phe Val Ile Glu Ala Ala
225                 230                 235                 240

Arg Glu Arg Arg Val Pro Asn Val Thr Val Ala His Ile Ser Ser Leu
                245                 250                 255

Ser Val Gln Thr Asp Asp Val Ala Arg Ser Thr Ile Ala Ala Leu Ala
            260                 265                 270

Asp Ala Asp Val Asn Val Val Asn Pro Ile Ile Val Lys Ile Thr
        275                 280                 285

Arg Leu Ser Glu Leu Leu Asp Ala Gly Val Ser Val Met Phe Gly Ser
    290                 295                 300

Asp Asn Leu Arg Asp Pro Phe Tyr Pro Leu Gly Ala Ala Asn Pro Leu
305                 310                 315                 320

Gly Ser Ala Ile Phe Ala Cys Gln Ile Ala Ala Leu Gly Thr Pro Gln
                325                 330                 335

Asp Leu Arg Arg Val Phe Asp Ala Val Thr Ile Asn Ala Ala Arg Met
            340                 345                 350

Leu Gly Phe Pro Ser Leu Leu Gly Val Val Glu Gly Ala Val Ala Asp
        355                 360                 365

Leu Ala Val Phe Pro Ser Ala Thr Pro Glu Glu Val Val Leu Asp Gln
    370                 375                 380

Gln Ser Pro Leu Phe Val Leu Lys Gly Gly Arg Val Val Ala Met Arg
385                 390                 395                 400

Leu Ala Ala Gly Ser Thr Ser Phe Arg Asp Tyr Ser
                405                 410

<210> SEQ ID NO 40
<211> LENGTH: 241
<212> TYPE: PRT
<213> ORGANISM: Rhodococcus sp.

<400> SEQUENCE: 40

Met Ile Tyr Ser Thr Val Asn Ala Asn Pro Tyr Ala Trp Pro Tyr Asp
1               5                   10                  15

Gly Ser Ile Asp Pro Ala His Thr Ala Leu Ile Leu Ile Asp Trp Gln
            20                  25                  30

Ile Asp Phe Cys Gly Pro Gly Gly Tyr Val Asp Ser Met Gly Tyr Asp
        35                  40                  45

Leu Ser Leu Thr Arg Ser Gly Leu Glu Pro Thr Ala Arg Val Leu Ala
    50                  55                  60

Ala Ala Arg Asp Thr Gly Met Thr Val Ile His Thr Arg Glu Gly His
65                  70                  75                  80

Arg Pro Asp Leu Ala Asp Leu Pro Pro Asn Lys Arg Trp Arg Ser Ala
                85                  90                  95

Ser Ala Gly Ala Glu Ile Gly Ser Val Gly Pro Cys Gly Arg Ile Leu
            100                 105                 110

Val Arg Gly Glu Pro Gly Trp Glu Ile Val Pro Glu Val Ala Pro Arg
        115                 120                 125

Glu Gly Glu Pro Ile Ile Asp Lys Pro Gly Lys Gly Ala Phe Tyr Ala
    130                 135                 140

Thr Asp Leu Asp Leu Leu Leu Arg Thr Arg Gly Ile Thr His Leu Ile
```

```
            145                 150                 155                 160
Leu Thr Gly Ile Thr Thr Asp Val Cys Val His Thr Thr Met Arg Glu
                165                 170                 175
Ala Asn Asp Arg Gly Tyr Glu Cys Leu Ile Leu Ser Asp Cys Thr Gly
                180                 185                 190
Ala Thr Asp Arg Lys His His Glu Ala Ala Leu Ser Met Val Thr Met
                195                 200                 205
Gln Gly Gly Val Phe Gly Ala Thr Ala His Ser Asp Asp Leu Leu Ala
        210                 215                 220
Ala Leu Gly Thr Thr Val Pro Ala Ala Ala Gly Pro Arg Ala Arg Thr
225                 230                 235                 240
Glu

<210> SEQ ID NO 41
<211> LENGTH: 233
<212> TYPE: PRT
<213> ORGANISM: Rhizobium leguminosarum

<400> SEQUENCE: 41

Met Asp Ala Met Val Glu Thr Asn Arg His Phe Ile Asp Ala Asp Pro
1               5                   10                  15
Tyr Pro Trp Pro Tyr Asn Gly Ala Leu Arg Pro Asp Asn Thr Ala Leu
                20                  25                  30
Ile Ile Ile Asp Met Gln Thr Asp Phe Cys Gly Lys Gly Gly Tyr Val
            35                  40                  45
Asp His Met Gly Tyr Asp Leu Ser Leu Val Gln Ala Pro Ile Glu Pro
        50                  55                  60
Ile Lys Arg Val Leu Ala Ala Met Arg Ala Lys Gly Tyr His Ile Ile
65                  70                  75                  80
His Thr Arg Glu Gly His Arg Pro Asp Leu Ala Asp Leu Pro Ala Asn
                85                  90                  95
Lys Arg Trp Arg Ser Gln Arg Ile Gly Ala Gly Ile Gly Asp Pro Gly
                100                 105                 110
Pro Cys Gly Arg Ile Leu Thr Arg Gly Glu Pro Gly Trp Asp Ile Ile
            115                 120                 125
Pro Glu Leu Tyr Pro Ile Glu Gly Glu Thr Ile Ile Asp Lys Pro Gly
        130                 135                 140
Lys Gly Ser Phe Cys Ala Thr Asp Leu Glu Leu Val Leu Asn Gln Lys
145                 150                 155                 160
Arg Ile Glu Asn Ile Ile Leu Thr Gly Ile Thr Thr Asp Val Cys Val
                165                 170                 175
Ser Thr Thr Met Arg Glu Ala Asn Asp Arg Gly Tyr Glu Cys Leu Leu
                180                 185                 190
Leu Glu Asp Cys Cys Gly Ala Thr Asp Tyr Gly Asn His Leu Ala Ala
            195                 200                 205
Ile Lys Met Val Lys Met Gln Gly Gly Val Phe Gly Ser Val Ser Asn
        210                 215                 220
Ser Ala Ala Leu Val Glu Ala Leu Pro
225                 230

<210> SEQ ID NO 42
<211> LENGTH: 4268
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 42

```
gtttgtggaa gcggtattcg caatttaatt aagtttaaac ggcgcgcctt tccataggct      60
ccgcccccct gacgagcatc acaaaaatcg acgctcaagt cagaggtggc gaaacccgac     120
aggactataa agataccagg cgtttccccc tggaagctcc ctcgtgcgct ctcctgttcc     180
gaccctgccg cttaccggat acctgtccgc ctttctccct cgggaagcg tggcgctttc      240
tcatagctca cgctgtaggt atctcagttc ggtgtaggtc gttcgctcca agctgggctg     300
tgtgcacgaa ccccccgttc agcccgaccg ctgcgcctta ccggtaact atcgtcttga      360
gtccaacccg gtaagacacg acttatcgcc actggcagca gccactggta acaggattag     420
cagagcgagg tatgtaggcg gtgctacaga gttcttgaag tggtggccta actacggcta     480
cactagaaga acagtatttg gtatctgcgc tctgctgaag ccagttacct cggaaaaag      540
agttggtagc tcttgatccg gcaaacaaac caccgctggt agcggtggtt ttttgtttg      600
caagcagcag attacgcgca gaaaaaagg atctcaagaa gatcctttga tcttttctac      660
ggggtctgac gctcagtgga acgaaaactc acgttaaggg attttggtca tgagattatc     720
aaaaaggatc ttcacctaga tcctttttaaa ttaaaaatga agttttaaat caatctaaag    780
tatatatgag taaacttggt ctgacagtta ccaatgctta atcagtgagg cacctatctc     840
agcgatctgt ctatttcgtt catccatagt tgcctgactc ccgtcgtgt agataactac      900
gatacgggag ggcttaccat ctggccccag tgctgcaatg ataccgcgag acccacgctc     960
accggctcca gatttatcag caataaacca gccagccgga agggccgagc gcagaagtgg    1020
tcctgcaact ttatccgcct ccatccagtc tattaattgt tgccgggaag ctagagtaag    1080
tagttcgcca gttaatagtt tgcgcaacgt tgttgccatt gctacaggca tcgtggtgtc    1140
acgctcgtcg tttggtatgg cttcattcag ctccggttcc caacgatcaa ggcgagttac    1200
atgatccccc atgttgtgca aaaaagcggt tagctccttc ggtcctccga tcgttgtcag    1260
aagtaagttg gccgcagtgt tatcactcat ggttatggca gcactgcata attctcttac    1320
tgtcatgcca tccgtaagat gcttttctgt gactggtgag tactcaacca agtcattctg    1380
agaatagtgt atgcggcgac cgagttgctc ttgcccggcg tcaatacggg ataataccgc    1440
gccacatagc agaactttaa aagtgctcat cattggaaaa cgttcttcgg ggcgaaaact    1500
ctcaaggatc ttaccgctgt tgagatccag ttcgatgtaa cccactcgtg cacccaactg    1560
atcttcagca tcttttactt tcaccagcgt ttctgggtga gcaaaaacag gaaggcaaaa    1620
tgccgcaaaa aagggaataa gggcgacacg gaaatgttga atactcatac tcttcctttt    1680
tcaatattat tgaagcattt atcagggtta ttgtctcatg agcggataca tatttgaatg    1740
tatttagaaa aataaacagc gatcgcgcgg ccgcgggtaa taactgatat aattaaattg    1800
aagctctaat ttgtgagttt agtatacatg catttactta taatacagtt ttttagtttt    1860
gctggccgca tcttctcaaa tatgcttccc agcctgcttt tctgtaacgt tcaccctcta    1920
ccttagcatc ccttcccttt gcaaatagtc ctcttccaac aataataatg tcagatcctg    1980
tagagaccac atcatccacg gttctatact gttgacccaa tgcgtctccc ttgtcatcta    2040
aacccacacc gggtgtcata atcaaccaat cgtaaccttc atctcttcca cccatgtctc    2100
tttgagcaat aaagccgata acaaaatctt tgtcgctctt cgcaatgtca acagtaccct    2160
tagtatattc tccagtagct agggagccct tgcatgacaa ttctgctaac atcaaaaggc    2220
ctctaggttc ctttgttact tcttccgccg cctgcttcaa accgctaaca atacctgggc    2280
```

```
ccaccacacc gtgtgcattc gtaatgtctg cccattctgc tattctgtat acacccgcag    2340
agtactgcaa tttgactgta ttaccaatgt cagcaaattt tctgtcttcg aagagtaaaa    2400
aattgtactt ggcggataat gcctttagcg gcttaactgt gccctccatg gaaaaatcag    2460
tcaagatatc cacatgtgtt tttagtaaac aaatttgggg acctaatgct caactaact     2520 ccagtaattc cttggtggta cgaacatcca atgaagcaca caagtttgtt tgcttttcgt    2580
gcatgatatt aaatagcttg gcagcaacag gactaggatg agtagcagca cgttccttat    2640
atgtagcttt cgacatgatt tatcttcgtt tcctgcaggt ttttgttctg tgcagttggg    2700
ttaagaatac tgggcaattt catgtttctt caacaccaca tatgcgtata tataccaatc    2760
taagtctgtg ctccttcctt cgttcttcct tctgctcgga gattaccgaa tcaaagctag    2820
cttatcgatg ataagctgtc aaagatgaga attaattcca cggactatag actatactag    2880
atactccgtc tactgtacga tacacttccg ctcaggtcct tgtcctttaa cgaggcctta    2940
ccactctttt gttactctat tgatccagct cagcaaaggc agtgtgatct aagattctat    3000
cttcgcgatg tagtaaaact agctagaccg agaaagagac tagaaatgca aaaggcactt    3060
ctacaatggc tgccatcatt attatccgat gtgacgctgc agcttctcaa tgatattcga    3120
atacgctttg aggagataca gcctaatatc cgacaaactg ttttacagat ttacgatcgt    3180
acttgttacc catcattgaa ttttgaacat ccgaacctgg gagttttccc tgaaacagat    3240
agtatatttg aacctgtata ataatatata gtctagcgct ttacggaaga caatgtatgt    3300
atttcggttc ctggagaaac tattgcatct attgcatagg taatcttgca cgtcgcatcc    3360
ccggttcatt ttctgcgttt ccatcttgca cttcaatagc atatctttgt taacgaagca    3420
tctgtgcttc attttgtaga acaaaaatgc aacgcgagag cgctaatttt tcaaacaaag    3480
aatctgagct gcattttac agaacagaaa tgcaacgcga agcgctatt ttaccaacga     3540 agaatctgtg cttcatttttt gtaaaacaaa atgcaacgc gacgagagcg ctaattttc     3600 aaacaaagaa tctgagctgc attttacag aacagaaatg caacgcgaga gcgctatttt    3660
accaacaaag aatctatact ctttttttgt tctacaaaaa tgcatcccga gagcgctatt    3720
tttctaacaa agcatcttag attactttt ttctcctttg tgcgctctat aatgcagtct    3780
cttgataact ttttgcactg taggtccgtt aaggttagaa gaaggctact ttggtgtcta    3840
ttttctcttc cataaaaaaa gcctgactcc acttcccgcg tttactgatt actagcgaag    3900
ctgcgggtgc atttttcaa gataaaggca tccccgatta tattctatac cgatgtggat     3960
tgcgcatact ttgtgaacag aaagtgatag cgttgatgat tcttcattgg tcagaaaatt    4020
atgaacggtt tcttctattt tgtctctata tactacgtat aggaaatgtt tacattttcg    4080
tattgttttc gattcactct atgaatagtt cttactacaa ttttttttgtc taaagagtaa    4140 tactagagat aaacataaaa aatgtagagg tcgagtttag atgcaagttc aaggagcgaa    4200
aggtggatgg gtaggttata tagggatata gcacagagat atatagcaaa gagatacttt    4260
tgagcaat                                                            4268
```

<210> SEQ ID NO 43
<211> LENGTH: 4399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
gtttgtggaa gcggtattcg caatttaatt aaagctggtg acaattaatc atcggctcgt    60
ataatgtgtg gaattgaatc gatataagga ggttaatcat gtttaaaccc tcaaaatata   120
ttttccctct atcttctcgt tgcgcttaat ttgactaatt ctcattagcg aggcgcgcct   180
ttccataggc tccgccccc tgacgagcat cacaaaaatc gacgctcaag tcagaggtgg   240
cgaaacccga caggactata aagataccag gcgtttcccc ctggaagctc cctcgtgcgc   300
tctcctgttc cgaccctgcc gcttaccgga tacctgtccg cctttctccc ttcgggaagc   360
gtggcgcttt ctcatagctc acgctgtagg tatctcagtt cggtgtaggt cgttcgctcc   420
aagctgggct gtgtgcacga acccccgtt cagcccgacc gctgcgcctt atccggtaac   480
tatcgtcttg agtccaaccc ggtaagacac gacttatcgc cactggcagc agccactggt   540
aacaggatta gcagagcgag gtatgtaggc ggtgctacag agttcttgaa gtggtggcct   600
aactacggct acactagaag aacagtattt ggtatctgcg ctctgctgaa gccagttacc   660
ttcggaaaaa gagttggtag ctcttgatcc ggcaaacaaa ccaccgctgg tagcggtggt   720
ttttttgttt gcaagcagca gattacgcgc agaaaaaaag gatctcaaga agatcctttg   780
atcttttcta cggggtctga cgctcagtgg aacgaaaact cacgttaagg gattttggtc   840
atgagattat caaaaggat cttcacctag atccttttaa attaaaaatg aagttttaaa   900
tcaatctaaa gtatatatga gtaaacttgg tctgacagtt accatgctt aatcagtgag   960
gcacctatct cagcgatctg tctatttcgt tcatccatag ttgcctgact ccccgtcgtg  1020
tagataacta cgatacggga gggcttacca tctggcccca gtgctgcaat gataccgcga  1080
gacccacgct caccggctcc agatttatca gcaataaacc agccagccgg aagggccgag  1140
cgcagaagtg gtcctgcaac tttatccgcc tccatccagt ctattaattg ttgccgggaa  1200
gctagagtaa gtagttcgcc agttaatagt ttgcgcaacg ttgttgccat tgctacaggc  1260
atcgtggtgt cacgctcgtc gtttggtatg gcttcattca gctccggttc caacgatca   1320
aggcgagtta catgatcccc catgttgtgc aaaaaagcgg ttagctcctt cggtcctccg  1380
atcgttgtca gaagtaagtt ggccgcagtg ttatcactca tggttatggc agcactgcat  1440
aattctctta ctgtcatgcc atccgtaaga tgcttttctg tgactggtga gtactcaacc  1500
aagtcattct gagaatagtg tatgcggcga ccgagttgct cttgcccggc gtcaatacgg  1560
gataataccg cgccacatag cagaacttta aaagtgctca tcattggaaa acgttcttcg  1620
gggcgaaaac tctcaaggat cttaccgctg ttgagatcca gttcgatgta acccactcgt  1680
gcacccaact gatcttcagc atcttttact ttcaccagcg tttctgggtg agcaaaaaca  1740
ggaaggcaaa atgccgcaaa aaagggaata agggcgacac ggaaatgttg aatactcata  1800
ctcttccttt tcaatatta ttgaagcatt tatcagggtt attgtctcat gagcggatac  1860
atatttgaat gtatttagaa aaataaacag cgatcgcgcg gccgcgggta ataactgata  1920
taattaaatt gaagctctaa tttgtgagtt tagtatacat gcatttactt ataatacagt  1980
ttttttagttt tgctggccgc atcttctcaa atatgcttcc cagcctgctt ttctgtaacg  2040
ttcaccctct accttagcat cccttcccctt tgcaaatagt cctcttccaa caataataat  2100
gtcagatcct gtagagacca catcatccac ggttctatac tgttgaccca atgcgtctcc  2160
cttgtcatct aaacccacac cgggtgtcat aatcaaccaa tcgtaacctt catctcttcc  2220
acccatgtct ctttgagcaa taaagccgat aacaaaatct ttgtcgctct tcgcaatgtc  2280
aacagtaccc ttagtatatt ctccagtagc tagggagccc ttgcatgaca attctgctaa  2340
```

| | |
|---|---|
| catcaaaagg cctctaggtt cctttgttac ttcttccgcc gcctgcttca aaccgctaac | 2400 |
| aatacctggg cccaccacac cgtgtgcatt cgtaatgtct gcccattctg ctattctgta | 2460 |
| tacacccgca gagtactgca atttgactgt attaccaatg tcagcaaatt ttctgtcttc | 2520 |
| gaagagtaaa aaattgtact tggcggataa tgcctttagc ggcttaactg tgccctccat | 2580 |
| ggaaaaatca gtcaagatat ccacatgtgt ttttagtaaa caaattttgg gacctaatgc | 2640 |
| ttcaactaac tccagtaatt ccttggtggt acgaacatcc aatgaagcac acaagtttgt | 2700 |
| ttgcttttcg tgcatgatat taaatagctt ggcagcaaca ggactaggat gagtagcagc | 2760 |
| acgttcctta tatgtagctt tcgacatgat ttatcttcgt ttcctgcagg ttttttgttct | 2820 |
| gtgcagttgg gttaagaata ctgggcaatt tcatgtttct tcaacaccac atatgcgtat | 2880 |
| atataccaat ctaagtctgt gctccttcct tcgttcttcc ttctgctcgg agattaccga | 2940 |
| atcaaagcta gcttatcgat gataagctgt caaagatgag aattaattcc acggactata | 3000 |
| gactatacta gatactccgt ctactgtacg atacacttcc gctcaggtcc ttgtcctta | 3060 |
| acgaggcctt accactcttt tgttactcta ttgatccagc tcagcaaagg cagtgtgatc | 3120 |
| taagattcta tcttcgcgat gtagtaaaac tagctagacc gagaaagaga ctagaaatgc | 3180 |
| aaaaggcact tctacaatgg ctgccatcat tattatccga tgtgacgctg cagcttctca | 3240 |
| atgatattcg aatacgcttt gaggagatac agcctaatat ccgacaaact gttttacaga | 3300 |
| tttacgatcg tacttgttac ccatcattga attttgaaca tccgaacctg ggagttttcc | 3360 |
| ctgaaacaga tagtatattt gaacctgtat aataatatat agtctagcgc tttacggaag | 3420 |
| acaatgtatg tatttcggtt cctggagaaa ctattgcatc tattgcatag gtaatcttgc | 3480 |
| acgtcgcatc cccggttcat tttctgcgtt tccatcttgc acttcaatag catatctttg | 3540 |
| ttaacgaagc atctgtgctt cattttgtag aacaaaaatg caacgcgaga gcgctaattt | 3600 |
| ttcaaacaaa gaatctgagc tgcatttttta cagaacagaa atgcaacgcg aaagcgctat | 3660 |
| tttaccaacg aagaatctgt gcttcatttt tgtaaaacaa aaatgcaacg cgacgagagc | 3720 |
| gctaattttt caaacaaaga atctgagctg cattttttaca gaacagaaat gcaacgcgag | 3780 |
| agcgctattt taccaacaaa gaatctatac ttcttttttg ttctacaaaa atgcatcccg | 3840 |
| agagcgctat ttttctaaca aagcatctta gattacttttt tttctccttt gtgcgctcta | 3900 |
| taatgcagtc tcttgataac ttttttgcact gtaggtccgt taaggttaga agaaggctac | 3960 |
| tttggtgtct atttttctctt ccataaaaaa agcctgactc cacttcccgc gtttactgat | 4020 |
| tactagcgaa gctgcgggtg catttttttca agataaaggc atccccgatt atattctata | 4080 |
| ccgatgtgga ttgcgcatac tttgtgaaca gaaagtgata gcgttgatga ttcttcattg | 4140 |
| gtcagaaaat tatgaacggt ttcttctatt ttgtctctat atactacgta taggaaatgt | 4200 |
| ttacattttc gtattgtttt cgattcactc tatgaatagt tcttactaca attttttttgt | 4260 |
| ctaaagagta atactagaga taaacataaa aaatgtagag gtcgagttta gatgcaagtt | 4320 |
| caaggagcga aggtggatg ggtaggttat atagggatat agcacagaga tatatagcaa | 4380 |
| agagatactt ttgagcaat | 4399 |

<210> SEQ ID NO 44
<211> LENGTH: 8762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
gtttgtggaa gcggtattcg caatcattta gtcgtgcaat gtatgacttt aagatttgtg      60
agcaggaaga aagggagaa tcttctaacg ataaacccttgaaaaactgggtagactacg        120
ctatgttgag ttgctacgca ggctgcacaa ttacacgaga atgctcccgc ctaggattta    180
aggctaaggg acgtgcaatg cagacgacag atctaaatga ccgtgtcggt gaagtgttcg    240
ccaaactttt cggttaacac atgcagtgat gcacgcgcga tggtgctaag ttacatatat    300
atatatatat atatatatat atatatatag ccatagtgat gtctaagtaa cctttatggt    360
atatttctta atgtggaaag atactagcgc gcgcacccac acacaagctt cgtcttttct    420
tgaagaaaag aggaagctcg ctaaatggga ttccactttc cgttccctgc cagctgatgg    480
aaaaaggtta gtgaacgat gaagaataaa aagagagatc cactgaggtg aaatttcagc     540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
accttccttt gtaattttttt ttgtaattat tcttcttaat aatccaaaca aacacacata    780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caacttggac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg cgcgccgtc tgaagaatga atgatttgat gatttctttt     1860
tccctccatt tttcttactg aatatatcaa tgatatagac ttgtatagtt tattatttca    1920
aattaagtag ctatatatag tcaagataac gtttgtttga cacgattaca ttattcgtcg    1980
acatcttttt tcagcctgtc gtggtagcaa tttgaggagt attattaatt gaataggttc    2040
attttgcgct cgcataaaca gttttcgtca gggacagtat gttggaatga gtggtaatta    2100
atggtgacat gacatgttat agcaataacc ttgatgttta catcgtagtt taatgtacac    2160
cccgcgaatt cgttcaagta gggagtgcacc aattgcaaag ggaaaagctg aatgggcagt   2220
tcgaatagta cttttccat aggctccgcc ccctgacga gcatcacaaa aatcgacgct      2280
caagtcagag gtggcgaaac ccgacaggac tataaagata ccaggcgttt cccctggaa     2340
```

```
gctccctcgt gcgctctcct gttccgaccc tgccgcttac cggatacctg tccgcctttc    2400
tcccttcggg aagcgtggcg ctttctcata gctcacgctg taggtatctc agttcggtgt    2460
aggtcgttcg ctccaagctg ggctgtgtgc acgaacccccc cgttcagccc gaccgctgcg    2520
ccttatccgg taactatcgt cttgagtcca acccggtaag acacgactta tcgccactgg    2580
cagcagccac tggtaacagg attagcagag cgaggtatgt aggcggtgct acagagttct    2640
tgaagtggtg cctaactac ggctacacta gaagaacagt atttggtatc tgcgctctgc     2700
tgaagccagt taccttcgga aaaagagttg gtagctcttg atccggcaaa caaaccaccg    2760
ctggtagcgg tggttttttt gtttgcaagc agcagattac gcgcagaaaa aaggatctc    2820 aagaagatcc tttgatcttt tctacggggt ctgacgctca gtggaacgaa actcacgtt    2880 aagggatttt ggtcatgaga ttatcaaaaa ggatcttcac ctagatcctt ttaaattaaa   2940
aatgaagttt taaatcaatc taaagtatat atgagtaaac ttggtctgac agttaccaat    3000
gcttaatcag tgaggcacct atctcagcga tctgtctatt tcgttcatcc atagttgcct    3060
gactccccgt cgtgtagata actacgatac gggagggctt accatctggc cccagtgctg    3120
caatgatacc gcgagaccca cgctcaccgg ctccagattt atcagcaata aaccagccag    3180
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa acaggaagg caaaatgccg caaaaaaggg aataagggcg acacggaaat     3840
gttgaatact catactcttc cttttcaat attattgaag catttatcag ggttattgtc     3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca aagaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagttttac tgtacaaaca cctgtgtagc     4380
tccttctagc attttaagt tattcacacc tcaggggag ggataaatta ataaattcc       4440 aaaagcgaag atcgagaaac taaattaaaa ttccaaaaac gaagtggaa cacaccccc     4500 cgaaaaaaaa caacaaacaa aaacccaac aaaataaaca aaaacaaaat aaatatataa     4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
```

```
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gatttttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaagag accgcctcgt ttcttttttct tcgtcgaaaa aggcaataaa   5220
aatttttatc acgtttcttt ttcttgaaaa ttttttttt tgattttttt ctctttcgat   5280
gacctcccat tgatatttaa gttaataaac ggtcttcaat ttctcaagtt tcagtttcat   5340
ttttcttgtt ctattacaac ttttttttact tcttgctcat tagaaagaaa gcatagcaat   5400
ctaatctaag ttttaattac aaaatgacca ctctggatga caccgcttac cgataccgaa   5460
cttccgttcc tggcgatgcc gaggctattg aggctctgga tggatctttc accactgaca   5520
ccgttttccg agtgaccgct actggcgacg gcttcaccct gcgagaggtg cctgtcgacc   5580
ctcctctcac caaggttttc cctgacgatg agtcggacga tgagtctgac gctggagagg   5640
acggcgaccc tgactctcga actttcgtgg cttacggcga cgatggagac ctggccggct   5700
ttgtggtcgt ttcttactcc ggatggaacc gacgactgac cgtggaggac atcgaggtcg   5760
ctcctgagca ccgaggtcat ggtgtcggac gagctctgat gggtctcgct actgagttcg   5820
ctcgagagcg aggtgctggc cacctgtggc tcgaggtcac caacgttaac gcccctgcta   5880
ttcatgccta ccgacgaatg ggttttaccc tgtgtggcct cgatactgcc ctgtacgacg   5940
gaaccgcttc cgatggagag caggccctct acatgtcgat gccctgccct taaacaggcc   6000
ccttttcctt tgtcgatatc atgtaattag ttatgtcacg cttacattca cgccctcctc   6060
ccacatccgc tctaaccgaa aaggaaggag ttagacaacc tgaagtctag gtccctattt   6120 attttttta atagttatgt tagtattaag aacgttattt atatttcaaa ttttctttt   6180 ttttctgtac aaacgcgtgt acgcatgtaa cattatactg aaaaccttgc ttgagaaggt   6240
tttgggacgc tcgaaggctt taatttgcgg gtaataactg atataattaa attgaagctc   6300
taatttgtga gtttagtata catgcattta cttataatac agttttttag ttttgctggc   6360
cgcatcttct caaatatgct tcccagcctg ctttttctgta acgttcaccc tctaccttag   6420
catcccttcc ctttgcaaat agtcctcttc caacaataat aatgtcagat cctgtagaga   6480
ccacatcatc cacggttcta tactgttgac ccaatgcgtc tcccttgtca tctaaaccca   6540
caccgggtgt cataatcaac caatcgtaac cttcatctct tccacccatg tctctttgag   6600
caataaagcc gataacaaaa tctttgtcgc tcttcgcaat gtcaacagta cccttagtat   6660
attctccagt agctagggag cccttgcatg acaattctgc taacatcaaa aggcctctag   6720
gttcctttgt tacttcttcc gccgcctgct tcaaaccgct aacaatacct gggcccacca   6780
caccgtgtgc attcgtaatg tctgcccatt ctgctattct gtatacaccc gcagagtact   6840
gcaatttgac tgtattacca atgtcagcaa atttttctgtc ttcgaagagt aaaaaattgt   6900
acttggcgga taatgccttt agcggcttaa ctgtgccctc catggaaaaa tcagtcaaga   6960
tatccacatg tgttttagt aaacaaattt tgggacctaa tgcttcaact aactccagta   7020
attccttggt ggtacgaaca tccaatgaag cacacaagtt tgtttgcttt tcgtgcatga   7080
```

```
tattaaatag cttggcagca acaggactag gatgagtagc agcacgttcc ttatatgtag    7140
ctttcgacat gatttatctt cgtttcctgc aggttttgt tctgtgcagt tgggttaaga    7200
atactgggca atttcatgtt tcttcaacac cacatatgcg tatatatacc aatctaagtc    7260
tgtgctcctt ccttcgttct tccttctgct cggagattac cgaatcaaag ctagcttatc    7320
gatgataagc tgtcaaagat gagaattaat tccacggact atagactata ctagatactc    7380
cgtctactgt acgatacact tccgctcagg tccttgtcct ttaacgaggc cttaccactc    7440
ttttgttact ctattgatcc agctcagcaa aggcagtgtg atctaagatt ctatcttcgc    7500
gatgtagtaa aactagctag accgagaaag agactagaaa tgcaaaaggc acttctacaa    7560
tggctgccat cattattatc cgatgtgacg ctgcagcttc tcaatgatat tcgaatacgc    7620
tttgaggaga tacagcctaa tatccgacaa actgttttac agatttacga tcgtacttgt    7680
tacccatcat tgaattttga acatccgaac ctgggagttt tccctgaaac agatagtata    7740
tttgaacctg tataataata tatagtctag cgctttacgg aagacaatgt atgtatttcg    7800
gttcctggag aaactattgc atctattgca taggtaatct tgcacgtcgc atccccggtt    7860
cattttctgc gtttccatct tgcacttcaa tagcatatct ttgttaacga agcatctgtg    7920
cttcattttg tagaacaaaa atgcaacgcg agagcgctaa ttttcaaac aaagaatctg    7980 agctgcattt ttacagaaca gaaatgcaac gcgaaagcgc tatttaccaa acgaagaatc    8040
tgtgcttcat ttttgtaaaa caaaaatgca acgcgacgag agcgctaatt tttcaaacaa    8100
agaatctgag ctgcattttt acagaacaga aatgcaacgc gagagcgcta ttttaccaac    8160
aaagaatcta tacttctttt ttgttctaca aaaatgcatc ccgagagcgc tattttttcta    8220 acaaagcatc ttagattact ttttttctcc tttgtgcgct ctataatgca gtctcttgat    8280 aacttttgc actgtaggtc cgttaaggtt agaagaaggc tactttggtg tctatttct    8340 cttccataaa aaaagcctga ctccacttcc cgcgtttact gattactagc gaagctgcgg    8400
gtgcattttt tcaagataaa ggcatccccg attatattct ataccgatgt ggattgcgca    8460
tactttgtga acagaaagtg atagcgttga tgattcttca ttggtcagaa aattatgaac    8520
ggtttcttct attttgtctc tatatactac gtataggaaa tgtttacatt ttcgtattgt    8580
tttcgattca ctctatgaat agttcttact acaatttttt tgtctaaaga gtaatactag    8640
agataaacat aaaaaatgta gaggtcgagt ttagatgcaa gttcaaggag cgaaaggtgg    8700
atgggtaggt tatatagga tatagcacag agatatatag caaagagata cttttgagca    8760
at                                                                   8762
```

<210> SEQ ID NO 45
<211> LENGTH: 5824
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gtttgtggaa gcggtattcg caatttaatt aaagctggtg acaattaatc atcggctcgt      60
ataatgtgtg gaattgaatc gatataagga ggttaatcat atgcaaacgc tcagcatcca     120
gcacggtacc ctcgtcacga tggatcagta ccgcagagtc cttggggata gctgggttca     180
cgtgcaggat ggacggatcg tcgcgctcgg agtgcacgcc gagtcggtgc ctccgccagc     240
ggatcgggtg atcgatgcac gcggcaaggt cgtgttaccc ggtttcatca atgcccacac     300
```

```
ccatgtgaac cagatcctcc tgcgcggagg ccctcgcac gggcgtcaac tctatgactg    360
gctgttcaac gttttgtatc cgggacaaaa ggcgatgaga ccggaggacg tagcggtggc    420
ggtgaggttg tattgtgcgg aagctgtgcg cagcgggatt acgacgatca acgacaacgc    480
cgattcggcc atctacccag gcaacatcga ggccgcgatg gcggtctatg gtgaggtggg    540
tgtgagggtc gtctacgccc gcatgttctt tgatcggatg gacgggcgca ttcaagggta    600
tgtggacgcc ttgaaggctc gctctcccca agtcgaactg tgctcgatca tggaggaaac    660
ggctgtggcc aaagatcgga tcacagccct gtcagatcag tatcatggca cggcaggagg    720
tcgtatatca gtttggcccg ctcctgccat taccccggcg gtgacagttg aaggaatgcg    780
atgggcacaa gccttcgccc gtgatcgggc ggtaatgtgg acgcttcaca tggcggagag    840
cgatcatgat gagcggcttc attggatgag tcccgccgag tacatggagt gttacggact    900
cttggatgag cgtctgcagg tcgcgcattg cgtgtacttt gaccggaagg atgttcggct    960
gctgcaccgc cacaatgtga aggtcgcgtc gcaggttgtg agcaatgcct acctcggctc    1020
aggggtggcc ccgtgccag agatggtgga gcgcggcatg gccgtgggca ttggaacaga    1080
tgacgggaat tgtaatgact ccgtaaacat gatcggagac atgaagttta tggcccatat    1140
tcaccgcgcg gtgcatcggg atgcggacgt gctgacccca gagaagattc ttgaaatggc    1200
gacgatcgat ggggcgcgtt cgttgggaat ggaccacgag attggttcca tcgaaaccgg    1260
caagcgcgcg gaccttatcc tgcttgacct gcgtcaccct cagacgactc ctcaccatca    1320
tttggcggcc acgatcgtgt ttcaggctta cggcaatgag gtggacactg tcctgattga    1380
cggaaacgtt gtgatggaga accgccgctt gagctttctt cccccctgaac gtgagttggc    1440 gttccttgag gaagcgcaga gccgcgccac agctattttg cagcgggcga acatggtggc    1500
taacccagct tggcgcagcc tctaggttta aaccctcaaa atatattttc cctctatctt    1560
ctcgttgcgc ttaatttgac taattctcat tagcgaggcg cgccttttcca taggctccgc    1620 cccctgacg agcatcacaa aaatcgacgc tcaagtcaga ggtggcgaaa cccgacagga    1680
ctataaagat accaggcgtt ccccctgga agctccctcg tgcgctctcc tgttccgacc    1740
ctgccgctta ccggatacct gtccgccttt ctcccttcgg gaagcgtggc gctttctcat    1800
agctcacgct gtaggtatct cagttcggtg taggtcgttc gctccaagct gggctgtgtg    1860
cacgaacccc ccgttcagcc cgaccgctgc gccttatccg gtaactatcg tcttgagtcc    1920
aacccggtaa gacacgactt atcgccactg gcagcagcca ctggtaacag gattagcaga    1980
gcgaggtatg taggcggtgc tacagagttc ttgaagtggt ggcctaacta cggctacact    2040
agaagaacag tatttggtat ctgcgctctg ctgaagccag ttaccttcgg aaaaagagtt    2100
ggtagctctt gatccggcaa acaaaccacc gctggtagcg gtggtttttt tgtttgcaag    2160
cagcagatta cgcgcagaaa aaaggatctc aagaagatc ctttgatctt ttctacgggg    2220
tctgacgctc agtggaacga aaactcacgt taagggattt tggtcatgag attatcaaaa    2280
aggatcttca cctagatcct tttaaattaa aaatgaagtt ttaaatcaat ctaaagtata    2340
tatgagtaaa cttggtctga cagttaccaa tgcttaatca gtgaggcacc tatctcagcg    2400
atctgtctat ttcgttcatc catagttgcc tgactccccg tcgtgtagat aactacgata    2460
cgggagggct taccatctgg ccccagtgct gcaatgatac cgcgagaccc acgctcaccg    2520
gctccagatt tatcagcaat aaaccagcca gccggaaggg ccgagcgcag aagtggtcct    2580
gcaactttat ccgcctccat ccagtctatt aattgttgcc gggaagctag agtaagtagt    2640
```

```
tcgccagtta atagtttgcg caacgttgtt gccattgcta caggcatcgt ggtgtcacgc    2700
tcgtcgtttg gtatggcttc attcagctcc ggttcccaac gatcaaggcg agttacatga    2760
tcccccatgt tgtgcaaaaa agcggttagc tccttcggtc ctccgatcgt tgtcagaagt    2820
aagttggccg cagtgttatc actcatggtt atggcagcac tgcataattc tcttactgtc    2880
atgccatccg taagatgctt ttctgtgact ggtgagtact caaccaagtc attctgagaa    2940
tagtgtatgc ggcgaccgag ttgctcttgc ccggcgtcaa tacgggataa taccgcgcca    3000
catagcagaa ctttaaaagt gctcatcatt ggaaaacgtt cttcggggcg aaaactctca    3060
aggatcttac cgctgttgag atccagttcg atgtaaccca ctcgtgcacc caactgatct    3120
tcagcatctt ttactttcac cagcgtttct gggtgagcaa aaacaggaag gcaaaatgcc    3180
gcaaaaaagg gaataagggc gacacggaaa tgttgaatac tcatactctt ccttttcaa     3240
tattattgaa gcatttatca gggttattgt ctcatgagcg gatacatatt tgaatgtatt    3300
tagaaaaata acagcgatc gcgcggccgc gggtaataac tgatataatt aaattgaagc     3360
tctaatttgt gagtttagta tacatgcatt tacttataat acagtttttt agttttgctg    3420
gccgcatctt ctcaaatatg cttcccagcc tgcttttctg taacgttcac cctctacctt    3480
agcatccctt ccctttgcaa atagtcctct tccaacaata ataatgtcag atcctgtaga    3540
gaccacatca tccacggttc tatactgttg acccaatgcg tctcccttgt catctaaacc    3600
cacaccgggt gtcataatca accaatcgta accttcatct cttccaccca tgtctctttg    3660
agcaataaag ccgataacaa aatctttgtc gctcttcgca atgtcaacag tacccttagt    3720
atattctcca gtagctaggg agcccttgca tgacaattct gctaacatca aaaggcctct    3780
aggttccttt gttacttctt ccgccgcctg cttcaaaccg ctaacaatac ctgggcccac    3840
cacaccgtgt gcattcgtaa tgtctgccca ttctgctatt ctgtatacac ccgcagagta    3900
ctgcaatttg actgtattac caatgtcagc aaattttctg tcttcgaaga gtaaaaaatt    3960
gtacttggcg gataatgcct ttagcggctt aactgtgccc tccatggaaa atcagtcaa     4020
gatatccaca tgtgttttta gtaaacaaat tttgggacct aatgcttcaa ctaactccag    4080
taattccttg gtggtacgaa catccaatga agcacacaag tttgtttgct tttcgtgcat    4140
gatattaaat agcttggcag caacaggact aggatgagta gcagcacgtt ccttatatgt    4200
agctttcgac atgattttatc ttcgtttcct gcaggttttt gttctgtgca gttgggttaa    4260
gaatactggg caatttcatg tttcttcaac accacatatg cgtatatata ccaatctaag    4320
tctgtgctcc ttccttcgtt cttccttctg ctcggagatt accgaatcaa agctagctta    4380
tcgatgataa gctgtcaaag atgagaatta attccacgga ctatagacta tactagatac    4440
tccgtctact gtacgataca cttccgctca ggtccttgtc ctttaacgag gccttaccac    4500
tcttttgtta ctctattgat ccagctcagc aaaggcagtg tgatctaaga ttctatcttc    4560
gcgatgtagt aaaactagct agaccgagaa agagactaga aatgcaaaag gcacttctac    4620
aatggctgcc atcattatta tccgatgtga cgctgcagct tctcaatgat attcgaatac    4680
gctttgagga gatacagcct aatatccgac aaactgtttt acagatttac gatcgtactt    4740
gttacccatc attgaatttt gaacatccga acctgggagt tttccctgaa acagatagta    4800
tatttgaacc tgtataataa tatatagtct agcgctttac ggaagacaat gtatgtattt    4860
cggttcctgg agaaactatt gcatctattg cataggtaat cttgcacgtc gcatccccgg    4920
ttcatttct gcgtttccat cttgcacttc aatagcatat ctttgttaac gaagcatctg     4980
tgcttcattt tgtagaacaa aaatgcaacg cgagagcgct aattttttcaa acaaagaatc    5040
```

```
tgagctgcat ttttacagaa cagaaatgca acgcgaaagc gctattttac caacgaagaa      5100
tctgtgcttc atttttgtaa aacaaaaatg caacgcgacg agagcgctaa ttttttcaaac     5160 aaagaatctg agctgcattt ttacagaaca gaaatgcaac gcgagagcgc tattttacca     5220
acaaagaatc tatacttctt ttttgttcta caaaaatgca tcccgagagc gctatttttc     5280
taacaaagca tcttagatta cttttttttct cctttgtgcg ctctataatg cagtctcttg    5340 ataactttt gcactgtagg tccgttaagg ttagaagaag gctactttgg tgtctatttt      5400
ctcttccata aaaaaagcct gactccactt cccgcgttta ctgattacta gcgaagctgc     5460
gggtgcattt tttcaagata aaggcatccc cgattatatt ctataccgat gtggattgcg     5520
catactttgt gaacagaaag tgatagcgtt gatgattctt cattggtcag aaaattatga     5580 acggttctt ctattttgtc tctatatact acgtatagga aatgtttaca ttttcgtatt      5640
gttttcgatt cactctatga atagttctta ctacaatttt tttgtctaaa gagtaatact     5700
agagataaac ataaaaaatg tagaggtcga gtttagatgc aagttcaagg agcgaaaggt     5760
ggatgggtag gttatatagg gatatagcac agagatatat agcaaagaga acttttgag      5820 caat                                                                  5824
```

<210> SEQ ID NO 46
<211> LENGTH: 8336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
gtttgtggaa gcggtattcg caatttaatt aaagctggtg acaattaatc atcggctcgt       60
ataatgtgtg gaattgaatc gatataagga ggttaatcat atgactagaa tcgctatcac     120
aggtggtaga gttttgacta tggacccaga aagaagagta ttagaaccag gtacagttgt     180
tgttgaagat caattcattg cacaagtcgg ttcaccagat gacgtagaca tcagaggtgc     240
tgaaattata gatgccactg gtatggctgt attaccaggt ttcgttaata cacatacccca    300 cgttcctcaa attttgttaa gaggtggtgc ttcacatgat agaaatttgt tggaatggtt    360
gcacaacgtc ttatatccag gtttggctgc atacactgat gacgtatca gagttggtac     420 attgttatat tgtgctgaag cattgagatc cggtattact acagttgtcg acaatgaaga     480
tgttagacct aacgattttg ccagagctgg tgccgctggt attggtgcat tcactgatgc     540
cggtatcaga gcaatctatg ccagaatgta ctttgatgct ccaagagcag aattggaaga     600
attagtcgca acaatacatg caaaagcccc tggtgccgta agaatggacg aatctgcttc     660
aaccgatcat gttttggcag acttagatca attgattacc agacatgaca gaactgctga     720
tggtagaatt agagtatggc cagctcctgc aataccattc atggttctg aaaagggtat      780 gaaggcagcc caagaaatag ctgcatccag aactgacggt tggacaatgc atgttagtga     840
agatccaatc gaagccagag tccactctat gaatgctcct gaatatttgc atcacttggg     900
ttgtttagac gatagattgt tagccgctca ttgcgttcac atagactcaa gagatatcag     960
attgtttaga caacatgatg ttaagatatc cacacaacct gtctccaata gttacttagc    1020
agccggtata gcaccagttc ctgaaatgtt ggctcatggt gtcacagtag gtattggtac    1080
cgacgatgct aattgtaacg actccgtaaa cttaatcagt gatatgaagg ttttggcatt    1140
gatacataga gctgcacaca gagatgctag tatcattacc ccagaaaaga taatcgaaat    1200
```

```
ggccactatt gacggtgcta gatgcattgg tatggctgat caaatcggtt ctttggaagc    1260
tggtaaaaga gcagacataa tcactttgga tttgagacat gcacaaacca ctcctgccca    1320
cgatttggcc gctacaattg tctttcaagc ttatggtaat gaagtaaacg atgttttggt    1380
caacggttct gtagttatga gagatagagt tttgtcattc ttaccaaccc ctcaagaaga    1440
aaaggcttta tacgacgatg catctgaaag atcagcagcc atgttagcca gagctggttt    1500
gactggtaca agaacctggc aaactttggg ttcttaagga aatccattat gatgtcagga    1560
gaacacacgt taaaagcggt acgaggcagt tttattgatg tcacccgtac gatcgataac    1620
ccggaagaga ttgcctctgc gctgcggttt attgaggatg gtttattact cattaaacag    1680
ggaaaagtgg aatggtttgg cgaatgggaa aacggaaagc atcaaattcc tgacaccatt    1740
cgcgtgcgcg actatcgcgg caaactgata gtaccgggct tgtcgatac acatatccat    1800 tatccgcaaa gtgaaatggt gggggcctat ggtgagcaat tgctggagtg gttgaataaa    1860
cacaccttcc ctactgaacg tcgttatgag gatttagagt acgcccgcga aatgtcggcg    1920
ttcttcatca agcagctttt acgtaacgga accaccacgg cgctggtgtt tggcactgtt    1980
catccgcaat ctgttgatgc gctgtttgaa gccgccagtc atatcaatat gcgtatgatt    2040
gccggtaagg tgatgatgga ccgcaacgca ccggattatc tgctcgacac tgccgaaagc    2100
agctatcacc aaagcaaaga actgatcgaa cgctggcaca aaaatggtcg tctgctatat    2160
gcgattacgc cacgcttcgc cccgacctca tctcctgaac agatggcgat ggcgcaacgc    2220
ctgaaagaag aatatccgga tacgtgggta catacccatc tctgtgaaaa caaagatgaa    2280
attgcctggg tgaaatcgct ttatcctgac catgatggtt atctggatgt ttaccatcag    2340
tacggcctga ccgtaaaaa ctgtgtcttt gctcactgcg tccatctcga agaaaaagag    2400
tgggatcgtc tcagcgaaac caaatccagc attgctttct gtccgacctc caacctttac    2460
ctcggcagcg gcttattcaa cttgaaaaaa gcatggcaga agaaagttaa agtgggcatg    2520
ggaacggata tcggtgccgg aaccactttc aacatgctgc aaacgctgaa cgaagcctac    2580
aaagtattgc aattacaagg ctatcgcctc tcggcatatg aagcgtttta cctggccacg    2640
ctcggcggag cgaaatctct gggccttgac gatttgattg caacttttt acctggcaaa    2700 gaggctgatt tcgtggtgat ggaacccacc gccactccgc tacagcagct gcgctatgac    2760
aactctgttt ctttagtcga caaattgttc gtgatgatga cgttgggcga tgaccgttcg    2820
atctaccgca cctacgttga tggtcgtctg gtgtacgaac gcaactaagg aacgaccatg    2880
agagaagtcc aattgttaga tggtagaaga gttgatgtcg cctgtgctgg tccttttgatt    2940 agtgaaatag gtgcccactt agatttgact gctccagttg aaattgattg tggtggtggt    3000
ttagcaacta gaccttttac tgaacctcat ttgcacttag acaaagcagg tactgccgat    3060
agattgcctg ccggtgcttc cacaatcggt gacgctattg ctgcaatgca agtgtcaag    3120 gtaaccgaaa gagataatgt cgccgctgta gcagccagaa tgcatagagt tttaaacaga    3180
atcgtcgatg acggttccca cgctattaga gcattggttg atgtcgacga gtttgggggt    3240
ttaacagctt ttcatgctgc acaacaagtc caagccgctt tggccccaag agctgttgtc    3300
caaattgtcg ctttcccaca acacggttta acccctcaag tattggcaat gttagaacaa    3360
gcagccgctg aaggtgcagg tgccttgggt gctcatactg atgttgaccc agatcctgca    3420
gcccacgttg gtgccgtcgc tgcaatagcc gctggtgctt ccttgccatt agaagttcat    3480
actgacgaag gtgctagtcc agataaattt tatttgcctg cagtattgga agttttagat    3540
```

```
agattcccag gtttgtctac tacattagct cattgtttgt cattaggtac aattgcacct    3600
aagcaacaac aacattggat cgaagaatta gctcacagag atatcaaagt atgcgttgca    3660
ccatctattt tgggtttcgg tttgccatta gcacctgtta gagccttaat agaagctggt    3720
gtcggtatct tagtaggttc agacaatttg caagatgttt tctttccttt gggtacaggt    3780
agagcaattg aaaacgttag attgttagcc accgcagccc aattaactgc accagaattg    3840
gccggtcctt taattgctgg tgtaaccgac atagcttacg caaccgttac tggtgctgca    3900
gatgccttgg ctgttgaatc tccagctaca ttagtagttc atgatgctac ctcacctgca    3960
gaattgttaa gaggtataga cggtacaaga attaccgtta tagatggttt gttgacatct    4020
ccattgcaat tggataaagg tatcaagtaa gtttaaacta atcccacagc cgccagttcc    4080
gctggcggca ttttaacttt ctttaatggg cgcgcctttc cataggctcc gccccctga    4140
cgagcatcac aaaaatcgac gctcaagtca gaggtggcga acccgacag gactataaag    4200
ataccaggcg tttcccctg gaagctccct cgtgcgctct cctgttccga ccctgccgct    4260
taccggatac ctgtccgcct ttctcccttc gggaagcgtg gcgctttctc atagctcacg    4320
ctgtaggtat ctcagttcgg tgtaggtcgt tcgctccaag ctgggctgtg tgcacgaacc    4380
ccccgttcag cccgaccgct cgccttatc ggtaactat cgtcttgagt ccaacccggt    4440
aagacacgac ttatcgccac tggcagcagc cactggtaac aggattagca gagcgaggta    4500
tgtaggcggt gctacagagt tcttgaagtg gtggcctaac tacggctaca ctagaagaac    4560
agtatttggt atctgcgctc tgctgaagcc agttaccttc ggaaaaagag ttggtagctc    4620
ttgatccggc aaacaaacca ccgctggtag cggtggtttt tttgtttgca agcagcagat    4680
tacgcgcaga aaaaaggat ctcaagaaga tcctttgatc ttttctacgg gtctgacgc    4740
tcagtggaac gaaaactcac gttaagggat tttggtcatg agattatcaa aaaggatctt    4800
cacctagatc cttttaaatt aaaaatgaag ttttaaatca atctaaagta tatatgagta    4860
aacttggtct gacagttacc aatgcttaat cagtgaggca cctatctcag cgatctgtct    4920
atttcgttca tccatagttg cctgactccc cgtcgtgtag ataactacga tacgggaggg    4980
cttaccatct ggccccagtg ctgcaatgat accgcgagac ccacgctcac cggctccaga    5040
tttatcagca ataaaccagc cagccggaag ggccgagcgc agaagtggtc ctgcaacttt    5100
atccgcctcc atccagtcta ttaattgttg ccgggaagct agagtaagta gttcgccagt    5160
taatagtttg cgcaacgttg ttgccattgc tacaggcatc gtggtgtcac gctcgtcgtt    5220
tggtatggct tcattcagct ccggttccca acgatcaagg cgagttacat gatcccccat    5280
gttgtgcaaa aaagcggtta gctccttcgg tcctccgatc gttgtcagaa gtaagttggc    5340
cgcagtgtta tcactcatgg ttatggcagc actgcataat tctcttactg tcatgccatc    5400
cgtaagatgc ttttctgtga ctggtgagta ctcaaccaag tcattctgag aatagtgtat    5460
gcggcgaccg agttgctctt gcccggcgtc aatacgggat aataccgcgc cacatagcag    5520
aactttaaaa gtgctcatca ttggaaaacg ttcttcgggg cgaaaactct caaggatctt    5580
accgctgttg agatccagtt cgatgtaacc cactcgtgca cccaactgat cttcagcatc    5640
ttttactttc accagcgttt ctgggtgagc aaaaacagga aggcaaaatg ccgcaaaaaa    5700
gggaataagg gcgacacgga aatgttgaat actcatactc ttccttttc aatattattg    5760
aagcatttat cagggttatt gtctcatgag cggatacata tttgaatgta tttagaaaaa    5820
taaacagcga tcgcgcggcc gcgggtaata actgatataa ttaaattgaa gctctaattt    5880
gtgagtttag tatacatgca tttacttata atacagtttt ttagttttgc tggccgcatc    5940
```

```
ttctcaaata tgcttcccag cctgcttttc tgtaacgttc accctctacc ttagcatccc    6000
ttccctttgc aaatagtcct cttccaacaa taataatgtc agatcctgta gagaccacat    6060
catccacggt tctatactgt tgacccaatg cgtctccctt gtcatctaaa cccacaccgg    6120
gtgtcataat caaccaatcg taaccttcat ctcttccacc catgtctctt tgagcaataa    6180
agccgataac aaaatcttg tcgctcttcg caatgtcaac agtacccta gtatattctc    6240 cagtagctag ggagcccttg catgacaatt ctgctaacat caaaaggcct ctaggttcct    6300
ttgttacttc ttccgccgcc tgcttcaaac cgctaacaat acctgggccc accacaccgt    6360
gtgcattcgt aatgtctgcc cattctgcta ttctgtatac acccgcagag tactgcaatt    6420
tgactgtatt accaatgtca gcaaattttc tgtcttcgaa gagtaaaaaa ttgtacttgg    6480
cggataatgc ctttagcggc ttaactgtgc cctccatgga aaaatcagtc aagatatcca    6540
catgtgtttt tagtaaacaa attttgggac ctaatgcttc aactaactcc agtaattcct    6600
tggtggtacg aacatccaat gaagcacaca agtttgtttg cttttcgtgc atgatattaa    6660
atagcttggc agcaacagga ctaggatgag tagcagcacg ttccttatat gtagctttcg    6720
acatgattta tcttcgtttc ctgcaggttt tgttctgtg cagttgggtt aagaatactg    6780
ggcaatttca tgtttcttca acaccacata tgcgtatata taccaatcta agtctgtgct    6840
ccttccttcg ttcttcctc tgctcggaga ttaccgaatc aaagctagct tatcgatgat    6900
aagctgtcaa agatgagaat taattccacg gactatagac tatactagat actccgtcta    6960
ctgtacgata cacttccgct caggtccttg tcctttaacg aggccttacc actcttttgt    7020
tactctattg atccagctca gcaaaggcag tgtgatctaa gattctatct tcgcgatgta    7080
gtaaaactag ctagaccgag aaagagacta gaaatgcaaa aggcacttct acaatggctg    7140
ccatcattat tatccgatgt gacgctgcag cttctcaatg atattcgaat acgctttgag    7200
gagatacagc ctaatatccg acaaactgtt ttacagattt acgatcgtac ttgttaccca    7260
tcattgaatt ttgaacatcc gaacctggga gttttccctg aaacagatag tatatttgaa    7320
cctgtataat aatatatagt ctagcgcttt acggaagaca atgtatgtat ttcggttcct    7380
ggagaaacta ttgcatctat tgcataggta atcttgcacg tcgcatcccc ggttcatttt    7440 ctgcgttcc atcttgcact tcaatagcat atctttgtta acgaagcatc tgtgcttcat    7500
tttgtagaac aaaaatgcaa cgcgagagcg ctaatttttc aaacaaagaa tctgagctgc    7560 attttacag aacagaaatg caacgcgaaa gcgctatttt accaacgaag aatctgtgct    7620 tcattttgt aaaacaaaaa tgcaacgcga cgagagcgct aatttttcaa acaaagaatc    7680
tgagctgcat tttacagaa cagaaatgca acgcgagagc gctatttac caacaaagaa    7740 tctatacttc ttttttgttc tacaaaaatg catcccgaga gcgctatttt ctaacaaag    7800 catcttagat tactttttt ctcctttgtg cgctctataa tgcagtctct tgataacttt    7860
ttgcactgta ggtccgttaa ggttagaaga aggctacttt ggtgtctatt ttctcttcca    7920 taaaaaagc ctgactccac ttcccgcgtt tactgattac tagcgaagct gcgggtgcat    7980
tttttcaaga taaaggcatc cccgattata ttctataccg atgtggattg cgcatacttt    8040
gtgaacagaa agtgatagcg ttgatgattc ttcattggtc agaaaattat gaacggtttc    8100 ttctatttg tctctatata ctacgtatag gaaatgttta catttcgta ttgttttcga    8160 ttcactctat gaatagttct tactacaatt ttttgtccta aagagtaata ctagagataa    8220
acataaaaaa tgtagaggtc gagtttagat gcaagttcaa ggagcgaaag gtggatgggt    8280
```
aggttatata gggatatagc acagagatat atagcaaaga gatacttttg agcaat        8336

<210> SEQ ID NO 47
<211> LENGTH: 8063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
gtttgtggaa gcggtattcg caatttaatt aaagctggtg acaattaatc atcggctcgt    60
ataatgtgtg gaattgaatc gatataagga ggttaatcat atgtcctcca cagcattata   120
caccgttcct accgcaggtc cagacgatgt tgccgccttg aaagcattag atggtcattc   180
cgcctccgat attttggctg taataggtaa acagagggt aatggttgtg ttaacgactt    240
tagtagaacc ttatctgctg cagtttggca tccattgtta aagagattcag ccattacagt   300
cttttccggt ggtgcagaag gtgtaataag tccacatgta aacatcttcg ttagagatga   360
aagacaatat tctggtcacc ctagaggttt ggtaactgct gttggtagaa caagagttat   420
cggtccagaa gaaattggta gacctgctca agtcgatgca gtacatgaaa ccgttgtcgc   480
attgttaact gaattgggtg ttggtccaga tgacgttcac ttggtcttga ttaaatgccc   540
tttgttatct tcagacgcta tagcaggtgt tcatagaaga ggtttaagac ctgtcactac   600
agatacttac gaatctatgt caagatccag agccgcttct gctttgggta tagccatggc   660
tttaaaggaa tgtgatagag acagagcatt gttagccttg gaaggtagag atgacgtttg   720
gtcagcaaga gcctccgctt ccagtggtgc tgaattggat gactgccaca ttttagtagt   780
tgcagaatca gatgcagccg ctaatccatt aagagcagcc catactgcca tgagagatgc   840
tttggacatc caagctttaa cagaagtttt tgacagaatt gctgcagaag gtggtaccgt   900
cagacaaata ttcgcaaagg ccgaagctga tccttcaggt gctatcagag ttatagaca    960
taccatgtta actgattccg acgtcaatgc aacaagacac gccagagccg ctgtaggtgg  1020
tttgattgca gccttacatg gtaacggtgc tgtctatgta tcaggtggtg cagaacacca  1080
aggtccaagt ggtggtggtt ctgttactgt tatatatgat gttcctgcaa cagccaacgc  1140
taccggtgaa gcttctagat aaggaaatcc attatgatat actcaacagt caacgctaat  1200
ccttacgctt ggccttacga tggttcaata gaccctgctc acaccgcttt aatcttaatc  1260
gattggcaaa tagacttttg tggtccaggt ggttatgtcg attccatggg ttacgactta  1320
tccttgacta gaagtggttt agaacctaca gcaagagtat tggctgcagc cagagatact  1380
ggtatgacag ttatccatac tagagaaggt cacagaccag atttggctga cttgccacct  1440
aataagagat ggagatctgc atcagccggt gctgaaatcg ttcagttgg tccatgtggt  1500
agaattttag tcagaggtga acctggttgg gaaatagtac cagaagttgc acctagagaa  1560
ggtgaaccaa ttatagataa acctggtaaa ggtgctttct acgcaacaga tttggacttg  1620
ttgttgagaa caagaggtat cacccatttg attttgaccg gtataactac agatgtttgc  1680
gtccacacca ctatgagaga agccaacgat agaggttacg aatgtttaat tttgtctgat  1740
tgcaccggtg ctactgacag aaagcatcac gaagctgcat tatctatggt caccatgcaa  1800
ggtggtgtat tcggtgcaac tgcccattca gatgacttat ggccgctttt gggtacaacc  1860
gttccagcag ccgctggtcc tagagctaga acagaataag gaacgaccat gacagttagt  1920
tccgatacaa ctgctgaaat atcgttaggt tggtcaatcc aagactggat tgattccac   1980
```

```
aagtcatcaa gctcccaggc ttcactaagg cttcttgaat cactactaga ctctcaaaat    2040
gttgcgccag tcgataatgc gtggatatcg ctaatttcaa aggaaatttt actgcaccaa    2100
ttccaaattt taaagagcag agaaaataaa gaaactctac ctctctacgg tgtccctatt    2160
gctgttaagg acaacatcga cgttagaggt ctacccacca ccgctgcatg tccatccttt    2220
gcatatgagc cttccaaaga ctctaaagta gtagaactac taagaaatgc aggtgcgata    2280
atcgtgggta agacaaactt ggaccaattt gccacaggat tagtcggcac acggtctcca    2340
tatgggaaaa caccttgcgc ttttagcaaa gagcatgtat ctggtggttc ctccgctggg    2400
tcagcatcgg tggtcgccag aggtatcgta ccaattgcat tgggtactga tacagcaggt    2460
tctggtagag tcccagccgc cttgaacaac ctgattggcc taaagccaac aaagggcgtc    2520
ttttcctgtc aaggtgtagt tcccgcttgt aaatctttag actgcgtctc catctttgca    2580
ttaaacctaa gtgatgctga acgctgcttc cgcatcatgt gccagccaga tcctgataat    2640
gatgaatatt ctagaccta tgtttccaac cctttgaaaa aattttcaag caatgtaacg    2700
attgctattc ctaaaaatat cccatggtat ggtgaaacca agaatcctgt actgttttcc    2760
aatgctgtcg aaaatctatc aagaacgggc gctaacgtca tagaaattga ttttgagcct    2820
cttttagagt tagctcgctg tttatacgaa ggtacttggg tggccgagcg ttatcaagct    2880
attcaatcgt ttttggacag taaaccacca aaggaatctt tggaccctac tgttatttca    2940
attatagaag gggccaagaa atacagtgca gtagactgct tcagttttga atacaaaaga    3000
caaggcatct tgcaaaaagt gagacgactt ctcgaatcag tcgatgtatt gtgtgtgccc    3060
acatgtcctt taaatcctac tatgcaacaa gttgcggatg aaccagtcct agtcaattca    3120
agacaaggca catggactaa ttttgtcaac ttggcagatt tggcagccct tgctgttccc    3180
gcagggttcc gagacgatgg tttgccaaat ggtattactt taatcggtaa aaaattcaca    3240
gattacgcac tattagagtt ggctaaccgc tatttccaaa atatattccc caacggttcc    3300
agaacatacg gtactttac ctcttcttca gtaaagccag caaacgatca attagtggga    3360
ccagactatg acccatctac gtccataaaa ttggctgttg tcggtgcaca tcttaagggt    3420
ctgcctctac attggcaatt ggaaaaggtc aatgcaacat atttatgtac aacaaaaaca    3480
tcaaaagctt accagctttt tgctttgccc aaaaatggac cagttttaaa acctggtttg    3540
agaagagttc aagatagcaa tggctctcaa atcgaattag aagtgtacag tgttccaaaa    3600
gaactgttcg gtgcttttat ttccatggtt cctgaaccat taggaatagg ttcagtggag    3660
ttagaatctg gtgaatggat caaatccttt atttgtgaag aatctggtta caaagccaaa    3720
ggtacagttg atatcacaaa gtatggtgga tttagagcat attttgaaat gttgtaagtt    3780
taaactaatc ccacagccgc cagttccgct ggcggcattt taactttctt taatgggcgc    3840
gcctttccat aggctccgcc ccctgacga gcatcacaaa aatcgacgct caagtcagag    3900
gtggcgaaac ccgacaggac tataaagata ccaggcgttt ccccctggaa gctccctcgt    3960
gcgctctcct gttccgaccc tgccgcttac cggatacctg tccgcctttc tcccttcggg    4020
aagcgtggcg ctttctcata gctcacgctg taggtatctc agttcggtgt aggtcgttcg    4080
ctccaagctg ggctgtgtgc acgaaccccc cgttcagccc gaccgctgcg ccttatccgg    4140
taactatcgt cttgagtcca acccggtaag acacgactta tcgccactgg cagcagccac    4200
tggtaacagg attagcagag cgaggtatgt aggcggtgct acagagttct tgaagtggtg    4260
gcctaactac ggctacacta agaacagt atttggtatc tgcgctctgc tgaagccagt    4320
taccttcgga aaaagagttg gtagctcttg atccggcaaa caaaccaccg ctggtagcgg    4380
```

```
tggttttttt gtttgcaagc agcagattac gcgcagaaaa aaaggatctc aagaagatcc    4440
tttgatcttt tctacggggt ctgacgctca gtggaacgaa aactcacgtt aagggatttt    4500
ggtcatgaga ttatcaaaaa ggatcttcac ctagatcctt ttaaattaaa aatgaagttt    4560
taaatcaatc taaagtatat atgagtaaac ttggtctgac agttaccaat gcttaatcag    4620
tgaggcacct atctcagcga tctgtctatt tcgttcatcc atagttgcct gactccccgt    4680
cgtgtagata actacgatac gggagggctt accatctggc cccagtgctg caatgatacc    4740
gcgagaccca cgctcaccgg ctccagattt atcagcaata accagccag ccggaagggc    4800 cgagcgcaga agtggtcctg caactttatc cgcctccatc cagtctatta attgttgccg    4860
ggaagctaga gtaagtagtt cgccagttaa tagtttgcgc aacgttgttg ccattgctac    4920
aggcatcgtg gtgtcacgct cgtcgtttgg tatggcttca ttcagctccg gttcccaacg    4980
atcaaggcga gttacatgat cccccatgtt gtgcaaaaaa gcggttagct ccttcggtcc    5040
tccgatcgtt gtcagaagta agttggccgc agtgttatca ctcatggtta tggcagcact    5100
gcataattct cttactgtca tgccatccgt aagatgcttt tctgtgactg gtgagtactc    5160
aaccaagtca ttctgagaat agtgtatgcg gcgaccgagt tgctcttgcc cggcgtcaat    5220
acgggataat accgcgccac atagcagaac tttaaaagtg ctcatcattg gaaaacgttc    5280
ttcggggcga aaactctcaa ggatcttacc gctgttgaga tccagttcga tgtaacccac    5340
tcgtgcaccc aactgatctt cagcatcttt tactttcacc agcgtttctg ggtgagcaaa    5400
aacaggaagg caaaatgccg caaaaaaggg aataagggcg acacggaaat gttgaatact    5460
catactcttc cttttcaat attattgaag catttatcag ggttattgtc tcatgagcgg    5520
atacatattt gaatgtattt agaaaaataa acagcgatcg cgcggccgcg ggtaataact    5580
gatataatta aattgaagct ctaatttgtg agtttagtat acatgcattt acttataata    5640 cagttttta gttttgctgg ccgcatcttc tcaaatatgc ttcccagcct gcttttctgt    5700
aacgttcacc ctctaccttt gcatcccttc cctttgcaaa tagtcctctt ccaacaataa    5760
taatgtcaga tcctgtagag accacatcat ccacggttct atactgttga cccaatgcgt    5820
ctcccttgtc atctaaaccc acaccgggtg tcataatcaa ccaatcgtaa ccttcatctc    5880
ttccacccat gtctctttga gcaataaagc cgataacaaa atctttgtcg ctcttcgcaa    5940
tgtcaacagt acccttagta tattctccag tagctaggga gcccttgcat gacaattctg    6000
ctaacatcaa aaggcctcta ggttcctttg ttacttcttc cgccgcctgc ttcaaaccgc    6060
taacaatacc tgggcccacc acaccgtgtg cattcgtaat gtctgcccat tctgctattc    6120
tgtatacacc cgcagagtac tgcaatttga ctgtattacc aatgtcagca aattttctgt    6180
cttcgaagag taaaaaattg tacttggcgg ataatgcctt tagcggctta actgtgccct    6240
ccatggaaaa atcagtcaag atatccacat gtgtttttag taaacaaatt ttgggaccta    6300
atgcttcaac taactccagt aattccttgg tggtacgaac atccaatgaa gcacacaagt    6360
ttgtttgctt ttcgtgcatg atattaaata gcttggcagc aacaggacta ggatgagtag    6420
cagcacgttc cttatatgta gctttcgaca tgatttatct tcgtttcctg caggttttg     6480 ttctgtgcag ttgggttaag aatactgggc aatttcatgt ttcttcaaca ccacatatgc    6540
gtatatatac caatctaagt ctgtgctcct tccttcgttc ttccttctgc tcggagatta    6600
ccgaatcaaa gctagcttat cgatgataag ctgtcaaaga tgagaattaa ttccacggac    6660
tatagactat actagatact ccgtctactg tacgatacac ttccgctcag gtccttgtcc    6720
```

| | |
|---|---|
| tttaacgagg ccttaccact cttttgttac tctattgatc cagctcagca aaggcagtgt | 6780 |
| gatctaagat tctatcttcg cgatgtagta aaactagcta gaccgagaaa gagactagaa | 6840 |
| atgcaaaagg cacttctaca atggctgcca tcattattat ccgatgtgac gctgcagctt | 6900 |
| ctcaatgata ttcgaatacg ctttgaggag atacagccta atatccgaca aactgtttta | 6960 |
| cagatttacg atcgtacttg ttacccatca ttgaattttg aacatccgaa cctgggagtt | 7020 |
| ttccctgaaa cagatagtat atttgaacct gtataataat atatagtcta gcgctttacg | 7080 |
| gaagacaatg tatgtatttc ggttcctgga gaaactattg catctattgc ataggtaatc | 7140 |
| ttgcacgtcg catccccggt tcattttctg cgtttccatc ttgcacttca atagcatatc | 7200 |
| tttgttaacg aagcatctgt gcttcatttt gtagaacaaa aatgcaacgc gagagcgcta | 7260 |
| attttttcaaa caaagaatct gagctgcatt tttacagaac agaaatgcaa cgcgaaagcg | 7320 |
| ctattttacc aacgaagaat ctgtgcttca tttttgtaaa acaaaaatgc aacgcgacga | 7380 |
| gagcgctaat ttttcaaaca aagaatctga gctgcatttt tacagaacag aaatgcaacg | 7440 |
| cgagagcgct attttaccaa caaagaatct atacttcttt tttgttctac aaaaatgcat | 7500 |
| cccgagagcg ctattttttct aacaaagcat cttagattac tttttttctc ctttgtgcgc | 7560 |
| tctataatgc agtctcttga taactttttg cactgtaggt ccgttaaggt tagaagaagg | 7620 |
| ctactttggt gtctattttc tcttccataa aaaagcctg actccacttc ccgcgtttac | 7680 |
| tgattactag cgaagctgcg ggtgcatttt ttcaagataa aggcatcccc gattatattc | 7740 |
| tataccgatg tggattgcgc atactttgtg aacagaaagt gatagcgttg atgattcttc | 7800 |
| attggtcaga aaattatgaa cggtttcttc tattttgtct ctatatacta cgtataggaa | 7860 |
| atgtttacat tttcgtattg ttttcgattc actctatgaa tagttcttac tacaattttt | 7920 |
| ttgtctaaag agtaatacta gagataaaca taaaaaatgt agaggtcgag tttagatgca | 7980 |
| agttcaagga gcgaaaggtg gatgggtagg ttatataggg atatagcaca gagatatata | 8040 |
| gcaaagagat acttttgagc aat | 8063 |

<210> SEQ ID NO 48
<211> LENGTH: 8927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

| | |
|---|---|
| gtttgtggaa gcggtattcg caatcattta gtcgtgcaat gtatgacttt aagatttgtg | 60 |
| agcaggaaga aaagggagaa tcttctaacg ataaaccctt gaaaaactgg gtagactacg | 120 |
| ctatgttgag ttgctacgca ggctgcacaa ttacacgaga atgctcccgc ctaggattta | 180 |
| aggctaaggg acgtgcaatg cagacgacag atctaaatga ccgtgtcggt gaagtgttcg | 240 |
| ccaaactttt cggttaacac atgcagtgat gcacgcgcga tggtgctaag ttacatatat | 300 |
| atatatatat atatatatat atatatatag ccatagtgat gtctaagtaa cctttatggt | 360 |
| atatttctta atgtggaaag atactagcgc gcgcacccac acacaagctt cgtcttttct | 420 |
| tgaagaaaag aggaagctcg ctaaatggga ttccactttc cgttccctgc cagctgatgg | 480 |
| aaaaaggtta gtggaacgat gaagaataaa aagagagatc cactgaggtg aaatttcagc | 540 |
| tgacagcgag tttcatgatc gtgatgaaca atggtaacga gttgtggctg ttgccaggga | 600 |
| gggtggttct caacttttaa tgtatggcca aatcgctact tgggtttgtt ataataacaaa | 660 |

```
gaagaaataa tgaactgatt ctcttcctcc ttcttgtcct ttcttaattc tgttgtaatt    720 accttcctttt gtaattttttt ttgtaattat tcttcttaat aatccaaaca aacacacata   780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980 acatctttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta cttttttccat aggctccgcc cccctgacga gcatcacaaa aatcgacgct   2280
caagtcagag gtggcgaaac ccgacaggac tataaagata ccaggcgttt cccctggaa    2340 gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaggatctc    2820 aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taagtatat atgagtaaac ttggtctgac agttaccaat   3000
gcttaatcag tgaggcacct atctcagcga tctgtctatt tcgttcatcc atagttgcct   3060
```

```
gactccccgt cgtgtagata actacgatac gggagggctt accatctggc cccagtgctg    3120
caatgatacc gcgagaccca cgctcaccgg ctccagattt atcagcaata aaccagccag    3180
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa aacaggaagg caaaatgccg caaaaagggg ataagggcg acacggaaat    3840 gttgaatact catactcttc ctttttcaat attattgaag catttatcag ggttattgtc    3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca aagaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagttttttac tgtacaaaca cctgtgtagc    4380
tccttctagc attttttaagt tattcacacc tcaaggggag ggataaatta aataaattcc    4440
aaaagcgaag atcgagaaac taaattaaaa ttccaaaaac gaagttggaa cacaaccccc    4500
cgaaaaaaaa caacaaacaa aaacccaac aaaataaaca aaaacaaaat aaatatataa    4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttattttatt ttatttaata aagaaaaca acaagatggg    4740 ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttacatttca cagtctgaac ttttgcagat tacctaattt ggtaagatat    4980
taattatgaa ctgaaagttg atggcggccg catagcttca aaatgtttct actccttttt    5040
tactcttcca gattttctcg gactccgcgc atcgccgtac cacttcaaaa cacccaagca    5100
cagcatacta aatttcccct ctttcttcct ctagggtgtc gttaattacc cgtactaaag    5160
gtttggaaaa gaaaaagag accgcctcgt ttcttttttct tcgtcgaaaa aggcaataaa    5220
aatttttatc acgtttcttt ttcttgaaaa tttttttttt tgattttttt ctctttcgat    5280
gacctcccat tgatatttaa gttaataaac ggtcttcaat ttctcaagtt tcagtttcat    5340
ttttcttgtt ctattacaac ttttttttact tcttgctcat tagaaagaaa gcatagcaat    5400
```

```
ctaatctaag ttttaattac aaaatgtcat cctcagaagt aaaagcaaat ggttggaccg    5460
cagttcctgt ttccgcaaaa gcaatagtag actccttggg taaattagga gatgtctctt    5520
catattccgt agaagatatt gccttttccag ctgcagacaa attggtagcc gaagctcaag    5580
cattcgttaa ggctagatta tctcctgaaa cctacaacca ttcaatgaga gttttctatt    5640
ggggtactgt cattgccaga agattgttac cagaacaagc taaagatttg tctccttcaa    5700
catgggcatt aacctgtttg ttacacgacg ttggtactgc cgaagcttat tttacctcca    5760
ctagaatgag tttcgatatc tacggtggta ttaaagctat ggaagtattg aaggttttag    5820
gttccagtac agatcaagca gaagccgttg ctgaagcaat tataagacat gaagatgttg    5880
gtgtcgacgg taacatcaca ttttttgggtc aattgatcca attggcaaca ttgtacgata    5940
acgtcggtgc ctacgacggt attgatgact tcggttcctg ggttgatgac actacaagaa    6000
acagtataaa cactgctttc ccaagacatg gttggtgttc ttggttcgca tgcacagtta    6060
gaaaagaaga atcaaacaag ccttggtgcc acaccacaca cataccacaa ttcgacaaac    6120
aaatggaagc aaacaccttg atgaaacctt gggaataaac aggcccctttt tcctttgtcg    6180 atatcatgta attagttatg tcacgcttac attcacgccc tcctcccaca tccgctctaa    6240
ccgaaaagga aggagttaga caacctgaag tctaggtccc tatttatttt ttttaatagt    6300
tatgttagta ttaagaacgt tatttatatt tcaaatttt ctttttttc tgtacaaacg    6360 cgtgtacgca tgtaacatta tactgaaaac cttgcttgag aaggttttgg gacgctcgaa    6420
ggctttaatt tgcgggtaat aactgatata attaaattga agctctaatt tgtgagttta    6480
gtatacatgc atttacttat aatacagttt tttagttttg ctggccgcat cttctcaaat    6540
atgcttccca gcctgctttt ctgtaacgtt caccctctac cttagcatcc cttccctttg    6600
caaatagtcc tcttccaaca ataataatgt cagatcctgt agagaccaca tcatccacgg    6660
ttctatactg ttgacccaat gcgtctccct tgtcatctaa acccacaccg ggtgtcataa    6720
tcaaccaatc gtaaccttca tctcttccac ccatgtctct ttgagcaata aagccgataa    6780
caaaatcttt gtcgctcttc gcaatgtcaa cagtaccctt agtatattct ccagtagcta    6840 gggagcccctt gcatgacaat tctgctaaca tcaaaaggcc tctaggttcc tttgttactt    6900
cttccgccgc ctgcttcaaa ccgctaacaa tacctgggcc caccacaccg tgtgcattcg    6960
taatgtctgc ccattctgct attctgtata cacccgcaga gtactgcaat ttgactgtat    7020
taccaatgtc agcaaatttt ctgtcttcga agagtaaaaa attgtacttg gcggataatg    7080
cctttagcgg cttaactgtg ccctccatgg aaaaatcagt caagatatcc acatgtgttt    7140
ttagtaaaca aattttggga cctaatgctt caactaactc cagtaattcc ttggtggtac    7200
gaacatccaa tgaagcacac aagtttgttt gcttttcgtg catgatatta aatagcttgg    7260
cagcaacagg actaggatga gtagcagcac gttccttata tgtagctttc gacatgattt    7320
atcttcgttt cctgcaggtt tttgttctgt gcagttgggt taagaatact gggcaatttc    7380
atgtttcttc aacaccacat atgcgtatat ataccaatct aagtctgtgc tccttccttc    7440
gttcttcctt ctgctcggag attaccgaat caaagctagc ttatcgatga taagctgtca    7500
aagatgagaa ttaattccac ggactataga ctatactaga tactccgtct actgtacgat    7560
acacttccgc tcaggtcctt gtcctttaac gaggccttac cactcttttg ttactctatt    7620
gatccagctc agcaaaggca gtgtgatcta agattctatc ttcgcgatgt agtaaaacta    7680
gctagaccga gaaagagact agaaatgcaa aaggcacttc tacaatggct gccatcatta    7740
ttatccgatg tgacgctgca gcttctcaat gatattcgaa tacgctttga ggagatacag    7800
```

```
cctaatatcc gacaaactgt tttacagatt tacgatcgta cttgttaccc atcattgaat    7860
tttgaacatc cgaacctggg agttttccct gaaacagata gtatatttga acctgtataa    7920
taatatatag tctagcgctt tacggaagac aatgtatgta tttcggttcc tggagaaact    7980
attgcatcta ttgcataggt aatcttgcac gtcgcatccc cggttcattt tctgcgtttc    8040
catcttgcac ttcaatagca tatctttgtt aacgaagcat ctgtgcttca ttttgtagaa    8100
caaaaatgca acgcgagagc gctaattttt caaacaaaga atctgagctg cattttaca     8160 gaacagaaat gcaacgcgaa agcgctattt taccaacgaa gaatctgtgc ttcattttg     8220 taaaacaaaa atgcaacgcg acgagagcgc taattttca aacaaagaat ctgagctgca     8280
tttttacaga acagaaatgc aacgcgagag cgctatttta ccaacaaaga atctatactt    8340 ctttttgtt ctacaaaaat gcatcccgag agcgctattt tctaacaaa gcatcttaga      8400 ttactttttt tctcctttgt gcgctctata atgcagtctc ttgataactt tttgcactgt    8460
aggtccgtta aggttagaag aaggctactt tggtgtctat tttctcttcc ataaaaaaag    8520
cctgactcca cttcccgcgt ttactgatta ctagcgaagc tgcgggtgca ttttttcaag    8580
ataaaggcat ccccgattat attctatacc gatgtggatt gcgcatactt tgtgaacaga    8640
aagtgatagc gttgatgatt cttcattggt cagaaaatta tgaacggttt cttctatttt    8700
gtctctatat actacgtata ggaaatgttt acattttcgt attgttttcg attcactcta    8760
tgaatagttc ttactacaat ttttttgtct aaagagtaat actagagata aacataaaaa    8820
atgtagaggt cgagtttaga tgcaagttca aggagcgaaa ggtggatggg taggttatat    8880
agggatatag cacagagata tatagcaaag agatacttt gagcaat                   8927

<210> SEQ ID NO 49
<211> LENGTH: 8918
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gtttgtggaa gcggtattcg caatcattta gtcgtgcaat gtatgacttt aagatttgtg      60
agcaggaaga aaagggagaa tcttctaacg ataaacccct gaaaaactgg gtagactacg     120
ctatgttgag ttgctacgca ggctgcacaa ttacacgaga atgctcccgc ctaggattta     180
aggctaaggg acgtgcaatg cagacgcacg atctaaatga ccgtgtcggt gaagtgttcg     240
ccaaactttt cggttaacac atgcagtgat gcacgcgcga tggtgctaag ttacatatat     300
atatatatat atatatatat atatatatag ccatagtgat gtctaagtaa cctttatggt     360
atatttctta atgtggaaag atactagcgc gcgcacccac acacaagctt cgtcttttct     420
tgaagaaaag aggaagctcg ctaaatggga ttccactttc cgttccctgc cagctgatgg     480
aaaaaggtta gtggaacgat gaagaataaa aagagagatc cactgaggtg aaatttcagc     540
tgacagcgag tttcatgatc gtgatgaaca atggtaacga gttgtggctg ttgccaggga     600
gggtggttct caacttttaa tgtatggcca atcgctact tgggtttgtt atataacaaa      660
gaagaaataa tgaactgatt ctcttcctcc ttcttgtcct ttcttaattc tgttgtaatt     720
accttccttt gtaatttttt ttgtaattat tcttcttaat aatccaaaca aacacacata     780
ttacaataat gaagaagccc gagctgaccg ctacctctgt tgagaagttc ctgattgaga     840
agtttgattc cgtttccgac ctgatgcagc tgtccgaggg cgaggagtct cgagccttct     900
```

```
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc cccttggac    1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgacccct  1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta cttttttccat aggctccgcc cccctgacga gcatcacaaa aatcgacgct   2280
caagtcagag gtggcgaaac ccgacaggac tataaagata ccaggcgttt cccctggaa    2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg gctgtgtgc acgaacccc cgttcagccc gaccgctgcg    2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta agaacagt atttggtatc tgcgctctgc    2700
tgaagccagt taccttcgga aaaagagttg gtagctcttg atccggcaaa caaccaccg    2760
ctggtagcgg tggttttttt gtttgcaagc agcagattac gcgcagaaaa aaggatctc    2820
aagaagatcc tttgatcttt tctacggggt ctgacgctca gtggaacgaa actcacgtt   2880
aagggatttt ggtcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
```

```
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa aacaggaagg caaaatgccg caaaaaaggg aataagggcg acacggaaat    3840
gttgaatact catactcttc ctttttcaat attattgaag catttatcag ggttattgtc    3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca aagaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagttttac tgtacaaaca cctgtgtagc    4380
tccttctagc attttaagt tattcacacc tcaaggggag ggataaatta ataaaattcc    4440
aaaagcgaag atcgagaaac taaattaaaa ttccaaaaac gaagttggaa cacaaccccc    4500
cgaaaaaaaa caacaaacaa aaacccaac aaaataaaca aaaacaaaat aaatatataa    4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttatttatt ttatttaata aaagaaaaca acaagatggg    4740
ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttcatttca cagtctgaac ttttgcagat tacctaattt ggtaagatat    4980
taattatgaa ctgaaagttg atggcggccg catagcttca aaatgtttct actccttttt    5040
tactcttcca gattttctcg gactccgcgc atcgccgtac cacttcaaaa cacccaagca    5100
cagcatacta aatttcccct ctttcttcct ctagggtgtc gttaattacc cgtactaaag    5160
gtttggaaaa gaaaaagag accgcctcgt ttcttttct tcgtcgaaaa aggcaataaa    5220
aattttatc acgtttcttt ttcttgaaaa ttttttttt tgatttttt ctctttcgat    5280
gacctcccat tgatatttaa gttaataaac ggtcttcaat ttctcaagtt tcagtttcat    5340
ttttcttgtt ctattacaac ttttttact tcttgctcat tagaaagaaa gcatagcaat    5400
ctaatctaag ttttaattac aaaatgatat actcaacagt caacgctaat ccttacgctt    5460
ggccttacga tggttcaata gaccctgctc acaccgcttt aatcttaatc gattggcaaa    5520
tagacttttg tggtccaggt ggttatgtcg attccatggg ttacgactta tccttgacta    5580
gaagtggttt agaacctaca gcaagagtat tggctgcagc cagagatact ggtatgacag    5640
```

-continued

```
ttatccatac tagagaaggt cacagaccag atttggctga cttgccacct aataagagat      5700
ggagatctgc atcagccggt gctgaaatcg gttcagttgg tccatgtggt agaattttag      5760
tcagaggtga acctggttgg gaaatagtac cagaagttgc acctagagaa ggtgaaccaa      5820
ttatagataa acctggtaaa ggtgcttcct acgcaacaga tttggacttg ttgttgagaa      5880
caagaggtat cacccatttg attttgaccg gtataactac agatgtttgc gtccacacca      5940
ctatgagaga agccaacgat agaggttacg aatgtttaat tttgtctgat tgcaccggtg      6000
ctactgacag aaagcatcac gaagctgcat tatctatggt caccatgcaa ggtggtgtat      6060
tcggtgcaac tgcccattca gatgacttat tggccgcttt gggtacaacc gttccagcag      6120
ccgctggtcc tagagctaga acagaataaa caggccccct ttccttttgtc gatatcatgt      6180 aattagttat gtcacgctta cattcacgcc ctcctcccac atccgctcta accgaaaagg      6240
aaggagttag acaacctgaa gtctaggtcc ctatttattt tttttaatag ttatgttagt      6300
attaagaacg ttatttatat ttcaaatttt tcttttttt ctgtacaaac gcgtgtacgc      6360
atgtaacatt atactgaaaa ccttgcttga aaggttttg ggacgctcga aggctttaat      6420
ttgcgggtaa taactgatat aattaaattg aagctctaat ttgtgagttt agtatacatg      6480
catttactta taatacagtt ttttagtttt gctggccgca tcttctcaaa tatgcttccc      6540
agcctgcttt tctgtaacgt tcaccctcta ccttagcatc ccttccctt gcaaatagtc      6600 ctcttccaac aataataatg tcagatcctg tagagaccac atcatccacg gttctatact      6660
gttgacccaa tgcgtctccc ttgtcatcta aacccacacc gggtgtcata atcaaccaat      6720
cgtaaccttc atctcttcca cccatgtctc tttgagcaat aaagccgata acaaaatctt      6780
tgtcgctctt cgcaatgtca acagtaccct tagtatattc tccagtagct agggagccct      6840
tgcatgacaa ttctgctaac atcaaaaggc ctctaggttc ctttgttact tcttccgccg      6900
cctgcttcaa accgctaaca ataccctggc ccaccacacc gtgtgcattc gtaatgtctg      6960
cccattctgc tattctgtat acacccgcag agtactgcaa tttgactgta ttaccaatgt      7020
cagcaaattt tctgtcttcg aagagtaaaa aattgtactt ggcggataat gcctttagcg      7080
gcttaactgt gccctccatg gaaaaatcag tcaagatatc cacatgtgtt tttagtaaac      7140 aaatttggg acctaatgct tcaactaact ccagtaattc cttggtggta cgaacatcca      7200
atgaagcaca caagtttgtt tgcttttcgt gcatgatatt aaatagcttg gcagcaacag      7260
gactaggatg agtagcagca cgttccttat atgtagcttt cgacatgatt tatcttcgtt      7320
tcctgcaggt ttttgttctg tgcagttggg ttaagaatac tgggcaattt catgtttctt      7380
caacaccaca tatgcgtata tataccaatc taagtctgtg ctccttcctt cgttcttcct      7440
tctgctcgga gattaccgaa tcaaagctag cttatcgatg ataagctgtc aaagatgaga      7500
attaattcca cggactatag actatactag atactccgtc tactgtacga tacacttccg      7560
ctcaggtcct tgtcctttaa cgaggcctta ccactctttt gttactctat tgatccagct      7620
cagcaaaggc agtgtgatct aagattctat cttcgcgatg tagtaaaact agctagaccg      7680
agaaagagac tagaaatgca aaaggcactt ctacaatggc tgccatcatt attatccgat      7740
gtgacgctgc agcttctcaa tgatattcga atacgctttg aggagataca gcctaatatc      7800
cgacaaactg ttttacagat ttacgatcgt acttgttacc catcattgaa ttttgaacat      7860
ccgaacctgg gagttttccc tgaaacagat agtatatttg aacctgtata ataatatata      7920
gtctagcgct ttacggaaga caatgtatgt atttcggttc ctggagaaac tattgcatct      7980
```

```
attgcatagg taatcttgca cgtcgcatcc ccggttcatt ttctgcgttt ccatcttgca    8040
cttcaatagc atatctttgt taacgaagca tctgtgcttc attttgtaga acaaaaatgc    8100
aacgcgagag cgctaattt tcaaacaaag aatctgagct gcattttac agaacagaaa     8160 tgcaacgcga aagcgctatt ttaccaacga agaatctgtg cttcattttt gtaaaacaaa   8220
aatgcaacgc gacgagagcg ctaattttc aaacaaagaa tctgagctgc attttacag    8280 aacagaaatg caacgcgaga gcgctatttt accaacaaag aatctatact tcttttttgt   8340
tctacaaaaa tgcatcccga gagcgctatt tttctaacaa agcatcttag attacttttt   8400
ttctcctttg tgcgctctat aatgcagtct cttgataact ttttgcactg taggtccgtt   8460
aaggttagaa gaaggctact ttggtgtcta tttttctcttc cataaaaaa gcctgactcc    8520 acttcccgcg tttactgatt actagcgaag ctgcgggtgc atttttcaa gataaaggca   8580 tccccgatta tattctatac cgatgtggat tgcgcatact ttgtgaacag aaagtgatag    8640
cgttgatgat tcttcattgg tcagaaaatt atgaacggtt tcttctattt tgtctctata   8700
tactacgtat aggaaatgtt tacattttcg tattgtttc gattcactct atgaatagtt    8760
cttactacaa tttttttgtc taaagagtaa tactagagat aaacataaaa aatgtagagg    8820
tcgagtttag atgcaagttc aaggagcgaa aggtggatgg gtaggttata tagggatata    8880
gcacagagat atatagcaaa gagatacttt tgagcaat                            8918

<210> SEQ ID NO 50
<211> LENGTH: 8894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gtttgtggaa gcggtattcg caatcattta gtcgtgcaat gtatgacttt aagatttgtg      60
agcaggaaga aaagggagaa tcttctaacg ataaacccctt gaaaaactgg gtagactacg    120
ctatgttgag ttgctacgca ggctgcacaa ttacacgaga atgctcccgc ctaggattta    180
aggctaaggg acgtgcaatg cagacgacag atctaaatga ccgtgtcggt gaagtgttcg    240
ccaaactttt cggttaacac atgcagtgat gcacgcgcga tggtgctaag ttacatatat    300
atatatatat atatatatat atatatatag ccatagtgat gtctaagtaa cctttatggt    360
atatttctta atgtggaaag atactagcgc gcgcacccac acacaagctt cgtcttttct    420
tgaagaaaag aggaagctcg ctaaatggga ttccactttc cgttccctgc cagctgatgg    480
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
accttccttt gtaatttttt ttgtaattat tcttcttaat aatccaaaca aacacacata    780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
```

```
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gataggttc    2040 attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc ccctgacga gcatcacaaa atcgacgct    2280 caagtcagag gtgcgaaac ccgacaggac tataaagata ccaggcgttt ccccctggaa    2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaacccc cgttcagccc gaccgctgcg    2520
ccttatccgg taactatcgt cttgagtcca acccggtaag acgacactta tcgccactgg   2580
cagcagccac tggtaacagg attagcagag cgaggtatgt aggcggtgct acagagttct   2640
tgaagtggtg gcctaactac ggctacacta gaagaacagt attggtatc tgcgctctgc    2700 tgaagccagt taccttcgga aaaagagttg gtagctcttg atccggcaaa caaccaccg    2760 ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat ccccatgtt gtgcaaaaaa gcggttagct   3420
ccttcggtcc tccgatcgtt gtcagaagta agttggccgc agtgttatca ctcatggtta   3480
```

```
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa aacaggaagg caaaatgccg caaaaaggg aataagggcg acacggaaat     3840
gttgaatact catactcttc cttttcaat attattgaag catttatcag ggttattgtc      3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca agaatttat tcgtacgaat cacagggacg      4260
gccgccctca ccgaaccagc gaatacctca gcggtcccct gcagtgactc aacaaagcga    4320
tatgaacatc ttgcgatggt atcctgctga tagttttac tgtacaaaca cctgtgtagc      4380
tccttctagc attttaagt tattcacacc tcaggggag ggataaatta aataaattcc       4440
aaaagcgaag atcgagaaac taaattaaaa ttccaaaaac gaagttggaa cacaacccc     4500 cgaaaaaaaa caacaacaa aaacccaac aaaataaaca aaaacaaaat aaatatataa      4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttatttatt ttatttaata aagaaaaca acaagatggg       4740 ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttacatttca cagtctgaac ttttgcagat tacctaattt ggtaagatat    4980
taattatgaa ctgaaagttg atggcggccg catagcttca aaatgtttct actccttttt    5040
tactcttcca gattttctcg gactccgcgc atcgccgtac cacttcaaaa cacccaagca    5100
cagcatacta aatttcccct ctttcttcct ctagggtgtc gttaattacc cgtactaaag    5160
gtttggaaaa gaaaaagag accgcctcgt ttcttttct tcgtcgaaaa aggcaataaa       5220 aattttatc acgtttcttt ttcttgaaaa tttttttttt tgattttttt ctctttcgat      5280
gacctcccat tgatatttaa gttaataaac ggtcttcaat ttctcaagtt tcagtttcat    5340
ttttcttgtt ctattacaac tttttttact tcttgctcat tagaaagaaa gcatagcaat    5400
ctaatctaag ttttaattac aaaatggacg caatggtaga aacaaataga cacttcatag    5460
atgccgaccc ttacccttgg ccttacaacg gtgccttgag acctgataac acagccttga    5520
ttataatcga tatgcaaacc gacttttgtg gtaaaggtgg ttatgtcgat catatgggtt    5580
acgacttatc attggtacaa gccccaatcg aacctattaa aagagtttta gctgcaatga    5640
gagctaaggg ttatcatatt atacacacaa gagaaggtca cagaccagat ttggctgact    5700
tacctgcaaa caagagatgg agatctcaaa gaataggtgc tggtatcggt gacccaggtc    5760
cttgtggtag aattttgacc agaggtgaac caggttggga tatcattcca gaattgtacc    5820
```

```
ctatagaagg tgaaactatc atcgataaac ctggtaaagg tagtttttgc gcaacagact    5880
tagaattggt tttgaaccaa aagagaatcg aaaacatcat cttgaccggt atcactacag    5940
atgtttgtgt ctctaccact atgagagaag caaacgatag aggttacgaa tgcttgttgt    6000
tggaagattg ttgcggtgcc actgactacg gtaaccattt ggccgctatt aaaatggtca    6060
agatgcaagg tggtgtattc ggttctgttt caaattccgc agccttggtt gaagcattac    6120
cataaacagg ccccttttcc tttgtcgata tcatgtaatt agttatgtca cgcttacatt    6180
cacgccctcc tcccacatcc gctctaaccg aaaaggaagg agttagacaa cctgaagtct    6240
aggtccctat ttatttttt taatagttat gttagtatta agaacgttat ttatatttca    6300 aattttctt ttttttctgt acaaacgcgt gtacgcatgt aacattatac tgaaaacctt    6360
gcttgagaag gttttgggac gctcgaaggc tttaatttgc gggtaataac tgatataatt    6420
aaattgaagc tctaatttgt gagtttagta tacatgcatt tacttataat acagtttttt    6480
agttttgctg gccgcatctt ctcaaatatg cttcccagcc tgcttttctg taacgttcac    6540
cctctacctt agcatccctt cccttttgcaa atagtcctct tccaacaata ataatgtcag    6600
atcctgtaga gaccacatca tccacggttc tatactgttg acccaatgcg tctcccttgt    6660
catctaaacc cacaccgggt gtcataatca accaatcgta accttcatct cttccaccca    6720
tgtctctttg agcaataaag ccgataacaa aatctttgtc gctcttcgca atgtcaacag    6780
tacccttagt atattctcca gtagctaggg agcccttgca tgacaattct gctaacatca    6840
aaaggcctct aggttccttt gttacttctt ccgccgcctg cttcaaaccg ctaacaatac    6900
ctgggcccac cacccgtgt gcattcgtaa tgtctgccca ttctgctatt ctgtatacac    6960
ccgcagagta ctgcaatttg actgtattac caatgtcagc aaattttctg tcttcgaaga    7020
gtaaaaaatt gtacttggcg gataatgcct ttagcggctt aactgtgccc tccatggaaa    7080
aatcagtcaa gatatccaca tgtgttttta gtaaacaaat tttgggacct aatgcttcaa    7140
ctaactccag taattccttg gtggtacgaa catccaatga agcacacaag tttgtttgct    7200
tttcgtgcat gatattaaat agcttggcag caacaggact aggatgagta gcagcacgtt    7260
ccttatatgt agcttcgac atgatttatc ttcgttttcct gcaggttttt gttctgtgca    7320
gttgggttaa gaatactggg caatttcatg tttcttcaac accacatatg cgtatatata    7380
ccaatctaag tctgtgctcc ttccttcgtt cttccttctg ctcggagatt accgaatcaa    7440
agctagctta tcgatgataa gctgtcaaag atgagaatta attccacgga ctatagacta    7500
tactagatac tccgtctact gtacgataca cttccgctca ggtccttgtc ctttaacgag    7560
gccttaccac tcttttgtta ctctattgat ccagctcagc aaaggcagtg tgatctaaga    7620
ttctatcttc gcgatgtagt aaaactagct agaccgagaa agagactaga aatgcaaaag    7680
gcacttctac aatggctgcc atcattatta tccgatgtga cgctgcagct tctcaatgat    7740 attgaatac gctttgagga gatacagcct aatatccgac aaactgtttt acagatttac    7800
gatcgtactt gttacccatc attgaatttt gaacatccga acctgggagt tttccctgaa    7860
acagatagta tatttgaacc tgtataataa tatatagtct agcgctttac ggaagacaat    7920
gtatgtattt cggttcctgg agaaactatt gcatcattg cataggtaat cttgcacgtc    7980
gcatccccgg ttcattttct gcgtttccat cttgcacttc aatagcatat ctttgttaac    8040
gaagcatctg tgcttcattt tgtagaacaa aaatgcaacg cgagagcgct aattttttcaa    8100 acaaagaatc tgagctgcat ttttacagaa cagaaatgca acgcgaaagc gctattttac    8160
caacgaagaa tctgtgcttc atttttgtaa aacaaaaatg caacgcgacg agagcgctaa    8220
``` ttttttcaaac aaagaatctg agctgcattt ttacagaaca gaaatgcaac gcgagagcgc    8280 tatttttacca acaaagaatc tatacttctt ttttgttcta caaaaatgca tcccgagagc    8340 gctattttc taacaaagca tcttagatta ctttttttct cctttgtgcg ctctataatg    8400
cagtctcttg ataactttt gcactgtagg tccgttaagg ttagaagaag ctactttgg    8460 tgtctatttt ctcttccata aaaaagcct gactccactt cccgcgttta ctgattacta    8520
gcgaagctgc gggtgcattt tttcaagata aaggcatccc cgattatatt ctataccgat    8580
gtggattgcg catactttgt gaacagaaag tgatagcgtt gatgattctt cattggtcag    8640
aaaattatga acgtttctt ctattttgtc tctatatact acgtatagga aatgtttaca    8700
ttttcgtatt gttttcgatt cactctatga atagttctta ctacaattttt tttgtctaaa    8760 gagtaatact agagataaac ataaaaaatg tagaggtcga gtttagatgc aagttcaagg    8820
agcgaaaggt ggatgggtag gttatatagg gatatagcac agagatatat agcaaagaga    8880
tacttttgag caat    8894

<210> SEQ ID NO 51
<211> LENGTH: 8395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gtttgtggaa gcggtattcg caatttaatt aaagctggtg acaattaatc atcggctcgt     60
ataatgtgtg gaattgaatc gatataagga ggttaatcat atgtcaatgg aaacccatag    120
ttatgtagac gtcgcaattc gtaacgcgcg tcttgccgat acgagggaa ttgtcgatat    180 tcttattcac gatgggcgca ttgcgtccat cgtgaagtcg acaaaaacaa aaggatcggt    240
ggagatcgat gctcatgagg gtctggtcac ttccggcctg gtagagcctc acatccatct    300
cgataaggcc ctgacggcag atcgggttcc cgcaggaagc attggcgacc ttcgaacgcg    360
acgaggcctt gagatggcaa ttcgggccac ccgtgatatc aagcgtacgt tcacggttga    420
agatgttcga gaacgggcca tacgtgcggc cctgatggca tcccgtgcgg gaaccaccgc    480
attgcggaca cacgtcgatg tcgacccgat tgtcggcctc gcaggtatcc gtggtgtcct    540
tgaggcgcgt gaagtctgcg cgggattgat cgatatccag atcgtcgcct tccctcagga    600
gggactcttc tgctctgcgg gggccgtgga cctcatgcgg gaggcgatca aactgggcgc    660
ggatgccgtc ggcggcgcac ccgcgctgga tgatcgcccg caggaccatg tccgagccgt    720
ttttgacctt gctgctgagt tcggcctgcc cgtagacatg cacgtcgatg agtccgaccg    780
gcgggaagac tttacgcttc cctttgtgat tgaagctgcc cgtgaacggc gtgtgcccaa    840
tgtgaccgtc gcgcacatca gctcgctgtc cgtacagacg gatgacgtag cacggtcgac    900
cattgccgcc cttgcggacg ccgatgttaa tgtcgtggtt aatccgatca ttgtcaaaat    960
tacgcggctg agtgaattac tcgatgccgg agtctccgta atgtttggct cggacaacct    1020
gcgggatccg ttctatccgc tcggagcggc gaatcccctt ggatcagcca ttttttgcctg    1080 tcaaattgcc gcgctgggaa caccgcaaga tctcagacgg gtattcgatg cggtcaccat    1140
caacgctgcc cgcatgctgg gattcccctc actttttaggc gtcgtggaag gggcagtcgc    1200
ggatctcgca gtattcccat cggcgacgcc cgaggaggtt gttctggatc aacagtctcc    1260
gctcttcgta ctcaagggcg gacgtgtcgt tgccatgcga ttggccgctg gatcaacgtc    1320

```
gttccgcgac tactcatgag gaaatccatt atgatgtcag gagaacacac gttaaaagcg    1380
gtacgaggca gttttattga tgtcacccgt acgatcgata acccggaaga gattgcctct    1440
gcgctgcggt ttattgagga tggtttatta ctcattaaac agggaaaagt ggaatggttt    1500
ggcgaatggg aaaacggaaa gcatcaaatt cctgacacca ttcgcgtgcg cgactatcgc    1560
ggcaaactga tagtaccggg ctttgtcgat acacatatcc attatccgca aagtgaaatg    1620
gtgggggcct atggtgagca attgctggag tggttgaata acacaccttt ccctactgaa    1680
cgtcgttatg aggatttaga gtacgcccgc gaaatgtcgg cgttcttcat caagcagctt    1740
ttacgtaacg gaaccaccac ggcgctggtg tttggcactg ttcatccgca atctgttgat    1800
gcgctgtttg aagccgccag tcatatcaat atgcgtatga ttgccggtaa ggtgatgatg    1860
gaccgcaacg caccggatta tctgctcgac actgccgaaa gcagctatca ccaaagcaaa    1920
gaactgatcg aacgctggca caaaaatggt cgtctgctat atgcgattac gccacgcttc    1980
gccccgacct catctcctga acagatggcg atggcgcaac gcctgaaaga gaatatccg    2040
gatacgtggg tacataccca tctctgtgaa aacaaagatg aaattgcctg ggtgaaatcg    2100
ctttatcctg accatgatgg ttatctggat gtttaccatc agtacggcct gaccggtaaa    2160
aactgtgtct ttgctcactg cgtccatctc gaagaaaaag agtgggatcg tctcagcgaa    2220
accaaatcca gcattgcttt ctgtccgacc tccaaccttt acctcggcag cggcttattc    2280
aacttgaaaa aagcatggca gaagaaagtt aaagtgggca tgggaacgga tatcggtgcc    2340
ggaaccactt tcaacatgct gcaaacgctg aacgaagcct acaaagtatt gcaattacaa    2400
ggctatcgcc tctcggcata tgaagcgttt tacctggcca cgctcggcgg agcgaaatct    2460
ctgggccttg acgatttgat tgcaactttt ttacctggca aagaggctga tttcgtggtg    2520
atggaaccca ccgccactcc gctacagcag ctgcgctatg acaactctgt ttctttagtc    2580
gacaaattgt tcgtgatgat gacgttgggc gatgaccgtt cgatctaccg cacctacgtt    2640
gatggtcgtc tggtgtacga acgcaactaa ggaacgacca tgcaaacgct cagcatccag    2700
cacggtaccc tcgtcacgat ggatcagtac cgcagagtcc ttggggatag ctgggttcac    2760
gtgcaggatg gacggatcgt cgcgctcgga gtgcacgcca gtcggtgcc tccgccagcg    2820
gatcgggtga tcgatgcacg cggcaaggtc gtgttacccg gtttcatcaa tgcccacacc    2880
catgtgaacc agatcctcct gcgcggaggg ccctcgcacg ggcgtcaact ctatgactgg    2940
ctgttcaacg ttttgtatcc gggacaaaag gcgatgagac cggaggacgt agcggtggcg    3000
gtgaggttgt attgtgcgga agctgtgcgc agcgggatta cgacgatcaa cgacaacgcc    3060
gattcggcca tctacccagg caacatcgag gccgcgatgg cggtctatgg tgaggtgggt    3120
gtgagggtcg tctacgcccg catgttcttt gatcggatgg acgggcgcat tcaagggtat    3180
gtggacgcct tgaaggctcg ctctccccaa gtcgaactgt gctcgatcat ggaggaaacg    3240
gctgtggcca aagatcggat cacagccctg tcagatcagt atcatggcac ggcaggaggt    3300
cgtatatcag tttggcccgc tcctgccatt accccggcgg tgacagttga aggaatgcga    3360
tgggcacaag ccttcgcccg tgatcgggcg gtaatgtgga cgcttcacat ggcggagagc    3420
gatcatgatg agcggcttca ttggatgagt cccgccgagt acatggagtg ttacggactc    3480
ttggatgagc gtctgcaggt cgcgcattgc gtgtactttg accggaagga tgttcggctg    3540
ctgcaccgcc acaatgtgaa ggtcgcgtcg caggttgtga gcaatgccta cctcggctca    3600
ggggtggccc ccgtgccaga gatggtggag cgcggcatgg ccgtgggcat tggaacagat    3660
```

```
gacgggaatt gtaatgactc cgtaaacatg atcggagaca tgaagtttat ggcccatatt    3720
caccgcgcgg tgcatcggga tgcggacgtg ctgaccccag agaagattct tgaaatggcg    3780
acgatcgatg gggcgcgttc gttgggaatg gaccacgaga ttggttccat cgaaaccggc    3840
aagcgcgcgg accttatcct gcttgacctg cgtcaccctc agacgactcc tcaccatcat    3900
ttggcggcca cgatcgtgtt tcaggcttac ggcaatgagg tggacactgt cctgattgac    3960
ggaaacgttg tgatggagaa ccgccgcttg agctttcttc ccctgaacg tgagttggcg     4020
ttccttgagg aagcgcagag ccgcgccaca gctattttgc agcgggcgaa catggtggct    4080
aacccagctt ggcgcagcct ctagcctcaa aatatatttt ccctctatct tctcgttgcg    4140
cttaatttga ctaattctca ttagcgaggc gcgcctttcc ataggctccg ccccctgac     4200
gagcatcaca aaaatcgacg ctcaagtcag aggtggcgaa acccgacagg actataaaga    4260
taccaggcgt ttcccctgg aagctccctc gtgcgctctc ctgttccgac cctgccgctt     4320
accggatacc tgtccgcctt tctcccttcg ggaagcgtgg cgctttctca tagctcacgc    4380
tgtaggtatc tcagttcggt gtaggtcgtt cgctccaagc tgggctgtgt gcacgaaccc    4440
cccgttcagc ccgaccgctg cgccttatcc ggtaactatc gtcttgagtc caacccggta    4500
agacacgact tatcgccact ggcagcagcc actggtaaca ggattagcag agcgaggtat    4560
gtaggcggtg ctacagagtt cttgaagtgg tggcctaact acggctacac tagaagaaca    4620
gtatttggta tctgcgctct gctgaagcca gttaccttcg gaaaaagagt tggtagctct    4680
tgatccggca aacaaaccac cgctggtagc ggtggttttt ttgtttgcaa gcagcagatt    4740
acgcgcagaa aaaaggatc tcaagaagat cctttgatct tttctacggg gtctgacgct     4800
cagtggaacg aaaactcacg ttaagggatt ttggtcatga gattatcaaa aaggatcttc    4860
acctagatcc ttttaaatta aaaatgaagt tttaaatcaa tctaaagtat atatgagtaa    4920
acttggtctg acagttacca atgcttaatc agtgaggcac ctatctcagc gatctgtcta    4980
tttcgttcat ccatagttgc ctgactcccc gtcgtgtaga taactacgat acgggagggc    5040
ttaccatctg gccccagtgc tgcaatgata ccgcgagacc cacgctcacc ggctccagat    5100
ttatcagcaa taaaccagcc agccggaagg gccgagcgca gaagtggtcc tgcaacttta    5160
tccgcctcca tccagtctat taattgttgc cgggaagcta gagtaagtag ttcgccagtt    5220
aatagtttgc gcaacgttgt tgccattgct acaggcatcg tggtgtcacg ctcgtcgttt    5280
ggtatggctt cattcagctc cggttcccaa cgatcaaggc gagttacatg atcccccatg    5340
ttgtgcaaaa aagcggttag ctccttcggt cctccgatcg ttgtcagaag taagttggcc    5400
gcagtgttat cactcatggt tatggcagca ctgcataatt ctcttactgt catgccatcc    5460
gtaagatgct tttctgtgac tggtgagtac tcaaccaagt cattctgaga atagtgtatg    5520
cggcgaccga gttgctcttg cccggcgtca atacgggata ataccgcgcc acatagcaga    5580
actttaaaag tgctcatcat tggaaaacgt tcttcggggc gaaaactctc aaggatctta    5640
ccgctgttga tccagttcga tgtaaccca ctcgtgcac ccaactgatc ttcagcatct      5700
tttactttca ccagcgtttc tgggtgagca aaaacaggaa ggcaaaatgc cgcaaaaaag    5760
ggaataaggg cgacacggaa atgttgaata ctcatactct tcctttttca atattattga    5820
agcatttatc agggttattg tctcatgagc ggatacatat ttgaatgtat ttagaaaaat    5880
aaacagcgat cgcgcggccg cgggtaataa ctgatataat taattgaag ctctaatttg     5940
tgagtttagt atacatgcat ttacttataa tacagttttt tagttttgct ggccgcatct    6000
tctcaaatat gcttcccagc ctgcttttct gtaacgttca ccctctacct tagcatccct    6060
```

```
tcccttttgca aatagtcctc ttccaacaat aataatgtca gatcctgtag agaccacatc   6120
atccacggtt ctatactgtt gacccaatgc gtctcccttg tcatctaaac ccacaccggg   6180
tgtcataatc aaccaatcgt aaccttcatc tcttccaccc atgtctcttt gagcaataaa   6240
gccgataaca aaatctttgt cgctcttcgc aatgtcaaca gtacccttag tatattctcc   6300
agtagctagg gagcccttgc atgacaattc tgctaacatc aaaaggcctc taggttcctt   6360
tgttacttct tccgccgcct gcttcaaacc gctaacaata cctgggccca ccacaccgtg   6420
tgcattcgta atgtctgccc attctgctat tctgtataca cccgcagagt actgcaattt   6480
gactgtatta ccaatgtcag caaattttct gtcttcgaag agtaaaaaat tgtacttggc   6540
ggataatgcc tttagcggct taactgtgcc ctccatggaa aaatcagtca agatatccac   6600
atgtgttttt agtaaacaaa ttttgggacc taatgcttca actaactcca gtaattcctt   6660
ggtggtacga acatccaatg aagcacacaa gtttgtttgc ttttcgtgca tgatattaaa   6720
tagcttggca gcaacaggac taggatgagt agcagcacgt tccttatatg tagctttcga   6780
catgatttat cttcgtttcc tgcaggtttt tgttctgtgc agttgggtta agaatactgg   6840
gcaatttcat gtttcttcaa caccacatat gcgtatatat accaatctaa gtctgtgctc   6900
cttccttcgt tcttccttct gctcggagat taccgaatca aagctagctt atcgatgata   6960
agctgtcaaa gatgagaatt aattccacgg actatagact atactagata ctccgtctac   7020
tgtacgatac acttccgctc aggtccttgt cctttaacga ggccttacca ctcttttgtt   7080
actctattga tccagctcag caaaggcagt gtgatctaag attctatctt cgcgatgtag   7140
taaaactagc tagaccgaga aagagactag aaatgcaaaa ggcacttcta caatggctgc   7200
catcattatt atccgatgtg acgctgcagc ttctcaatga tattcgaata cgctttgagg   7260
agatacagcc taatatccga caaactgttt tacagattta cgatcgtact tgttacccat   7320
cattgaattt tgaacatccg aacctgggag ttttccctga aacagatagt atatttgaac   7380
ctgtataata atatatagtc tagcgcttta cggaagacaa tgtatgtatt tcggttcctg   7440
gagaaactat tgcatctatt gcataggtaa tcttgcacgt cgcatccccg gttcattttc   7500
tgcgtttcca tcttgcactt caatagcata tctttgttaa cgaagcatct gtgcttcatt   7560
ttgtagaaca aaaatgcaac gcgagagcgc taattttttca aacaaagaat ctgagctgca   7620
tttttacaga acagaaatgc aacgcgaaag cgctatttta ccaacgaaga atctgtgctt   7680
cattttttgta aaacaaaaat gcaacgcgac gagagcgcta attttttcaaa caagaatct   7740
gagctgcatt tttacagaac agaaatgcaa cgcgagagcg ctattttacc aacaaagaat   7800
ctatacttct ttttgttct acaaaaatgc atcccgagag cgctatttttt ctaacaaagc   7860
atcttagatt acttttttttc tcctttgtgc gctctataat gcagtctctt gataactttt   7920
tgcactgtag gtccgttaag gttagaagaa ggctactttg gtgtctattt tctcttccat   7980
aaaaaaagcc tgactccact tcccgcgttt actgattact agcgaagctg cgggtgcatt   8040
ttttcaagat aaaggcatcc ccgattatat tctataccga tgtggattgc gcatactttg   8100
tgaacagaaa gtgatagcgt tgatgattct tcattggtca gaaaattatg aacggtttct   8160
tctatttttgt ctctatatac tacgtatagg aaatgtttac attttcgtat tgttttcgat   8220
tcactctatg aatagttctt actacaattt ttttgtctaa agagtaatac tagagataaa   8280
cataaaaaat gtagaggtcg agtttagatg caagttcaag gagcgaaagg tggatgggta   8340
ggttatatag ggatatagca cagagatata tagcaaagag atacttttga gcaat         8395
```

<210> SEQ ID NO 52
<211> LENGTH: 12133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

| | | | | | |
|---|---|---|---|---|---|
| gtttgtggaa | gcggtattcg | caatttaatt | aaagctggtg | acaattaatc | atcggctcgt | 60 |
| ataatgtgtg | gaattgaatc | gatataagga | ggttaatcat | atgcaagcgc | aagtttttcg | 120 |
| agttccaatg | agtaatccag | ccgatgttag | tggcgtagcc | aagctcatcg | atgagggagt | 180 |
| gatccgtgcc | gaagaggtcg | tctgcgttct | cggcaagacc | gaaggcaacg | gctgtgtcaa | 240 |
| tgacttcacg | cgtggctaca | ccaccctcgc | gttcaaggtc | tacttctccg | agaaactggg | 300 |
| cgtgtcccgg | caagaggtcg | gcgagcgcat | cgctttcatc | atgtccggcg | gtaccgaagg | 360 |
| cgtcatggcg | cctcactgca | ccatcttcac | cgtgcagaag | acggacaaca | agcagaagac | 420 |
| cgccgctgaa | ggcaagcgac | ttgccgttca | gcagatcttt | acccgcgagt | tcctgccgga | 480 |
| ggagatcggc | cgcatgccgc | aggtcacgga | aacagccgac | gctgttcgcc | gcgccatgcg | 540 |
| cgaagccggc | atcgcggatg | catccgatgt | ccacttcgtt | caggtcaagt | gcccactgct | 600 |
| cactgccggc | cgcatgcatg | acgctgtcga | gcgcgggcat | acggttgcca | ccgaagatac | 660 |
| ctatgagtcc | atgggctact | cccgcggcgc | atccgcgctt | ggtatcgccc | tggccctcgg | 720 |
| ggaagtcgag | aaggccaacc | tcagtgatga | agttattacc | gcagactaca | gtctctactc | 780 |
| ctcggttgcc | tcaacttcgg | cgggtatcga | gttgatgaac | aacgagatca | tcgtcatggg | 840 |
| caacagccgc | gcatgggtg | gtgacctcgt | catcggccac | gccgagatga | aggacgccat | 900 |
| cgacggtgca | gcggtccggc | aggccctgcg | cgacgtcggg | tgctgcgaga | acgacctgcc | 960 |
| gaccgtcgac | gagctcggcc | gcgtggtcaa | tgtatttgcc | aaggctgaag | cctccccgga | 1020 |
| cggtgaggtt | cgtaaccgcc | gccacacgat | gctggacgat | tcggacatta | acagcacgcg | 1080 |
| ccatgcgcga | gcggtcgtca | atgcagttat | cgcttcgatc | gtgggagatc | ccatggttta | 1140 |
| tgtctccggc | ggctccgagc | atcagggccc | cgccggtggc | ggtcccgttg | cagttatcgc | 1200 |
| gcgcacagct | taaggaaatc | cattatgata | tactcaacag | tcaacgctaa | tccttacgct | 1260 |
| tggccttacg | atggttcaat | agaccctgct | cacaccgctt | taatcttaat | cgattggcaa | 1320 |
| atagactttt | gtggtccagg | tggttatgtc | gattccatgg | ttacgactt | atccttgact | 1380 |
| agaagtggtt | tagaacctac | agcaagagta | ttggctgcag | ccagagatac | tggtatgaca | 1440 |
| gttatccata | ctagagaagg | tcacagacca | gatttggctg | acttgccacc | taataagaga | 1500 |
| tggagatctg | catcagccgg | tgctgaaatc | ggttcagttg | gtccatgtgg | tagaattta | 1560 |
| gtcagaggtg | aacctggttg | ggaaatagta | ccagaagttg | cacctagaga | aggtgaacca | 1620 |
| attatagata | aacctggtaa | aggtgctttc | tacgcaacag | atttggactt | gttgttgaga | 1680 |
| acaagaggta | tcacccattt | gattttgacc | ggtataacta | cagatgtttg | cgtccacacc | 1740 |
| actatgagag | aagccaacga | tagaggttac | gaatgtttaa | ttttgtctga | ttgcaccggt | 1800 |
| gctactgaca | gaaagcatca | cgaagctgca | ttatctatgg | tcaccatgca | aggtggtgta | 1860 |
| ttcggtgcaa | ctgcccattc | agatgactta | ttggccgctt | tgggtacaac | cgttccagca | 1920 |
| gccgctggtc | ctagagctag | aacagaataa | ggaacgacca | tgcagttag | ttccgataca | 1980 |
| actgctgaaa | tatcgttagg | ttggtcaatc | caagactgga | ttgatttcca | caagtcatca | 2040 |

```
agctcccagg cttcactaag gcttcttgaa tcactactag actctcaaaa tgttgcgcca    2100
gtcgataatg cgtggatatc gctaatttca aaggaaaatt tactgcacca attccaaatt    2160
ttaaagagca gagaaaataa agaaactcta cctctctacg gtgtccctat tgctgttaag    2220
gacaacatcg acgttagagg tctacccacc accgctgcat gtccatcctt tgcatatgag    2280
ccttccaaag actctaaagt agtagaacta ctaagaaatg caggtgcgat aatcgtgggt    2340
aagacaaact tggaccaatt tgccacagga ttagtcggca cacggtctcc atatgggaaa    2400
acaccttgcg cttttagcaa agagcatgta tctggtggtt cctccgctgg gtcagcatcg    2460
gtggtcgcca gaggtatcgt accaattgca ttgggtactg atacagcagg ttctggtaga    2520
gtcccagccg ccttgaacaa cctgattggc ctaaagccaa caagggcgt cttttcctgt     2580 caaggtgtag ttcccgcttg taaatcttta gactgcgtct ccatctttgc attaaaccta    2640
agtgatgctg aacgctgctt ccgcatcatg tgccagccag atcctgataa tgatgaatat    2700
tctagaccct atgttccaa cccttttgaaa aaattttcaa gcaatgtaac gattgctatt     2760
cctaaaaata tcccatggta tggtgaaacc aagaatcctg tactgttttc caatgctgtc    2820
gaaaatctat caagaacggg cgctaacgtc atagaaattg attttgagcc tcttttagag    2880
ttagctcgct gtttatacga aggtacttgg gtggccgagc gttatcaagc tattcaatcg    2940
tttttggaca gtaaaccacc aaaggaatct ttggaccta ctgttatttc aattatagaa      3000
ggggccaaga aatacagtgc agtagactgc ttcagttttg aatacaaaag acaaggcatc    3060
ttgcaaaaag tgagacgact tctcgaatca gtcgatgtat tgtgtgtgcc cacatgtcct    3120
ttaaatccta ctatgcaaca agttgcggat gaaccagtcc tagtcaattc aagacaaggc    3180
acatggacta attttgtcaa cttggcagat ttggcagccc ttgctgttcc cgcagggttc    3240
cgagacgatg gtttgccaaa tggtattact ttaatcggta aaaaattcac agattacgca    3300
ctattagagt tggctaaccg ctatttccaa aatatattcc ccaacggttc cagaacatac    3360 ggtacttttta cctcttcttc agtaaagcca gcaaacgatc aattagtggg accagactat    3420
gacccatcta cgtccataaa attggctgtt gtcggtgcac atcttaaggg tctgcctcta    3480
cattggcaat tggaaaaggt caatgcaaca tatttatgta caacaaaaac atcaaaagct    3540
taccagcttt ttgctttgcc caaaaatgga ccagttttaa aacctggttt gagaagagtt    3600
caagatagca atggctctca aatcgaatta gaagtgtaca gtgttccaaa agaactgttc    3660
ggtgctttta tttccatggt tcctgaacca ttaggaatag gttcagtgga gttagaatct    3720
ggtgaatgga tcaaatcctt tatttgtgaa gaatctggtt acaaagccaa aggtacagtt    3780
gatatcacaa agtatggtgg atttagagca tattttgaaa tgttgtaagg acacgataat    3840
gtcaatggaa acccatagtt atgtagacgt cgcaattcgt aacgcgcgtc ttgccgatac    3900
ggagggaatt gtcgatattc ttattcacga tgggcgcatt gcgtccatcg tgaagtcgac    3960
aaaaacaaaa ggatcggtgg agatcgatgc tcatgagggt ctggtcactt ccggcctggt    4020
agagcctcac atccatctcg ataaggccct gacggcagat cgggttcccg caggaagcat    4080
tggcgacctt cgaacgcgac gaggccttga tggcaatt cgggccaccc gtgatatcaa     4140
gcgtacgttc acggttgaag atgttcgaga acgggccata cgtgcggccc tgatggcatc    4200
ccgtgcggga accaccgcat tgcggacaca cgtcgatgtc gacccgattg tcggcctcgc    4260
aggtatccgt ggtgtccttg aggcgcgtga agtctgcgcg ggattgatcg atatccagat    4320
cgtcgccttc cctcaggagg gactcttctg ctctgcgggg gccgtggacc tcatgcggga    4380
ggcgatcaaa ctgggcgcgg atgccgtcgg cggcgcaccc gcgctggatg atcgcccgca    4440
```

```
ggaccatgtc cgagccgttt ttgaccttgc tgctgagttc ggcctgcccg tagacatgca    4500
cgtcgatgag tccgaccggc gggaagactt tacgcttccc tttgtgattg aagctgcccg    4560
tgaacggcgt gtgcccaatg tgaccgtcgc gcacatcagc tcgctgtccg tacagacgga    4620
tgacgtagca cggtcgacca ttgccgccct tgcggacgcc gatgttaatg tcgtggttaa    4680
tccgatcatt gtcaaaatta cgcggctgag tgaattactc gatgccggag tctccgtaat    4740
gtttggctcg gacaacctgc gggatccgtt ctatccgctc ggagcggcga atccccttgg    4800
atcagccatt tttgcctgtc aaattgccgc gctgggaaca ccgcaagatc tcagacgggt    4860
attcgatgcg gtcaccatca acgctgcccg catgctggga ttcccctcac ttttaggcgt    4920
cgtggaaggg gcagtcgcgg atctcgcagt attcccatcg gcgacgcccg aggaggttgt    4980
tctggatcaa cagtctccgc tcttcgtact caagggcgga cgtgtcgttg ccatgcgatt    5040
ggccgctgga tcaacgtcgt tccgcgacta ctcatgagga aatccattat gatgtcagga    5100
gaacacacgt taaagcggt acgaggcagt tttattgatg tcacccgtac gatcgataac     5160
ccggaagaga ttgcctctgc gctgcggttt attgaggatg gtttattact cattaaacag    5220
ggaaaagtgg aatggtttgg cgaatgggaa acggaaagc atcaaattcc tgacaccatt      5280
cgcgtgcgcg actatcgcgg caaactgata gtaccgggct tgtcgatac acatatccat      5340 tatccgcaaa gtgaaatggt gggggcctat ggtgagcaat tgctgagtg gttgaataaa      5400 cacaccttcc ctactgaacg tcgttatgag gatttagagt acgcccgcga aatgtcggcg    5460
ttcttcatca gcagcttttt acgtaacgga accaccacgg cgctggtgtt tggcactgtt    5520
catccgcaat ctgttgatgc gctgtttgaa gccgccagtc atatcaatat gcgtatgatt    5580
gccggtaagg tgatgatgga ccgcaacgca ccggattatc tgctcgacac tgccgaaagc    5640
agctatcacc aaagcaaaga actgatcgaa cgctggcaca aaaatggtcg tctgctatat    5700
gcgattacgc cacgcttcgc cccgacctca tctcctgaac agatggcgat ggcgcaacgc    5760
ctgaaagaag aatatccgga tacgtgggta catacccatc tctgtgaaaa caaagatgaa    5820
attgcctggg tgaaatcgct ttatcctgac catgatggtt atctgatgt ttaccatcag      5880 tacggcctga ccggtaaaaa ctgtgtcttt gctcactgcg tccatctcga agaaaaagag    5940
tgggatcgtc tcagcgaaac caaatccagc attgctttct gtccgacctc caacctttac    6000
ctcggcagcg gcttattcaa cttgaaaaaa gcatggcaga agaaagttaa agtgggcatg    6060
ggaacggata tcggtgccgg aaccactttc aacatgctgc aaacgctgaa cgaagcctac    6120
aaagtattgc aattacaagg ctatcgcctc tcggcatatg aagcgtttta cctggccacg    6180
ctcggcggag cgaaatctct gggccttgac gatttgattg caacttttt acctggcaaa     6240 gaggctgatt tcgtggtgat ggaacccacc gccactccgc tacagcagct gcgctatgac    6300
aactctgttt ctttagtcga caaattgttc gtgatgatga cgttgggcga tgaccgttcg    6360
atctaccgca cctacgttga tggtcgtctg gtgtacgaac gcaactaagg aacgaccatg    6420
caaacgctca gcatccagca cggtaccctc gtcacgatgg atcagtaccg cagagtcctt    6480
ggggatagct gggttcacgt gcaggatgga cggatcgtcg cgctcggagt gcacgccgag    6540
tcggtgcctc cgccagcgga tcgggtgatc gatgcacgcg gcaaggtcgt gttacccggt    6600
ttcatcaatg cccacaccca tgtgaaccag atcctcctgc gcggagggcc ctcgcacggg    6660
cgtcaactct atgactggct gttcaacgtt ttgtatccgg acaaaaggc gatgagaccg     6720 gaggacgtag cggtggcggt gaggttgtat tgtgcggaag ctgtgcgcag cgggattacg    6780
```

```
acgatcaacg acaacgccga ttcggccatc tacccaggca acatcgaggc cgcgatggcg   6840
gtctatggtg aggtgggtgt gagggtcgtc tacgcccgca tgttctttga tcggatggac   6900
gggcgcattc aagggtatgt ggacgccttg aaggctcgct ctccccaagt cgaactgtgc   6960
tcgatcatga aggaaacggc tgtggccaaa gatcggatca cagccctgtc agatcagtat   7020
catggcacgg caggaggtcg tatatcagtt tggcccgctc ctgccattac cccggcggtg   7080
acagttgaag gaatgcgatg ggcacaagcc ttcgcccgtg atcgggcggt aatgtggacg   7140
cttcacatgg cggagagcga tcatgatgag cggcttcatt ggatgagtcc cgccgagtac   7200
atggagtgtt acggactctt ggatgagcgt ctgcaggtcg cgcattgcgt gtactttgac   7260
cggaaggatg ttcggctgct gcaccgccac aatgtgaagg tcgcgtcgca ggttgtgagc   7320
aatgcctacc tcggctcagg ggtggccccc gtgccagaga tggtggagcg cggcatggcc   7380
gtgggcattg aacagatgac gggaattgt aatgactccg taaacatgat cggagacatg   7440
aagtttatgg cccatattca ccgcgcggtg catcggatg cggacgtgct gaccccagag   7500
aagattcttg aaatggcgac gatcgatggg gcgcgttcgt tgggaatgga ccacgagatt   7560
ggttccatcg aaaccggcaa gcgcgcggac cttatcctgc ttgacctgcg tcaccctcag   7620
acgactcctc accatcattt ggcggccacg atcgtgtttc aggcttacgg caatgaggtg   7680
gacactgtcc tgattgacgg aaacgttgtg atggagaacc gccgcttgag ctttcttccc   7740
cctgaacgtg agttggcgtt ccttgaggaa gcgcagagcc gcgccacagc tattttgcag   7800
cgggcgaaca tggtggctaa cccagcttgg cgcagcctct agcctcaaaa tatattttcc   7860
ctctatcttc tcgttgcgct taatttgact aattctcatt agcgaggcgc gccttttccat  7920
aggctccgcc cccctgacga gcatcacaaa aatcgacgct caagtcagag gtggcgaaac   7980
ccgacaggac tataaagata ccaggcgttt ccccctggaa gctccctcgt gcgctctcct   8040
gttccgaccc tgccgcttac cggatacctg tccgcctttc tcccttcggg aagcgtggcg   8100
ctttctcata gctcacgctg taggtatctc agttcggtgt aggtcgttcg ctccaagctg   8160
ggctgtgtgc acgaaccccc cgttcagccc gaccgctgcg ccttatccgg taactatcgt   8220
cttgagtcca acccggtaag acacgactta tcgccactgg cagcagccac tggtaacagg   8280
attagcagag cgaggtatgt aggcggtgct acagagttct tgaagtggtg gcctaactac   8340
ggctacacta agaacagt atttggtatc tgcgctctgc tgaagccagt taccttcgga   8400
aaaagagttg gtagctcttg atccggcaaa caaaccaccg ctggtagcgg tggtttttt   8460
gtttgcaagc agcagattac gcgcagaaaa aaaggatctc aagaagatcc tttgatcttt   8520
tctacggggt ctgacgctca gtggaacgaa aactcacgtt aagggatttt ggtcatgaga   8580
ttatcaaaaa ggatcttcac ctagatcctt ttaaattaaa aatgaagttt taaatcaatc   8640
taaagtatat atgagtaaac ttggtctgac agttaccaat gcttaatcag tgaggcacct   8700
atctcagcga tctgtctatt tcgttcatcc atagttgcct gactccccgt cgtgtagata   8760
actacgatac gggagggctt accatctggc cccagtgctg caatgatacc gcgagaccca   8820
cgctcaccgg ctccagattt atcagcaata aaccagccag ccggaagggc cgagcgcaga   8880
agtggtcctg caactttatc cgcctccatc cagtctatta attgttgccg ggaagctaga   8940
gtaagtagtt cgccagttaa tagtttgcgc aacgttgttg ccattgctac aggcatcgtg   9000
gtgtcacgct cgtcgtttgg tatggcttca ttcagctccg gttcccaacg atcaaggcga   9060
gttacatgat cccccatgtt gtgcaaaaaa gcggttagct ccttcggtcc tccgatcgtt   9120
gtcagaagta agttggccgc agtgttatca ctcatggtta tggcagcact gcataattct   9180
```

```
cttactgtca tgccatccgt aagatgcttt tctgtgactg gtgagtactc aaccaagtca    9240
ttctgagaat agtgtatgcg gcgaccgagt tgctcttgcc cggcgtcaat acgggataat    9300
accgcgccac atagcagaac tttaaaagtg ctcatcattg gaaaacgttc ttcggggcga    9360
aaactctcaa ggatcttacc gctgttgaga tccagttcga tgtaacccac tcgtgcaccc    9420
aactgatctt cagcatcttt tactttcacc agcgtttctg ggtgagcaaa acaggaagg     9480 caaaatgccg caaaaaggg aataagggcg acacggaaat gttgaatact catactcttc     9540 cttttcaat attattgaag catttatcag ggttattgtc tcatgagcgg atacatattt     9600
gaatgtattt agaaaaataa acagcgatcg cgcggccgcg ggtaataact gatataatta    9660
aattgaagct ctaatttgtg agtttagtat acatgcattt acttataata cagttttta    9720 gttttgctgg ccgcatcttc tcaaatatgc ttcccagcct gcttttctgt aacgttcacc    9780
ctctacctta gcatcccttc cctttgcaaa tagtcctctt ccaacaataa taatgtcaga    9840
tcctgtagag accacatcat ccacggttct atactgttga cccaatgcgt ctcccttgtc    9900
atctaaaccc acaccgggtg tcataatcaa ccaatcgtaa ccttcatctc ttccacccat    9960
gtctctttga gcaataaagc cgataacaaa atctttgtcg ctcttcgcaa tgtcaacagt   10020
acccttagta tattctccag tagctaggga gcccttgcat gacaattctg ctaacatcaa   10080
aaggcctcta ggttcctttg ttacttcttc cgccgcctgc ttcaaaccgc taacaatacc   10140
tgggcccacc acaccgtgtg cattcgtaat gtctgcccat tctgctattc tgtatacacc   10200
cgcagagtac tgcaatttga ctgtattacc aatgtcagca aattttctgt cttcgaagag   10260
taaaaaattg tacttggcgg ataatgcctt tagcggctta actgtgccct ccatggaaaa   10320
atcagtcaag atatccacat gtgttttag taaacaaatt ttgggaccta atgcttcaac    10380
taactccagt aattccttgg tggtacgaac atccaatgaa gcacacaagt ttgtttgctt   10440
ttcgtgcatg atattaaata gcttggcagc aacaggacta ggatgagtag cagcacgttc   10500
cttatatgta gctttcgaca tgatttatct tcgtttcctg caggttttg ttctgtgcag    10560 ttgggttaag aatactgggc aatttcatgt ttcttcaaca ccacatatgc gtatatatac    10620
caatctaagt ctgtgctcct tccttcgttc ttccttctgc tcggagatta ccgaatcaaa   10680
gctagcttat cgatgataag ctgtcaaaga tgagaattaa ttccacggac tatagactat   10740
actagatact ccgtcactg tacgatacac ttccgctcag gtccttgtcc tttaacgagg    10800
ccttaccact cttttgttac tctattgatc cagctcagca aaggcagtgt gatctaagat   10860
tctatcttcg cgatgtagta aaactagcta gaccgagaaa gagactagaa atgcaaaagg   10920
cacttctaca atggctgcca tcattattat ccgatgtgac gctgcagctt ctcaatgata   10980
ttcgaatacg ctttgaggag atacagccta atatccgaca aactgtttta cagatttacg   11040
atcgtacttg ttacccatca ttgaattttg aacatccgaa cctgggagtt ttccctgaaa   11100
cagatagtat atttgaacct gtataataat atatagtcta gcgctttacg gaagacaatg   11160
tatgtatttc ggttcctgga gaaactattg catctattgc ataggtaatc ttgcacgtcg   11220
catccccggt tcattttctg cgtttccatc ttgcacttca atagcatatc tttgttaacg   11280
aagcatctgt gcttcatttt gtagaacaaa atgcaacgc gagagcgcta attttcaaa     11340 caaagaatct gagctgcatt tttacagaac agaaatgcaa cgcgaaagcg ctattttacc   11400
aacgaagaat ctgtgcttca ttttttgtaaa acaaaaatgc aacgcgacga gagcgctaat   11460
ttttcaaaca aagaatctga gctgcatttt tacagaacag aaatgcaacg cgagagcgct   11520
```

| | | | | |
|---|---|---|---|---|
| attttaccaa | caaagaatct | atacttcttt | tttgttctac | aaaaatgcat | cccgagagcg | 11580 |
| ctattttct | aacaaagcat | cttagattac | ttttttctc | ctttgtgcgc | tctataatgc | 11640 |
| agtctcttga | taacttttg | cactgtaggt | ccgttaaggt | tagaagaagg | ctactttggt | 11700 |
| gtctattttc | tcttccataa | aaaaagcctg | actccacttc | ccgcgtttac | tgattactag | 11760 |
| cgaagctgcg | ggtgcatttt | ttcaagataa | aggcatcccc | gattatattc | tataccgatg | 11820 |
| tggattgcgc | atactttgtg | aacagaaagt | gatagcgttg | atgattcttc | attggtcaga | 11880 |
| aaattatgaa | cggtttcttc | tattttgtct | ctatatacta | cgtataggaa | atgtttacat | 11940 |
| tttcgtattg | ttttcgattc | actctatgaa | tagttcttac | tacaatttt | ttgtctaaag | 12000 |
| agtaatacta | gagataaaca | taaaaatgt | agaggtcgag | tttagatgca | agttcaagga | 12060 |
| gcgaaaggtg | gatgggtagg | ttatataggg | atatagcaca | gagatatata | gcaaagagat | 12120 |
| actttttgagc | aat | | | | | 12133 |

<210> SEQ ID NO 53
<211> LENGTH: 12112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

| | | | | | |
|---|---|---|---|---|---|
| gtttgtggaa | gcggtattcg | caatttaatt | aaagctggtg | acaattaatc | atcggctcgt | 60 |
| ataatgtgtg | gaattgaatc | gatataagga | ggttaatcat | atgtaccata | tagatgtatt | 120 |
| cagaatccct | tgccatagtc | caggtgacac | ttcaggttta | gaagatttga | tagaaacagg | 180 |
| tagagtcgct | ccagcagata | ttgttgctgt | catgggtaaa | acagagggta | atggttgtgt | 240 |
| taacgactat | acaagagaat | acgccaccgc | tatgttggct | gcatgcttag | gtagacattt | 300 |
| gcaattacca | cctcacgaag | ttgaaaagag | agtagcttt | gttatgtccg | gtggtacaga | 360 |
| aggtgtattg | tctccacatc | acaccgtttt | cgctagaaga | ccagcaatag | atgcccatag | 420 |
| acctgcaggt | aaaagattga | cttttaggtat | cgcttttaca | agagatttct | tgcctgaaga | 480 |
| aattggtaga | catgcacaaa | taaccgaaac | tgcaggtgcc | gttaagagag | ctatgagaga | 540 |
| tgctggtatc | gcatcaatag | atgacttaca | tttcgtacag | gttaagtgtc | cattgttgac | 600 |
| tcctgcaaag | atcgcttcag | caagatccag | aggttgcgct | ccagtcacta | cagatacata | 660 |
| tgaaagtatg | ggttactcta | gaggtgcctc | agctttgggt | attgcattag | ccaccgaaga | 720 |
| agttccttct | tcaatgttgg | tcgatgaatc | cgtattaaat | gactggagtt | tgtccagttc | 780 |
| tttagcttca | gcatccgccg | gtatagaatt | ggaacataac | gttgtcattg | ccataggcat | 840 |
| gtccgaacaa | gctacaagtg | aattagttat | cgcacacggt | gtcatgtctg | atgccattga | 900 |
| cgccgcttca | gttagaagaa | ctatagaatc | tttgggtatc | agatcagatg | acgaaatgga | 960 |
| tagaatagtc | aacgtattcg | ctaaagcaga | agcctctcca | gacggtgtag | ttagaggcat | 1020 |
| gagacatact | atgttgagtg | attctgacat | caactctacc | agacacgcta | gagcagttac | 1080 |
| tggtgcagcc | atagcttctg | tcgtaggtca | tggtatggtt | tatgtctcag | gtggtgccga | 1140 |
| acaccaaggt | ccagctggtg | gtggtccttt | cgcagttatt | gccagagctt | aaggaaatcc | 1200 |
| attatgatat | actcaacagt | caacgctaat | ccttacgctt | ggccttacga | tggttcaata | 1260 |
| gaccctgctc | acaccgcttt | aatcttaatc | gattggcaaa | tagacttttg | tggtccaggt | 1320 |
| ggttatgtcg | attccatggg | ttacgactta | tccttgacta | gaagtggttt | agaacctaca | 1380 |

-continued

```
gcaagagtat tggctgcagc cagagatact ggtatgacag ttatccatac tagagaaggt    1440
cacagaccag atttggctga cttgccacct aataagagat ggagatctgc atcagccggt    1500
gctgaaatcg gttcagttgg tccatgtggt agaattttag tcagaggtga acctggttgg    1560
gaaatagtac cagaagttgc acctagagaa ggtgaaccaa ttatagataa acctggtaaa    1620
ggtgctttct acgcaacaga tttggacttg ttgttgagaa caagaggtat cacccatttg    1680
attttgaccg gtataactac agatgtttgc gtccacacca ctatgagaga agccaacgat    1740
agaggttacg aatgttttaat tttgtctgat tgcaccggtg ctactgacag aaagcatcac    1800
gaagctgcat tatctatggt caccatgcaa ggtggtgtat tcggtgcaac tgcccattca    1860
gatgacttat tggccgcttt gggtacaacc gttccagcag ccgctggtcc tagagctaga    1920
acagaataag gaacgaccat gacagttagt tccgatacaa ctgctgaaat atcgttaggt    1980
tggtcaatcc aagactggat tgatttccac aagtcatcaa gctcccaggc ttcactaagg    2040
cttcttgaat cactactaga ctctcaaaat gttgcgccag tcgataatgc gtggatatcg    2100
ctaatttcaa aggaaaattt actgcaccaa ttccaaattt taaagagcag agaaaataaa    2160
gaaactctac ctctctacgg tgtccctatt gctgttaagg acaacatcga cgttagaggt    2220
ctacccacca ccgctgcatg tccatccttt gcatatgagc cttccaaaga ctctaaagta    2280
gtagaactac taagaaatgc aggtgcgata atcgtgggta agacaaactt ggaccaattt    2340
gccacaggat tagtcggcac acggtctcca tatgggaaaa caccttgcgc ttttagcaaa    2400
gagcatgtat ctggtggttc ctccgctggg tcagcatcgg tggtcgccag aggtatcgta    2460
ccaattgcat gggtactga tacagcaggt tctggtagag tcccagccgc cttgaacaac    2520
ctgattggcc taaagccaac aaagggcgtc ttttcctgtc aaggtgtagt tcccgcttgt    2580
aaatctttag actgcgtctc catctttgca ttaaacctaa gtgatgctga acgctgcttc    2640
cgcatcatgt gccagccaga tcctgataat gatgaatatt ctagacccta tgtttccaac    2700
cctttgaaaa aattttcaag caatgtaacg attgctattc ctaaaaatat cccatggtat    2760
ggtgaaacca agaatcctgt actgtttttcc aatgctgtcg aaaatctatc aagaacgggc    2820
gctaacgtca tagaaattga ttttgagcct ctttttagagt tagctcgctg tttatacgaa    2880
ggtacttggg tggccgagcg ttatcaagct attcaatcgt ttttggacag taaaccacca    2940
aaggaatctt tggaccctac tgttatttca attatagaag gggccaagaa atacagtgca    3000
gtagactgct tcagttttga atacaaaaga caaggcatct tgcaaaaagt gagacgactt    3060
ctcgaatcag tcgatgtatt gtgtgtgccc acatgtcctt taaatcctac tatgcaacaa    3120
gttgcggatg aaccagtcct agtcaattca agacaaggca catggactaa ttttgtcaac    3180
ttggcagatt tggcagccct tgctgttccc gcagggttcc gagacgatgg tttgccaaat    3240
ggtattactt taatcggtaa aaaattcaca gattacgcac tattagagtt ggctaaccgc    3300
tatttccaaa atatattccc caacggttcc agaacatacg gtactttac ctcttcttca    3360 gtaaagccag caaacgatca attagtggga ccagactatg acccatctac gtccataaaa    3420
ttggctgttg tcggtgcaca tcttaagggt ctgcctctac attggcaatt ggaaaaggtc    3480
aatgcaacat atttatgtac aacaaaaaca tcaaagcctt accagctttt tgctttgccc    3540
aaaaatggac cagttttaaa acctggttgg agaagagttc aagatagcaa tggctctcaa    3600
atcgaattag aagtgtacag tgttccaaaa gaactgttcg gtgcttttat ttccatggtt    3660
cctgaaccat taggaatagg ttcagtggag ttagaatctg gtgaatggat caaatccttt    3720
atttgtgaag aatctggtta caaagccaaa ggtacagttg atatcacaaa gtatggtgga    3780
```

```
tttagagcat attttgaaat gttgtaagga cacgataatg tcaatggaaa cccatagtta    3840
tgtagacgtc gcaattcgta acgcgcgtct tgccgatacg gagggaattg tcgatattct    3900
tattcacgat gggcgcattg cgtccatcgt gaagtcgaca aaaacaaaag gatcggtgga    3960
gatcgatgct catgagggtc tggtcacttc cggcctggta gagcctcaca tccatctcga    4020
taaggccctg acggcagatc gggttcccgc aggaagcatt ggcgaccttc gaacgcgacg    4080
aggccttgag atggcaattc gggccacccg tgatatcaag cgtacgttca cggttgaaga    4140
tgttcgagaa cgggccatac gtgcggccct gatggcatcc cgtgcgggaa ccaccgcatt    4200
gcggacacac gtcgatgtcg acccgattgt cggcctcgca ggtatccgtg gtgtccttga    4260
ggcgcgtgaa gtctgcgcgg gattgatcga tatccagatc gtcgccttcc ctcaggaggg    4320
actcttctgc tctgcggggg ccgtggacct catgcgggag gcgatcaaac tgggcgcgga    4380
tgccgtcggc ggcgcacccg cgctggatga tcgcccgcag gaccatgtcc gagccgtttt    4440
tgaccttgct gctgagttcg gcctgccgt agacatgcac gtcgatgagt ccgaccggcg    4500
ggaagacttt acgcttccct tgtgattga agctgcccgt gaacggcgtg tgcccaatgt    4560
gaccgtcgcg cacatcagct cgctgtccgt acagacggat gacgtagcac ggtcgaccat    4620
tgccgccctt gcggacgccg atgttaatgt cgtggttaat ccgatcattg tcaaaattac    4680
gcggctgagt gaattactcg atgccggagt ctccgtaatg tttggctcgg acaacctgcg    4740
ggatccgttc tatccgctcg gagcggcgaa tccccttgga tcagccattt ttgcctgtca    4800
aattgccgcg ctgggaacac cgcaagatct cagacgggta ttcgatgcgg tcaccatcaa    4860
cgctgcccgc atgctgggat ccctcact tttaggcgtc gtggaagggg cagtcgcgga    4920
tctcgcagta ttcccatcgg cgacgcccga ggaggttgtt ctggatcaac agtctccgct    4980
cttcgtactc aagggcggac gtgtcgttgc catgcgattg gccgctggat caacgtcgtt    5040
ccgcgactac tcatgaggaa atccattatg atgtcaggag aacacacgtt aaaagcggta    5100
cgaggcagtt ttattgatgt caccccgtacg atcgataacc cggaagagat tgcctctgcg    5160
ctgcggttta ttgaggatgg tttattactc attaaacagg gaaaagtgga atggtttggc    5220
gaatgggaaa acgaaaagca tcaaattcct gacaccattc gcgtgcgcga ctatcgcggc    5280
aaactgatag taccgggctt tgtcgataca catatccatt atccgcaaag tgaaatggtg    5340
ggggcctatg tgagcaatt gctggagtgg ttgaataaac acaccttccc tactgaacgt    5400
cgttatgagg atttagagta cgcccgcgaa atgtcggcgt tcttcatcaa gcagctttta    5460
cgtaacggaa ccaccacggc gctggtgttt ggcactgttc atccgcaatc tgttgatgcg    5520
ctgtttgaag ccgccagtca tatcaatatg cgtatgattg ccggtaaggt gatgatggac    5580
cgcaacgcac cggattatct gctcgacact gccgaaagca gctatcacca aagcaaagaa    5640
ctgatcgaac gctggcacaa aaatggtcgt ctgctatatg cgattacgcc acgcttcgcc    5700
ccgacctcat ctcctgaaca gatggcgatg gcgcaacgcc tgaaagaaga atatccggat    5760
acgtgggtac ataccccatct ctgtgaaaac aaagatgaaa ttgcctgggt gaaatcgctt    5820
tatcctgacc atgatggtta tctggatgtt taccatcagt acggcctgac cggtaaaaac    5880
tgtgtctttg ctcactgcgt ccatctcgaa gaaaaagagt gggatcgtct cagcgaaacc    5940
aaatccagca ttgctttctg tccgacctcc aaccttacc tcggcagcgg cttattcaac    6000
ttgaaaaaag catggcagaa gaaagttaaa gtgggcatgg aacggatat cggtgccgga    6060 accactttca acatgctgca aacgctgaac gaagcctaca agtattgca attacaaggc    6120
```

-continued

```
tatcgcctct cggcatatga agcgttttac ctggccacgc tcggcggagc gaaatctctg    6180
ggccttgacg atttgattgg caacttttta cctggcaaag aggctgattt cgtggtgatg    6240
gaacccaccg ccactccgct acagcagctg cgctatgaca actctgtttc tttagtcgac    6300
aaattgttcg tgatgatgac gttgggcgat gaccgttcga tctaccgcac ctacgttgat    6360
ggtcgtctgg tgtacgaacg caactaagga acgaccatgc aaacgctcag catccagcac    6420
ggtaccctcg tcacgatgga tcagtaccgc agagtccttg gggatagctg ggttcacgtg    6480
caggatggac ggatcgtcgc gctcggagtg cacgccgagt cggtgcctcc gccagcggat    6540
cgggtgatcg atgcacgcgg caaggtcgtg ttacccggtt tcatcaatgc ccacacccat    6600
gtgaaccaga tcctcctgcg cggagggccc tcgcacgggc gtcaactcta tgactggctg    6660
ttcaacgttt tgtatccggg acaaaaggcg atgagaccgg aggacgtagc ggtggcggtg    6720
aggttgtatt gtgcggaagc tgtgcgcagc gggattacga cgatcaacga caacgccgat    6780
tcggccatct acccaggcaa catcgaggcc gcgatggcgg tctatggtga ggtgggtgtg    6840
agggtcgtct acgcccgcat gttctttgat cggatggacg gcgcattca agggtatgtg    6900
gacgccttga aggctcgctc tccccaagtc gaactgtgct cgatcatgga ggaaacggct    6960
gtggccaaag atcggatcac agccctgtca gatcagtatc atggcacggc aggaggtcgt    7020
atatcagttt ggcccgctcc tgccattacc ccggcggtga cagttgaagg aatgcgatgg    7080
gcacaagcct tcgcccgtga tcgggcggta atgtggacgc ttcacatggc ggagagcgat    7140
catgatgagc ggcttcattg gatgagtccc gccgagtaca tggagtgtta cggactcttg    7200
gatgagcgtc tgcaggtcgc gcattgcgtg tactttgacc ggaaggatgt tcggctgctg    7260
caccgccaca atgtgaaggt cgcgtcgcag gttgtgagca atgcctacct cggctcaggg    7320
gtggccccg tgccagagat ggtggagcgc ggcatggccg tgggcattgg aacagatgac    7380
gggaattgta atgactccgt aaacatgatc ggagacatga agtttatggc ccatattcac    7440
cgcgcggtgc atcgggatgc ggacgtgctg accccagaga agattcttga aatgggcgacg    7500
atcgatgggg cgcgttcgtt gggaatggac cacgagattg gttccatcga aaccggcaag    7560
cgcgcggacc ttatcctgct tgacctgcgt caccctcaga cgactcctca ccatcatttg    7620
gcggccacga tcgtgtttca ggcttacggc aatgaggtgg acactgtcct gattgacgga    7680
aacgttgtga tggagaaccg ccgcttgagc tttcttcccc ctgaacgtga gttggcgttc    7740
cttgaggaag cgcagagccg cgccacagct attttgcagc gggcgaacat ggtggctaac    7800
ccagcttggc gcagcctcta gcctcaaaat atattttccc tctatcttct cgttgcgctt    7860
aatttgacta attctcatta gcgaggcgcg cctttccata ggctccgccc ccctgacgag    7920
catcacaaaa atcgacgctc aagtcagagg tggcgaaacc cgacaggact ataaagatac    7980
caggcgtttc cccctggaag ctccctcgtg cgctctcctg ttccgaccct gccgcttacc    8040
ggatacctgt ccgcctttct cccttcggga agcgtggcgc tttctcatag ctcacgctgt    8100
aggtatctca gttcggtgta ggtcgttcgc tccaagctgg gctgtgtgca cgaacccccc    8160
gttcagcccg accgctgcgc cttatccggt aactatcgtc ttgagtccaa cccggtaaga    8220
cacgacttat cgccactggc agcagccact ggtaacagga ttagcagagc gaggtatgta    8280
ggcggtgcta cagagttctt gaagtggtgg cctaactacg gctacactag aagaacagta    8340
tttggtatct gcgctctgct gaagccagtt accttcggaa aaagagttgg tagctcttga    8400
tccggcaaac aaaccaccgc tggtagcggt ggttttttg tttgcaagca gcagattacg    8460
cgcagaaaaa aaggatctca agaagatcct ttgatctttt ctacggggtc tgacgctcag    8520
```

```
tggaacgaaa actcacgtta agggattttg gtcatgagat tatcaaaaag gatcttcacc    8580
tagatccttt taaattaaaa atgaagtttt aaatcaatct aaagtatata tgagtaaact    8640
tggtctgaca gttaccaatg cttaatcagt gaggcaccta tctcagcgat ctgtctattt    8700
cgttcatcca tagttgcctg actcccgtc gtgtagataa ctacgatacg ggagggctta    8760
ccatctggcc ccagtgctgc aatgataccg cgagacccac gctcaccggc tccagattta    8820
tcagcaataa accagccagc cggaagggcc gagcgcagaa gtggtcctgc aactttatcc    8880
gcctccatcc agtctattaa ttgttgccgg gaagctagag taagtagttc gccagttaat    8940
agtttgcgca acgttgttgc cattgctaca ggcatcgtgg tgtcacgctc gtcgtttggt    9000
atggcttcat tcagctccgg ttcccaacga tcaaggcgag ttacatgatc ccccatgttg    9060
tgcaaaaaag cggttagctc cttcggtcct ccgatcgttg tcagaagtaa gttggccgca    9120
gtgttatcac tcatggttat ggcagcactg cataattctc ttactgtcat gccatccgta    9180
agatgctttt ctgtgactgg tgagtactca accaagtcat tctgagaata gtgtatgcgg    9240
cgaccgagtt gctcttgccc ggcgtcaata cgggataata ccgcgccaca tagcagaact    9300
ttaaaagtgc tcatcattgg aaaacgttct cggggcgaa aactctcaag gatcttaccg    9360
ctgttgagat ccagttcgat gtaacccact cgtgcaccca actgatcttc agcatctttt    9420
actttcacca gcgtttctgg gtgagcaaaa acaggaaggc aaaatgccgc aaaaaaggga    9480
ataagggcga cacggaaatg ttgaatactc atactcttcc ttttcaata ttattgaagc    9540
atttatcagg gttattgtct catgagcgga tacatatttg aatgtattta gaaaataaaa    9600
cagcgatcgc gcggccgcgg gtaataactg atataattaa attgaagctc taatttgtga    9660
gtttagtata catgcattta cttataatac agtttttag ttttgctggc cgcatcttct    9720
caaatatgct tcccagcctg cttttctgta acgttcaccc tctaccttag catcccttcc    9780
ctttgcaaat agtcctcttc caacaataat aatgtcagat cctgtagaga ccacatcatc    9840
cacggttcta tactgttgac ccaatgcgtc tcccttgtca tctaaaccca caccgggtgt    9900
cataatcaac caatcgtaac cttcatctct tccacccatg tctctttgag caataaagcc    9960
gataacaaaa tctttgtcgc tcttcgcaat gtcaacagta cccttagtat attctccagt   10020
agctagggag cccttgcatg acaattctgc taacatcaaa aggcctctag gttcctttgt   10080
tacttcttcc gccgcctgct tcaaaccgct aacaatacct gggcccacca caccgtgtgc   10140
attcgtaatg tctgcccatt ctgctattct gtatacaccc gcagagtact gcaatttgac   10200
tgtattacca atgtcagcaa attttctgtc ttcgaagagt aaaaaattgt acttggcgga   10260
taatgccttt agcggcttaa ctgtgccctc catggaaaaa tcagtcaaga tatccacatg   10320
tgtttttagt aaacaaattt tgggacctaa tgcttcaact aactccagta attccttggt   10380
ggtacgaaca tccaatgaag cacacaagtt tgtttgcttt tcgtgcatga tattaaatag   10440
cttggcagca acaggactag gatgagtagc agcacgttcc ttatatgtag ctttcgacat   10500
gatttatctt cgtttcctgc aggttttgt tctgtgcagt tgggttaaga atactgggca   10560
atttcatgtt tcttcaacac cacatatgcg tatatatacc aatctaagtc tgtgctcctt   10620
ccttcgttct tccttctgct cggagattac cgaatcaaag ctagcttatc gatgataagc   10680
tgtcaaagat gagaattaat tccacggact atagactata ctagatactc cgtctactgt   10740
acgatacact tccgctcagg tccttgtcct ttaacgaggc cttaccactc ttttgttact   10800
ctattgatcc agctcagcaa aggcagtgtg atctaagatt ctatcttcgc gatgtagtaa   10860
```

| | | | | |
|---|---|---|---|---|
| aactagctag | accgagaaag | agactagaaa | tgcaaaaggc | acttctacaa tggctgccat | 10920 |
| cattattatc | cgatgtgacg | ctgcagcttc | tcaatgatat | cgaatacgc tttgaggaga | 10980 |
| tacagcctaa | tatccgacaa | actgttttac | agatttacga | tcgtacttgt tacccatcat | 11040 |
| tgaattttga | acatccgaac | ctgggagttt | tccctgaaac | agatagtata tttgaacctg | 11100 |
| tataataata | tatagtctag | cgctttacgg | aagacaatgt | atgtatttcg gttcctggag | 11160 |
| aaactattgc | atctattgca | taggtaatct | tgcacgtcgc | atccccggtt cattttctgc | 11220 |
| gtttccatct | tgcacttcaa | tagcatatct | tgttaacga | agcatctgtg cttcattttg | 11280 |
| tagaacaaaa | atgcaacgcg | agagcgctaa | ttttcaaac | aaagaatctg agctgcattt | 11340 |
| ttacagaaca | gaaatgcaac | gcgaaagcgc | tattttacca | acgaagaatc tgtgcttcat | 11400 |
| ttttgtaaaa | caaaaatgca | acgcgacgag | agcgctaatt | tttcaaacaa agaatctgag | 11460 |
| ctgcatttt | acagaacaga | aatgcaacgc | gagagcgcta | ttttaccaac aaagaatcta | 11520 |
| tacttctttt | ttgttctaca | aaaatgcatc | ccgagagcgc | tattttctta caaagcatc | 11580 |
| ttagattact | ttttttctcc | tttgtgcgct | ctataatgca | gtctcttgat aacttttgc | 11640 |
| actgtaggtc | cgttaaggtt | agaagaaggc | tactttggtg | tctatttct cttccataaa | 11700 |
| aaaagcctga | ctccacttcc | cgcgtttact | gattactagc | gaagctgcgg gtgcattttt | 11760 |
| tcaagataaa | ggcatccccg | attatattct | ataccgatgt | ggattgcgca tactttgtga | 11820 |
| acagaaagtg | atagcgttga | tgattcttca | ttggtcagaa | aattatgaac ggtttcttct | 11880 |
| attttgtctc | tatatactac | gtataggaaa | tgtttacatt | ttcgtattgt tttcgattca | 11940 |
| ctctatgaat | agttccttact | acaattttt | tgtctaaaga | gtaatactag agataaacat | 12000 |
| aaaaaatgta | gaggtcgagt | ttagatgcaa | gttcaaggag | cgaaaggtgg atgggtaggt | 12060 |
| tatataggga | tatagcacag | agatatatag | caaagagata | cttttgagca at | 12112 |

<210> SEQ ID NO 54
<211> LENGTH: 1173
<212> TYPE: DNA
<213> ORGANISM: Rhodococcus sp.

<400> SEQUENCE: 54

| | | | | |
|---|---|---|---|---|
| ttgcgggaag | tccaactgct | cgacggccgc | cgagttgatg | ttgcatgcgc cggaccgttg | 60 |
| atctccgaaa | tcggcgccca | tctcgacctc | accgctccag | tggagatcga ctgtggcggc | 120 |
| ggcctggcga | cgcgaccgtt | caccgaaccc | catttgcacc | tcgacaaggc ggggaccgcc | 180 |
| gatcgtctac | cggcaggcgc | cagcaccatc | ggtgatgcga | tcgccgccat gcaatcggtg | 240 |
| aaagtcactg | agcgcgacaa | tgtggcggcg | gtcgccgcac | gaatgcaccg cgtcctgaac | 300 |
| cgcattgtcg | acgatggttc | ccacgccatt | cgcgctctcg | tcgacgtcga tgaggtctgg | 360 |
| ggattgaccg | cttttcatgc | agcccaacaa | gtccaagctg | ctctcgcgcc gcgcgcggta | 420 |
| gtacaaatcg | tggccttccc | acaacatggc | ctcaccccgc | aggtacttgc catgctcgag | 480 |
| caagcggccg | cagaaggtgc | aggagcactc | ggcgcccaca | ccgacgtcga ccctgaccca | 540 |
| gcggcgcacg | tcggtgctgt | ggccgccatt | gccgccgggg | catcgctacc gctcgaagtc | 600 |
| cacactgatg | aaggcgccag | tcccgacaag | ttctacttgc | ctgcagtact ggaggtcctc | 660 |
| gaccggtttc | ctggactctc | gacgaccctc | gcacactgtc | tgtcactcgg aacgatcgcg | 720 |
| ccgaaacaac | agcagcactg | gattgaggaa | ctggcccatc | gggacatcaa agtctgtgtc | 780 |
| gcgcctagca | ttttaggttt | cggcctgccc | ttggcgccag | tccgggcact catcgaggcc | 840 |
| ggcgtcggaa | tacttgtcgg | atcagacaac | ctgcaggacg | ttttctttcc gctcggtacg | 900 |

-continued

| | |
|---|---|
| ggccgcgcca tcgaaaacgt gcgtctgctg gcgaccgcag cacagctcac cgcacctgag | 960 |
| ctcgctggcc cgctcatcgc aggtgtcacc gacatcgcgt acgccaccgt gaccggcgca | 1020 |
| gcagatgcac tggcggtgga atccccgca accctcgtcg tccacgacgc gacctcgccg | 1080 |
| gcggagctgc ttcgcggcat cgacggtact cgaatcaccg ttatcgacgg cctgttgaca | 1140 |
| tccccgctcc aactcgacaa aggaatcaag tga | 1173 |

<210> SEQ ID NO 55
<211> LENGTH: 1239
<212> TYPE: DNA
<213> ORGANISM: Pseudomonas sp.

<400> SEQUENCE: 55

| | |
|---|---|
| atgtcaatgg aaacccatag ttatgtagac gtcgcaattc gtaacgcgcg tcttgccgat | 60 |
| acggagggaa ttgtcgatat tcttattcac gatgggcgca ttgcgtccat cgtgaagtcg | 120 |
| acaaaaacaa aaggatcggt ggagatcgat gctcatgagg gtctggtcac ttccggcctg | 180 |
| gtagagcctc acatccatct cgataaggcc ctgacggcag atcgggttcc cgcaggaagc | 240 |
| attggcgacc ttcgaacgcg acgaggcctt gagatggcaa ttcgggccac ccgtgatatc | 300 |
| aagcgtacgt tcacggttga agatgttcga gaacgggcca tacgtgcggc cctgatggca | 360 |
| tcccgtgcgg gaaccaccgc attgcggaca cacgtcgatg tcgacccgat tgtcggcctc | 420 |
| gcaggtatcc gtggtgtcct tgaggcgcgt gaagtctgcg cgggattgat cgatatccag | 480 |
| atcgtcgcct tccctcagga gggactcttc tgctctgcgg gggccgtgga cctcatgcgg | 540 |
| gaggcgatca aactgggcgc ggatgccgtc ggcggcgcac ccgcgctgga tgatcgcccg | 600 |
| caggaccatg tccgagccgt ttttgaccct tgctgctgagt tcggcctgcc cgtagacatg | 660 |
| cacgtcgatg agtccgaccg gcgggaagac tttacgcttc cctttgtgat tgaagctgcc | 720 |
| cgtgaacggc gtgtgcccaa tgtgaccgtc gcgcacatca gctcgctgtc cgtacagacg | 780 |
| gatgacgtag cacggtcgac cattgccgcc cttgcggacg ccgatgttaa tgtcgtggtt | 840 |
| aatccgatca ttgtcaaaat tacgcggctg agtgaattac tcgatgccgg agtctccgta | 900 |
| atgtttggct cggacaacct gcgggatccg ttctatccgc tcggagcggc gaatccccctt | 960 |
| ggatcagcca tttttgcctg tcaaattgcc gcgctgggaa caccgcaaga tctcagacgg | 1020 |
| gtattcgatg cggtcaccat caacgctgcc cgcatgctgg gattcccctc acttttaggc | 1080 |
| gtcgtggaag gggcagtcgc ggatctcgca gtattcccat cggcgacgcc cgaggaggtt | 1140 |
| gttctggatc aacagtctcc gctcttcgta ctcaagggcg gacgtgtcgt tgccatgcga | 1200 |
| ttggccgctg gatcaacgtc gttccgcgac tactcatga | 1239 |

<210> SEQ ID NO 56
<211> LENGTH: 726
<212> TYPE: DNA
<213> ORGANISM: Rhodococcus sp.

<400> SEQUENCE: 56

| | |
|---|---|
| atgatatact caacagtcaa cgctaatcct tacgcttggc cttacgatgg ttcaatagac | 60 |
| cctgctcaca ccgctttaat cttaatcgat tggcaaatag acttttgtgg tccaggtggt | 120 |
| tatgtcgatt ccatgggtta cgacttatcc ttgactagaa gtggtttaga acctacagca | 180 |
| agagtattgg ctgcagccag agatactggt atgacagtta tccatactag agaaggtcac | 240 |
| agaccagatt tggctgactt gccacctaat aagagatgga gatctgcatc agccggtgct | 300 |

-continued

```
gaaatcggtt cagttggtcc atgtggtaga attttagtca gaggtgaacc tggttgggaa      360
atagtaccag aagttgcacc tagagaaggt gaaccaatta tagataaacc tggtaaaggt      420
gctttctacg caacagattt ggacttgttg ttgagaacaa gaggtatcac ccatttgatt      480
ttgaccggta taactacaga tgtttgcgtc cacaccacta tgagaaagc caacgataga      540 ggttacgaat gtttaatttt gtctgattgc accggtgcta ctgacagaaa gcatcacgaa      600
gctgcattat ctatggtcac catgcaaggt ggtgtattcg gtgcaactgc ccattcagat      660
gacttattgg ccgctttggg tacaaccgtt ccagcagccg ctggtcctag agctagaaca      720
gaataa                                                                 726
```

<210> SEQ ID NO 57
<211> LENGTH: 702
<212> TYPE: DNA
<213> ORGANISM: Rhizobium leguminosarum

<400> SEQUENCE: 57

```
atggacgcga tggtcgaaac caaccggcat tttatcgacg ccgatccgta tccgtggccc      60
tataacggag ctctgaggcc tgacaatacc gccctcatca tcatcgacat gcagacggat     120
ttctgcggca agggcggtta tgtcgaccac atgggctacg acctgtcgct ggtgcaggcg     180
ccgatcgaac ccatcaaacg cgtgcttgcc gccatgcggg ccaagggtta tcacatcatc     240
cacacccgcg agggccaccg ccccgacctc gccgatctgc agcaaacaa acgctggcgc     300 tcgcaacgga tcgggccgg catcggtgat cccggcccct gcggccgaat cctgacgcgt     360
ggcgaacccg gctgggacat catccccgaa ctctacccga tcgaaggcga cgatcatc      420 gacaagcccg gcaagggttc gttctgcgcc accgacctcg aactcgtcct caaccagaaa     480
cgcatcgaga acattatcct caccgggatc accaccgatg tctgcgtctc gacgacgatg     540
cgcgaggcga acgaccgcgg ctacgaatgc ctgctgctgg aggactgctg tggtgcgacc     600
gactacggaa accacctcgc cgccatcaag atggtgaaga tgcagggcgg cgtcttcggc     660
tcggtctcca attccgcggc tctagtcgag gcgctgccct ga                        702
```

<210> SEQ ID NO 58
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Ala Asp
            35                  40                  45

Arg Val Ile Asp Ala Arg Gly Lys Val Val Leu Pro Gly Phe Ile Asn
        50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Leu Tyr Pro Gly Gln
                85                  90                  95

Lys Ala Met Arg Pro Glu Asp Val Ala Val Ala Val Arg Leu Tyr Cys
                100                 105                 110
```

Ala Glu Ala Val Arg Ser Gly Ile Thr Thr Ile Asn Asp Asn Ala Asp
            115                 120                 125

Ser Ala Ile Tyr Pro Gly Asn Ile Glu Ala Ala Met Ala Val Tyr Gly
        130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Ile Thr Pro Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asp Gly Asn Cys Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470

<210> SEQ ID NO 59
<211> LENGTH: 423
<212> TYPE: DNA
<213> ORGANISM: Saccharomyces cerevisiae

<400> SEQUENCE: 59
aggaacccat caggttggtg gaagattacc cgttctaaga cttttcagct tcctctattg    60

```
atgttacacc tggacacccc ttttctggca tccagttttt aatcttcagt ggcatgtgag    120
attctccgaa attaattaaa gcaatcacac aattctctcg gataccacct cggttgaaac    180
tgacaggtgg tttgttacgc atgctaatgc aaaggagcct ataccctttt ggctcggctg    240
ctgtaacagg gaatataaag ggcagcataa tttaggagtt tagtgaactt gcaacattta    300
ctattttccc ttcttacgta aatattttc tttttaattc taaatcaatc ttttcaatt     360 ttttgtttgt attcttttct tgcttaaatc tataactaca aaaacacat acataaacta    420 aaa                                                                 423
```

`<210>` SEQ ID NO 60
`<211>` LENGTH: 658
`<212>` TYPE: DNA
`<213>` ORGANISM: Saccharomyces cerevisiae

`<400>` SEQUENCE: 60

```
ttgctacgca ggctgcacaa ttacacgaga atgctcccgc ctaggattta aggctaaggg     60
acgtgcaatg cagacgacag atctaaatga ccgtgtcggt gaagtgttcg ccaaactttt    120
cggttaacac atgcagtgat gcacgcgcga tggtgctaag ttacatatat atatatatat    180
atatatatat atatatatag ccatagtgat gtctaagtaa cctttatggt atatttctta    240
atgtggaaag atactagcgc gcgcacccac acacaagctt cgtcttttct tgaagaaaag    300
aggaagctcg ctaaatggga ttccactttc cgttccctgc cagctgatgg aaaaaggtta    360
gtggaacgat gaagaataaa aagagagatc cactgaggtg aaatttcagc tgacagcgag    420
tttcatgatc gtgatgaaca atggtaacga gttgtggctg ttgccaggga gggtggttct    480
caacttttaa tgtatggcca aatcgctact tgggtttgtt atataacaaa gaagaaataa    540
tgaactgatt ctcttcctcc ttcttgtcct ttcttaattc tgttgtaatt accttccttt    600
gtaatttttt ttgtaattat tcttcttaat aatccaaaca aacacacata ttacaata     658
```

`<210>` SEQ ID NO 61
`<211>` LENGTH: 573
`<212>` TYPE: DNA
`<213>` ORGANISM: Saccharomyces cerevisiae

`<400>` SEQUENCE: 61

```
tgctgtaacc cgtacatgcc caaaataggg ggcgggttac acagaatata taacatcgta     60
ggtgtctggg tgaacagttt attcctggca tccactaaat ataatggagc ccgcttttta    120
agctggcatc cagaaaaaaa aagaatccca gcaccaaaat attgttttct tcaccaacca    180
tcagttcata ggtccattct cttagcgcaa ctacagagaa caggggcaca aacaggcaaa    240
aaacgggcac aacctcaatg gagtgatgca acctgcctgg agtaaatgat gacacaaggc    300 aattgacccca cgcatgtatc tatctcattt tcttacacct tctattacct tctgctctct    360
ctgatttgga aaaagctgaa aaaaaaggtt gaaccagtc ccctgaaatt attcccctac    420
ttgactaata agtatataaa gacggtaggt attgattgta attctgtaaa tctatttctt    480
aaacttctta aattctactt ttatagttag tctttttttt agttttaaaa caccaagaac    540
ttagtttcga ataaacacac ataaacaaac aaa                                573
```

`<210>` SEQ ID NO 62
`<211>` LENGTH: 812
`<212>` TYPE: DNA
`<213>` ORGANISM: Saccharomyces cerevisiae

<400> SEQUENCE: 62

```
gcaccgctgg cttgaacaac aataccagcc ttccaacttc tgtaaataac ggcggtacgc    60
cagtgccacc agtaccgtta cctttcggta tacctccttt ccccatgttt ccaatgccct   120
tcatgcctcc aacggctact atcacaaatc ctcatcaagc tgacgcaagc cctaagaaat   180
gaataacaat actgacagta ctaaataatt gcctacttgg cttcacatac gttgcatacg   240
tcgatataga taataatgat aatgacagca ggattatcgt aatacgtaat agttgaaaat   300
ctcaaaaatg tgtgggtcat tacgtaaata atgataggaa tgggattctt ctatttttcc   360
tttttccatt ctagcagccg tcgggaaaac gtggcatcct ctctttcggg ctcaattgga   420
gtcacgctgc cgtgagcatc ctctctttcc atatctaaca actgagcacg taaccaatgg   480
aaaagcatga gcttagcgtt gctccaaaaa agtattggat ggttaatacc atttgtctgt   540
tctcttctga ctttgactcc tcaaaaaaaa aaaatctaca atcaacagat cgcttcaatt   600
acgccctcac aaaaactttt ttccttcttc ttcgcccacg ttaaatttta tccctcatgt   660
tgtctaacgg atttctgcac ttgatttatt ataaaaagac aaagacataa tacttctcta   720
tcaatttcag ttattgttct tccttgcgtt attcttctgt tcttcttttt cttttgtcat   780
atataaccat aaccaagtaa tacatattca aa                                 812
```

<210> SEQ ID NO 63
<211> LENGTH: 625
<212> TYPE: DNA
<213> ORGANISM: Yarrowia lipolytica

<400> SEQUENCE: 63

```
tataaacggt attttcacaa ttgcacccca gccagaccga tagccggtcg caatccgcca    60
cccacaaccg tctacctccc acagaacccc gtcacttcca ccctttcca ccagatcata   120
tgtcccaact tgccaaatta aaaccgtgcg aattttcaaa ataaactttg gcaaagaggc   180
tgcaaaggag gggctggtga gggcgtctgg aagtcgacca gagaccgggt tggcggcgca   240
tttgtgtccc aaaaaacagc cccaattgcc ccaattgacc ccaaattgac ccagtagcgg   300
gcccaaccc ggcgagagcc cccttctccc cacatatcaa acctccccg gttcccacac   360
ttgccgttaa gggcgtaggg tactgcagtc tggaatctac gcttgttcag actttgtact   420
agtttctttg tctggccatc cgggtaaccc atgccggacg caaatagac tactgaaaat   480
ttttttgctt tgtggttggg actttagcca agggtataaa agaccaccgt ccccgaatta   540
cctttcctct tcttttctct ctctccttgt caactcacac ccgaaatcgt taagcatttc   600
cttctgagta taagaatcat tcaaa                                         625
```

<210> SEQ ID NO 64
<211> LENGTH: 318
<212> TYPE: DNA
<213> ORGANISM: Saccharomyces cerevisiae

<400> SEQUENCE: 64

```
gcataatatt gtccgctgcc cgttttctg ttagacggtg tcttgatcta cttgctatcg    60
ttcaacacca ccttattttc taactatttt tttttagct catttgaatc agcttatggt   120
gatggcacat ttttgcataa acctagctgt cctcgttgaa cataggaaaa aaaaatatat   180
aaacaaggct ctttcactct ccttggaatc agatttgggt tgttcccctt tattttcata   240
ttcttgtca tattctttc tcaattatta tcttctactc ataacctcac gcaaaataac   300
acagtcaaat caatcaaa                                                 318
```

<210> SEQ ID NO 65
<211> LENGTH: 413
<212> TYPE: DNA
<213> ORGANISM: Saccharomyces cerevisiae

<400> SEQUENCE: 65

| | | | | | |
|---|---|---|---|---|---|
| catagcttca | aaatgtttct | actccttttt | tactcttcca | gattttctcg | gactccgcgc | 60 |
| atcgccgtac | cacttcaaaa | cacccaagca | cagcatacta | aatttcccct | ctttcttcct | 120 |
| ctagggtgtc | gttaattacc | cgtactaaag | gtttggaaaa | gaaaaaagag | accgcctcgt | 180 |
| ttcttttcct | tcgtcgaaaa | aggcaataaa | aattttatc | acgttctttt | tcttgaaaa | 240 |
| tttttttttt | tgattttttt | ctctttcgat | gacctcccat | tgatatttaa | gttaataaac | 300 |
| ggtcttcaat | ttctcaagtt | tcagtttcat | ttttcttgtt | ctattacaac | ttttttact | 360 |
| tcttgctcat | tagaaagaaa | gcatagcaat | ctaatctaag | ttttaattac | aaa | 413 |

<210> SEQ ID NO 66
<211> LENGTH: 330
<212> TYPE: DNA
<213> ORGANISM: Saccharomyces cerevisiae

<400> SEQUENCE: 66

| | | | | | |
|---|---|---|---|---|---|
| taagattaat | ataattatat | aaaaatatta | tcttcttttc | tttatatcta | gtgttatgta | 60 |
| aaataaattg | atgactacgg | aaagcttttt | tatattgttt | cttttcatt | ctgagccact | 120 |
| taaatttcgt | gaatgttctt | gtaagggacg | gtagatttac | aagtgataca | acaaaaagca | 180 |
| aggcgctttt | tctaataaaa | agaagaaaag | catttaacaa | ttgaacacct | ctatatcaac | 240 |
| gaagaatatt | actttgtctc | taaatccttg | taaaatgtgt | acgatctcta | tatgggttac | 300 |
| tcataagtgt | accgaagact | gcattgaaag | | | | 330 |

<210> SEQ ID NO 67
<211> LENGTH: 377
<212> TYPE: DNA
<213> ORGANISM: Saccharomyces cerevisiae

<400> SEQUENCE: 67

| | | | | | |
|---|---|---|---|---|---|
| gtctgaagaa | tgaatgattt | gatgatttct | ttttccctcc | attttctta | ctgaatatat | 60 |
| caatgatata | gacttgtata | gtttattatt | tcaaattaag | tagctatata | tagtcaagat | 120 |
| aacgtttgtt | tgacacgatt | acattattcg | tcgacatctt | ttttcagcct | gtcgtggtag | 180 |
| caatttgagg | agtattatta | attgaatagg | ttcattttgc | gctcgcataa | acagttttcg | 240 |
| tcagggacag | tatgttggaa | tgagtggtaa | ttaatggtga | catgacatgt | tatagcaata | 300 |
| accttgatgt | ttcatcgta | gtttaatgta | caccccgcga | attcgttcaa | gtaggagtgc | 360 |
| accaattgca | aagggaa | | | | | 377 |

<210> SEQ ID NO 68
<211> LENGTH: 506
<212> TYPE: DNA
<213> ORGANISM: Saccharomyces cerevisiae

<400> SEQUENCE: 68

| | | | | | |
|---|---|---|---|---|---|
| gtgaatttac | tttaaatctt | gcatttaaat | aaattttctt | tttatagctt | tatgacttag | 60 |
| tttcaattta | tatactattt | taatgacatt | ttcgattcat | tgattgaaag | ctttgtgttt | 120 |
| tttcttgatg | cgctattgca | ttgttcttgt | cttttttcgcc | acatgtaata | tctgtagtag | 180 |

```
atacctgata cattgtggat gctgagtgaa attttagtta ataatggagg cgctcttaat        240
aattttgggg atattggctt ttttttttaa agtttacaaa tgaattttt ccgccaggat         300 aacgattctg aagttactct tagcgttcct atcggtacag ccatcaaatc atgcctataa       360
atcatgccta tatttgcgtg cagtcagtat catctcacatg aaaaaaactc ccgcaatttc      420
ttatagaata cgttgaaaat taaatgtacg cgccaagata agataacata tatctagatg      480
cagtaatata cacagattcc cgcgga                                            506

<210> SEQ ID NO 69
<211> LENGTH: 199
<212> TYPE: DNA
<213> ORGANISM: Saccharomyces cerevisiae

<400> SEQUENCE: 69
gttaattcaa attaattgat atagtttttt aatgagtatt gaatctgttt agaaataatg        60
gaatattatt tttatttatt tatttatatt attggtcggc tcttttcttc tgaaggtcaa       120
tgacaaaatg atatgaagga ataatgatt tctaaaattt tacaacgtaa gatattttta       180
caaaagccta gctcatctt                                                    199

<210> SEQ ID NO 70
<211> LENGTH: 400
<212> TYPE: DNA
<213> ORGANISM: Yarrowia lipolytica

<400> SEQUENCE: 70
gctgcttgta cctagtgcaa ccccagtttg ttaaaaatta gtagtcaaaa acttctgagt        60
tagaaatttg tgagtgtagt gagattgtag agtatcatgt gtgtccgtaa gtgaagtgtt      120
attgactctt agttagttta tctagtactc gtttagttga cactgatcta gtattttacg      180
aggcgtatga ctttagccaa gtgttgtact tagtcttctc tccaaacatg agagggctct      240
gtcactcagt cggcctatgg gtgagatggc ttggtgagat ctttcgatag tctcgtcaag     300
atggtaggat gatgggggaa tacattactg ctctcgtcaa ggaaaccaca atcagatcac      360
accatcctcc atggtatccg atgactctct tctccacagt                              400

<210> SEQ ID NO 71
<211> LENGTH: 203
<212> TYPE: DNA
<213> ORGANISM: Saccharomyces cerevisiae

<400> SEQUENCE: 71
acaagctaag ttgactgctg ctaccaacgc taagcaataa gcgatttaat ctctaattat       60
tagttaaagt tttataagca ttttttatgta acgaaaaata aattggttca tattattact    120
gcactgtcac ttaccatgga aagaccagac aagaagttgc cgacacgaca gtctgttgaa      180
ttggcttaag tctgggtccg ctt                                               203

<210> SEQ ID NO 72
<211> LENGTH: 274
<212> TYPE: DNA
<213> ORGANISM: Saccharomyces cerevisiae

<400> SEQUENCE: 72 caggccccctt ttcctttgtc gatatcatgt aattagttat gtcacgctta cattcacgcc      60
ctcctcccac atccgctcta accgaaaagg aaggagttag acaacctgaa gtctaggtcc     120
ctatttattt tttttaatag ttatgttagt attaagaacg ttatttatat ttcaaatttt     180
```

```
tcttttttttt ctgtacaaac gcgtgtacgc atgtaacatt atactgaaaa ccttgcttga    240
gaaggttttg ggacgctcga aggctttaat ttgc                                 274

<210> SEQ ID NO 73
<211> LENGTH: 67
<212> TYPE: DNA
<213> ORGANISM: Escherichia coli

<400> SEQUENCE: 73
agctggtgac aattaatcat cggctcgtat aatgtgtgga attgaatcga tataaggagg    60
ttaatca                                                               67

<210> SEQ ID NO 74
<211> LENGTH: 89
<212> TYPE: DNA
<213> ORGANISM: Escherichia coli

<400> SEQUENCE: 74
ctcaaaatat attttccctc tatcttctcg ttgcgcttaa tttgactaat tctcattagc    60
gaggcgcgcc tttccatagg ctccgcccc                                       89

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaaatccat t                                                          11

<210> SEQ ID NO 76
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76 ggaacgacc                                                             9
```